(12) United States Patent
Ma et al.

(10) Patent No.: US 11,957,760 B2
(45) Date of Patent: Apr. 16, 2024

(54) FOLATE RECEPTOR TARGETED NANOPARTICLE DRUG CONJUGATES AND USES THEREOF

(71) Applicant: Elucida Oncology, Inc., Monmouth Junction, NJ (US)

(72) Inventors: Kai Ma, Montgomery, NJ (US); Aranapakam M. Venkatesan, Rego Park, NY (US); Feng Chen, Princeton, NJ (US); Fei Wu, Plainsboro, NJ (US); Melik Ziya Türker, Princeton, NJ (US); Thomas Courtney Gardinier, II, Raritan, NJ (US); Geno J. Germano, Jr., Philadelphia, PA (US); Gregory Paul Adams, Hatboro, PA (US); Francis Y. F. Lee, Yardley, PA (US)

(73) Assignee: Elucida Oncology, Inc., Monmouth Junction, NJ (US)

( * ) Notice: Subject to any disclaimer, the term of this patent is extended or adjusted under 35 U.S.C. 154(b) by 0 days.

(21) Appl. No.: 18/183,328

(22) Filed: Mar. 14, 2023

(65) Prior Publication Data

US 2023/0263899 A1 Aug. 24, 2023

Related U.S. Application Data

(60) Division of application No. 17/867,025, filed on Jul. 18, 2022, and a continuation of application No. PCT/US2021/056610, filed on Oct. 26, 2021.

(Continued)

(51) Int. Cl.
*A61K 9/00* (2006.01)
*A61K 31/4192* (2006.01)

(Continued)

(52) U.S. Cl.
CPC ........ *A61K 47/552* (2017.08); *A61K 31/4192* (2013.01); *A61K 47/10* (2013.01);
(Continued)

(58) Field of Classification Search
CPC .................................................. A61K 47/6929
See application file for complete search history.

(56) References Cited

U.S. PATENT DOCUMENTS

| 6,214,345 B1 | 4/2001 | Firestone et al. |
| 6,548,264 B1 | 4/2003 | Tan et al. |

(Continued)

FOREIGN PATENT DOCUMENTS

| CN | 111001012 A | 4/2020 |
| EP | 0624377 B1 | 1/2002 |

(Continued)

OTHER PUBLICATIONS

Nakada, Novel antibody drug conjugates containing exatacn derivative-based cytotoxic payloads, Bioorganic & Medicinal Chemistry Letters 26, 1542-1545 (Year: 2016).*

(Continued)

*Primary Examiner* — Paul W Dickinson
(74) *Attorney, Agent, or Firm* — Hogan Lovells US LLP

(57) ABSTRACT

The disclosure relates to nanoparticle drug conjugates (NDC) that comprise ultrasmall nanoparticles, folate receptor (FR) targeting ligands, and linker-drug conjugates, and methods of making and using them to treat cancer.

30 Claims, 34 Drawing Sheets
Specification includes a Sequence Listing.

Related U.S. Application Data

(60) Provisional application No. 63/254,837, filed on Oct. 12, 2021, provisional application No. 63/242,201, filed on Sep. 9, 2021, provisional application No. 63/222,181, filed on Jul. 15, 2021, provisional application No. 63/155,043, filed on Mar. 1, 2021, provisional application No. 63/117,110, filed on Nov. 23, 2020, provisional application No. 63/116,393, filed on Nov. 20, 2020, provisional application No. 63/105,995, filed on Oct. 27, 2020.

(51) Int. Cl.
| | | |
|---|---|---|
| *A61K 47/10* | (2017.01) | |
| *A61K 47/54* | (2017.01) | |
| *A61K 47/55* | (2017.01) | |
| *A61K 47/60* | (2017.01) | |
| *A61K 47/69* | (2017.01) | |
| *A61K 49/00* | (2006.01) | |
| *A61P 35/00* | (2006.01) | |

(52) U.S. Cl.
CPC .......... *A61K 47/545* (2017.08); *A61K 47/551* (2017.08); *A61K 47/558* (2017.08); *A61K 47/60* (2017.08); *A61K 47/6923* (2017.08); *A61K 47/6929* (2017.08); *A61K 49/0032* (2013.01); *A61K 49/0093* (2013.01); *A61P 35/00* (2018.01)

(56) References Cited

U.S. PATENT DOCUMENTS

| | | |
|---|---|---|
| 7,223,837 B2 | 5/2007 | De Groot et al. |
| 7,498,298 B2 | 3/2009 | Doronina et al. |
| 7,601,332 B2 | 10/2009 | Vlahov et al. |
| 7,754,681 B2 | 7/2010 | Feng |
| 7,989,434 B2 | 8/2011 | Feng |
| 8,084,001 B2 | 12/2011 | Burns et al. |
| 8,236,319 B2 | 8/2012 | Chari et al. |
| 8,298,677 B2 | 10/2012 | Wiesner et al. |
| 8,409,876 B2 | 4/2013 | Wiesner et al. |
| 8,802,773 B2 | 8/2014 | Rozema et al. |
| 8,961,825 B2 | 4/2015 | Wiesner et al. |
| 9,011,735 B2 | 4/2015 | Wang et al. |
| 9,192,682 B2 | 11/2015 | Leamon et al. |
| 9,625,456 B2 | 4/2017 | Bradbury et al. |
| 9,931,407 B2 | 4/2018 | Foreman et al. |
| 9,999,694 B2 | 6/2018 | Bradbury et al. |
| 10,039,847 B2 | 8/2018 | Bradbury et al. |
| 10,064,855 B2 | 9/2018 | Langecker et al. |
| 10,111,963 B2 | 10/2018 | Yoo et al. |
| 10,293,053 B2 | 5/2019 | Nguyen et al. |
| 10,335,501 B2 | 7/2019 | Bradbury et al. |
| 10,485,881 B2 | 11/2019 | Bradbury et al. |
| 10,520,500 B2 | 12/2019 | El Harrak et al. |
| 10,548,989 B2 | 2/2020 | Bradbury et al. |
| 10,548,997 B2 | 2/2020 | Bradbury et al. |
| 10,548,998 B2 | 2/2020 | Bradbury et al. |
| 10,732,115 B2 | 8/2020 | Wiesner et al. |
| 10,808,039 B2 | 10/2020 | Doronina et al. |
| 10,940,216 B2 | 3/2021 | Bradbury et al. |
| 10,986,997 B2 | 4/2021 | Bradbury et al. |
| 10,987,430 B2 | 4/2021 | Shen et al. |
| 11,291,737 B2 | 4/2022 | Wiesner et al. |
| 11,419,955 B2 | 4/2022 | Bradbury et al. |
| 11,419,952 B2 | 8/2022 | Ma et al. |
| 11,559,591 B2 | 1/2023 | Bradbury et al. |
| 11,744,897 B2 | 9/2023 | Ma et al. |
| 2010/0179075 A1 | 7/2010 | Lau et al. |
| 2013/0039848 A1 | 2/2013 | Bradbury et al. |
| 2015/0174268 A1 | 6/2015 | Li |
| 2019/0343828 A1 | 11/2019 | Jeffrey et al. |
| 2022/0378924 A1 | 12/2022 | Ma |
| 2023/0021059 A1 | 1/2023 | Ma |
| 2023/0241243 A1 | 8/2023 | Venkatesan et al. |
| 2023/0263898 A1 | 8/2023 | Ma et al. |

FOREIGN PATENT DOCUMENTS

| | | |
|---|---|---|
| EP | 3546448 A1 | 10/2019 |
| WO | 2004/063387 A2 | 7/2004 |
| WO | 2004/074504 A2 | 9/2004 |
| WO | 2006/119087 A2 | 11/2006 |
| WO | 2007/136413 A2 | 11/2007 |
| WO | 2009/029870 A2 | 3/2009 |
| WO | 2010/121064 A2 | 10/2010 |
| WO | 2011/003109 A1 | 1/2011 |
| WO | 2013/127949 A1 | 9/2013 |
| WO | 2013/192609 A1 | 12/2013 |
| WO | 2014/130643 A1 | 8/2014 |
| WO | 2014/145606 A1 | 9/2014 |
| WO | 2015/103420 A1 | 7/2015 |
| WO | 2015/183882 A1 | 12/2015 |
| WO | 2016/100340 A1 | 6/2016 |
| WO | 2016/164578 A1 | 10/2016 |
| WO | 2016/179260 A1 | 11/2016 |
| WO | 2016/196201 A1 | 12/2016 |
| WO | 2017/189961 A1 | 2/2017 |
| WO | 2017/084645 A1 | 5/2017 |
| WO | 2017/106525 A1 | 6/2017 |
| WO | 2018/003739 A1 | 1/2018 |
| WO | 2018/009379 A1 | 1/2018 |
| WO | 2018/102372 A1 | 1/2018 |
| WO | 2018/191316 A1 | 10/2018 |
| WO | 2018/213851 A1 | 11/2018 |
| WO | 2018/237253 A1 | 12/2018 |
| WO | 2019/034176 A1 | 2/2019 |
| WO | 2019/081455 A1 | 2/2019 |
| WO | 2019/113004 A1 | 6/2019 |
| WO | 2019/195858 A1 | 10/2019 |
| WO | 2018/217528 A1 | 11/2019 |
| WO | 2019/213456 A1 | 11/2019 |
| WO | 2019/217893 A1 | 11/2019 |
| WO | 2020/214741 A1 | 10/2020 |
| WO | 2020/236825 A2 | 11/2020 |
| WO | 2021/092065 A1 | 5/2021 |
| WO | 2022/093793 A1 | 5/2022 |
| WO | 2022/093794 A1 | 5/2022 |
| WO | 2022/093800 A2 | 5/2022 |
| WO | 2022/093800 A3 | 6/2022 |

OTHER PUBLICATIONS

Adams Gregory P., "A targeted C'Dot drug conjugate (CDC) for the treatment of folate receptor alpha (FR[alpha]) overexpressing cancers", (2021) Retrieved from the Internet: URL: https://cancerres.aacrjournals.org/content/81/13_Supplement/305.abstract [retrieved on Feb. 6, 2022], whole document.

Adams Gregory P., et al., "ELU001, a targeted C'Dot drug conjugate (CDC) for the treatment of folate receptor alpha (FR[alpha]) overexpressing cancers", (2021) Retrieved from the Internet: URL: https://dlio3yog0oux5.cloudfront.net/elucidaoncology/files/doc/publications/20210422/Elucida+AACR+2021+Poster.pdf [retrieved on Feb. 6, 2022], the whole document.

Anonymous, "1085 / 12-PRO1184, a novel folate receptor alpha-directed antibody-drug conjugate, demonstrates robust anti-tumor activity in mouse carcinoma models," AACR Annual Meeting, 2022 New Orleans, Abstract, retrieved from the Internet: URL https://www.abstractsonline.com/pp8/#!/10517/presentation/12260, [retrieved on Sep. 21, 2022].

Anonymous, "Elucida Oncology to Present Preclinical Data on ELU001 at the American Association for Cancer Research Annual Meeting . . . ", (2021), Retrieved from the Internet: URL: https://ww.biospace.com/article/releases/elucida-oncology-to-presnet-preclinical-data-on-elu001-at-the-american-association-for-cancer-research-annual-meetingelu001-is-elucida-s-lead-c-dot-drug-conjugate-designed-to-target-fr[alpha]-overexpressing-cancers, [retrieved on Feb. 6, 2022] whole document.

(56) References Cited

OTHER PUBLICATIONS

Anonymous, "A Study to Evaluate ELU001 in Patients With Solid Tumors that Overexpress Folate Receptor Alpha (FR [alpha])", (2021), Retrieved from the Internet: URL:https://clinicaltrials.gov/ct2/show/record/NCT05001282?term=elucida+oncology&draw=2&rank=1, [retrieved on Feb. 6, 2022], whole document.
Badahur K.C. et al, "Redox potential ultrasensitive nanoparticle for the targeted delivery of camptothecin to HER2-positive cancer cells," Mol. Pharmaceutics (2014) 11:1897-1905.
Bargh, Jonathan D, et al., "Cleavable linkers in antibody-drug conjugates", Chemical Society Reviews, Royal Society of Chemistry, UK, vol. 48, No. 16, (2019), pp. 4361-4374.
Burns et al. "Fluorescent silica nanoparticles with efficient urinary excretion for nanomedicine", Nano Letters (2009) 9(1):442-448.
Cheung, A., et al. "Targeting Folate Receptor Alpha For Cancer Treatment," Oncotarget (2016) 7 (32):52553.
Doronina, et al. "Novel peptide linkers for highly potent antibody-auristatin conjugate," Bioconjugate Chem. (2008) 19:1960-1963.
Dubowchik, et al. "Cathepsin B-labile dipeptide linkers for lysosomal release of doxorubicin from internalizing immunoconjugates: model studies of enzymatic drug release and antigen-specific in vitro anticancer activity," Bioconjugate Chem. (2002) 13:855-869.
Kolb et al. Angew. Chem. Int. Ed. (2001) 40:2004-2021.
Hilderbrand, et al., "Near-infrared fluorescence: application to in vivo molecular imaging", Chemical Biology, (2010), 14:71-79.
Leamon, et al., "Comparative preclinical activity of the folate-targeted Vinca alkaloid conjugates EC140 and EC145," Int. J. Cancer (2007) 121:1585-1592.
Leamon, et al., "Folate-Vinca Alkaloid Conjugates for Cancer Therapy: A Structure-Activity Relationship," Bioconjugate Chemistry (2014) 25, pp. 560-568.
Ledermann, J. A. et al., "Targeting the folate receptor: diagnostic and therapeutic approaches to personalize cancer treatments," Annals of Oncology (2015), 26:2034-2043.
Ma et al. "Control of ultrasmall sub-10 nm ligand-functionalized fluorescent core-shell silica nanoparticle growth in water," Chem. Mater. (2015) 27:4119-4133.
Ma et al. "Controlling growth of ultrasmall sub-10 nm fluorescent mesoporous silica nanoparticles," Chem. Mater. (2013) 25:677-691.
Ma et al. "Early formation pathways of surfactant micelle directed ultrasmall silica ring and cage structures," J. Am. Chem. Soc. (2018) 140:17343-17348.
Ma et al. "Modular and orthogonal Post-PEGylation surface modifications by insertion enabling penta-functional ultrasmall organic-silica hybrid nanoparticles," Chem. Mater. (2017) 29:6840-6855.
Ma et al. "Elucidating the mechanism of silica nanoparticle PEGylation processes using fluorescence correlation spectroscopies," Chem. Mater. (2016), 28:1537-1545.
Phillips, et al. "Clinical translation of an ultrasmall inorganic optical-PET imaging nanoparticle probe," Science Translational Medicine, (2014) vol. 6, Issue 260, p. 260ra149.
Scaranti, et al., "Exploiting the folate receptor a in oncology", Nature Reviews, vol. 17, (2020), pp. 349-359.
St. Amant, "Novel Conjugation Strategies Using the Diels Alder Reaction", PHD. Thesis US Santa Barbara, (2018), pp. 1-226.
St. Amant,, "A Reactive Antibody Platform for One-Step Production of Antibody Drug Conjugates through a Diels Alder Reaction with Maleimide", Bioconjugate Chemistry, (2019), pp. 1-10.
St. Amant, et al., "Tuning the Diels Alder Reaction for Bioconjugation to Maleimide Drug-Linkers", Bioconjugate Chemistry, vol. 29, No. 7, (2018), pp. 2406-2414.
Turker et al. "Inner and outer surface functionalizations of ultrasmall fluorescent silica nanorings as shown by high-performance liquid chromatography," Chem. Mater. (2019) 31:5519-5528.
Turker et al. "Bimodal morphology transition pathway in the synthesis of ultrasmall fluorescent mesoporous silica nanoparticles," J. Phys. Chem. C (2019) 123:9582-9589.
Yoo et al., "Ultrasmall dual-modality silica nanoparticle drug conjugates: Design, synthesis, and characterization," Bioorg. Med. Chem. (2015) 23:7119-7130.
Written Opinion and International Searching Authority in PCT/US2021/056611, dated Feb. 23, 2022.
Written Opinion of the International Searching Authority in PCT/US2021/056621, dated May 3, 2022.
Written Opinion of the International Searching Authority in PCT/US2021/056610, dated May 5, 2022.
Choi et al., "Targeting kidney mesangium by nanoparticles of defined size", PNAS, vol. 108 (2011), 6656-6661.
Destito, et al. "Folic Acid-Mediated Targeting of Cowpea Mosaic Virus Particles to Tumor Cells", Chemistry & Biology 14, (2007), 1152-1162.
Lin et al., "Well-Ordered Mesoporous Silica Nanoparticles as Cell Markers", Chem. Matter (2005), 17, 4570-4573.
Lu et al. "Linkers having a crucial role in antibody-drug conjugates," Int. J. Mol. Sci. (2016), 17, 561.
Liu et al., pH-Reversible Cationic RNase A Conjugates for Enhanced Cellular Delivery and Tumor Cell Killing, Biomacromolecules, (2016), 17, 173-182.
Liu et al., "In Vitro and in Vivo Studies on the Transport of PEGylated Silica Nanoparticle across the Blood-Brain Barrier", American Chemical Society, (2014), pp. 2131-2136.
Venkatesan, et. al., Unpublished U.S. Appl. No. 18/297,200.
Ma, et. al., Unpublished U.S. Appl. No. 18/183,305.
Kettenbach, et al., "A 18F-lableled dibenzocyclooctyne (DBCO) derivative for copper-free click labeling of biomolecules", Med. Chem. Commun., (2016) 7, 654-657.
Schladt et al., "Multifunctional superparamagnetic MnO@SiO2 core/shell nanoparticles and their application for optical and magnetic resonance imaging," J. Mater. Chem. (2012), 22, 9253.
Chen, et al., "In vivo tumor targeting and image-guided drug delivery with antibody-conjugated, radiolabeled mesoporous silica nanoparticles," ACSNano (2013) 7(10), 9027-9039.

\* cited by examiner

| Compound names | DPR* | 7-day exposure (CellTiter-Glo® cytotoxic assay) ||||||
|---|---|---|---|---|---|---|---|
| | | KB(++++) | IGROV-1(++) | SK-OV-3(++) | HCC827(++) | A549(-) | BT549(-) |
| FA-CDC | 43 | 0.02 nM | 0.10 nM | 0.20 nM | 0.2 nM | 0.6 nM | 0.1 nM |
| FA-CDC | 20 | 0.23 nM | 0.44 nM | 0.70 nM | 0.3 nM | 1.9 nM | 0.33 nM |
| FA-CDC | 8 | 0.70 nM | 0.63 nM | 2.3 nM | 0.6 nM | 2.4 nM | 0.62 nM |
| Free Exatecan | 1 | 1.6 nM | 0.84 nM | 0.5 nM | 0.6 nM | 3.2 nM | 0.4 nM |

| Compound names | DPR* | 6-hour exposure (CellTiter-Glo® cytotoxic assay) ||||||
|---|---|---|---|---|---|---|---|
| | | KB(++++) | IGROV-1(++) | SK-OV-3(++) | HCC827(++) | A549(-) | BT549(-) |
| FA-CDC | 43 | 2.0 nM | 1.8 nM | 2.7 nM | 1.1 nM | 6.1 nM | 1.2 nM |
| FA-CDC | 20 | 3.6 nM | 6.2 nM | 44.5 nM | 2.7 nM | 38.8 nM | 4.4 nM |
| FA-CDC | 8 | 6.0 nM | 8.2 nM | 50.7 nM | 6.9 nM | 49.5 nM | 24.5 nM |
| Free Exatecan | 1 | 74.4 nM | 25.6 nM | 55.8 nM | 2.7 nM | 39.7 nM | 8.8 nM |

*DPR : Drug-to-Particle Ratio

FIG. 23

| Histology | Model | FR alpha positivity (IHC score) | Cytotoxicity IC50 (nM) | | Fold increase in potency (Targeted vs. Free) | |
|---|---|---|---|---|---|---|
| | | | NDC | Exatecan | NDC vs. Exatecan | Mean |
| Ovarian | ST004 | 3+ | 2.8 | 74.7 | 26.6 | |
| Ovarian | ST3308 | 3+ | 1.8 | 7.7 | 4.4 | |
| Ovarian | ST024 | 3+ | 0.4 | 3.9 | 9.6 | 13.5 |
| Ovarian | ST182B | 2+ | 0.2 | 0.7 | 4.4 | |
| Ovarian | ST206 | 2+ | 17.4 | 202.8 | 11.7 | |
| Ovarian | ST2442 | 2+ | 0.8 | 1.7 | 2.2 | 6.1 |
| Ovarian | ST182 | 1+ | 0.3 | 2.8 | 8.5 | |
| Ovarian | ST419 | 1+ | 0.16 | 0.34 | 2.1 | |
| Ovarian | ST4321 | 1+ | 0.3 | 0.7 | 2.4 | 4.3 |
| Ovarian | ST2199 | 1+ | - | - | - | - |

| Histology | Model | FR alpha positivity (IHC score) | Cytotoxicity IC50 (nM) | | Fold increase in potency (Targeted vs. Free) | |
|---|---|---|---|---|---|---|
| | | | NDC | Exatecan | NDC vs. Exatecan | Mean |
| NSCL | ST1931 | 3+ | 0.25 | 2.13 | 8.5 | |
| NSCL | ST1989 | 3+ | 2.4 | 17.4 | 7.3 | 7.9 |
| NSCL | ST1243 | 2+ | 0.46 | 4.74 | 10.3 | |
| NSCL | ST3647 | 2+ | 0.31 | 2.87 | 9.3 | |
| Breast (HR-, HER2+) | ST353 | 2+ | 1.69 | 5.79 | 3.4 | |
| Breast (HR+, HER2+) | ST430 | 2+ | 0.42 | 1.58 | 3.8 | |
| Breast (HR+, HER2+) | STF040 | 2+ | 3.18 | 33.64 | 10.6 | 7.5 |
| TNBC | ST1248 | 1+ | 1.93 | 161.9 | 83.9 | |
| TNBC | ST1599 | 1+ | 3.20 | 157.5 | 49.2 | 66.6 |

| Histology | Model | FR alpha positivity (IHC score) | Cytotoxicity IC50 (nM) | | Fold increase in potency (Targeted vs. Free) | |
|---|---|---|---|---|---|---|
| | | | NDC | Exatecan | NDC vs. Exatecan | Mean |
| Endometrium | ST1392 | 3+ | 0.39 | 3.44 | 8.8 | |
| Endometrium | ST2043 | 3+ | 36.6 | 409.5 | 11.2 | |
| Endometrium | ST4413 | 3+ | 2.47 | 25.82 | 10.5 | 10.2 |
| Endometrium | ST2073 | 2+ | 3.15 | 7.9 | 2.5 | |
| Endometrium | ST2136 | 2+ | 6.13 | 21.4 | 3.5 | |
| Endometrium | ST2846 | 2+ | 0.80 | 16.67 | 20.8 | |
| Head&Neck | ST1203 | 2+ | 0.22 | 2.29 | 10.4 | |
| Head&Neck | ST2216 | 2+ | 1.21 | 9.74 | 8.0 | |
| Head&Neck | ST2430 | 2+ | 0.37 | 2.0 | 5.3 | |
| NSCL | ST3898 | 2+ | 4.04 | 61.6 | 15.2 | 9.4 |

FIG. 24

FOLATE RECEPTOR TARGETED NANOPARTICLE DRUG CONJUGATES AND USES THEREOF

RELATED APPLICATIONS

This application is a divisional of U.S. application Ser. No. 17/867,025, which was filed on Jul. 18, 2022, under 35 U.S.C. 111(a) as a continuation of International Application No. PCT/US2021/056610, filed on Oct. 26, 2021, which claims the benefit of U.S. Provisional Application No. 63/105,995, filed on Oct. 27, 2020, U.S. Provisional Application No. 63/116,393, filed on Nov. 20, 2020, U.S. Provisional Application No. 63/117,110, filed on Nov. 23, 2020, U.S. Provisional Application No. 63/155,043, filed on Mar. 1, 2021, U.S. Provisional Application No. 63/222,181, filed on Jul. 15, 2021, U.S. Provisional Application No. 63/242,201, filed on Sep. 9, 2021, and U.S. Provisional Application No. 63/254,837, filed on Oct. 12, 2021, the contents of which are each incorporated herein by reference in their entireties.

SEQUENCE LISTING

The instant application contains a Sequence Listing which has been submitted electronically in XML format and is hereby incorporated by reference in its entirety. Said XML file, created on Sep. 13, 2022, is named 761825_291000_SL.xml and is 9,091 bytes in size.

BACKGROUND OF THE INVENTION

Targeted delivery of therapeutics (e.g., cytotoxic drugs) to cancer cells is an emerging approach for cancer treatment. The toxicity of the delivered therapeutics to healthy tissue or organs in a subject can be greatly reduced by the selective delivery of drugs to a targeted disease area, leading to improved therapeutic outcomes. Antibody drug conjugates (ADCs) are a popular platform for targeted drug delivery, which typically feature a highly toxic drug substance covalently attached to a monoclonal antibody that can target cancer, wherein the toxic drug substance is released upon targeting of the cancer. However, many challenges remain with conventional targeted drug delivery platforms, such as ADCs, including difficulties in production, limitations in drug loading capacity, poor tumor penetration, and lack of ability to overcome tumor heterogeneity.

Cornell University and Memorial Sloan Kettering Cancer Center developed ultrasmall sub-10 nm silica-organic hybrid nanoparticles, referred to as Cornell prime dots (C'Dots), which have significant potential in diagnostics and therapeutic applications. For example, C'Dots can be conjugated with epidermal growth factor receptor inhibitors, e.g., gefitinib, which is a cancer-targeted agent that inhibits cancer growth (WO 2015/183882 A1). However, the mechanism of action (MOA) of EGFR inhibitors requires active binding to the epidermal growth factor receptor, so a continuous high concentration of the payload in the targeted cancer cell is required to effectively inhibit cancer cell proliferation. This type of MOA is generally not compatible with the fast blood circulation half-life of C'Dots.

Folate receptor alpha (FRα), also known as FOLR1, has received significant attention from the scientific community as a potential target for cancer therapy, and other isoforms of FR have also been identified as potential biological targets. See, e.g., Targeting Folate Receptor Alpha For Cancer Treatment, Cheung, A., et al. *Oncotarget* (2016) 7 (32): 52553; Targeting the folate receptor: diagnostic and therapeutic approaches to personalize cancer treatments, Ledermann, J. A. et al., *Annals of Oncology* (2015), 26:2034-2043; each of which are incorporated herein by reference in their entireties. Folate receptor (FR) is an ideal target for cancer therapy, as FR can be overexpressed in tumors, such as those of the ovary, endometrium, breast, colon, and lung, but its distribution in normal tissues is low and restricted. Emerging insights have suggested that FR may also exhibit cell-growth regulation and signaling functions, in addition to serving as a folate receptor and transporter. These features together render FR an attractive therapeutic target.

Folic acid is transported into the cells by various mechanisms, and the most prevalent mechanism is mediation through folate receptors, of which there are four glycopeptide members (FR alpha [FOLR1], FR beta [FOLR2], FR gamma [FOLR3], and FR delta [FOLR4]). Among these four members, the alpha isoform (FR alpha or FRα) is a glycosylphosphatidylinositol (GPI)-anchored membrane protein with high affinity for binding and transporting the active form of folate, 5-methyltetrahydrofolate (5MTF). The alpha isoform has been reported to be over-expressed in certain solid tumors, for example, in ovarian cancer, fallopian tube cancer, primary peritoneum cancer, uterus cancer, kidney cancer, lung cancer, brain cancer, gastrointestinal cancer, and breast carcinomas. The alpha isoform is also over-expressed in certain hematological malignancies, which can be exploited for treatment of these malignancies, e.g., for treatment of acute myeloid lymphoma (AML), including pediatric AML. This low and restricted distribution in normal tissues or cells, alongside emerging insights into tumor-promoting functions and association of expression with patient prognosis, together render FRα an attractive therapeutic target. Additionally, the beta isoform (FRβ) is overexpressed in certain cancers, e.g., hematological malignancies such as acute myeloid leukemia (AML) and chronic myelogenous leukemia (CML), providing the opportunity to develop targeted therapies for these cancers.

Although many FR-targeted drug delivery platforms have been developed and tested for cancer treatment in the past, e.g., using both ADCs and small-molecule drug conjugates, none of them are successfully approved for clinical use due to their limited therapeutic outcome (EP 0624377 A2, U.S. Pat. No. 9,192,682 B2, Leamon, et al., "Comparative preclinical activity of the folate-targeted Vinca alkaloid conjugates EC140 and EC145, *Int. J Cancer* (2007) 121:1585-1592; Leamon et al., "Folate-Vinca Alkaloid Conjugates for Cancer Therapy: A Structure-Activity Relationships, *Bioconjugate Chemistry* (2014) 25:560-568; Scaranti, M., et al. Exploiting the folate receptor a in oncology. *Nat Rev Clin Oncol.* (2020) 17: 349-359).

Therefore, successful development of a FR-targeted drug delivery platform remains highly desired.

SUMMARY OF THE INVENTION

The present disclosure provides a nanoparticle-drug conjugate (NDC) comprising: (a) a silica nanoparticle, and polyethylene glycol (PEG) covalently bonded to the surface of the nanoparticle; (b) a targeting ligand comprising folic acid, or a derivative or salt thereof, wherein the targeting ligand is attached to the nanoparticle directly or indirectly through a spacer group; and (c) a linker-payload conjugate, wherein: (i) the payload is exatecan; (ii) the linker-payload conjugate is attached to the nanoparticle directly or indirectly through a spacer group; (iii) the linker is a protease-cleavable linker; and (iv) the exatecan is released upon cleavage of the linker.

This disclosure also relates to nanoparticle-drug-conjugates (NDCs) comprising: (a) a nanoparticle that comprises a silica-based core and a silica shell surrounding at least a portion of the core; polyethylene glycol (PEG) covalently bonded to the surface of the nanoparticle, and a fluorescent compound covalently encapsulated within the core of the nanoparticle; (b) a targeting ligand that binds to folate receptor (FR), wherein the targeting ligand comprises folic acid, or a folate receptor binding derivative thereof, and wherein the targeting ligand is attached to the nanoparticle directly or indirectly through a spacer group; (c) a linker-payload conjugate, wherein the payload is a cytotoxic agent; wherein the linker-payload conjugate is attached to the nanoparticle directly or indirectly thorough a spacer group; wherein the cytotoxic agent is released upon cleavage of the linker; wherein the linker in the linker-payload conjugate is a protease-cleavable linker; and wherein the NDC has an average diameter between about 1 nm and about 10 nm, e.g., between about 3 nm and about 8 nm, or between about 3 nm and about 6 nm. The cytotoxic agent may be exatecan.

In the NDCs of the present disclosure, the average nanoparticle to payload ratio may range from 1 to 80, such as from 1 to 21 (e.g., 1 to 13, or 1 to 12) and the average nanoparticle to targeting ligand ratio may range from 1 to 50, such as from 1 to 25 (e.g., 1 to 11).

The NDCs of the present disclosure may have an average diameter of between about 1 nm and about 10 nm, e.g., between about 5 nm and about 8 nm, between about 3 nm and about 8 nm, or between about 3 nm and about 6 nm.

The NDCs of the present disclosure may comprise any suitable dye or detectable compound, such as a fluorescent compound. For example, in an NDC of the present disclosure, the fluorescent compound may be Cy5. The fluorescent compound may be encapsulated within the nanoparticle (e.g., covalently linked to the silica core). The NDCs of the present disclosure can comprise a targeting ligand that binds to a folate receptor (FR). The targeting ligand may comprise folic acid or a derivative thereof. It should be understood that "folic acid" may encompass an amide or an ester of folic acid, e.g., folic acid may be conjugated to the nanoparticle (or spacer group) at its carboxyl terminus via an amide or ester bond. For example, "folic acid" may refer to the folic acid amide present in the exemplary NDC illustrated in FIG. 1.

The NDCs of the present disclosure may comprise structure (S-1):

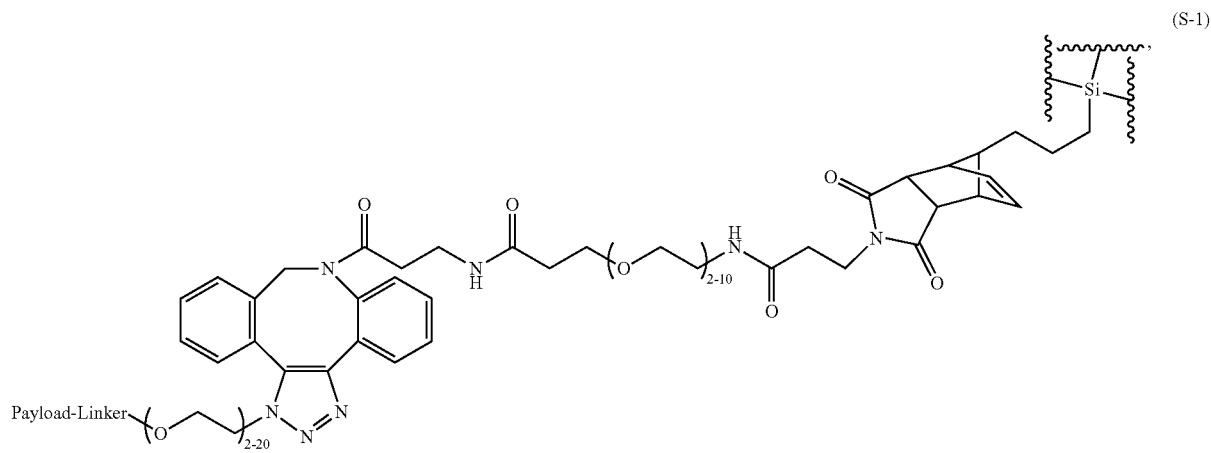

wherein Payload comprises exatecan; Linker comprises a protease-cleavable linker; and the silicon atom is a part of the nanoparticle.

For example, the NDCs of the present disclosure may comprise structure (S-1a):

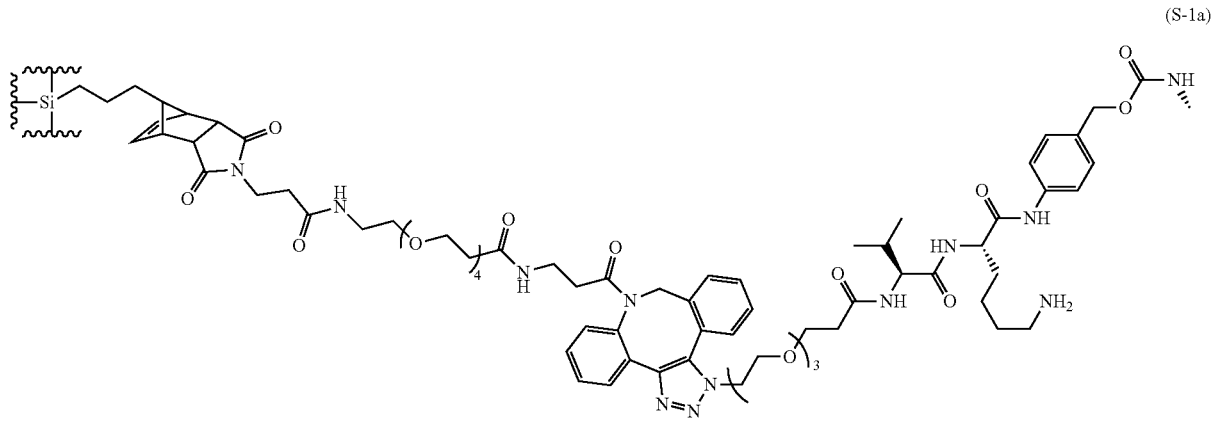

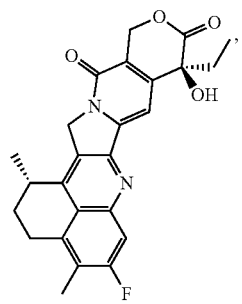

wherein the silicon atom is a part of the nanoparticle.

The NDCs of the present disclosure may comprise Structure (S-2):

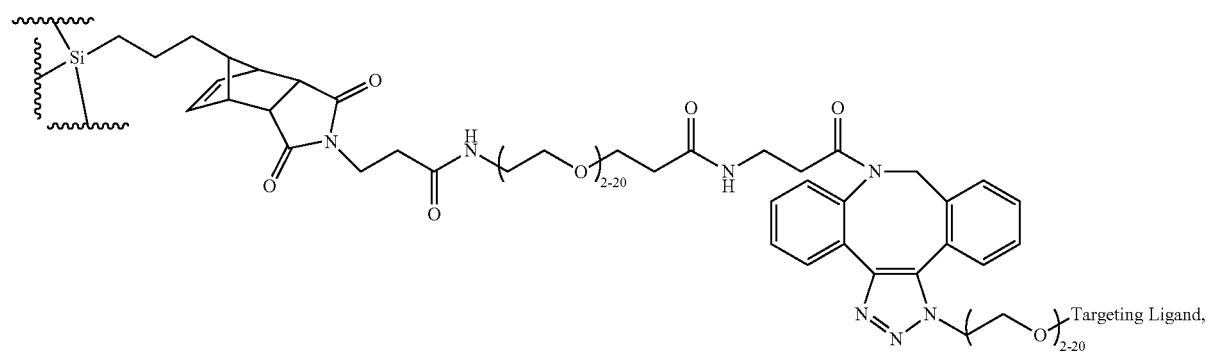

(S-2)

wherein Targeting Ligand is folic acid, or a folate receptor binding derivative thereof, and the silicon atom is a part of the nanoparticle.

For example, the NDCs of the present disclosure may comprise structure (S-2a):

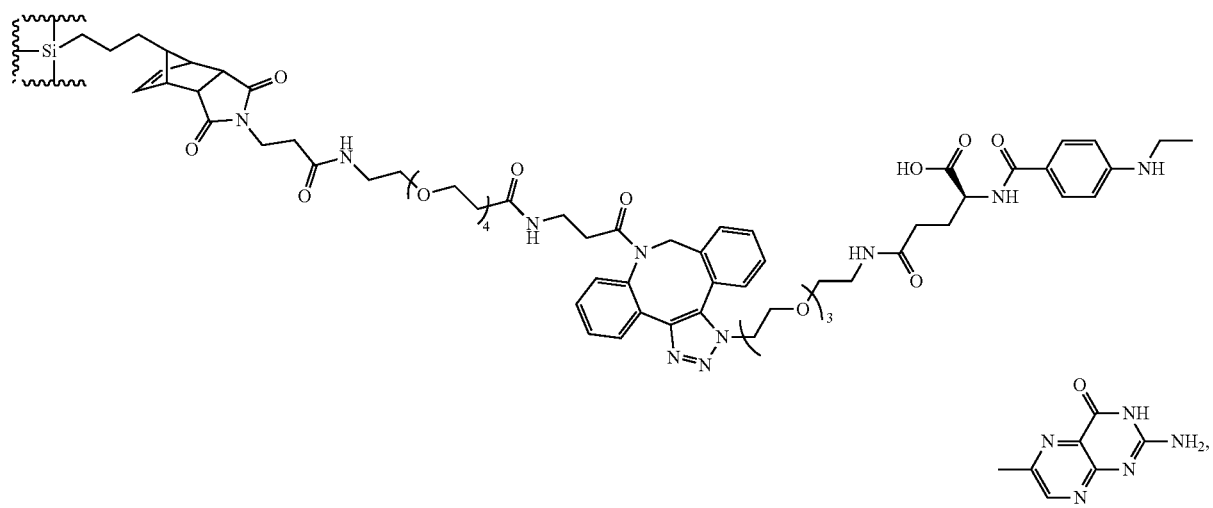

(S-2a)

wherein the silicon atom is a part of the nanoparticle.

The NDCs of the present disclosure may comprise a combination of Structures (S-1) and (S-2). For example, the NDCs may comprise both Structure (S-1a) and Structure (S-2a), e.g., as depicted in FIG. 1. Structures S-1, S-1a, S-2, or S-2a may be present in the NDC at any desired ratio, e.g., at a ratio disclosed herein.

The disclosure also relates to NDCs comprising a nanoparticle that comprises a silica-based core and a silica shell surrounding at least a portion of the core; polyethylene glycol (PEG) covalently bonded to the surface of the nanoparticle; a fluorescent compound covalently encapsulated within the core of the nanoparticle; a targeting ligand, wherein the targeting ligand is folic acid; a linker-payload conjugate, wherein the linker-payload conjugate is a protease cleavable linker that is capable of undergoing hydrolysis at a C-terminal end upon protease binding thereby releasing the payload from the nanoparticle, wherein the protease comprises a serine protease or a cysteine protease, wherein the payload in the linker-payload conjugate is exatecan, or an analog of exatecan; and wherein the fluorescent compound is Cy5.

The disclosure also relates to NDCs comprising a nanoparticle that comprises a silica-based core and a silica shell surrounding at least a portion of the core; polyethylene glycol (PEG) covalently bonded to the surface of the nanoparticle; a Cy5 dye covalently encapsulated within the core of the nanoparticle; a targeting ligand that binds to folate receptor, wherein the targeting ligand is folic acid, and wherein the targeting ligand is attached to the nanoparticle indirectly through a spacer group; a linker-payload conjugate, wherein the linker-payload conjugate is attached to the nanoparticle indirectly through a spacer group, wherein the linker-payload conjugate comprises a compound comprising the structure

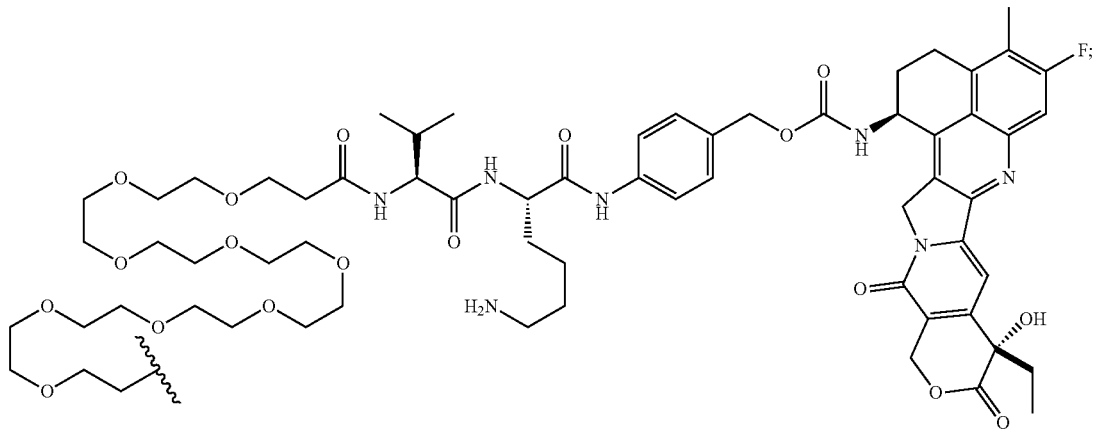 [SMILES: *CCOCCOCCOCCOCCOCCOCCOCCOCCOCCC(=O)N[C@H](C(=O)N[C@@H](CCCCN)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C]

and wherein the NDC has an average diameter between about 1 nm and about 10 nm (e.g., between about 1 and about 6 nm).

This disclosure also relates to nanoparticle drug conjugates (NDC) comprising: (a) a silica nanoparticle that comprises a silica-based core and a silica shell surrounding at least a portion of the core; and polyethylene glycol (PEG) covalently bonded to the surface of the nanoparticle; (b) an exatecan-linker moiety comprising the structure of Formula (NP-3):

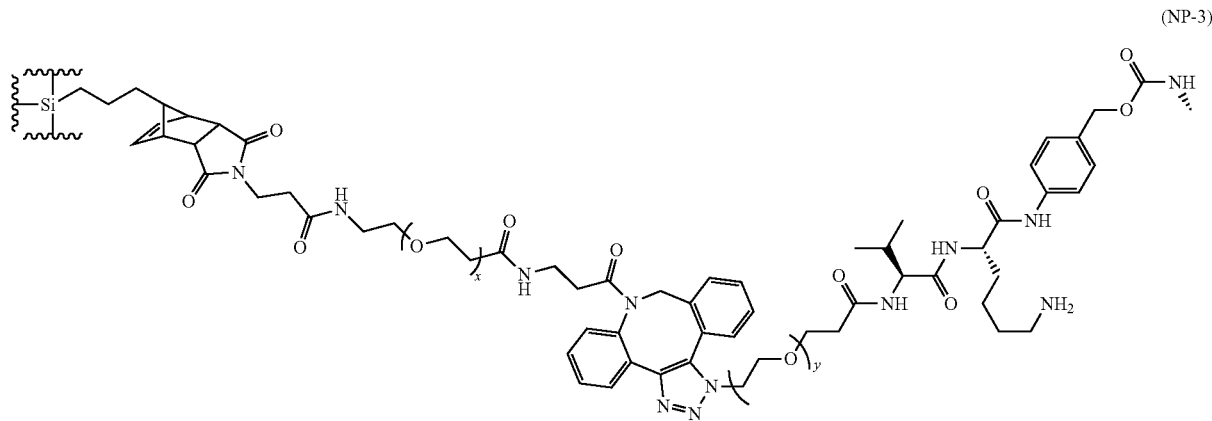

(NP-3)

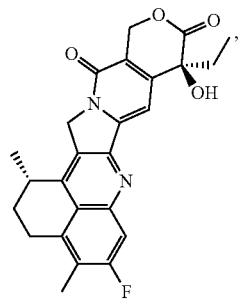

wherein x is 4 and y is 9; and (c) a targeting ligand moiety comprising the structure of Formula (NP-2)

(NP-2)

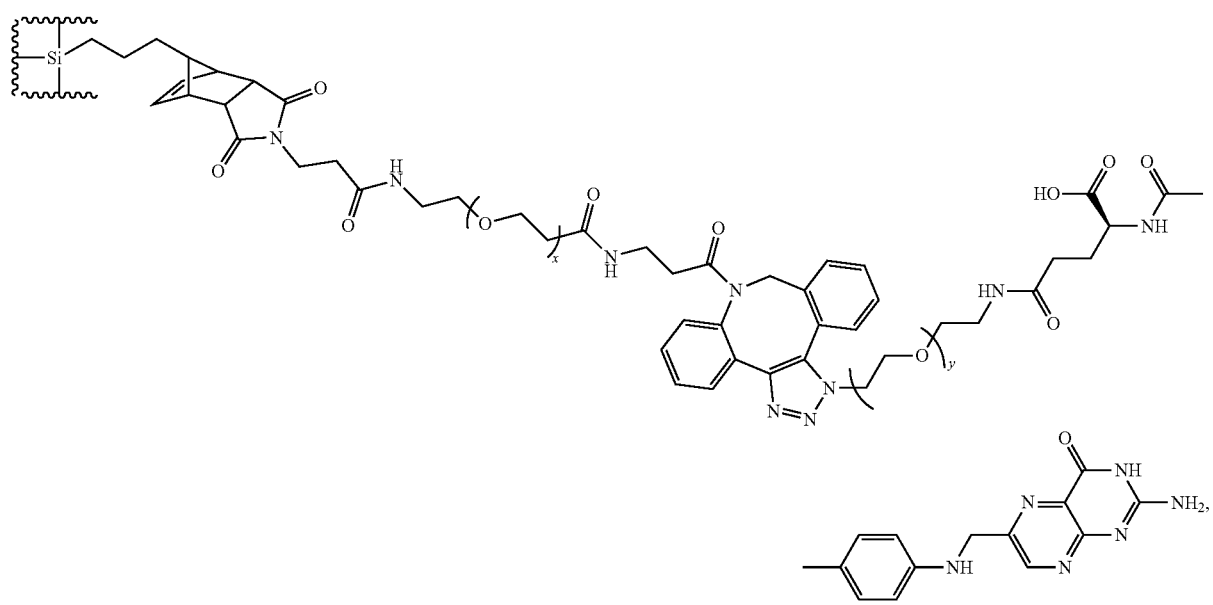

wherein x is 4 and y is 3, and wherein the exatecan-linker moiety and the targeting ligand moiety are each conjugated to a surface of the nanoparticle. The NDC may comprise a fluorescent dye (e.g., Cy5) covalently encapsulated within the core of the nanoparticle.

This disclosure also provides a method of treating a folate receptor (FR)-expressing cancer (e.g., a folate receptor (FR)-expressing tumor), comprising administering to a subject in need thereof an effective amount of an NDC described herein. The method may include administration of NDCs to the subject in need thereof intravenously. In the methods of the present disclosure, the subject may have a cancer selected from the group consisting of ovarian cancer, endometrial cancer, fallopian tube cancer, cervical cancer, breast cancer (including, e.g., HER2+ breast cancer, HR+ breast cancer, HR− breast cancer, and triple-negative breast cancer), lung cancer (e.g., non-small cell lung cancer (NSCLC), mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML). The NDCs of the present disclosure may also be used for targeting tumor associated macrophages, which may be used as a means to modify the immune status of a tumor in a subject. The NDCs of the present disclosure may be used in a method of treating an advanced, recurrent, or refractory solid tumor.

This disclosure provides use of an NDC for treating a folate receptor (FR)-expressing cancer (e.g., a folate receptor (FR)-expressing tumor). The use may include administration of NDCs intravenously to the subject in need thereof. In the use of the NDC, the subject may have a cancer selected from the group consisting of ovarian cancer, endometrial cancer, fallopian tube cancer, cervical cancer, breast cancer (including, e.g., HER2+ breast cancer, HR+ breast cancer, HR− breast cancer, and triple-negative breast cancer), lung cancer (e.g., non-small cell lung cancer (NSCLC), mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML). In the use of the NDC, the cancer may be an advanced, recurrent, or refractory solid tumor.

This disclosure provides NDCs for use in the manufacture of a medicament for treating a folate receptor (FR)-expressing cancer (e.g., a folate receptor (FR)-expressing tumor). The use in the manufacture of a medicament may include administration of NDCs intravenously to the subject in need thereof. The use in the manufacture of a medicament may include administration of NDCs to a subject, wherein the subject has a cancer selected from the group consisting of ovarian cancer, endometrial cancer, fallopian tube cancer, cervical cancer, breast cancer (including, e.g., HER2+ breast cancer, HR+ breast cancer, HR− breast cancer, and triple-negative breast cancer), lung cancer (e.g., non-small cell lung cancer (NSCLC), mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML). The NDCs of the present disclosure may be used in the manufacture of a medicament for treating an advanced, recurrent, or refractory solid tumors.

This disclosure also relates to a pharmaceutical composition comprising an NDC and a pharmaceutically acceptable excipient. The pharmaceutical compositions disclosed herein may be used for treating a folate receptor (FR)-expressing cancer (e.g., a folate receptor (FR)-expressing tumor).

BRIEF DESCRIPTION OF THE DRAWINGS

FIG. 10A depicts a representative HPLC chromatograph at 360 nm of the non-cleaved NDC showing a single peak at elution time around 6.3 min which corresponds to the non-released payload retained on the NDC. FIG. 10B depicts a representative HPLC chromatograph at 360 nm of a cleaved NDC, showing an additional peak at elution time around 3 to 4 min which corresponds to the released exatecan payload. The area under curve (AUC) of the released payload and the retained payload were used to calculate the percentage of released payload.

FIG. 11A depicts the reverse-phase HPLC chromatograph of NDC B at different time points after incubation with Cathepsin-B. FIG. 11B depicts the reverse-phase HPLC chromatograph of NDC C at different time points after incubation with cathepsin-B. FIG. 11C depicts the reverse-phase HPLC chromatograph of NDC D (prepared using the exatecan-linker conjugate precursor 202, from Example 1) at different time points after incubation with cathepsin-B.

FIG. 12A depicts the $T_{1/2}$ as 2.9 hours for NDC B. FIG. 12B depicts the $T_{1/2}$ as 2.6 hours for NDC C. FIG. 12C depicts the $T_{1/2}$ as 1.4 hours for NDC D.

FIG. 21A shows the $IC_{50}$ curves of irinotecan in regular KB cells (naïve cells), and in KB cells treated four times with irinotecan (irinotecan-resistant cells). FIG. 21B shows the $IC_{50}$ curves of the exemplary NDC in the naïve cells, and in the irinotecan-resistant cells. The exatecan-linker conjugate precursor used to prepare the exemplary NDC of this study is described in Example 1 (Compound 202).

FIG. 21A shows the $IC_{50}$ curves of exatecan in regular KB cells (naïve cells), and in KB cells treated four times or seven times with exatecan (exatecan-resistant cells). FIG. 22A shows the $IC_{50}$ curves of the exemplary NDC in the naïve cells and in the exatecan-resistant cells (4-cycle and 7-cycle pretreatment). The exatecan-linker conjugate precursor used to prepare the exemplary NDC of this study is described in Example 1 (Compound 202).

FIG. 23 provides a table demonstrating the cytotoxicity of exemplary folate receptor targeting NDCs ("FA-CDC") with varying drug-to-particle ratios (DPRs), in different FR-alpha overexpressing cancer cell lines, compared to non-conjugated exatecan. The exatecan-linker conjugate precursor used to prepare the exemplary NDCs of this study is described in Example 1 (Compound 202).

FIG. 24 provides a table showing the cytotoxicity of an exemplary NDC in various 3D patient-derived platinum-resistant tumor spheroids. The exatecan-linker conjugate precursor used to prepare the exemplary NDC of this study is described in Example 1 (Compound 202).

FIG. 25A is the flow cytometry histogram of the FR targeting NDC (10 nM) and non-targeting NDC (negative control; 10 nM) in IGROV-1 cell line. FIG. 25B is the flow cytometry histogram of anti-FR alpha antibody-PE and isotype antibody-PE (negative control) in IGROV-1 cell line. FIG. 25C is the flow cytometry histogram of the FR targeting NDC (10 nM) and non-targeting NDC (negative control; 10 nM) in engineered AML MV4;11 cell line that overexpresses FR alpha. FIG. 25D is the flow cytometry histogram of anti-FR alpha antibody-PE and isotype antibody-PE (negative control) in engineered AML MV4;11 cell line that overexpresses FR alpha.

FIG. 33A compares the stability of an NDC produced using a diene-based functionalized nanoparticle (i.e., based on the protocol outlined in Example 3), and a comparative NDC produced using an amine-based functionalized nanoparticle, in human serum at 37° C., over 7 days. FIG. 33B compares the stability of the NDC produced using a diene-based bifunctional precursor, and the comparative NDC produced using an amine-based bifunctional precursor, in mouse serum at 37° C., over 7 days.

DETAILED DESCRIPTION OF THE INVENTION

Figure 1:
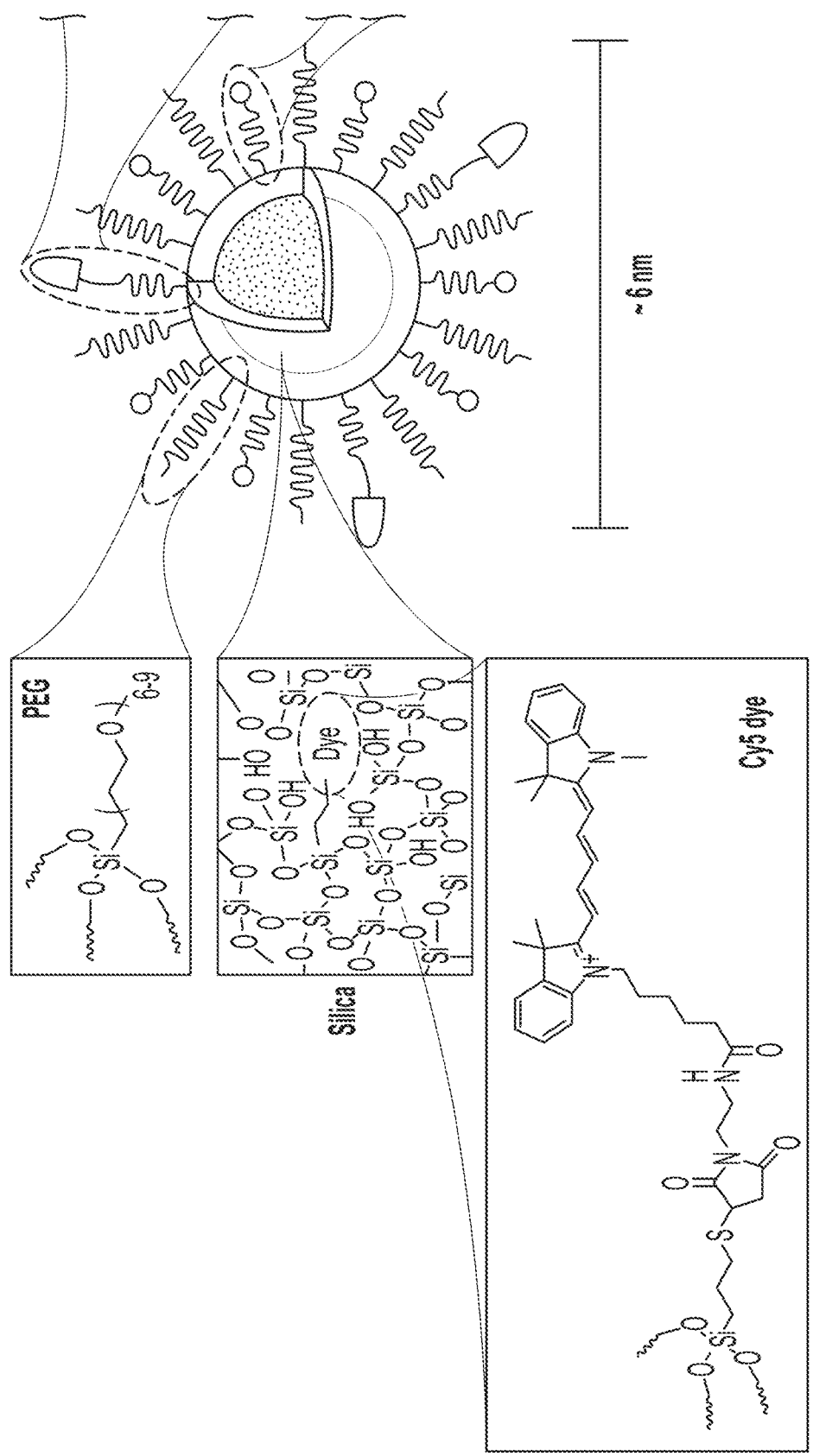
FIG. 1 illustrates a representative chemical structure of nanoparticle-drug conjugate (NDC).
Figure 1:
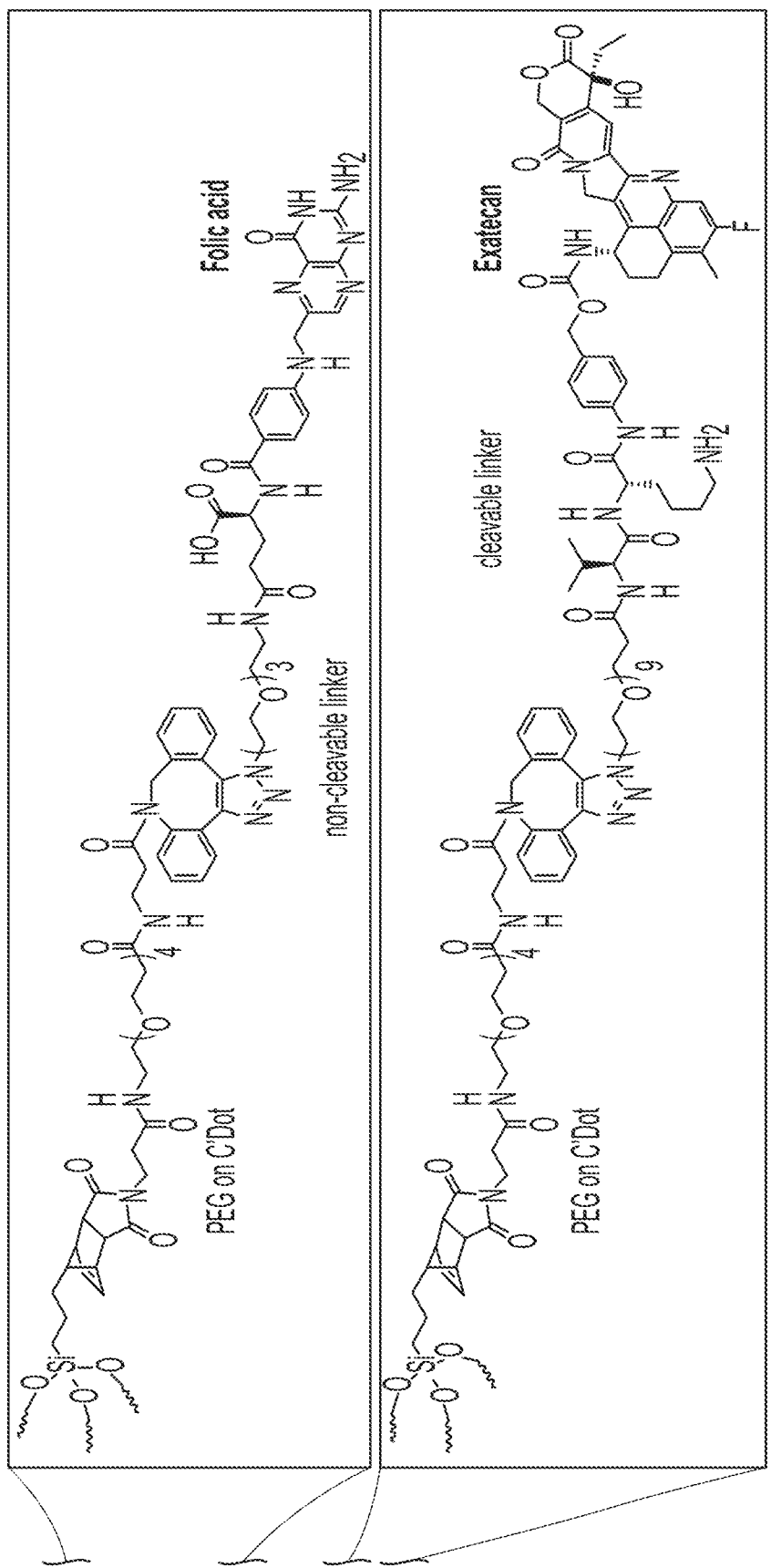

Described herein are nanoparticle drug conjugates (NDC), which comprise a nanoparticle (e.g., a silica nanoparticle, such as a multi-modal silica-based nanoparticle) that allows conjugation to targeting ligands and to cytotoxic payloads, for detection, prevention, monitoring, and/or treatment of a disease, such as cancer.

This disclosure provides compositions and methods of using a nanoparticle drug conjugate (NDC) comprising: a nanoparticle; a targeting ligand that binds to a folate receptor (e.g., folic acid, or a derivative or salt thereof), and a linker-payload conjugate, that may comprise exatecan and a protease-cleavable linker.

The conjugation of both targeting ligands and linker-drug conjugates to the nanoparticle can be achieved via a highly efficient "click chemistry" reaction, which is fast, simple to perform, versatile, and results in high product yields. The payload may be a cytotoxic agent comprising exatecan, or a salt or analog thereof, that is attached to the nanoparticle via a cleavable linker group. The cleavable linker group can be cleaved when the NDC is internalized in a cancer cell (e.g., in a tumor cell), such as in the endosome or lysosomal compartment of the cell, causing release of the active cytotoxic agent from the NDCs. The cleavage may be catalyzed by a protease (e.g., cathepsin B).

The NDCs disclosed herein provide an optimal platform for drug delivery, due in part to their physical properties. For example, the NDCs comprise nanoparticles that are ultrasmall in diameter (e.g., with average diameter between about 1 nm and about 10 nm, such as between about 5 nm and about 8 nm) and benefit from enhanced permeability and retention (EPR) effects in tumor microenvironments, while retaining desired clearance and pharmacokinetic properties.

The NDCs described herein have certain advantages over other drug delivery platforms (e.g., ADCs such as FR-targeted ADCs, and FR-targeted small molecule drugs (e.g., chemotherapeutics)). For example, a single NDC of the present disclosure may include up to about 80 drug molecules on each nanoparticle (e.g., 80 exatecan molecules). In contrast, in conventional ADCs, only about 4 to 8 therapeutic/drug molecules can be attached to the antibody, and conventional FR-targeted small molecule drugs are limited to only a single therapeutic/drug molecule. Thus, the NDCs described herein can carry at least 10 times more drug molecules NDC, relative to conventional drug delivery platforms, and deliver a relatively higher drug load to cells.

While conventional folate receptor (FR)-targeting drug-delivery platforms, such as ADCs and FR-targeted small molecular chemotherapeutics, usually exhibit high potency in cancer cells with high receptor expression level, their efficacy in cancer cells with medium or low FR expression level is limited. In contrast, the NDCs of the present disclosure can effectively target cancer cells with both high and low FR expression levels and provide potent therapy for cancers that have low FR expression (see, e.g., FIG. 23 and associated assay described in the Examples).

Without wishing to be bound by any particular theory of mechanism, it is believed that, because the NDCs disclosed herein can include multiple FR-targeting ligands on a single nanoparticle, there is a multivalent or avidity effect on binding to several FRs on the cell surface. In contrast, a single ADC generally can only bind to up to two FRs on the cell surface, and a single FR-targeted chemotherapy drug can only bind to one FR on the cell surface. Thus, the multivalent effect of the FR-targeted NDCs of the present disclosure can significantly enhance the binding of NDC to cells that express FR, leading to improved targeting efficiency and therapeutic outcomes. This multivalent effect can also render the NDCs of the present disclosure suitable for treating cancers that have low FR-expression, that cannot be effectively treated using conventional FR-targeted drug delivery platforms, such as ADCs or FR-targeted chemotherapy drugs.

The efficacy of ADCs in solid tumor treatment is usually greatly limited by their poor tumor penetration. In contrast, the FR-targeted NDCs disclosed herein exhibit highly effective tumor penetration, permitting the delivery of therapeutics throughout a tumor following administration, which improves therapeutic outcomes in treating solid tumors, relative to the use of ADCs.

The NDCs of the present disclosure have a smaller size than conventional drug delivery platforms, such as ADCs. Notably, the NDCs of the present disclosure are smaller than the particle size cut off for renal clearance, permitting the NDC to be renally clearable. As a result, NDCs that are administered to a subject but do not enter a cancer cell (i.e., non-targeted NDCs) can be rapidly cleared from the body via renal elimination. This target-and/or-clear approach reduces the toxicity of NDCs as compared to conventional drug delivery platforms, such as ADCs, and prevents undesirable accumulation of the NDCs (or their payloads) in healthy tissues or organs. The NDCs of the present disclosure exhibit improved biodistribution than conventional drug delivery platforms, such as ADCs, resulting in reduced side effect and toxicity.

Nanoparticles

This disclosure relates to NDCs comprising a nanoparticle, such as a silica nanoparticle. The nanoparticle may comprise a silica-based core and a silica shell surrounding at least a portion of the core. Alternatively, the nanoparticle may have only the core and no shell. The core of the nanoparticle may contain the reaction product of a reactive fluorescent compound and a co-reactive organo-silane compound. For example, the core of the nanoparticle may contain the reaction product of a reactive fluorescent compound and a co-reactive organo-silane compound, and silica. In preferred aspects of the present disclosure, the nanoparticle is a core-shell particle.

The diameter of the core may be from about 0.5 nm to about 100 nm, from about 0.1 nm to about 50 nm, from about 0.5 nm to about 25 nm, from about 0.8 nm to about 15 nm, or from about 1 nm to about 8 nm. For example, the diameter of the core may be from about 3 nm to about 8 nm, or 3 nm to about 6 nm, e.g., the diameter of the core may be from about 3 nm to about 4 nm, about 4 nm to about 5 nm, about 5 nm to about 6 nm, about 6 nm to about 7 nm, or about 7 nm to about 8 nm.

The shell of the nanoparticle can be the reaction product of a silica forming compound, such as a tetraalkyl orthosilicate, for example tetraethyl orthosilicate (TEOS). The shell of the nanoparticle may have a range of layers. For example, the silica shell may be from about 1 to about 20 layers, from about 1 to about 15 layers, from about 1 to about 10 layers, or from about 1 to about 5 layers. For example, the silica shell may comprise from about 1 to about 3 layers. The thickness of the shell may range from about 0.5 nm to about 90 nm, from about 0.5 nm to about 40 nm, from about 0.5 nm to about 20 nm, from about 0.5 nm to about 10 nm, or from about 0.5 nm to about 5 nm, e.g., about 1 nm, about 2 nm, about 3 nm, about 4 nm, or about 5 nm. For example, the thickness of the silica shell may be from about 0.5 nm to about 2 nm. The silica shell of the nanoparticle may cover only a portion of nanoparticle or the entire particle. For example, the silica shell may cover about 1 to about 100 percent, from about 10 to about 80 percent, from about 20 to about 60 percent, or from about 30 to about 50 percent of the nanoparticle. For example, the silica shell may cover about 50 to about 100 percent. The silica shell can be either solid, i.e., substantially non-porous, meso-porous, semi-porous, or the silica shell may be porous. The silica nanoparticle can be either solid, i.e., substantially non-porous, meso-porous, semi-porous, or the silica nanoparticle may be porous. In some embodiments, the nanoparticle is a non-mesoporous nanoparticle, e.g., a non-mesoporous silica nanoparticle, such as a non-mesoporous silica core-shell nanoparticle.

The surface of the nanoparticle may be modified to incorporate at least one functional group. An organic polymer may be attached to the nanoparticle and can be modified to incorporate at least one functional group by any known techniques in the art. The functional groups can include, but are not limited to, dibenzocyclooctyne (DBCO), maleimide, N-hydroxysuccinimide (NHS) ester, a diene (e.g., cyclopentadiene), an amine, or a thiol. For example, a bifunctional group comprising a silane at one terminus, and a DBCO, maleimide, NHS ester, diene (e.g., cyclopentadiene), amine, or thiol at the other terminus, may be condensed onto the surface of the silica nanoparticle via the silane group. The incorporation of the functional group can also be accomplished through known techniques in the art, such as using "click chemistry," amide coupling reactions, 1,2-additions such as a Michael addition, or Diels-Alder (2+4) cycloaddition reactions. This incorporation allows attachment of various targeting ligands, contrast agents and/or therapeutic agents to the nanoparticle.

The organic polymers that may be attached to the nanoparticle include, but are not limited to, poly(ethylene glycol) (PEG), polylactate, polylactic acids, sugars, lipids, polyglutamic acid (PGA), polyglycolic acid, poly(lactic-co-glycolic acid) (PLGA), polyvinyl acetate (PVA), and combinations thereof. In preferred aspects of the present disclosure, the organic polymer is poly(ethylene glycol) (PEG).

In preferred aspects of the present disclosure, the surface of the nanoparticle is functionalized. For example, the surface of the nanoparticle can have functional groups other than those resulting from the synthesis of the nanoparticles (e.g., —OH groups (resulting from terminal Si—OH groups on a nanoparticle surface) and PEG groups (resulting from Si-PEG groups on the nanoparticle surface). Such functionalization and functionalization methods are known in the art.

The nanoparticle may comprise a non-pore surface and a pore surface. In an embodiment, at least a portion of the individual nanoparticle non-pore surface and at least a portion of the individual nanoparticle pore surface are functionalized. In an embodiment, at least a portion of the nanoparticle non-pore surface and the at least a portion of the pore surface have different functionalization. The pore surface is also referred to herein as the interior surface. The nanoparticles may also have a non-pore surface (or non-porous surface). The non-pore surface is also referred to herein as the exterior nanoparticle surface.

The pore surface (e.g., at least a portion of the pore surface) and/or the non-pore surface (e.g., at least a portion of the non-pore surface) of the nanoparticle can be functionalized. For example, the nanoparticles can be reacted with compounds such that a functional group of the compound is presented on (e.g., covalently bonded to) the surface of the nanoparticle. The surface can be functionalized with hydrophilic groups (e.g., polar groups such as ketone groups, carboxylic acid, carboxylate groups, and ester groups), which provide a surface having hydrophilic character, or hydrophobic groups (e.g., nonpolar groups such as alkyl, aryl, and alkylaryl groups), which provide a surface having hydrophobic character. Such functionalization is known in the art. For example, diethoxydimethylsilane (DEDMS) can be condensed on at least a portion of the pore surface such that the pore surface has hydrophobic character, allowing increased loading performance of a hydrophobic cytotoxic payload relative to nanoparticles that are not functionalized so.

In preferred aspects of the present disclosure, the surface of the nanoparticle is at least partially functionalized with polyethylene glycol (PEG) groups. The attachment of PEG to the nanoparticle may be accomplished by a covalent bond or a non-covalent bond, such as by ionic bond, hydrogen bond, hydrophobic bond, coordination, adhesive, and physical absorption.

In certain aspects, the PEG groups are attached (e.g., covalently attached) to the surface of the nanoparticle. In a core-shell nanoparticle, the PEG groups are covalently bonded to the silica at the surface of the shell via a Si—O—C bond and or to the silica in the core. In a core nanoparticle, the PEG groups are covalently bonded to the silica in the core.

In preferred aspects, the nanoparticle is a core-shell nanoparticle, wherein the PEG groups are covalently bonded to the silica at the surface of the shell via a Si—O—C bond. The PEG groups on the nanoparticle surface can prevent adsorption of serum proteins to the nanoparticle in a physiological environment (e.g., in a subject), and may facilitate efficient urinary excretion and decrease aggregation of the nanoparticle (see, e.g., Burns et al. "Fluorescent silica nanoparticles with efficient urinary excretion for nanomedicine", *Nano Letters* (2009) 9(1):442-448).

The PEG groups may be derived from PEG polymer having a molecular weight (Mw) of 400 g/mol to 2000 g/mol, including all integer g/mol values and ranges therebetween. In an embodiment, the PEG groups are derived from PEG polymer having a Mw of 460 g/mol to 590 g/mol, which contain 6 to 9 ethylene glycol units. In various embodiments, the nanoparticles are at least 50%, at least 75%, at least 90%, or at least 95% functionalized with PEG groups. In an embodiment, the nanoparticles are functionalized with PEG groups with the maximum number of PEG groups such that, the pores remain accessible (e.g., the pores can be functionalized). In an embodiment, the pore surface is a silica surface having terminal silanol (Si—OH) groups.

A polyethylene glycol unit disclosed herein may be functionalized with a functional group, for example, a "click chemistry" group, such as dibenzocyclooctyne (DBCO) or azide, a diene (e.g., cyclopentadiene), a maleimide, an NHS ester, an amine, a thiol, or an activated acetylene moiety such as

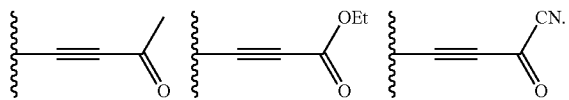

While DBCO can be used, the functional group may also be another alkyne, such as another strained alkyne (e.g., DIBO or a derivative thereof, or a derivative of DBCO). Also, the functional group may be a nitrone or a nitrile oxide.

Alternatively, or in addition to the foregoing, a functional group can be introduced to an NDC without necessarily requiring a PEG group. For example, an NDC may be functionalized with a functional group such as a "click chemistry" group, e.g., dibenzocyclooctyne (DBCO) or azide; a diene (e.g., cyclopentadiene); a maleimide; an NHS ester; an amine; a thiol; or an activated acetylene moiety such as

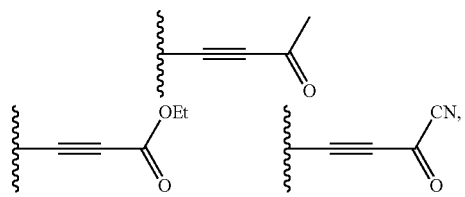

that may comprise any suitable linker, or may have no linker. While DBCO can be used to functionalize the nanoparticle, the functional group may also be another alkyne, such as another strained alkyne (e.g., DIBO or a derivative thereof, or a derivative of DBCO). Also, the functional group may be a nitrone or a nitrile oxide.

For example, a DBCO-functionalized linker may be introduced to a nanoparticle (e.g., a PEGylated C'Dot) by reacting the silane group on a DBCO-linker-silane compound with a silanol group on the surface of the nanoparticle (e.g., under the PEG layer on the C'Dot surface). Similarly, a diene-functionalized precursor (e.g., cyclopentadiene-functionalized precursor) may be introduced to a nanoparticle (e.g., a PEGylated C'Dot) by reacting the silane group on a diene-linker-silane or diene-silane precursor compound with a silanol group on the surface of the nanoparticle (e.g., under the PEG layer on the C'Dot surface), followed by functionalizing the diene on the nanoparticle with a second precursor that comprises a reactive group (e.g., DBCO) via a dienophile. The linker group in the DBCO-linker-silane or diene-linker-silane can comprise any structure (or sub-structure), including but not limited to PEG, a carbon chain (e.g., alkylene), a heteroalkylene group, or the like. The diene-functionalized linker covalently attached to the nanoparticle may be further modified, e.g., by reaction with a DBCO-functionalized group. For example, the diene-functionalized linker covalently attached to the nanoparticle may be contacted with a DBCO-linker-maleimide compound (or other suitable DBCO-linker-dienophile), to form a cycloadduct between the diene and maleimide, resulting in an NDC comprising DBCO groups attached to its surface, e.g., using cycloaddition chemistry, such as a Diels-Alder cycloaddition.

Functionalization (e.g., with one of the aforementioned functional groups, such as DBCO or cyclopentadiene) facilitates the conjugation of suitably functionalized FR-targeting ligands and/or functionalized drug payloads (such as azide-functionalized FR-targeting ligands and/or azide-functionalized drug payloads) to the nanoparticle by a coupling reaction, e.g., via click chemistry, (3+2) cycloaddition reactions, amide coupling, or Diels-Alder reaction. This functionalization approach also improves the versatility of the formulation chemistry and the stability of the FR-targeted NDC constructs.

An advantage of the NDCs disclosed herein is that they can be prepared using relatively stable linker or spacer groups, or precursors thereof. The linker or spacer groups, or their precursors, can avoid premature or undesired cleavage, which can occur using other linkers or precursors. For example, certain methods of functionalizing nanoparticles employ amine-silane precursors (to provide amine-functionalized nanoparticles) that are modified at the amine groups to conjugate other moieties to the nanoparticle. However, the amine-silane precursors can be unstable and can self-condense during reaction, causing undesired aggregation. The aggregates can be very difficult to separate from the functionalized nanoparticles. Additionally, the amine groups on the surface of the nanoparticle can promote undesired reactivity, that may lead to premature release of the payload, or undesired release of the targeting ligand.

Figure 33A:
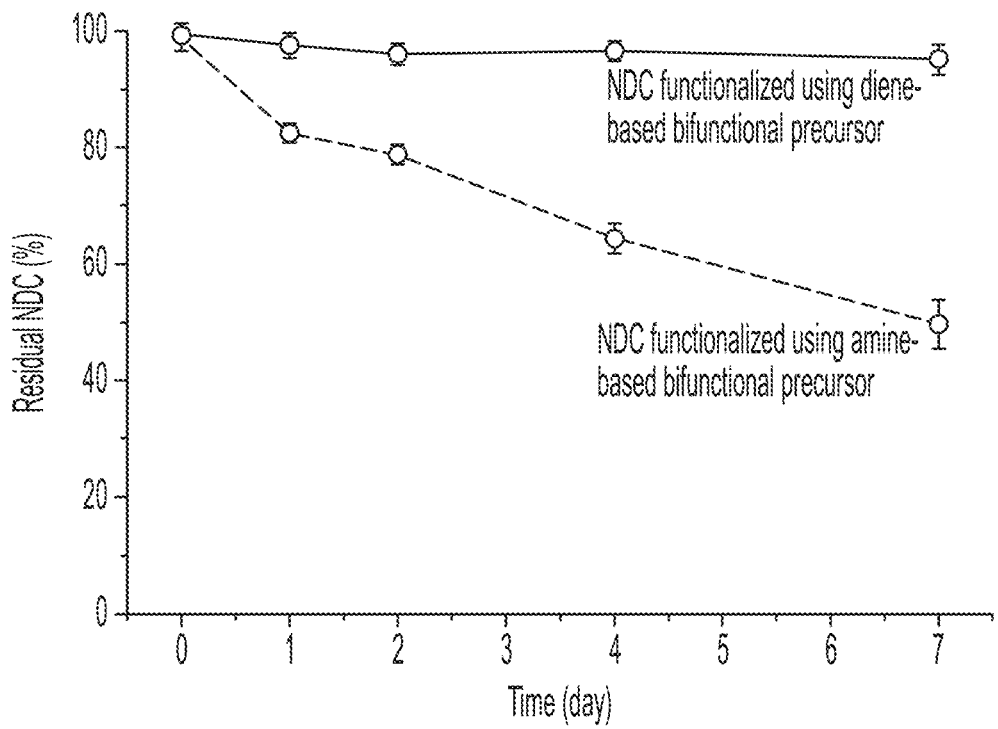
FIGS. 33A-33B are graphs demonstrating the stability of exemplary NDCs prepared using methods disclosed herein.
Figure 33B:
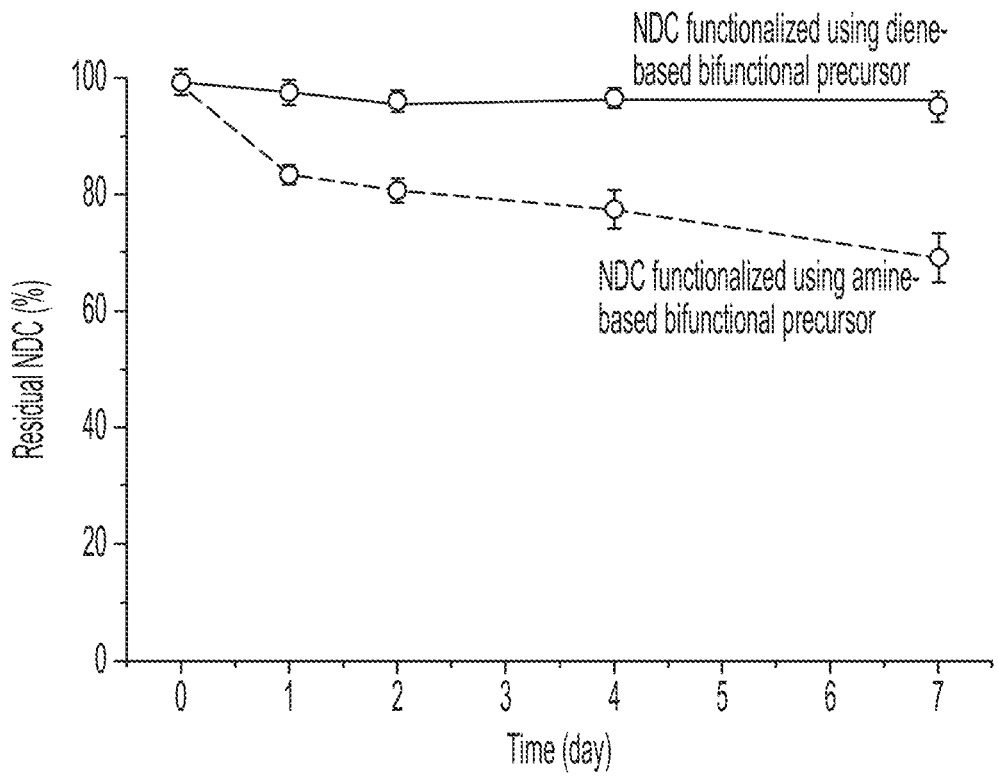

The NDCs disclosed herein can be produced using relatively stable precursors, and the NDCs are stable and highly pure. For example, the nanoparticles of the present NDCs can be prepared with a silane-diene precursor (such as a silane-cyclopentadiene precursor), to afford a nanoparticle functionalized with one or more diene groups. The diene groups may then be reacted with a second precursor, such as a dienophile-containing precursor (e.g., a PEG-maleimide derivative, e.g., a DBCO-PEG-maleimide), causing a stable cycloadduct to form. The resulting functionalized nanoparticle, comprising the cycloadduct, may optionally be reacted with one or more subsequent precursors (such as targeting ligand precursors and/or payload-linker conjugate precursors described herein), to further functionalize the nanoparticle. The diene-silane precursors, and the cycloadducts that are produced, do not exhibit the undesired qualities of other functionalized nanoparticles, e.g., they have relatively high serum stability, can be produced in high yield and purity (e.g., free of aggregated precursor). See, e.g., FIGS. 33A-33B. Additionally, as this nanoparticle functionalization approach is highly modular, any desired ratio of payload, targeting ligand, or otherwise, can be introduced to the nanoparticle. Examples of preparing nanoparticles using these methods, and their benefits, are provided in the Examples.

The NDCs of the present disclosure may comprise a structure of Formula (NP):

also other imaging techniques, such as positron emission tomography (PET), single photon emission computed tomography (SPECT), computerized tomography (CT), and magnetic resonance imaging (MRI), the nanoparticle may also be conjugated to a contrast agent, such as a radionuclide.

The nanoparticles may incorporate any suitable fluorescent compound, such as a fluorescent organic compound, a dye, a pigment, or a combination thereof. Such fluorescent compounds can be incorporated into the silica matrix of the core of the nanoparticle. A wide variety of suitable chemically reactive fluorescent dyes/fluorophores are known, see for example, MOLECULAR PROBES HANDBOOK OF FLUORESCENT PROBES AND RESEARCH CHEMICALS, $6^{th}$ ed., R. P. Haugland, ed. (1996). In preferred aspects of the present disclosure, the fluorescent compound is covalently encapsulated within the core of the nanoparticle.

In some aspects, fluorescent compound can be, but is not limited to, a near infrared fluorescent (NIRF) dye that is positioned within the silica core of the nanoparticle, that can provide greater brightness and fluorescent quantum yield relative to the free fluorescent dye. It is well-known that the near infrared-emitting probes exhibit decreased tissue attenuation and autofluorescence (Burns et al. "Fluorescent silica nanoparticles with efficient urinary excretion for nanomedicine", *Nano Letters* (2009) 9(1):442-448).

Fluorescent compounds that may be used (e.g., encapsulated by an NDC) in the present disclosure, include, but are not limited to, Cy5, Cy5.5 (also known as Cy5++), Cy2,

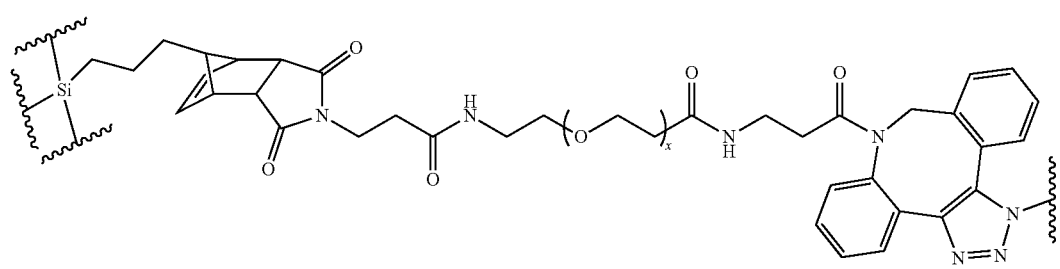

(NP)

wherein x is an integer of 0 to 20, e.g., 4; wherein the silicon atom is a part of the nanoparticle; and wherein the ⌇ adjacent to the triazole moiety denotes a point of attachment to a targeting ligand or payload-linker conjugate, either directly or indirectly, e.g., via a linker or spacer group, e.g., a PEG moiety. For example, the attachment may be to a linker or spacer group, e.g., the linker of a linker-payload conjugate, or a linker or spacer group of a folate receptor targeting ligand, e.g., a PEG moiety. The NDCs of the present disclosure may be prepared from diene (e.g., cyclopentadiene) functionalized nanoparticles, e.g., by conjugating a linker moiety (e.g., a linker comprising a dienophile, such as maleimide) to the diene with a cycloaddition reaction.

The silica shell surface of the nanoparticles can be modified by using known cross-linking agents to introduce surface functional groups. Crosslinking agents include, but are not limited to, divinyl benzene, ethylene glycol dimethacrylate, trimethylol propane trimethacrylate, N,N'-methylene-bis-acrylamide, alkyl ethers, sugars, peptides, DNA fragments, or other known functionally equivalent agents.

In order to permit the nanoparticle to be detectable by not only optical imaging (such as fluorescence imaging), but fluorescein isothiocyanate (FITC), tetramethylrhodamine isothiocyanate (TRITC), phycoerythrin, Cy7, fluorescein (FAM), Cy3, Cy3.5 (also known as Cy3++), Texas Red (sulforhodamine 101 acid chloride), LIGHTCYCLER®-Red 640, LIGHTCYCLER®-Red 705, tetramethylrhodamine (TMR), rhodamine, rhodamine derivative (ROX), hexachlorofluorescein (HEX), rhodamine 6G (R6G), the rhodamine derivative JA133, Alexa Fluorescent Dyes (such as ALEXA FLUOR® 488, ALEXA FLUOR® 546, ALEXA FLUOR® 633, ALEXA FLUOR® 555, and ALEXA FLUOR® 647), 4',6-diamidino-2-phenylindole (DAPI), propidium iodide, aminomethylcoumarin (AMCA), Spectrum Green, Spectrum Orange, Spectrum Aqua, LISSAMINE™, and fluorescent transition metal complexes, such as europium.

Fluorescent compounds that can be used also include fluorescent proteins, such as GFP (green fluorescent protein), enhanced GFP (EGFP), blue fluorescent protein and derivatives (BFP, EBFP, EBFP2, azurite, mKalama1), cyan fluorescent protein and derivatives (CFP, ECFP, Cerulean, CyPet) and yellow fluorescent protein and derivatives (YFP, Citrine, Venus, YPet) (WO 2008/142571, WO 2009/056282, WO 1999/22026).

In preferred aspects of the present disclosure, the fluorescent compound is selected from the group consisting of Cy5 and Cy5.5. In preferred aspects, the fluorescent compound is Cy5.

A fluorescent nanoparticle may be synthesized by the steps of: (1) covalently conjugating a fluorescent compound, such as a reactive fluorescent dye (e.g., Cy5), with a reactive moiety including, but not limited to, maleimide, iodoacetamide, thiosulfate, amine, N-hydroxysuccimide ester, 4-sulfo-2,3,5,6-tetrafluorophenyl (STP) ester, sulfosuccinimidyl ester, sulfodichlorophenol esters, sulfonyl chloride, hydroxyl, isothiocyanate, carboxyl, to an organo-silane compound, such as a co-reactive organo-silane compound, to form a fluorescent silica precursor, and reacting the fluorescent silica precursor to form a fluorescent core; or (2) reacting the fluorescent silica precursor with a silica forming compound, such as tetraalkoxysilane, to form a fluorescent core. The fluorescent core may then be reacted with a silica forming compound, such as a tetraalkoxysilane, to form a silica shell on the core, to provide the fluorescent nanoparticle.

Fluorescent silica-based nanoparticles are known in the art and are described by U.S. Pat. No. 8,298,677 B2, U.S. Pat. No. 9,625,456 B2, U.S. Ser. No. 10/548,997 B2, U.S. Pat. No. 9,999,694 B2, U.S. Ser. No. 10/039,847 B2 and U.S. Ser. No. 10/548,998 B2, the contents of which are each incorporated herein by reference in their entireties.

In preferred aspects of the present disclosure, the NDCs comprise a nanoparticle that comprises a silica-based core and a silica shell surrounding at least a portion of the core and polyethylene glycol (PEG) is covalently bonded to the surface of the nanoparticle, and a fluorescent compound is covalently encapsulated within the core of the nanoparticle.

Targeting Ligand

The NDCs of the present disclosure may comprise a targeting ligand that is attached to the nanoparticle directly or indirectly through a spacer group. NDCs with targeting ligands can enhance internalization of the payload/drugs in tumor cells and/or deliver drugs into tumor cells due to increased permeability, as well as the targeting ability of the NDC. The targeting ligand can allow the nanoparticle to target a specific cell type through the specific binding between the ligand and the cellular component. The targeting ligand may also facilitate entry of the nanoparticle into the cell or barrier transport, for example, for assaying the intracellular environment.

The targeting ligands of the present disclosure are capable of binding to receptors on tumor cells. Specifically, the targeting ligands can bind to the folate receptor (FR), including all four human isoforms of FR, including FR alpha (FRα, also known as FOLR1), FR beta (FRβ, also known as FOLR2), FR gamma (FRγ, also known as FOLR3), and FR delta (FRδ, also known as FOLR4). Conjugation of FR targeting ligand to the surface of the nanoparticle of the present disclosure allows for targeted therapy of FR-overexpressing cancerous cells, tissues, and tumors. For example, NDCs of the present disclosure comprising targeting ligands that can bind to folate receptor alpha (FRα), such as folic acid, may be used for targeting ovarian cancer, endometrial cancer, fallopian tube cancer, peritoneal cancer, cervical cancer, breast cancer, lung cancer, mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, and testicular cancer, acute myeloid leukemia (AML, e.g., pediatric AML). NDCs of the present disclosure comprising targeting ligands that can bind to folate receptor beta (FRβ) may be used for targeting acute myeloid leukemia (AML, e.g., pediatric AML), chronic myelogenous leukemia (CML), and tumor associated macrophages. Tumor associated macrophages can be targeted as a means to modify the immune status of the tumor. Without wishing to be bound by theory, the binding affinity of FR-targeted NDCs to folate receptors can be enhanced due to multivalence effect.

Folate receptor can be highly expressed in solid tumor cells, including ovarian, kidney, lung, brain, endometrial, colorectal, pancreatic, gastric, prostate, breast and non-small-cell lung cancers. FR is over-expressed in other cancers including fallopian tube cancer, cervical cancer, mesothelioma, uterine cancer, esophageal cancer, stomach cancer, bladder cancer, liver cancer, head and neck cancer, thyroid cancer, skin cancer, and testicular cancer. FR is also over-expressed in hematological malignancies, such as acute myeloid leukemia (AML) and chronic myelogenous leukemia (CML).

In preferred aspects of the present disclosure, the targeting ligands bind to folate receptor alpha (FRα), folate receptor beta (FRβ), or both.

The present disclosure provides FR-targeting ligands that are capable of binding to specific cell types having elevated levels of FRα, such as, but not limited to, cancer (e.g., adenocarcinomas) of uterus, ovary, breast, cervix, kidney, colon, testicles (e.g., testicular choriocarcinoma), brain (e.g., ependymal brain tumors), malignant pleural mesothelioma, and nonfunctioning pituitary adenocarcinoma. The present disclosure also provides FR-targeting ligands that are capable of targeting acute myeloid leukemia (AML, e.g., pediatric AML), chronic myelogenous leukemia (CML), and tumor associated macrophages. The targeting ligand can be any suitable molecule that can bind a FR, such as FRα, such as a small organic molecule (e.g., folate or a folate analog), an antigen-binding portion of an antibody (e.g. a Fab fragment, a Fab' fragment, a F(ab')2 fragment, a scFv fragment, a Fv fragment, a dsFv diabody, a dAb fragment, a Fd' fragment, a Fd fragment, or an isolated complementarity determining region (CDR) region), an antibody mimetic (e.g., aptamer, an affibody, affilin, affimer, anticalin, avimer, Darpin, and the like), a nucleic acid, lipid, and the like.

In aspects of the present disclosure, the targeting ligand is folic acid, or a folate receptor binding derivative thereof. It will be understood that "folic acid" can encompass any amide or ester derivative of folic acid. For example, free folic acid may be modified to be conjugated to the nanoparticle via a spacer group, such as PEG or a PEG derivative (e.g., by forming an amide bond between the terminal carboxylic acid of folic acid, and a nitrogen atom of the spacer group).

The FR-targeted NDCs may not only accumulate in a cancer cell or tumor, but may also penetrate the tumor tissue and deliver payloads to the entire tumor tissue for optimal treatment efficacy. Without wishing to be bound by any particular theory or mechanism, it is believed that the targeting ligands bind to the specific receptor groups on the surface of the cancer cell, resulting in receptor-mediated cell uptake of NDCs. This receptor-mediated cell uptake of NDCs happens via the endocytosis process, and eventually traffics NDCs to endosomes and lysosomes in cancer cells.

In aspects of the present disclosure, the NDCs comprise a targeting ligand that is attached to the nanoparticle directly or indirectly through a spacer group. For example, the targeting ligand can be attached to the nanoparticle directly via the silica of the nanoparticle (i.e., covalently bonded). In preferred aspects, the targeting ligand is attached to the nanoparticle indirectly through a suitable spacer group.

The spacer group can be any group that can act as a spacer, e.g., as a spacer between a targeting ligand and the nanoparticle, and attach the targeting ligand to the nanoparticle. The spacer group may be a divalent linker, such as a divalent linker that comprises a chain length of between about 5 and about 200 atoms (e.g., carbon atoms, heteroatoms, or a combination thereof), such as between about 5 and about 100 atoms, between about 5 and about 80 atoms, between about 10 and about 80 atoms, between about 10 and about 70 atoms, between about 10 and about 30 atoms, between about 20 and about 30 atoms, between about 30 and about 80 atoms, or between about 30 and about 60 atoms. Suitable spacer groups may comprise an alkylene, alkenylene, alkynylene, heteroalkylene (e.g., PEG), carbocyclyl, heterocyclyl, aryl, heteroaryl, or a combination thereof. For example, the spacer group may comprise a PEG group, an alkylene group, or a combination thereof. The spacer group may be substituted or unsubstituted, e.g., the spacer group may comprise a substituted alkylene, substituted heteroalkylene, or a combination thereof. For example, the spacer group may comprise a PEG group (or PEG spacer), an alkylene group (or alkylene spacer), one or more heteroatoms, and/or one or more cyclic groups (e.g., heterocyclylene groups, such as a piperazine).

The targeting ligand, such as folic acid, may be attached to the nanoparticle indirectly through a PEG spacer group. The folic acid may be present in the NDC as an amide, e.g., to facilitate conjugation to a PEG spacer group or other divalent linker, e.g., as shown in FIG. 1. The number of PEG monomers in a PEG spacer may range from 2 to 20, from 2 to 10, from 2 to 8, or from 2 to 5. In preferred aspects, the number of PEG groups as spacers in a functionalized FR-targeting ligand is 3.

The average nanoparticle to targeting ligand (e.g., folic acid) ratio may range from about 1 to about 50, from about 1 to about 40, from about 1 to about 30, or from about 1 to about 20. For example, the average nanoparticle to targeting ligand (e.g., folic acid) ratio may be about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:40, or 1:50. For example, the average nanoparticle to targeting ligand ratio may range from about 1 to about 20, e.g., the average number of folic acid molecules on each nanoparticle may be between about 5 and about 10, between about 10 and about 15, or between about 15 and about 20, e.g., about 1, about 2, about 3, about 4, about 5, about 6, about 7, about 8, about 9, about 10, about 11, about 12, about 13, about 14, or about 15 folic acid molecules per nanoparticle. An NDC disclosed herein may comprise about 10 folic acid molecules. An NDC disclosed herein may comprise about 11 folic acid molecules. An NDC disclosed herein may comprise about 12 folic acid molecules. An NDC disclosed herein may comprise about 13 folic acid molecules. An NDC disclosed herein may comprise about 14 folic acid molecules. An NDC disclosed herein may comprise about 15 folic acid molecules.

A smaller number of targeting ligands attached to the nanoparticle may help maintain the hydrodynamic diameter of the nanoparticle, e.g., to meet the renal clearance cutoff size range (Hilderbrand et al., Near-infrared fluorescence: Application to in vivo molecular imaging, *Curr. Opin. Chem. Biol.*, (2010) 14:71-79). The number of targeting ligands measured may be an average number of targeting ligands attached to more than one nanoparticle. Alternatively, one nanoparticle may be measured to determine the number of targeting ligands attached.

The number of targeting ligands attached to the nanoparticle can be measured by any suitable methods, such as, but not limited to, optical imaging, fluorescence correlation spectroscopy (FCS), UV-Vis, chromatography, mass spectroscopy, or indirect enzymatic analysis.

The targeting ligand can be attached to the nanoparticle via covalent bonding to the silica of the nanoparticle (e.g., indirectly through a spacer group). The ligand may be conjugated to a nanoparticle (e.g., via a functional group on the nanoparticle surface) described herein, for example, using coupling reactions, Click Chemistry (e.g., a 3+2 Click Chemistry reaction), cycloaddition (e.g., a 3+2 or 2+4 cycloaddition reaction, using the appropriate functional groups), or conjugation via a carboxylate, ester, alcohol, carbamide, aldehyde, amine, sulfur oxide, nitrile oxide, nitrone, nitrogen oxide, halide, or any other suitable compound known in the art.

In preferred aspects of the present disclosure, the conjugation of FR-targeting ligands can be accomplished by "click chemistry" reaction using a diarylcyclooctyne (DBCO) group. Any suitable reaction mechanism may be adapted in the present disclosure for "click chemistry", so long as facile and controlled attachment of the targeting ligand to the nanoparticle can be achieved.

In some aspects, a triple bond (e.g., alkyne, e.g., terminal alkyne) is introduced onto the surface of a nanoparticle (e.g., via a PEG covalently conjugated with the shell of the nanoparticle, or through another suitable linker or spacer group). Separately, an azide bond, or other group that is reactive with a triple bond, may be introduced onto the desired targeting ligand. For example, folic acid may be modified by conjugating the terminal carboxylic acid of folic acid with a spacer group (e.g., a PEG moiety), that comprises an azide at one terminus). The nanoparticle (e.g., PEGylated nanoparticle) comprising the free triple bond, and the targeting ligand (comprising a group reactive with the triple bond), can be mixed (with or without a copper or other metal catalyst) to effect cycloaddition of the group reactive with the triple bond (e.g., azide) to the triple bond, resulting in the conjugation of the targeting ligand with the nanoparticle (e.g., "Click Chemistry"). Many variations of this approach can also be used, as will be readily apparent to a person of ordinary skill in the art.

An azide functionalized FR-ligand (where the FR-ligand may comprise a spacer group, and the spacer group may possess the azide group) can be attached to the nanoparticle either directly or indirectly via an alkyne (e.g., DBCO group). Spacer groups, such as, but not limited to PEG groups, can be present in a FR-targeting ligand precursor, and may possess a terminal group (e.g., azide) to facilitate conjugation to the nanoparticle, and after conjugation, the spacer group may be disposed between the targeting ligand and the nanoparticle. For example, the FR-targeting ligand precursor may comprise a structure of Formula (D-1):

(D-1)

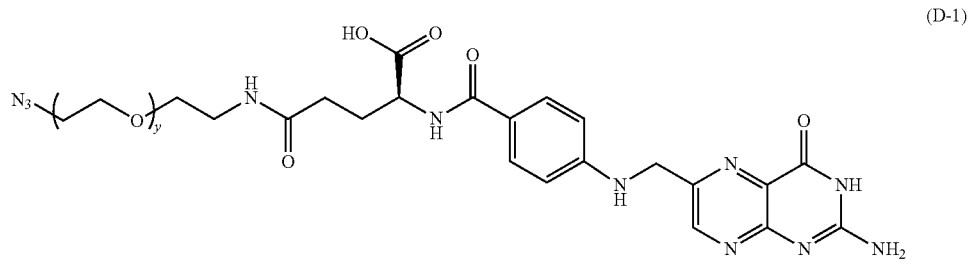

wherein y is an integer of 0 to 20 (e.g., 3). For example, y may be 1, 2, 3, 4, 5, 6, 7, 8, 9, 10, 11, 12, 13, 14, 15, 16, 17, 18, 19, or 20, e.g., 2, 3, or 4.

In some aspects, the FR-targeting ligand may be functionalized with a suitable terminal group, such as, but not limited to an azide group. The azide functionalized FR-ligand can be attached to the nanoparticle either directly or indirectly via the DBCO groups. Spacer groups, such as, but not limited to PEG groups can be present between the azide functionalized FR-ligand and the nanoparticle. In preferred aspects, the FR-targeting ligand is functionalized to include spacer groups, such as, but not limited to PEG groups that terminate with an azide group that reacts with the DBCO groups on the surface of the nanoparticle.

The functionalization of FR-targeting ligand may include hydrophilic PEG groups as spacers, that may enhance solubility in water, and may reduce or eliminate aggregation and precipitation of the nanoparticle.

In aspects of the present disclosure, the number of PEG groups as spacers that can be present in a functionalized FR-targeting ligand may be in the range of from 2 to 20, from 2 to 10, from 2 to 8, or from 2 to 5. In preferred aspects, the number of PEG groups as spacers in a functionalized FR-targeting ligand is 3.

The NDCs of the present disclosure comprising a targeting ligand may comprise a structure of Formula (NP-2):

(NP-2)

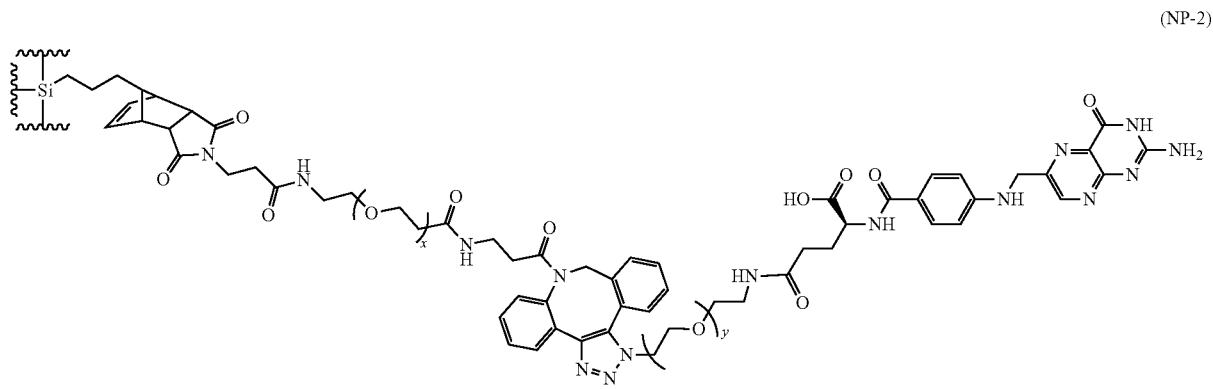

wherein x is an integer of 0 to 10 (e.g., 0, 1, 2, 3, 4, 5, 6, 7, 8, 9, 10, e.g., 4), and y is an integer of 0 to 20 (e.g., 1, 2, 3, 4, 5, 6, 7, 8, 9, 10, 11, 12, 13, 14, 15, 16, 17, 18, 19, or 20, e.g., 3), and the silicon atom is a part of the nanoparticle (e.g., bonded with the silica shell of a core-shell silica nanoparticle). For example, x may be 4, and y may be 3. Each nanoparticle of the NDCs disclosed herein may comprise more than one molecule of Formula (NP-2), for example, the nanoparticle may comprise between about 1 and about 20 molecules of Formula (NP-2), e.g., between about 5 and about 20 molecules of Formula (NP-2), between about 8 and about 15 molecules of Formula (NP-2), between about 10 and about 15 molecules of Formula (NP-2), e.g., about 1, about 2, about 3, about 4, about 5, about 6, about 7, about 8, about 9, about 10, about 11, about 12, about 13, about 14, about 15, about 16, about 17, about 18, about 19, or about 20 molecules of Formula (NP-2). An NDC disclosed herein may comprise about 12 molecules of Formula (NP-2). An NDC disclosed herein may comprise about 13 molecules of Formula (NP-2).

Linker-Payload Conjugate

The NDCs of the present disclosure can also comprise a linker-payload conjugate that is attached to the nanoparticle directly or indirectly through a spacer group. In preferred aspects, the linker-payload conjugate is attached to the nanoparticle through a spacer group. The payload may be exatecan, or a salt or analog thereof.

The spacer group can be any group that can act as a spacer, e.g., as a spacer between a payload/linker conjugate and the nanoparticle, and attach the linker-payload conjugate to the nanoparticle. The spacer group may be a divalent linker, such as a divalent linker that comprises a chain length of between about 5 and about 200 atoms (e.g., carbon atoms, heteroatoms, or a combination thereof), such as between about 5 and about 100 atoms, between about 5 and about 80 atoms, between about 10 and about 80 atoms, between about 10 and about 70 atoms, between about 10 and about 30 atoms, between about 20 and about 30 atoms, between about 30 and about 80 atoms, or between about 30 and about 60 atoms. Suitable spacer groups may comprise an alkylene, alkenylene, alkynylene, heteroalkylene (e.g., PEG), carbocyclyl, heterocyclyl, aryl, heteroaryl, or a combination thereof. For example, the spacer group may comprise a PEG group, an alkylene group, or a combination thereof. The spacer group may be substituted or unsubstituted, e.g., the spacer group may comprise a substituted alkylene, substituted heteroalkylene, or a combination thereof. For example, the spacer group may comprise a PEG group (or PEG spacer), an alkylene group (or alkylene spacer), one or more heteroatoms, and/or one or more or cyclic groups.

It will be understood that chemical modifications may be made to the payload in order to make reactions of the payload with linker more convenient for purposes of preparing conjugates of the present disclosure. For example, a functional group, e.g., amine, hydroxyl, or sulfhydryl, may be appended to the payload (e.g., exatecan) at a position which has minimal or an acceptable effect on the activity or other properties of the payload (e.g., exatecan). Alternatively, an existing functional group on the payload (e.g., pendant amine group) may be the point of attachment to the linker. For example, exatecan contains an amine functional group suitable for coupling to the linker moiety The payload (e.g., exatecan payload, or a salt or analog thereof) can be cleaved from the nanoparticle inside a cell, or a cell organelle, e.g., by an enzyme, thereby releasing exatecan, e.g., inside the cell or cell organelle). Exatecan is a topoisomerase 1 (Topo-1) inhibitor that can stabilize the complexes of DNA and Topo-1 enzyme, preventing DNA relegation and inducing lethal DNA strand breaks. The generation of these DNA lesions is effective for killing cancer cells, allowing NDCs of the present disclosure to achieve the desired therapeutic effect.

In preferred aspects of the present disclosure, the payload is exatecan, or a salt thereof. In other preferred aspects of the present disclosure, the payload is an analog of exatecan, or a salt thereof.

In aspects of the present disclosure, the average nanoparticle to payload ratio ranges from 1 to 80, from 1 to 70, from 1 to 60, from 1 to 50, from 1 to 40, from 1 to 30, from 1 to 20, from 1 to 15, from 1 to 12 and preferably from 1 to 10. For example, the average nanoparticle to payload (e.g., exatecan, or a salt or analog thereof) ratio may be about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:32, 1:34, 1:36, 1:38, 1:40, 1:45, 1:50, 1:55, 1:60, 1:65, 1:70, 1:75, or 1:80. For example, the average number of exatecan molecules on each nanoparticle may be between about 5 and about 10, between about 10 and about 15, between about 15 and about 20, between about 20 and about 25, or between about 25 and about 30, e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 exatecan molecules per nanoparticle. An NDC disclosed herein may comprise about 18 exatecan molecules. An NDC disclosed herein may comprise about 19 exatecan molecules. An NDC disclosed herein may comprise about 20 exatecan molecules. An NDC disclosed herein may comprise about 21 exatecan molecules. An NDC disclosed herein may comprise about 22 exatecan molecules. An NDC disclosed herein may comprise about 23 exatecan molecules. An NDC disclosed herein may comprise about 24 exatecan molecules. An NDC disclosed herein may comprise about 25 exatecan molecules. An NDC disclosed herein may comprise about 26 exatecan molecules. An NDC disclosed herein may comprise about 27 exatecan molecules.

Vintafolide, developed by Endocyte and Merck & Co. is a small molecule drug conjugate consisting of a small molecule targeting the Folate Receptor, which is over expressed on certain cancers, such as ovarian cancer, and a chemotherapy drug, Vinblastine (U.S. Pat. No. 7,601,332 B2 and U.S. Pat. No. 1,002,942 B2). However, vintafolide is capable of carrying single molecule of payload only, attached to the targeting moiety by a pH-cleavable linker. In contrast to that, in the present disclosure several cytotoxic payloads (e.g., exatecan molecules) can be incorporated onto the surface of single nanoparticle.

The linkers in the linker-payload conjugates can be self-immolative linkers that are capable of releasing the active payload in vitro as well as in vivo under conditions sufficient for enzymatic release of the active payload (e.g., a condition presenting an enzyme capable of catalyzing the release).

The linkers described herein can be used, for example, to attach a cytotoxic drug payload (e.g., exatecan) to a carrier and/or a targeting moiety (e.g., nanoparticle) that binds to a cancer cell (e.g., binds to a receptor on the surface of a cancer cell) and gets internalized into the cell (e.g., through the endosome and lysosomal compartment). Once internalized, the linkers can be cleaved or degraded to release active cytotoxic drug. Specifically, the protease-cleavable linkers can release their payload under the action of proteases such as cathepsin, trypsin or other proteases in the lysosomal compartment of the cell.

The cleavable linkers described herein may comprise a structure of Formula (F):

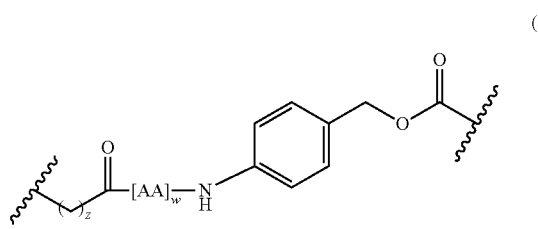

(F)

wherein each instance of [AA] is a natural or non-natural amino acid residue; z is an integer of 1 to 5; w is an integer of 1 to 4 (e.g., 2 or 3); and each ⌇ denotes a point of attachment, e.g., to a spacer group (e.g., PEG) or another portion of the linker, or to an exatecan molecule. For example, -[AA]$_w$- may comprise Val-Lys, Val-Cit, Phe-Lys, Trp-Lys, Asp-Lys, Val-Arg, or Val-Ala, and z may be 2, wherein one ⌇ denotes an attachment to the oxygen atom of a PEG group, and the other ⌇ denotes an attachment to the nitrogen atom of exatecan. For example, -[AA]$_w$- may comprise Val-Lys.

The cleavable linkers described herein may comprise a structure of Formula (F-1):

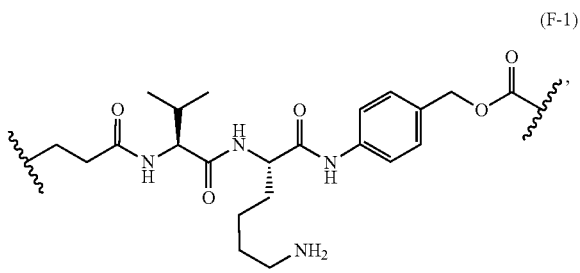 [SMILES: *CCC(=O)N[C@H](C(=O)N[C@@H](CCCCN)C(=O)Nc1ccc(COC(*)=O)cc1)C(C)C]

(F-1)

wherein one ⌇ denotes a point of attachment to the oxygen atom of a PEG group, and the other ⌇ of attachment to the nitrogen atom of exatecan.

The linkers of this disclosure can be prepared from linker precursors that contain reactive groups at one or both ends of the molecule. The reactive groups can be selected to allow conjugation to exatecan or an analog thereof at one end, and also facilitate conjugation to the nanoparticle at the other end. It is desirable for the payload to contain an amine, a hydroxyl, hydrazone, hydrazide or a sulfhydryl group in order to facilitate conjugation to the linker. For example, exatecan comprises a primary amine group that can facilitate its conjugation to the linker.

The linker-payload conjugate precursors can be attached to the nanoparticle using any suitable techniques and methods, and many such techniques are well-known in the art. See, e.g., WO 2017/189961, WO 2015/183882, WO 2013/192609, WO 2016/179260 and WO 2018/213851, each of which are hereby incorporated by reference in their entireties, which describe silica-based core-shell or silica-based core nanoparticles that can be used to prepare targeted nanoparticle-based drug delivery systems. Additionally, linker-payload conjugate precursors, or ligand-linker precursors, can be attached to a nanoparticle using a reaction or method described in Kolb et al. *Angew. Chem. Int. Ed.* (2001) 40:2004-2021, which is incorporated herein by reference in its entirety.

The linker-payload conjugate may be attached to the nanoparticle directly or indirectly through a spacer group, such as a spacer group described herein. Suitable spacer groups include, but are not limited to, a divalent linker (e.g., a divalent linker described herein), such as PEG spacer, or an alkylene spacer (e.g., a methylene spacer), which may further comprise a heteroatom or cyclic group (e.g., heterocyclylene group). The linker-payload conjugate can be absorbed into the interstices or pores of the silica shell, or coated onto the silica shell of the nanoparticle, such as a fluorescent nanoparticle (e.g., covalently attached to the surface of the nanoparticle). In other aspects, where the silica shell is not covering all of the surface of the nanoparticle, the linker-payload conjugate can be associated with the fluorescent core, such as by physical absorption or by bonding interaction.

In some aspects, the linker-payload conjugate may also be associated with the PEG groups that are covalently bonded to the surface of the nanoparticle. For example, the linker-payload conjugate may be attached to the nanoparticle through the PEG. The PEGs can have multiple functional groups for attachment to the nanoparticle and to the linker-payload conjugate.

In specific aspects of the present disclosure, the linker-payload conjugates (or linker-payload conjugate precursor) may be functionalized with a hydrophilic PEG spacer. The linker-payload conjugate precursor may be functionalized with a hydrophilic PEG spacer and/or suitable terminal group such as, but not limited to, an azide group, to facilitate covalently attaching the linker-payload conjugate (e.g., via the spacer group) to the surface of the nanoparticle, e.g., via reaction with a DBCO group on the nanoparticle surface). Other terminal groups can include a nitrile oxide or nitrone, e.g., for conjugation via a 3+2 cycloaddition reaction, to a suitable group on the nanoparticle (e.g., a diene moiety).

The number of PEG groups as spacers that can be present in a functionalized linker-payload conjugate (or precursor thereof) may range from 0 to 20, e.g., from 2 to 20, from 2 to 10, or from 5 to 8, e.g., 5, 6, 7, 8, 9, 10, 11, or 12. In preferred aspects, the number of PEG groups as spacers in a functionalized linker-payload conjugate is 9.

For example, exatecan can be conjugated to a protease-cleavable linker to form the linker-payload conjugate. This linker-conjugate can be prepared from a precursor functionalized with a PEG spacer that has a terminal reactive group, such as an azide, for further conjugation to the surface of the nanoparticle, e.g., via a DBCO group.

The protease-cleavable linker can be designed to be labile to cathepsin B (Cat-B), an enzyme that is over-expressed in malignant tumors, thereby effecting release of the cytotoxic agent, such as exatecan by a self-immolative process.

The linker payload conjugate precursor can comprise a structure of Formula (E-1):

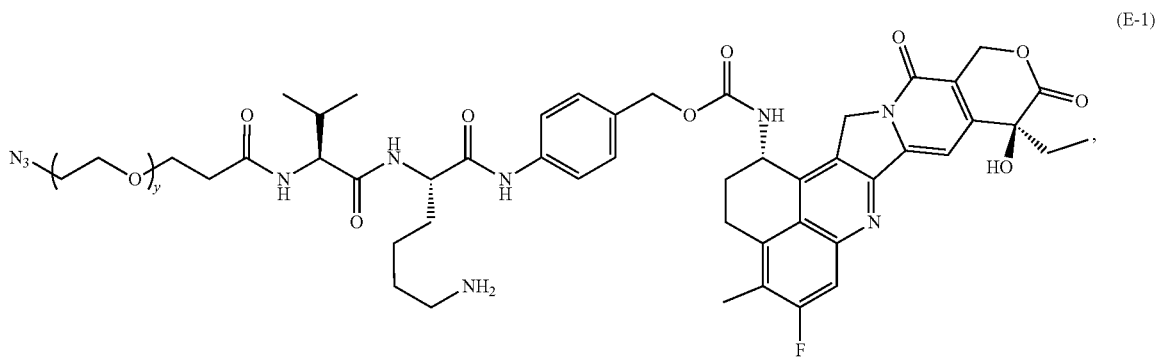

(E-1)

wherein y is an integer of 0 to 20, e.g., 5 to 15, e.g., 9.

The linker and linker-payload conjugates described in the present disclosure have several advantages, ranging from superior serum stability to faster release kinetics mechanism, relative to conventional drug delivery platforms, linkers, or linker-payload conjugates. Also, the ability to pair these linkers with a variety of chemical groups provides the opportunity for the selective release of free payload/drugs, with minimal derivatization, that is a significant advantage.

In preferred aspects of the present disclosure, the linker in the linker-payload conjugate is a protease-cleavable linker.

The NDCs of the present disclosure comprising a payload-linker moiety may comprise a structure of Formula (NP-3):

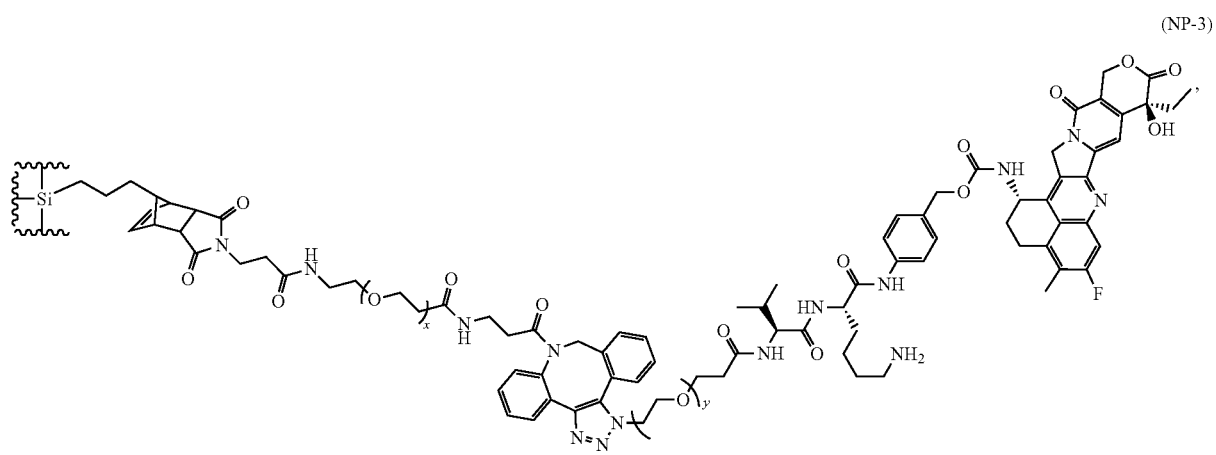

(NP-3)

wherein x is an integer of 0 to 10 (e.g., 0, 1, 2, 3, 4, 5, 6, 7, 8, 9, or 10, e.g., 4), and y is an integer of 0 to 20 (e.g., 0, 1, 2, 3, 4, 5, 6, 7, 8, 9, 10, 11, 12, 13, 14, 15, 16, 17, 18, 19, or 20, e.g., 9), and the silicon atom is a part of the nanoparticle (e.g., bonded with the silica shell of a core-shell silica nanoparticle. For example x may be 4, and y may be 9. An NDC disclosed herein may comprise more than one molecule of Formula (NP-3), for example, the nanoparticle may comprise between about 1 and about 80 molecules of Formula (NP-3), e.g., between about 1 and about 60 molecules of Formula (NP-3), between about 1 and about 40 molecules of Formula (NP-3), between about 1 and about 30 molecules of Formula (NP-3), between about 10 and about 30 molecules of Formula (NP-3), between about 15 and about 25 molecules of Formula (NP-3), e.g., about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 molecules of Formula (NP-3).

Upon contact with a protease (e.g., within a cancer cell, such as within the lysosome of a cancer cell), an NDC of the present disclosure may undergo cleavage to release free exatecan. The cleavage of an NDC disclosed herein may concomitantly release exatecan, carbon dioxide, and 4-aminobenzyl alcohol from the NDC. For example, the cleavage of an exemplary NDC disclosed herein is provided in Scheme 1 below.

Scheme 1. Exemplary cleavage mechanism of an NDC disclosed herein.

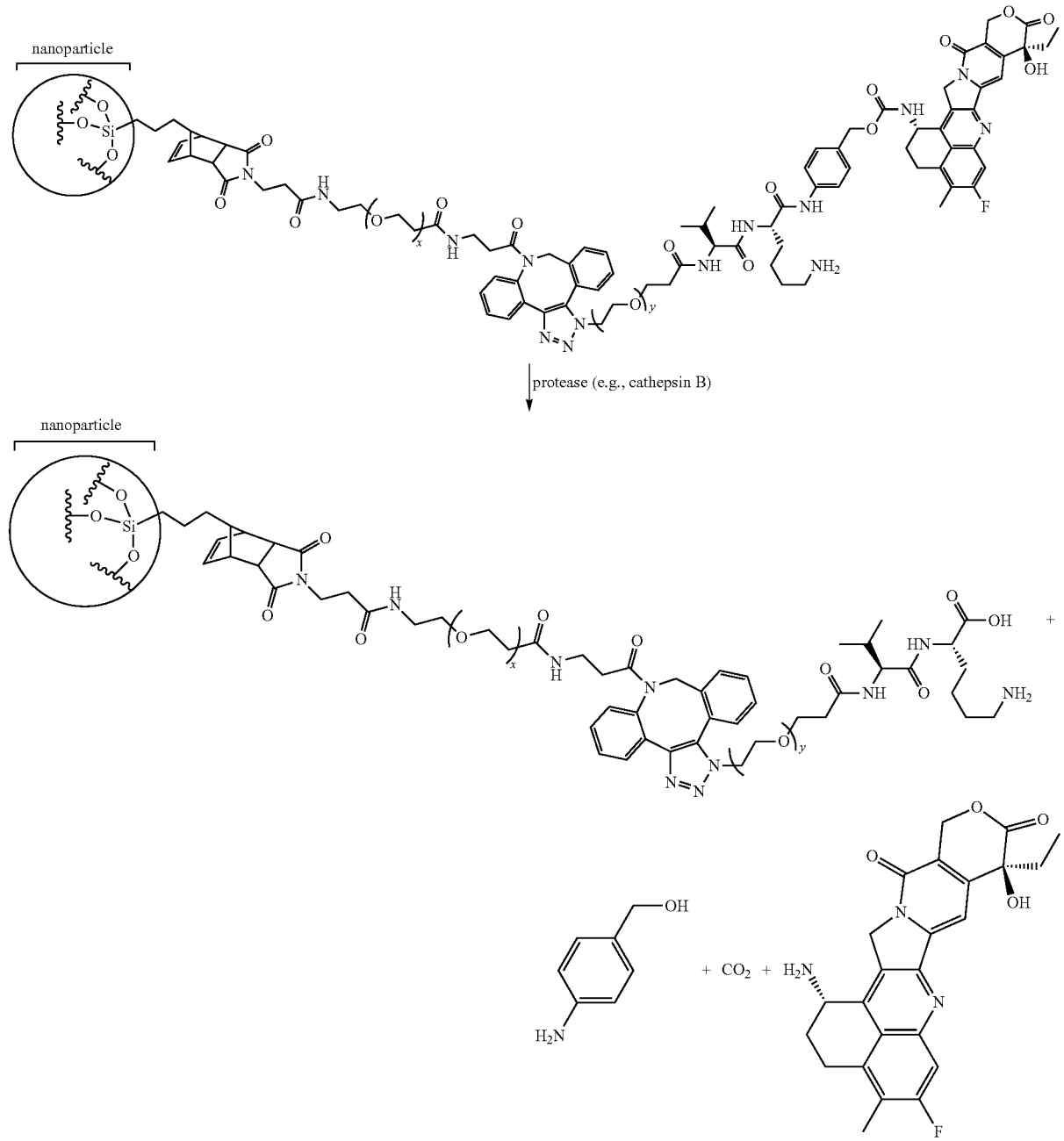

The NDCs disclosed herein may comprise both a molecule of Formula (NP-2), and a molecule of Formula (NP-3), e.g., each NDC may comprise about 1 and about 20 molecules of Formula (NP-2), and about 1 and about 30 molecules of Formula (NP-3). For example, each NDC may comprise about 10 and about 15 molecules of Formula (NP-2), and about 15 and about 25 molecules of Formula (NP-3). An NDC disclosed herein may comprise an average of 13 molecules of Formula (NP-2), and an average of 21 molecules of Formula (NP-3); an average of 12 molecules of Formula (NP-2), and an average of 25 molecules of Formula (NP-3); an average of 12 molecules of Formula (NP-2), and an average of 20 molecules of Formula (NP-3).

This disclosure provides compositions and methods directed to a nanoparticle-drug conjugate (NDC) comprising: a nanoparticle; a targeting ligand that binds to folate receptor; and a linker-payload conjugate, wherein the NDC has an average diameter between about 1 nm and about 10 nm. For example, a nanoparticle comprising folic acid as a targeting ligand, and a linker-payload conjugate comprising exatecan conjugated via a protease-cleavable linker, wherein the NDC has an average diameter between about 1 nm and about 10 nm.

FIG. 1 illustrates a representative nanoparticle-drug conjugate (NDC) that has an average diameter of about 6 nm, comprising a nanoparticle that comprises a silica-based core and a silica shell surrounding at least a portion of the core, polyethylene glycol (PEG) covalently bonded to the surface of the nanoparticle, and a fluorescent compound (Cy5) covalently encapsulated within the core of the nanoparticle, folic acid (FA) as the targeting ligand that can bind to a folate receptor, and a linker-payload conjugate that comprises a protease-cleavable linker-exatecan conjugate. It will be understood that "folic acid" is intended to encompass any amide or ester derivative of folic acid, e.g., as shown in FIG. 1 where folic acid is covalently attached to the spacer group (PEG) via an amide group.

Figure 6:
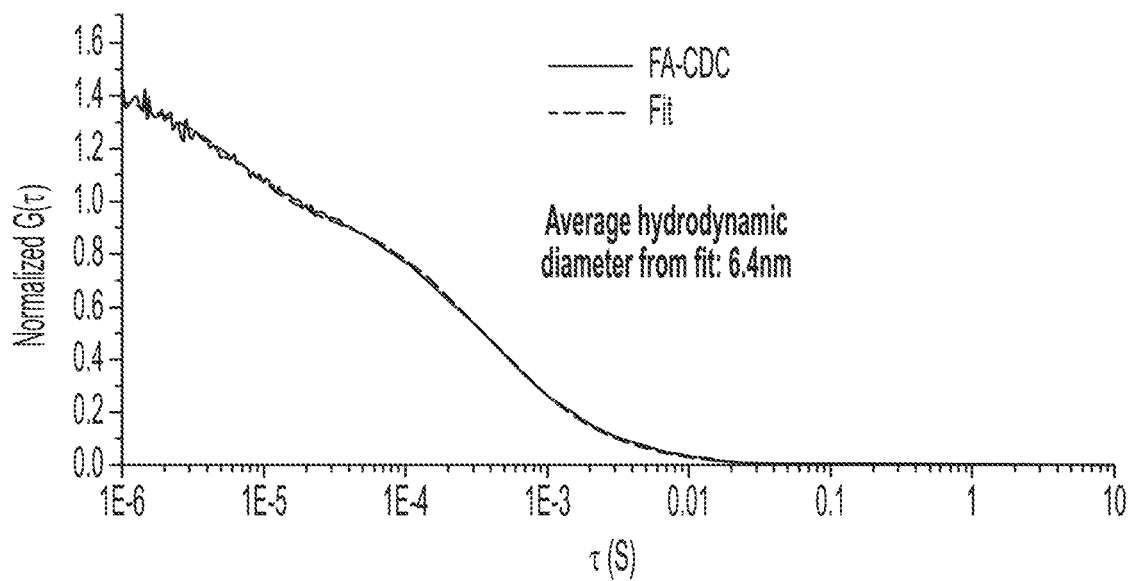
FIG. 6 depicts a fluorescence correlation spectroscopy (FCS) correlation curve of an exemplary NDC (folic acid (FA)-functionalized exatecan-linker conjugated C'Dot (FA-CDC)) that is fitted by a single-modal FCS correlation function. Average hydrodynamic diameter was obtained via fitting the FCS correlation curve.
Figure 7:
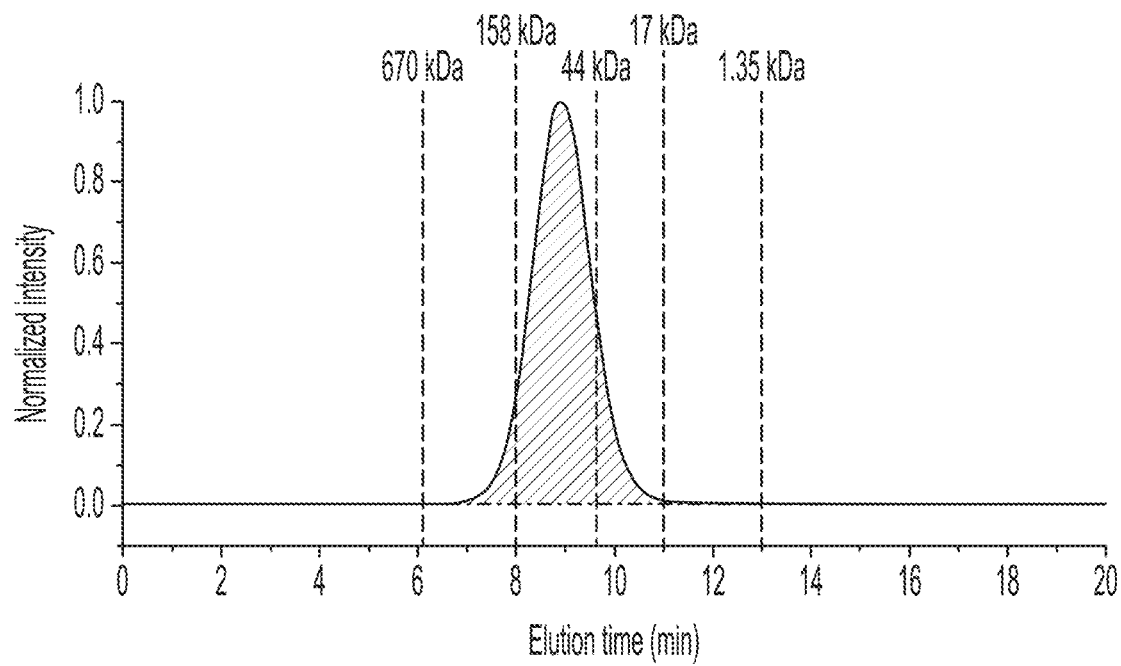
FIG. 7 depicts a chromatogram showing the elution of an exemplary NDC (folic acid (FA)-functionalized exatecan-linker conjugated C'Dot (FA-CDC)) by a gel permeation chromatography (GPC). The elution of FA-CDC (striped line under the curve) is compared to the elution time of protein standards with varying molecular weight (dashed line).

The NDC may have an average diameter between about 5 nm to about 8 nm, or between about 6 nm to about 7 nm. The average diameter of NDCs can be measured by any suitable methods, such as, but not limited to, fluorescence correlation spectroscopy (FCS) (see, e.g., FIG. 6) and gel permeation chromatography (GPC) (FIG. 7).

The NDCs of the present disclosure can comprise nanoparticles that can be functionalized with contrast agents for positron emission tomography (PET), single photon emission computed tomography (SPECT), computerized tomography (CT), magnetic resonance imaging (MRI), and optical imaging (such as fluorescence imaging including near-infrared fluorescence (NIRF) imaging, bio luminescence imaging, or combinations thereof).

A contrast agent, such as a radionuclide (radiolabel) including, but not limited to $^{89}$Zr, $^{64}$Cu, $^{68}$Ga, $^{86}$Y, $^{124}$I and $^{17}$Lu, may be attached to the nanoparticle. Alternatively, the nanoparticle can be attached to a chelator moiety, for example, DFO, DOTA, TETA and DTPA, that is adapted to bind a radionuclide. Such nanoparticle may be detected by PET, SPECT, CT, MRI, or optical imaging (such as fluorescence imaging including near-infrared fluorescence (NIRF) imaging, bio luminescence imaging, or combinations thereof).

The radionuclide can additionally serve as a therapeutic agent for creating a multitherapeutic platform. This coupling allows the therapeutic agent to be delivered to the specific cell type through the specific binding between the targeting ligand and the cellular component.

Protease-Cleavable Linker-Payload Conjugates

A linker-payload conjugate may comprise a compound of Formula (I)

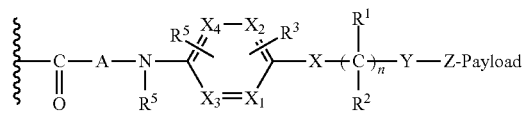

(I)

or a salt thereof, wherein,

⁀ line represents an attachment to the nanoparticle through a spacer group; A is a dipeptide selected from the group consisting of Val-Cit, Phe-Lys, Trp-Lys, Asp-Lys, Val-Lys, Val-Arg, and Val-Ala, or A is a tetrapeptide selected from the group consisting of Val-Phe-Gly-Sar (SEQ ID NO: 8), Val-Cit-Gly-Sar, Val-Lys-Gly-Sar (SEQ ID NO: 10), Val-Ala-Gly-Sar (SEQ ID NO: 11), Val-Phe-Gly-Pro (SEQ ID NO: 12), Val-Cit-Gly-Pro, Val-Lys-Gly-Pro (SEQ ID NO: 14), Val-Ala-Gly-Pro (SEQ ID NO: 15), Val-Cit-Gly-any natural or unnatural N-alkyl substituted alpha amino acid, Val-Lys-Gly-any natural or unnatural N-alkyl substituted alpha amino acid, Val-Phe-Gly-any natural or unnatural N-alkyl substituted alpha amino acid, Val-Ala-Gly-any natural or unnatural N-alkyl substituted alpha amino acid, Phe-Lys-Gly-any natural or unnatural N-alkyl substituted alpha amino acid, and Trp-Lys-Gly-any natural or unnatural N-alkyl substituted alpha amino acid; Payload is exatecan, and the primary amine group of exatecan is represented by Z; $R^1$ and $R^2$ in each occurrence is independently hydrogen, substituted or unsubstituted $C_{1-6}$ alkyl or substituted or unsubstituted $C_{1-6}$ alkoxy, or hydroxyl; $R^3$ and $R^4$ in each occurrence is independently hydrogen, halo, substituted or unsubstituted $C_{1-6}$ alkyl, or substituted or unsubstituted $C_{1-6}$ alkoxy; $R^5$ is selected from the group consisting of hydrogen, substituted or unsubstituted $C_{1-6}$ alkyl; substituted or unsubstituted $C_{3-7}$ cycloalkyl, substituted or unsubstituted aryl, substituted or unsubstituted heteroaryl, and substituted or unsubstituted $C_{5-6}$ heterocycloalkyl; with the proviso that, when A is a dipeptide, $R^5$ is H; $R^a$, $R^b$, and $R^c$ in each occurrence is independently hydrogen or substituted or unsubstituted $C_{1-6}$ alkyl; X is absent, —O—, —CO— or —NR$^a$—; Y is absent

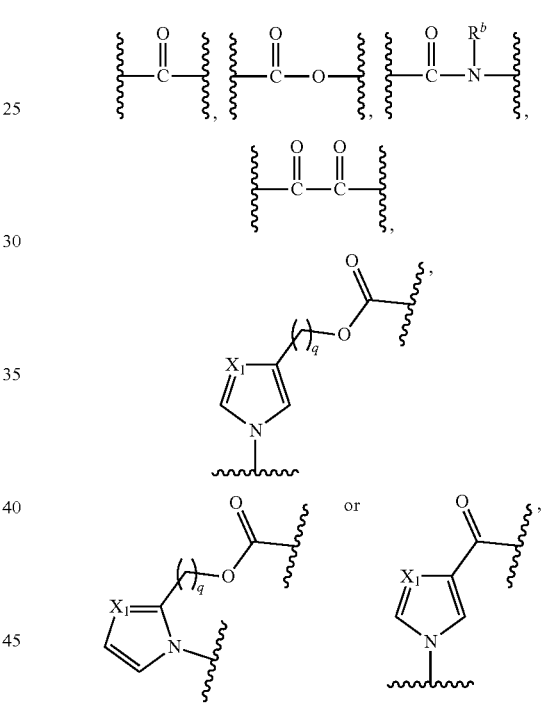

wherein the carbonyl in

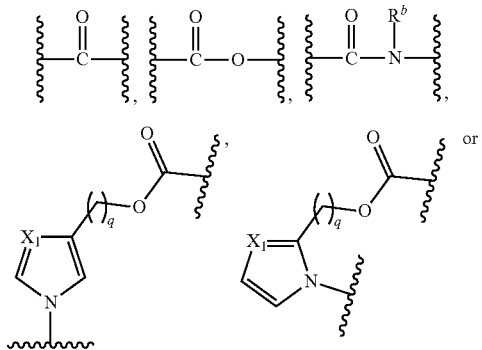

-continued

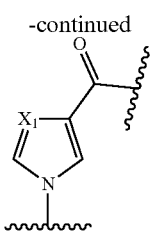

is bonded to Z;
with the proviso that, when Y is

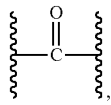

X is absent and n is 1; when Y is

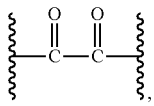

X is absent and n is 0; when Y is

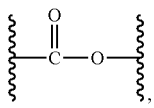

X is absent and n is 0; and/or when X is —CO—, Y is absent and n is 0; $X_1$ and $X_2$ are independently —CH— or —N—; $X_3$ is —CH—; $X_4$ is —CH—; Z is —NR$^c$— or —O—; n is 0 or 1; q is 1 to 3.

In preferred aspects of Formula (I), A is Val-Lys; $R^1$-$R^5$ are each independently hydrogen; X is absent; Y is

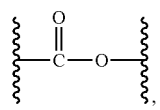

wherein the carbonyl in

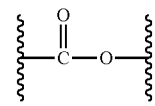 [SMILES: *OC(*)=O]

is bonded to Z; n is 1; $X_1$, $X_2$, $X_3$, and $X_4$ are each independently —CH—; Z is —NR$^c$— wherein R$^c$ is hydrogen, and wherein the N is the nitrogen atom present in the exatecan payload.

In the linker-payload conjugate of Formula (I), the payload may be exatecan, which has a functional group that is bonded to the linker, wherein the functional group is an amine (when exatecan is bonded to the linker, it is a secondary amine, and once released (or prior to conjugation), i.e., as a separate molecular entity, the amine of exatecan is a primary amine).

Exemplary Linker-payload Conjugates: Representative linker-payload conjugates of the present disclosure include, but are not limited to the following sub-structures, wherein ⁀ line represents a direct bond to the nanoparticle or an indirect bond to the nanoparticle through a spacer group. Suitable spacer groups include, but are not limited to a PEG spacer, or an alkylene spacer (e.g., methylene spacer), which may further comprise heteroatoms, or cyclic groups (e.g., heterocyclylene groups). In preferred aspects, the spacer group is a PEG spacer.

An exemplary linker-payload conjugate of Formula (I) of the present disclosure includes the following sub-structure:

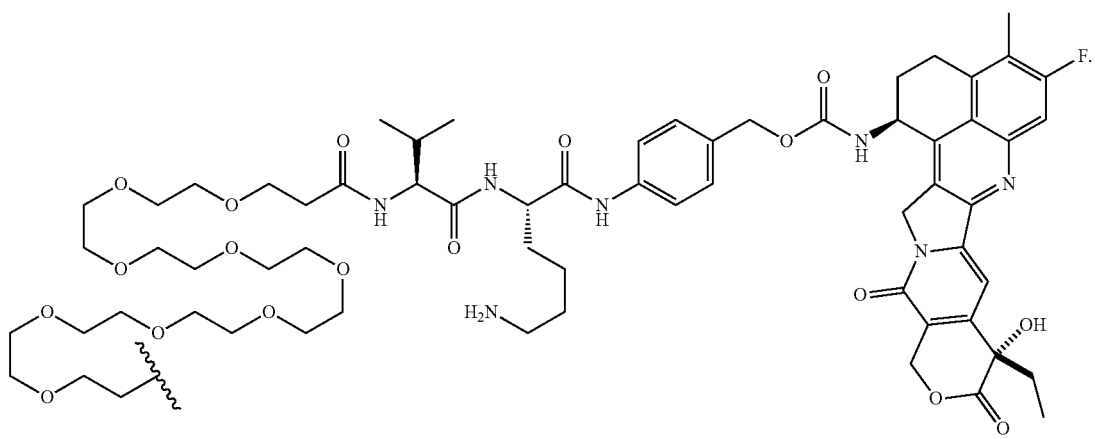 [SMILES: *CCOCCOCCOCCOCCOCCOCCOCCOCCOCCC(=O)N[C@H](C(=O)N[C@@H](CCCCN)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C]

Linkers and Precursors Thereof. The linkers of this disclosure, and/or their precursors, can contain reactive groups at both ends of the molecule. The reactive groups can be selected to allow conjugation to exatecan or a salt or analog thereof at one end, and also facilitate conjugation to a nanoparticle (e.g., via a spacer group) at the other end. For example, the linker can connect to exatecan via a chemically reactive functional group that is a part of the exatecan, such as the primary amine of exatecan (that becomes a secondary amine upon conjugation to the linker).

The linker can be conjugated to a functionalized polyethylene glycol or a $C_5$-$C_6$ alkyl chain via a chemically reactive functional group that is a part of the linker such as a primary or secondary amine or carboxyl group.

Protease-cleavable Linkers: Proteases are involved in all stages of cancer disease from tumor cells growth and survival, to angiogenesis and invasions. Therefore, they can be utilized to treat cancer as selective triggers towards activation of linker/payload system. This disclosure relates to linkers that are cleavable by the action of proteases thereby releasing the free payload (e.g., exatecan). Lysosomal proteases such as cathepsin B and serine proteases such as cathepsin A or tripeptidyl-peptidase I have been extensively studied in the context of prodrug development. Proteolytic enzymes such as caspases are also well-known to be utilized as biological triggers for the selective activation of payload or for specific cargo delivery to a target cell such as a cancer cell.

A linker (or precursor thereof) can comprise a compound of Formula (I-A)

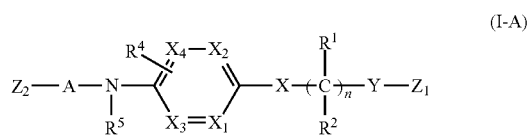

(I-A)

wherein: A is a dipeptide selected from the group consisting of Val-Cit, Phe-Lys, Trp-Lys, Asp-Lys, Val-Lys, Val-Arg, and Val-Ala, or A is a tetrapeptide selected from the group consisting of Val-Cit-Gly-Sar (SEQ ID NO: 8), Val-Cit-Gly-Sar, Val-Lys-Gly-Sar (SEQ ID NO: 10), Val-Ala-Gly-Sar (SEQ ID NO: 11), Val-Phe-Gly-Pro (SEQ ID NO: 12), Val-Cit-Gly-Pro, Val-Lys-Gly-Pro (SEQ ID NO: 14), Val-Ala-Gly-Pro (SEQ ID NO: 15), Val-Cit-Gly-any natural or unnatural N-alkyl substituted alpha amino acid, Val-Lys-Gly-any natural or unnatural N-alkyl substituted alpha amino acid, Val-Phe-Gly-any natural or unnatural N-alkyl substituted alpha amino acid, Val-Ala-Gly-any natural or unnatural N-alkyl substituted alpha amino acid, Phe-Lys-Gly-any natural or unnatural N-alkyl substituted alpha amino acid, and Trp-Lys-Gly-any natural or unnatural N-alkyl substituted alpha amino acid; R and $R^2$ in each occurrence is independently hydrogen, substituted or unsubstituted $C_{1-6}$ alkyl or substituted or unsubstituted $C_{1-6}$ alkoxy, or hydroxy; $R^3$ and $R^4$ in each occurrence is independently hydrogen, halo, substituted or unsubstituted $C_{1-6}$ alkyl or substituted or unsubstituted $C_{1-6}$ alkoxy; $R^5$ is selected from the group consisting of hydrogen, substituted or unsubstituted $C_{1-6}$ alkyl; substituted or unsubstituted $C_{3-7}$ cycloalkyl, substituted or unsubstituted aryl, substituted or unsubstituted heteroaryl, and substituted or unsubstituted $C_{5-6}$ heterocycloalkyl, with the proviso that, when A is a dipeptide, $R^5$ is H; $R^{1'}$, $R^{2'}$, $R^{3'}$, $R^{4'}$ and $R^{5'}$ in each occurrence is independently hydrogen, substituted or unsubstituted $C_{1-6}$ alkyl or substituted or unsubstituted $C_{1-6}$ cycloalkyl; X is absent, —O—, —CO— or —$NR^a$—; Y is absent

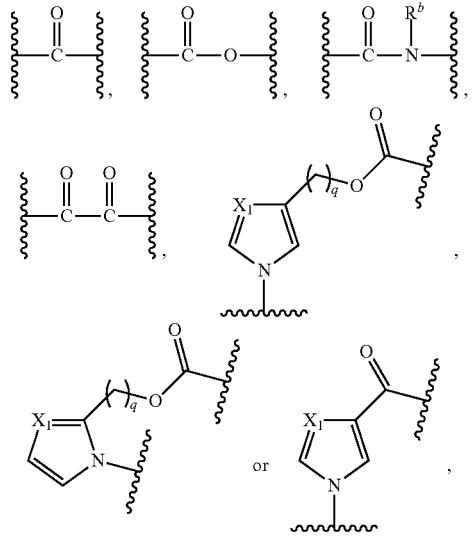

wherein the carbonyl in

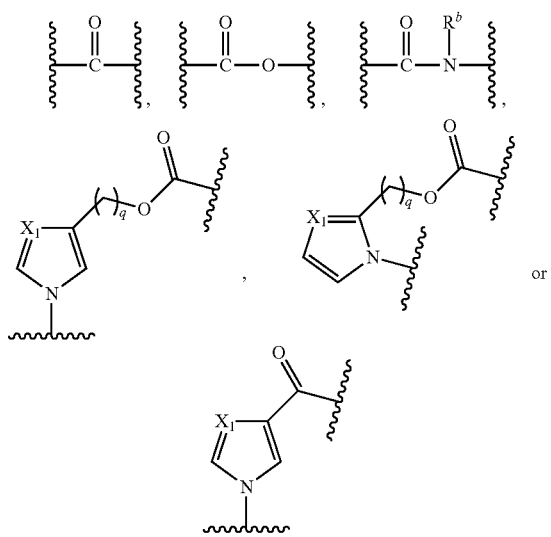

is bonded to $Z_1$, with the proviso that, when Y is

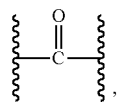

X is absent and n is 1; with the proviso that, when Y is

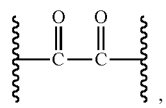 [SMILES: *C(=O)C(*)=O]

X is absent and n is 0, with the proviso that, when Y is

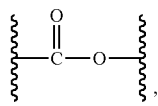 [SMILES: *OC(*)=O]

X is absent and n is 0 or 1; with the proviso that, when X is —CO—, Y is absent and n is 0; $X_3$ is —CH—; $X_4$ is —CH—; $Z_1$ is a functional group selected from the group consisting of halo, hydroxy, —OSO$_2$—CH$_3$, —OSO$_2$CF$_3$, 4-nitrophenoxy, —COCl, and —COOH; $Z_2$ is a functional group selected from the group consisting of —NH$_2$, —NHR$^c$, and —COOH; or $Z_2$ is —C(O)-T$_1$; T$_1$ is a functionalized polyethylene glycol or a $C_5$-$C_6$ alkyl chain that has a terminal group selected from the group consisting of azide,

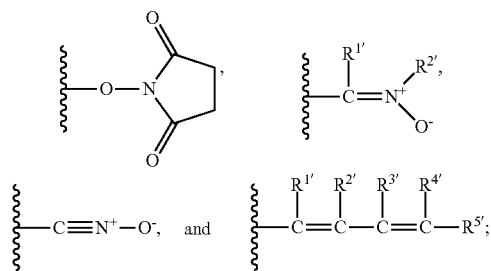

$R^a$, $R^b$ and $R^c$ in each occurrence is independently hydrogen or substituted or unsubstituted $C_{1-6}$ alkyl; n is 0 or 1; and q is 1 to 3. In certain aspects of Formula (I-A), A is Val-Lys; $R^1$-$R^5$ are each independently hydrogen; X is absent; Y is

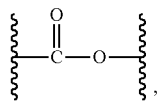 [SMILES: *OC(*)=O]

wherein the carbonyl in

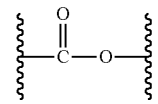

is bonded to Z; n is 1; $X_1$, $X_2$, $X_3$ and $X_4$ are each independently —CH—; $Z_1$ is a functional group selected from the group consisting of halo, hydroxy, —OSO$_2$—CH$_3$, —OSO$_2$CF$_3$, 4-nitrophenoxy, —COCl, and —COOH; $Z_2$ is a functional group selected from the group consisting of —NH$_2$, —NHR$^c$, and —COOH or $Z_2$ is —C(O)-T$_1$, wherein T$_1$ is as defined in Formula (I-A).

Pharmaceutical Compositions

The present disclosure further provides a pharmaceutical composition for treating a disease (e.g., cancer, such as a cancer associated with folate receptor expressing tumor), wherein the composition comprises an effective amount of an NDC described herein.

In specific aspects of the present disclosure, the pharmaceutical composition comprising the NDCs can be used to treat cancer selected from the group consisting of ovarian cancer, endometrial cancer, fallopian tube cancer, cervical cancer, breast cancer, lung cancer, mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML). The pharmaceutical composition comprising the NDCs may also be used for targeting tumor associated macrophages, e.g., to modify the immune status of a tumor in a subject.

The pharmaceutical compositions of the present disclosure may comprise a pharmaceutically acceptable excipient, such as a non-toxic carrier, adjuvant, diluent, or vehicle that does not negatively impact the pharmacological activity of the NDCs with which it is formulated. Pharmaceutically acceptable excipients useful in the manufacture of the pharmaceutical compositions of the present disclosure are any of those that are well known in the art of pharmaceutical formulation, and can include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the present disclosure include, but are not limited to, ion exchangers, alumina, aluminum stearate, lecithin, serum proteins (e.g., human serum albumin), buffer substances (e.g., phosphates), glycine, sorbic acid, potassium sorbate, glyceride mixtures (e.g., mixtures of saturated vegetable fatty acids), water, salts or electrolytes (e.g., protamine sulfate, disodium hydrogen phosphate, potassium hydrogen phosphate, sodium chloride, zinc salts), colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The pharmaceutical compositions of the present disclosure may be administered orally in the form of a suitable pharmaceutical unit dosage form. The pharmaceutical compositions of the present disclosure may be prepared in many forms that include tablets, hard or soft gelatin capsules, aqueous solutions, suspensions, liposomes, and other slow-release formulations, such as shaped polymeric gels.

Suitable modes of administration for the NDCs or composition include, but are not limited to, oral, intravenous, rectal, sublingual, mucosal, nasal, ophthalmic, subcutaneous, intramuscular, transdermal, spinal, intrathecal, intra-articular, intra-arterial, sub-arachnoid, bronchial, lymphatic administration, intra-tumoral, and other routes suitable for systemic delivery of active ingredients.

The present pharmaceutical composition may be administered by any method known in the art, including, without limitation, transdermal (passive via patch, gel, cream, ointment or iontophoretic); intravenous (bolus, infusion); subcutaneous (infusion, depot); transmucosal (buccal and sublingual, e.g., orodispersible tablets, wafers, film, and effervescent formulations); conjunctival (eyedrops); rectal (suppository, enema)); or intradermal (bolus, infusion, depot). The composition may be delivered topically.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The pharmaceutical compositions of the present disclosure may also be formulated for parenteral administration (e.g., by injection, for example, bolus injection or continuous infusion) and may be presented in unit dosage form in ampules, pre-filled syringes, infusion containers (e.g., small volume infusion containers), or multi-dose containers, that may contain an added preservative.

The pharmaceutical compositions may take such forms as suspensions, solutions, or emulsions in oily or aqueous vehicles, and may contain formulating agents such as suspending, stabilizing and/or dispersing agents. Alternatively, the pharmaceutical compositions of the present disclosure may be in powder form, obtained by aseptic isolation of sterile solid or by lyophilization from solution, for constitution with a suitable vehicle, e.g., sterile, pyrogen-free water, before use.

For topical administration (e.g., to the epidermis), the pharmaceutical compositions may be formulated as an ointment, cream, or lotion, or as the active ingredient of a transdermal patch. Suitable transdermal delivery systems are disclosed, for example, in A. Fisher et al. (U.S. Pat. No. 4,788,603), and R. Bawa et al. (U.S. Pat. Nos. 4,931,279; 4,668,506; and 4,713,224), which are incorporated herein by reference in their entireties. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The pharmaceutical compositions can also be delivered via ionophoresis, e.g., as disclosed in U.S. Pat. Nos. 4,140,122; 4,383,529; or 4,051,842, each of which are incorporated herein by reference in their entireties.

Pharmaceutical compositions suitable for topical administration in the mouth include unit dosage forms such as lozenges comprising a pharmaceutical composition of the present disclosure in a flavored base, such as sucrose and acacia or tragacanth; pastilles comprising the pharmaceutical composition in an inert base such as gelatin and glycerin or sucrose and acacia; mucoadherent gels, and mouthwashes comprising the pharmaceutical composition in a suitable liquid carrier.

For topical administration to the eye, the pharmaceutical compositions can be administered as drops, gels (S. Chrai et al, U.S. Pat. No. 4,255,415), gums (S. L. Lin et al, U.S. Pat. No. 4,136,177) or via a prolonged-release ocular insert (A. S. Michaels, U.S. Pat. No. 3,867,519 and H. M. Haddad et al., U.S. Pat. No. 3,870,791), each of which are incorporated herein by reference in their entireties.

When desired, the above-described pharmaceutical compositions can be adapted to give sustained release of a therapeutic compound employed, e.g., by combination with certain hydrophilic polymer matrices, e.g., comprising natural gels, synthetic polymer gels or mixtures thereof.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

Pharmaceutical compositions suitable for vaginal administration may be presented as pessaries, tampons, creams, gels, pastes, foams, or sprays containing, in addition to the nanoparticles and the therapeutic agent, a carrier. Such carriers are well known in the art.

For administration by inhalation, the pharmaceutical compositions according to the present disclosure are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the pharmaceutical compositions of the present disclosure may take the form of a dry powder composition, for example, a powder mix of the pharmaceutical composition and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the pharmaceutical compositions of the present disclosure may be administered via a liquid spray, such as via a plastic bottle atomizer. Typical of these are the MISTOMETER® (isoproterenol inhaler—Wintrop) and the MEDIHALER® (isoproterenol inhaler-Riker).

Pharmaceutical compositions of the present disclosure may also contain other adjuvants such as flavorings, colorings, anti-microbial agents, or preservatives.

It will be further appreciated that the amount of the pharmaceutical compositions suitable for use in treatment will vary not only with the therapeutic agent selected but also with the route of administration, the nature of the condition being treated and the age and condition of the patient and will be ultimately at the discretion of the attendant physician or clinician. For evaluations of these factors, see J. F. Brien et al., *Europ. J. Clin. Pharmacol.*, 14, 133 (1978); and Physicians' Desk Reference, Charles E. Baker, Jr., Pub., Medical Economics Co., Oradell, N.J. (41$^{st}$ ed., 1987), each of which are incorporated herein by reference in their entireties.

Administration and Methods of Treatment

NDCs of the present disclosure can be administered to a subject. The subject can be a mammal, preferably a human. Mammals include, but are not limited to, murines, rats, rabbits, simians, bovines, ovine, swine, canines, feline, farm animals, sport animals, pets, equine, and primates.

NDCs may be administered to a subject by, but not restricted to, the following routes: oral, intravenous, nasal, subcutaneous, local, intramuscular or transdermal. For example, the NDCs of the present disclosure may be administered to a subject intravenously.

The methods and compositions of the present disclosure can be used to help a physician or surgeon to identify and characterize areas of disease, such as cancers, including, but not restricted to, cancers that overexpress FR, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease.

The methods and compositions of the present disclosure may be used, but are not limited to, metastatic disease detection, treatment response monitoring, and targeted delivery of payload, including by passing the blood-brain barrier.

The methods and compositions of the present disclosure can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state.

The methods and compositions of the present disclosure can also be used to monitor and/or guide various therapeutic interventions, such as surgical and catheter-based procedures, and monitoring drug therapy, including cell based therapies. The methods of the present disclosure can also be used in prognosis of a disease or disease condition. Cellular subpopulations residing within or marginating the disease site, such as stem-like cells ("cancer stem cells") and/or inflammatory/phagocytic cells may be identified and characterized using the methods and compositions of the present disclosure.

With respect to each of the foregoing, examples of such disease or disease conditions that can be detected or monitored (before, during or after therapy) include cancer (for example, melanoma, thyroid, colorectal, ovarian, lung, breast, prostate, cervical, skin, brain, gastrointestinal, mouth, kidney, esophageal, bone cancer), that can be used to identify subjects that have an increased susceptibility for developing cancer and/or malignancies, i.e., they are predisposed to develop cancer and/or malignancies, inflammation (for example, inflammatory conditions induced by the presence of cancerous lesions), cardiovascular disease (for example, atherosclerosis and inflammatory conditions of blood vessels, ischemia, stroke, thrombosis), dermatologic disease (for example, Kaposi's Sarcoma, psoriasis), ophthalmic disease (for example, macular degeneration, diabetic retinopathy), infectious disease (for example, bacterial, viral, fungal and parasitic infections, including Acquired Immunodeficiency Syndrome (AIDS)), immunologic disease (for example, an autoimmune disorder, lymphoma, multiple sclerosis, rheumatoid arthritis, diabetes mellitus), central nervous system disease (for example, a neurodegenerative disease, such as Parkinson's disease or Alzheimer's disease), inherited diseases, metabolic diseases, environmental diseases (for example, lead, mercury and radioactive poisoning, skin cancer), bone-related disease (for example, osteoporosis, primary and metastatic bone tumors, osteoarthritis) and a neurodegenerative disease.

The methods and compositions of the present disclosure, therefore, can be used, for example, to determine the presence and/or localization of tumor and/or co-resident stem-like cells ("cancer stem cells"), the presence and/or localization of inflammatory cells, including the presence of activated macrophages, for instance in peritumoral regions, the presence and in localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the present disclosure can also be used in identification and evaluation of cell death, injury, apoptosis, necrosis, hypoxia and angiogenesis (PCT/US2006/049222).

The methods of the present disclosure comprise administering to a subject in need thereof an effective amount of an NDC described herein. For example, the NDC can be administered to the subject in need thereof intravenously. An "effective amount" is an amount of the NDC that elicits a desired biological or medicinal response under the conditions of administration, such as an amount that reduces the signs and/or symptoms of a disease or disorder being treated, e.g., reduces tumor size or tumor burden. The actual amount administered can be determined by an ordinarily skilled clinician based upon, for example, the subject's age, weight, sex, general heath and tolerance to drugs, severity of disease, dosage form selected, route of administration, and other factors.

In specific aspects of the method, the subject has a cancer selected from the group consisting of ovarian cancer, endometrial cancer, fallopian tube cancer, cervical cancer, breast cancer, lung cancer, mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML).

The present disclosure also includes use of NDCs for treating a folate receptor expressing tumor. For example, the use of NDC may comprise administration to the subject in need thereof intravenously.

The present disclosure also relates to the use of NDCs in a subject with cancer selected from the group consisting of ovarian cancer, endometrial cancer, fallopian tube cancer, cervical cancer, breast cancer, lung cancer, mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML).

The NDCs of the present disclosure may also be used in the manufacture of a medicament for treating a folate receptor expressing tumor, wherein the NDC is administered to the subject in need thereof intravenously and wherein the subject has a cancer selected from the group consisting of ovarian cancer, endometrial cancer, fallopian tube cancer, cervical cancer, breast cancer, lung cancer, mesothelioma, uterine cancer, gastrointestinal cancer (e.g., esophageal cancer, colon cancer, rectal cancer, and stomach cancer), pancreatic cancer, bladder cancer, kidney cancer, liver cancer, head and neck cancer, brain cancer, thyroid cancer, skin cancer, prostate cancer, testicular cancer, acute myeloid leukemia (AML, e.g., pediatric AML), and chronic myelogenous leukemia (CML).

The compositions and methods disclosed herein can include compositions and methods that include administering a NDC as disclosed herein in combination with one or more additional anti-cancer agents. In such circumstances the NDC can be administered before, substantially concurrently with, or after the additional agent or agents. Suitable additional agents, include, for example chemotherapeutic agents such as mechlorethamine, cyclophosphamide, melphalan, chlorambucil, ifosfamide, busulfan, N-nitroso-N-methylurea, carmustine, lomustine, semustine, fotemustine, streptozotocin, dacarbazine, mitozolomide, temozolomide, thiotepa, mitomycin, diaziquone, cisplatin, carboplatin, oxaliplatin, procarbazine, hexamethylmelamine, methotrexate, pemetrexed, fluorouracil (e.g. 5-fluorouracil), capecitabine, cytarabine, gemcitabine, decitabine, azacitidine, fludarabine, nelarabine, cladribine, clofarabine, pentostatin, thioguanine, mercaptopurine, vincristine, vinblastine, vinorelbine, vindesine, vinflunine, paclitaxel, docetaxel, irinotecan, topotecan, camptothecin, etoposide, mitoxantrone, teniposide, novobiocin, merbarone, doxorubicin, daunorubicin, epirubicin, idarubicin, pirarubicin, aclarubicin, mitomycin C, actinomycin, bleomycin, bisantrene, gemcitabine, cytarabine, and the like. Other anti-cancer agents that can be used with a NDC in the compositions and methods disclosed herein include, immune check point inhibitors (e.g., anti-PD1, anti-PDL1, anti-CTLA4 antibodies), hormone receptor antagonists, other chemotherapeutic conjugates (e.g., in the form of antibody-drug conjugates, nanoparticle drug conjugates, and the like), and the like.

The terminology used in the description of the invention herein is for the purpose of describing particular embodiments only and is not intended to be limiting of the invention. As used in the description of the embodiments of the invention and the appended claims, the singular forms of "a", "an" and "the" are intended to include the plural forms as well, unless the context clearly indicates otherwise. Also, as used herein, "and/or" refers to and encompasses any and all possible combinations of one or more of the associated listed items.

The term "about," when referring to a value means ±20%, or ±10. Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

It will be understood that in the detailed description and appended claims, the abbreviations and nomenclature employed are those which are standard in amino acid and peptide chemistry.

ABBREVIATIONS

The abbreviations used in this disclosure, unless otherwise indicated are as follows:
Fmoc: Fluorenylmethoxycarbonyl
MeOH: Methanol
Cit-OH: L-Citrulline
DCM: Dichloromethane
EEDQ: 2-Ethoxy-1-(ethoxycarbonyl)-1,2-dihydroquinoline
THF: Tetrahydrofuran
NMR: Nuclear Magnetic Resonance
DMSO: Dimethyl sulfoxide
LCMS: Liquid Chromatography-Mass Spectrometry
TEA: Triethylamine
HATU: (1-[Bis(dimethylamino)methylene]-1H-1,2,3-triazolo[4,5-b]pyridinium 3-oxide hexafluorophosphate
DMF: Dimethylformamide
DIPEA: N,N-Diisopropylethylamine
TMSCN: Trimethylsilyl cyanide
RP HPLC: Reverse Phase High-Pressure Liquid Chromatography
SFC: Supercritical fluid chromatography
CAN: Acetonitrile
NMP: N-Methyl pyrrolidone
r.t: Room Temperature
TEA: Triethylamine
TFA: Trifluoroacetic acid
MTBE: Methyl tert-butyl ether
EtOAC: Ethyl acetate
PyBOP: (Benzotrizole-1-yl-oxytripyrrolidinenophosphoniumhexafluorophosphate)

Definitions

As used herein, the term "alkyl" refers to monovalent aliphatic hydrocarbon group that may comprise 1 to 18 carbon atoms, such as 1 to about 12 carbon atoms, or 1 to about 6 carbon atoms ("$C_{1-18}$ alkyl"). An alkyl group can be straight chain, branched chain, monocyclic moiety or polycyclic moiety or combinations thereof. Examples of alkyl groups include methyl, ethyl, propyl, isopropyl, butyl, isobutyl, sec-butyl, tert-butyl, pentyl, hexyl, cyclopropyl, cyclobutyl, cyclopentyl, cyclohexyl, norbornyl, and the like. Each instance of an alkyl group may be independently optionally substituted, i.e., unsubstituted (an "unsubstituted alkyl") or substituted (a "substituted alkyl") with one or more substituents e.g., for instance from 1 to 5 substituents, 1 to 3 substituents, or 1 substituent.

As used herein, the term "alkenyl" refers to a monovalent straight-chain or branched hydrocarbon group having from 2 to 18 carbon atoms, one or more carbon-carbon double bonds, and no triple bonds ("$C_{2-18}$ alkenyl"). An alkenyl group may have 2 to 8 carbon atoms, 2 to 6 carbon atoms, 2 to 5 carbon atoms, 2 to 4 carbon atoms, or 2 to 3 carbon atoms. The one or more carbon-carbon double bonds can be internal (such as in 2-butenyl) or terminal (such as in 1-butenyl). Examples of alkenyl groups include ethenyl, 1-propenyl, 2-propenyl, 1-butenyl, 2-butenyl, butadienyl, pentenyl, pentadienyl, hexenyl, heptenyl, octenyl, octatrienyl, and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a monovalent straight-chain or branched hydrocarbon group having from 2 to 18 carbon atoms, one or more carbon-carbon triple bonds ("$C_{2-18}$ alkynyl"). The alkynyl group may have 2 to 8 carbon atoms, 2 to 6 carbon atoms, 2 to 5 carbon atoms, 2 to 4 carbon atoms, or 2 to 3 carbon atoms. The one or more carbon-carbon triple bonds can be internal (such as in 2-butynyl) or terminal (such as in 1-butynyl). Examples of alkynyl groups include ethynyl, 1-propynyl, 2-propynyl, 1-butynyl, 2-butynyl, and the like. Each instance of an alkynyl group may be independently optionally substituted, i.e., unsubstituted (an "unsubstituted alkynyl") or substituted (a "substituted alkynyl") with one or more substituents, e.g., for instance from 1 to 5 substituents, 1 to 3 substituents, or 1 substituent.

As used herein, the term "heteroalkyl" refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. The term "alkenylene," by itself or as part of another substituent, means, unless otherwise stated, a divalent radical derived from an alkene. An alkylene, alkenylene, alkynylene, or heteroalkylene group may be described as, e.g., a $C_{1-6}$-membered alkylene, $C_{1-6}$-membered alkenylene, $C_{1-6}$-membered alkynylene, or $C_{1-6}$-membered heteroalkylene, wherein the term "membered" refers to the non-hydrogen atoms within the moiety. In the case of heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— may represent both —C(O)$_2$R'— and —R'C(O)$_2$—. Each instance of an alkylene, alkenylene, alkynylene, or heteroalkylene group may be independently optionally substituted, i.e., unsubstituted (an "unsubstituted alkylene") or substituted (a "substituted heteroalkylene") with one or more substituents.

As used herein, the terms "substituted alkyl," "substituted alkenyl," "substituted alkynyl," "substituted heteroalkyl," "substituted heteroalkenyl," "substituted heteroalkynyl," "substituted cycloalkyl," "substituted heterocyclyl," "substituted aryl," and "substituted heteroaryl" refer to alkyl, alkenyl, alkynyl, heteroalkyl, heteroalkenyl, heteroalkynyl, cycloalkyl, heterocyclyl, aryl, and heteroaryl moieties, respectively, having substituents replacing one or more hydrogen atoms on one or more carbons or heteroatoms of the moiety. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above.

As used herein, the term "alkoxy" refers to a group of formula —O-alkyl. The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the term "aryl," refers to stable aromatic ring system, that may be monocyclic or polycyclic, of which all the ring atoms are carbon, and which may be substituted or unsubstituted. The aromatic ring system may have, for example, 3-7 ring atoms. Examples include phenyl, benzyl, naphthyl, anthracyl, and the like. Each instance of an aryl group may be independently optionally substituted, i.e., unsubstituted (an "unsubstituted aryl") or substituted (a "substituted aryl") with one or more substituents.

As used herein, the term "heteroaryl" refers to an aryl group that includes one or more ring heteroatoms. For example, a heteroaryl can include a stable 5-, 6-, or 7-membered monocyclic or 7-, 8-, or 9-membered bicyclic aromatic heterocyclic ring which consists of carbon atoms and one or more heteroatoms, independently selected from the group consisting of nitrogen, oxygen and sulfur. The nitrogen atom may be substituted or unsubstituted (e.g., N or $NR_4$ wherein $R_4$ is H or other substituents, as defined). Examples of heteroaryl groups include pyrrole, furan, indole, thiophene, thiazole, isothiazole, imidazole, triazole, tetrazole, pyrazole, oxazole, isoxazole, pyridine, pyrazine, pyridazine, pyrimidine, and the like.

As used herein, the terms "cycloalkylene," "heterocyclylene," "arylene," and "heteroarylene," alone or as part of another substituent, mean a divalent radical derived from a cycloalkyl, heterocyclyl, aryl, and heteroaryl, respectively. Each instance of a cycloalkylene, heterocyclylene, arylene, or heteroarylene may be independently optionally substituted, i.e., unsubstituted (an "unsubstituted arylene") or substituted (a "substituted heteroarylene") with one or more substituents.

As used herein, the term "cycloalkyl", is intended to include non-aromatic cyclic hydrocarbon rings, such as hydrocarbon rings having from three to eight carbon atoms in their ring structure. Cycloalkyl can include cyclobutyl, cyclopropyl, cyclopentyl, cyclohexyl and the like. The cycloalkyl group can be either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

As used herein, the term "heterocyclyl" refers to a monovalent cyclic molecular structure comprising atoms of at least two different elements in the ring or rings (i.e., a radical of a heterocyclic ring). Additional reference is made to: Oxford Dictionary of Biochemistry and Molecular Biology, Oxford University Press, Oxford, 1997 as evidence that heterocyclic ring is a term well-established in field of organic chemistry.

As used herein, the term "dipeptide" refers to a peptide that is composed of two amino-acid residues, that may be denoted herein as -$A_1$-$A_2$-. For example, dipeptides employed in the synthesis of protease-cleavable linker-payload conjugates of the present disclosure may be selected from the group consisting of Val-Cit, Phe-Lys, Trp-Lys, Asp-Lys, Val-Lys, and Val-Ala.

As used herein, the term "functionalized polyethylene glycol" refers to the polyethylene glycol comprising a functional group. For example, a functionalized polyethylene glycol may be polyethylene glycol functionalized with a terminal group selected from the group consisting of azide

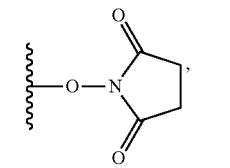 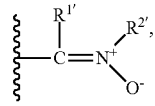

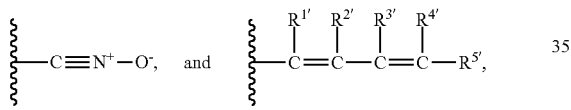

wherein $R^{1'}$, $R^{2'}$, $R^{3'}$, $R^{4'}$ and $R^5$ in each occurrence is independently hydrogen, substituted or unsubstituted $C_{1-6}$ alkyl or substituted or unsubstituted $C_{1-6}$ cycloalkyl. In preferred aspects, $R^{1'}$, $R^{2'}$, $R^{3'}$, $R^{4'}$ and $R^{5'}$ in each occurrence is hydrogen. In preferred aspects, $R^{1'}$, $R^{2'}$, $R^{3'}$, $R^{4'}$ and $R^{5'}$ in each occurrence is methyl.

In some aspects of the present disclosure, the term "functionalized polyethylene glycol" refers to, but is not limited to the following structures.

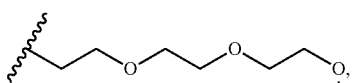

-continued

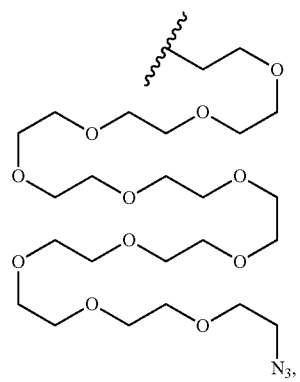

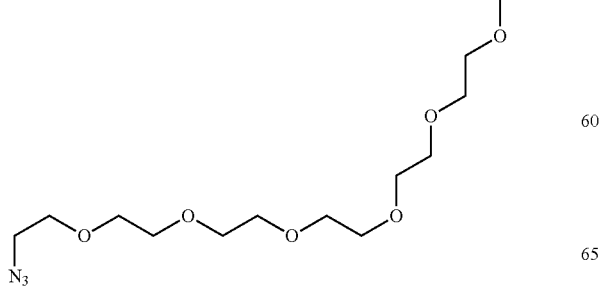

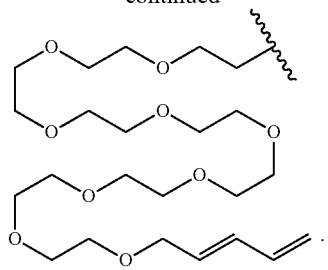

As used herein, $T_1$ may refer to a functionalized polyethylene glycol or a $C_5$-$C_6$ alkyl chain that has a terminal group selected from the group consisting of azide,

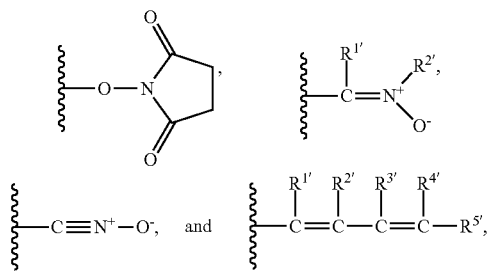

wherein $R^{1'}$, $R^{2'}$, $R^{3'}$, $R^{4'}$ and $R^{5'}$ in each occurrence is independently hydrogen, substituted or unsubstituted $C_{1-6}$ alkyl or substituted or unsubstituted $C_{1-6}$ cycloalkyl. In preferred aspects of $T^1$, $R^{1'}$, $R^{2'}$, $R^{3'}$, $R^{4'}$ and $R^{5'}$ in each occurrence is hydrogen. In preferred aspects of $T^1$, $R^{1'}$, $R^{2'}$, $R^{3'}$, $R^{4'}$ and $R^{5'}$ in each occurrence is methyl. In preferred aspects, $T_1$ is a functionalized polyethylene glycol that has an azide terminal group. In preferred aspects, $T_1$ is a $C_5$-$C_6$ alkyl chain that has an azide terminal group. The repeat unit (—O—$CH_2$—$CH_2$—) of polyethylene glycol (PEG) can range from 5-20 units, preferably 5-15 units and more preferably 6-12.

As used herein, $T_1$ may refer to a $C_5$-$C_6$ alkyl chain that has a terminal group selected from the group consisting of azide,

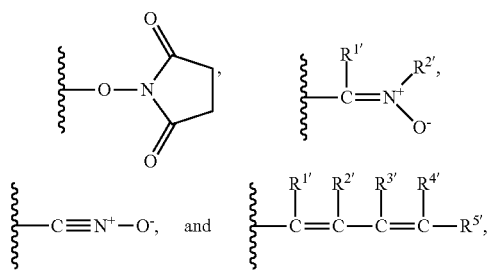

wherein $R^{1'}$, $R^2$, $R^{3'}$, $R^{4'}$ and $R^{5'}$ in each occurrence is independently hydrogen, substituted or unsubstituted $C_{1-6}$ alkyl or substituted or unsubstituted $C_{1-6}$ cycloalkyl. In preferred aspects, $R^{1'}$, $R^{2'}$, $R^{3'}$, $R^{4'}$ and $R^{5'}$ in each occurrence is hydrogen. In preferred aspects, $R^{1'}$, $R^{2'}$, $R^{3'}$, $R^{4'}$ and $R^{5'}$ in each occurrence is methyl.

Monofunctionalized azide-terminated PEG and monofunctionalized azide-terminated $C_5$-$C_6$ alkyl chain can be made from PEG using known procedures and suitable reagents, such as those disclosed in the Schemes provided herein.

As used herein, the term "halo" or "halogen" refers to F, Cl, Br, or I.

An aryl or heteroaryl group described herein can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "hydroxy" refers to a group of formula —OH.

As used herein, the term "hydroxyl" refers to a hydroxyl radical (·OH).

As used herein, the phrase "optionally substituted" means unsubstituted or substituted. In general, the term "substituted" means that at least one hydrogen present on a group (e.g., a carbon or nitrogen atom) is replaced with a permissible substituent, e.g., a substituent which upon substitution results in a stable compound. The term "substituted" can include substitution with all permissible substituents of organic compounds, such as any of the substituents described herein that result in the formation of a stable compound. For purposes of the present disclosure, heteroatoms such as nitrogen may have hydrogen substituents and/or any suitable substituent as described herein which satisfy the valencies of the heteroatoms and results in the formation of a stable moiety.

As used herein, the term "tetrapeptide" refers to a peptide that is composed of four amino-acid residues, that may be denoted herein as -$A_1$-$A_2$-$A_3$-$A_4$-. Tetrapeptides employed in the synthesis of protease-cleavable linker-payload conjugates of the present disclosure is selected from the group consisting of Val-Phe-Gly-Sar (SEQ ID NO: 8), Val-Cit-Gly-Sar, Val-Lys-Gly-Sar (SEQ ID NO: 10), Val-Ala-Gly-Sar (SEQ ID NO: 11), Val-Phe-Gly-Pro (SEQ ID NO: 12), Val-Cit-Gly-Pro, Val-Lys-Gly-Pro (SEQ ID NO: 14), Val-Ala-Gly-Pro (SEQ ID NO: 15), Val-Cit-Gly-any natural or unnatural N-alkyl substituted alpha amino acid, Val-Lys-Gly-any natural or unnatural N-alkyl substituted alpha amino acid, Val-Phe-Gly-any natural or unnatural N-alkyl substituted alpha amino acid, Val-Ala-Gly-any natural or unnatural N-alkyl substituted alpha amino acid, Phe-Lys-Gly-any natural or unnatural N-alkyl substituted alpha amino acid, and Trp-Lys-Gly-any natural or unnatural N-alkyl substituted alpha amino acid.

Furthermore, it will be appreciated by one of ordinary skill in the art that the synthetic methods, as described herein, utilize a variety of protecting groups. As used herein, the term "protecting group" refers to a particular functional moiety, e.g., O, S, or N, that is temporarily blocked so that a reaction can be carried out selectively at another reactive site in a multifunctional compound. Protecting groups may be introduced and removed at appropriate stages during the synthesis of a compound using methods that are known to one of ordinary skill in the art. The protecting groups are applied according to standard methods of organic synthesis as described in the literature (Theodora W. Greene and Peter G. M. Wuts (2007) *Protecting Groups in Organic Synthesis*, 4th edition, John Wiley and Sons, incorporated by reference with respect to protecting groups).

Exemplary protecting groups include, but are not limited to, oxygen, sulfur, nitrogen and carbon protecting groups. For example, oxygen protecting groups include, but are not limited to, methyl ethers, substituted methyl ethers (e.g., MOM (methoxymethyl ether), MTM (methylthiomethyl ether), BOM (benzyloxymethyl ether), PMBM (pimethoxybenzyloxymethyl ether), optionally substituted ethyl ethers, optionally substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), esters (e.g., formate, acetate, benzoate (Bz), trifluoroacetate, dichloroacetate) carbonates, cyclic acetals and ketals. In addition, nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives, etc. Amino protecting groups include, but are not limited to fluorenylmethyloxycarbonyl (Fmoc), tert-butyloxycarbonyl (Boc), carboxybenzyl (Cbz), acetamide, trifluoroacetamide, etc. Certain other exemplary protecting groups are detailed herein, however, it will be appreciated that the present disclosure is not intended to be limited to these protecting groups; rather, a variety of additional equivalent protecting groups may be utilized according to methods known to one skilled in the art.

Throughout this disclosure, a nanoparticle-drug-conjugate (NDC) may sometimes be referred to as a CDC (C'Dot-drug-conjugate), e.g., a FA-CDC.

The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

In order that the invention described herein may be more fully understood, the following examples are set forth. These examples are offered to illustrate the nanoparticle drug conjugates, methods of use, and methods of making, and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of suitable protecting group for a particular functional group as well as suitable conditions for protection and deprotection are well known in the art. For example, numerous protecting groups, and their introduction and removal, are described in Greene et al. *Protecting Groups in Organic Synthesis*, Second Edition, Wiley, New York, 1991, and references cited therein.

General Methods

Methods useful for making the compounds discussed herein are set forth in the following Examples and are generalized here. One of skill in the art will recognize that these Examples can be adapted to prepare the linker-payload conjugates, linkers and payloads and their pharmaceutically accepted salts thereof according to the present disclosure. In the reactions described, reactive functional groups, such as hydroxy, amino, imino, thio or carboxy groups, may be protected wherever desired, e.g., to avoid unwanted reactions. Conventional protecting groups may also be used in accordance with standard practice and techniques of synthesis. The materials needed to synthesize the novel linkers bearing payloads such as exatecan were obtained commercially, and their corresponding analogs are prepared as disclosed in the following examples.

Reagents were purchased from commercial suppliers (Combi-Blocks/SIGMA-ALDRICH) and used without further purification. All non-aqueous reactions were run in flame-dried glassware under a positive pressure of argon. Anhydrous solvents were purchased from commercial suppliers (RANKEM). All the amino acids such as Cit, Val, Phe, Lys, Trp, Asp are naturally occurring amino acids with S-configuration. In several examples, tetrapeptide and unnatural amino acids can also be used. Flash chromatography was performed on 230-400 mesh silica gel with the indicated solvent systems. Proton Nuclear magnetic resonance spectra were recorded on Bruker Spectrometer at 400 MHZ using DMSO as solvent. Peak positions are given in parts per million downfield from tetramethylsilane as the internal standard. J values are expressed in hertz. Mass analyses were performed on (Agilent/Shimadzu) spectrometer using electrospray (ES) technique. HPLC analyses were performed on (Agilent/Waters), PDA-UV detector equipped with a Gemini C-18 (1000×4.6 mm; 5 u) and all compounds tested were determined to be >95% pure using this method. As can be seen in many protease-cleavable linker-payload conjugates, two peaks were isolated at the end of the reaction. The Peak-A (or Peak-1) is the desired compound with the stereochemistry as shown.

Compounds prepared according to the procedures described herein may be isolated by preparative HPLC methods. Representative HPLC conditions and methods are provided below:

Agilent UPLC-MS; Column: Column-YMC Triart C18 (2.1×33 mm, 3 u)

Gradient Conditions: Flow rate: 1.0 ml/min; column temperature: 50° C.; Solvent A: 0.01% HCOOH in water and Solvent B: 0.01% HCOOH in $CH_3CN$; Mobile phase: 95% [0.01% HCOOH in water] and 5% [0.01% HCOOH in $CH_3CN$] held for 0.50 min, then to 1% [0.01% HCOOH in water] and 99% [0.01% HCOOH in $CH_3CN$] in 3.00 min, held this conditions up to 4.00 min and finally back to initial condition in 4.10 min and held for 4.50 min (Table 1).

TABLE 1

| HPLC Gradient Conditions. | | | |
|---|---|---|---|
| TIME | MODULE | % A | % B |
| 0.00 | Pumps | 95 | 5 |
| 0.50 | Pumps | 95 | 5 |
| 3.00 | Pumps | 1 | 99 |
| 4.00 | Pumps | 1 | 99 |
| 4.10 | Pumps | 95 | 5 |
| 4.50 | Pumps | 95 | 5 |

Example 1: Synthesis of Exatecan-Linker Conjugate Precursors

Exatecan-linker conjugate precursors suitable for preparing an NDC of the present disclosure can be synthesized according to the following protocols. As the exatecan-linker conjugate precursors comprise a terminal azide group, they are suitable for attaching to a nanoparticle functionalized with alkyne moieties (e.g., DBCO), using click chemistry.

Synthesis of (S)-2-amino-N-(4-(((tert-butyldiphenylsilyl)oxy)methyl)phenyl)-6-((diphenyl(p tolyl)methyl)amino)hexanamide (161)

Scheme 2: Synthesis of compound (161).

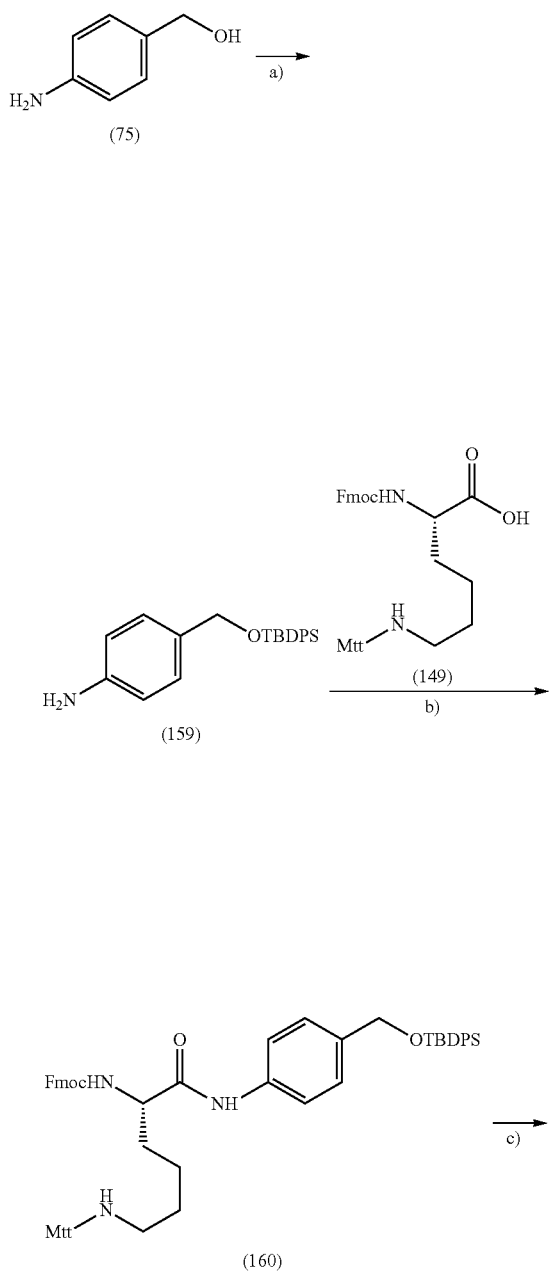

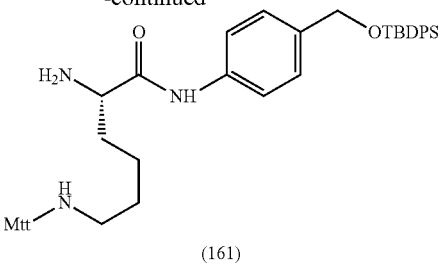

a) TBDPSCl, imidazole, DMF, 0° C. to rt, 16 h;
b) (149), HATU, DIPEA, DMF, rt, 16 h;
c) 30% Piperidine, DMF, rt, 3 h Synthesis of 4-(((tert-butyldiphenylsilyl)oxy)methyl)aniline (159): Imidazole (5.54 g, 81.22 mmol) was added to a solution of (4-aminophenyl)methanol (75) (5.0 g, 40.61 mmol) in DMF (25 mL) at 0° C., followed by tert-butyl (chloro)diphenylsilane (13.39 g, 48.73 mmol), and the reaction mixture was stirred at room temperature for 16 h. The progress of the reaction was monitored by TLC. After completion of starting material, the reaction mixture was quenched with water (20 mL) and extracted with EtOAc (2×200 mL). The combined organic layers were dried over anhydrous $Na_2SO_4$, concentrated under reduced pressure, and purified by column chromatography using silica gel (230-400 mesh) eluting with 10% EtOAc in petroleum ether to afford 4-(((tert-butyldiphenylsilyl)oxy)methyl)aniline (159; 6.6 g) as a gum. LCMS: m/z 362.31 [(M+H)$^+$]; $R_t$: 2.58 min; 93.68% purity.

Synthesis of (9H-fluoren-9-yl)methyl(S)-(1-((4-(((tert-butyldiphenylsilyl)oxy)methyl)phenyl)amino)-6-((diphenyl(p-tolyl)methyl)amino)-1-oxohexan-2-yl)carbamate (160): Diisopropylethylamine (4.18 mL, 24 mmol), HATU (6.08 g, 16 mmol) and 4-(((tert-butyldiphenylsilyl)oxy)methyl)aniline (159) (2.89 g, 8 mmol) were added to a solution of N2-(((9H-fluoren-9-yl)methoxy)carbonyl)-N6-(diphenyl(p-tolyl)methyl)-L-lysine (149) (5.0 g, 8 mmol) in DMF (50 mL) at 0° C., and the reaction mixture was stirred at room temperature for 16 h. The progress of the reaction was monitored by TLC. After completion of starting material, the reaction mixture was quenched with ice water. The precipitated solid was filtered and dried under vacuum to afford (9H-fluoren-9-yl)methyl (S)-(1-((4-(((tert-butyldiphenylsilyl)oxy)methyl)phenyl)amino)-6-((diphenyl(p-tolyl)methyl)amino)-1-oxohexan-2-yl)carbamate (160; 5.5 g) as a solid. LCMS: m/z 990.37 [(M+H)$^+$]; $R_t$: 2.84 min; 96.79% purity.

Synthesis of (S)-2-amino-N-(4-(((tert-butyldiphenylsilyl)oxy)methyl)phenyl)-6-((diphenyl(p tolyl)methyl)amino)hexanamide (161): Piperidine (16.5 mL) was added to a solution of (9H-fluoren-9-yl)methyl (S)-(1-((4-(((tert-butyldiphenylsilyl)oxy)methyl)phenyl)amino)-6-((diphenyl(p-tolyl)methyl)amino)-1-oxohexan-2-yl)carbamate (160) (5.5 g, 5.68 mmol) in DMF (38.5 mL) at room temperature, and the reaction mixture was stirred at room temperature for 3 h. The progress of the reaction was monitored by TLC. After completion of starting material, the reaction mixture was concentrated under reduced pressure, and purified by column chromatography using silica gel (230-400 mesh) eluting with 100% EtOAc to afford (S)-2-amino-N-(4-(((tert-butyldiphenylsilyl)oxy)methyl)phenyl)-6-((diphenyl(p-tolyl)methyl)amino)hexanamide (160; 3.5 g) as a gum. LCMS: m/z 744.24 [(M−H)$^−$]; $R_t$: 2.20 min; 90.16% purity.

Synthesis of 4-((32S,35S)-1-azido-35-(4-((diphenyl(p-tolyl)methyl)amino)butyl)-32-isopropyl-30,33-dioxo-3,6,9,12,15,18,21,24,27-nonaoxa-31,34-diaza-hexatriacontan-36-amido)benzyl (4-nitrophenyl) carbonate (191)
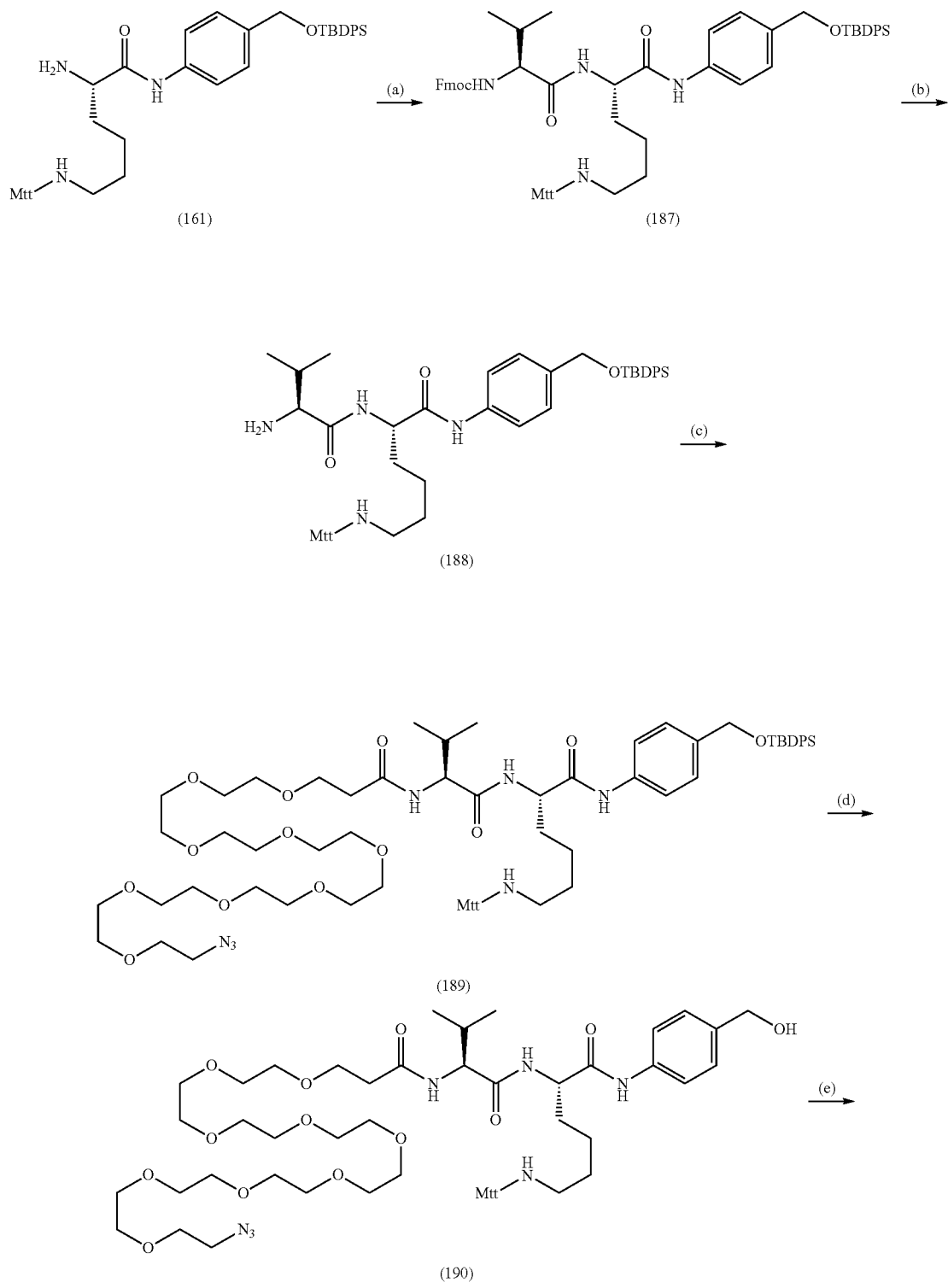
Scheme 3: Synthesis of compound (191).

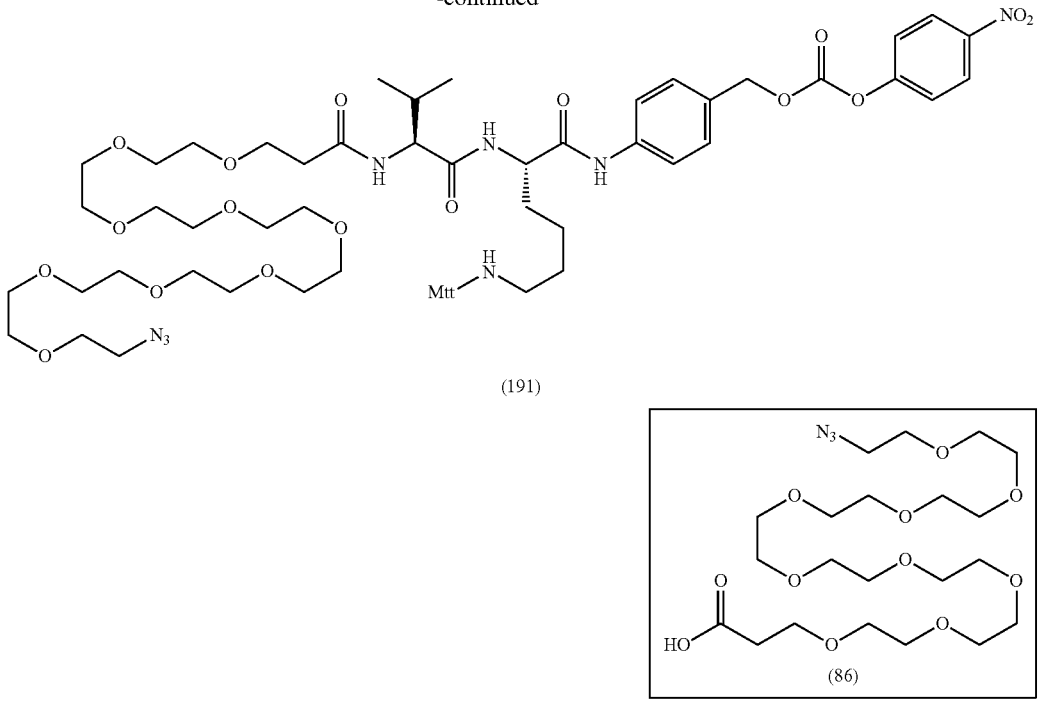

(191)

(86)

(a) Fmoc-Val-OH, HATU, DIPEA, DMF, RT;
(b) Piperidine, DMF, 0° C. to RT;
(c) Azido-PEG9-Acid (86), HATU, DIPEA, DMF, RT;
(d) NH$_4$F, MeOH, RT;
(e) p-Nitrophenyl chloroformate, pyridine, DCM, 0° C. to RT Synthesis of (9H-Fluoren-9-yl)methyl((S)-1-(((S)-1-((4-(((tert-butyldiphenylsilyl)oxy)methyl)phenyl)amino)-6-((diphenyl(p-tolyl)methyl)amino)-1-oxohexan-2-yl)amino)-3-methyl-1-oxobutan-2-yl)carbamate (187): Diisopropylethylamine (1.54 mL, 8.83 mmol), HATU (2.24 g, 5.89 mmol) and (S)-2-amino-N-(4-(((tert-butyldiphenylsilyl)oxy)methyl)phenyl)-6-((diphenyl(p-tolyl)methyl)amino)hexanamide (161) (2.19 g, 2.94 mmol) were added to a solution of (((N-(9-Fluorenylmethoxycarbonyl)-L-valine (1 g, 2.94 mmol), in DMF (20 mL) at 0° C., and the reaction mixture was stirred at room temperature for 3 h. The progress of the reaction was monitored by TLC. After completion of starting material, the reaction mixture was quenched with ice water. The precipitated solid was filtered and dried under vacuum to afford (((9H-fluoren-9-yl)methyl ((S)-1-(((S)-1-((4-(((tert-butyldiphenylsilyl)oxy)methyl) phenyl)amino)-6-((diphenyl(p-tolyl)methyl)amino)-1-oxohexan-2-yl)amino)-3-methyl-1-oxobutan-2-yl)carbamate (187; 2.5 g) as a solid. LCMS: MH$^+$ 1067, retention time 2.42 min.

Synthesis of (S)-2-((S)-2-Amino-3-methylbutanamido)-N-(4-(((tert-butyldiphenylsilyl)oxy)methyl)phenyl)-6-((diphenyl(p-tolyl)methyl)amino)hexanamide (188): A 30% solution of piperidine in DMF (4.5 mL) was added to a solution of (((9H-fluoren-9-yl)methyl ((S)-1-(((S)-1-((4-(((tert-butyldiphenylsilyl)oxy)methyl)phenyl)amino)-6-((diphenyl(p-tolyl)methyl)amino)-1-oxohexan-2-yl)amino)-3-methyl-1-oxobutan-2-yl)carbamate (187) (1.5 g, 1.40 mmol) in DMF (6 mL) at room temperature, and the reaction mixture was stirred at room temperature for 2 h. The progress of the reaction was monitored by TLC. After completion of starting material, the reaction mixture was concentrated under reduced and purified by flash chromatography eluting with 100% EtOAc, to afford (S)-2-((S)-2-amino-3-methylbutanamido)-N-(4-(((tert-butyldiphenylsilyl)oxy)methyl)phenyl)-6-((diphenyl(p-tolyl)methyl)amino) hexanamide (188; 1.1 g) as a solid. $^1$H NMR (400 MHz, DMSO-d$_6$): δ 10.07 (s, 1H), 7.64-7.63 (d, 4H), 7.56-7.54 (d, 2H), 7.46-7.35 (m, 9H), 7.27-7.24 (m, 8H), 7.185-7.11 (m, 2H), 7.05-7.03 (d, 2H), 4.71 (s, 2H), 4.44 (d, 1H), 3.25-3.16 (d, 1H), 3.01-3.00 (m, 1H), 2.21 (s, 3H), 1.98-1.93 (m, 2H), 1.68-1.38 (m, 4H), 1.15 (s, 10H), LCMS: MH$^+$ 845, retention time 3.63 min.

Synthesis of 1-azido-N—((S)-1-(((S)-1-((4-(((tert-butyldiphenylsilyl)oxy)methyl)phenyl)amino)-6-((diphenyl(p-tolyl)methyl)amino)-1-oxohexan-2-yl)amino)-3-methyl-1-oxobutan-2-yl)-3,6,9,12,15,18,21,24,27-nonaoxatriacontan-30-amide (189): Diisopropylethylamine (0.49 mL, 2.83 mmol), HATU (719.47 mg, 1.89 mmol) and (S)-2-((S)-2-amino-3-methylbutanamido)-N-(4-(((tert-butyldiphenylsilyl)oxy)methyl)phenyl)-6-((diphenyl(p-tolyl)methyl)amino) hexanamide (188) (800 mg, 0.94 mmol) were added to a solution of 1-azido-3,6,9,12,15,18,21,24,27-nonaoxatriacontan-30-oic acid (86) (484 mg, 0.94 mmol) in DMF (8 mL) at 0° C., and the reaction mixture was stirred at room temperature for 6 h. The progress of the reaction was monitored by TLC. After completion of starting material, the reaction mixture was quenched with water (15 mL) and extracted with EtOAc (2×30 mL). The combined organic layers were dried over anhydrous Na$_2$SO$_4$, concentrated under reduced, and purified by flash chromatography eluting with 3% MeOH in DCM to provide 1-azido-N—((S)-1-(((S)-1-((4-(((tert-butyldiphenylsilyl)oxy)methyl)phenyl) amino)-6-((diphenyl(p-tolyl)methyl)amino)-1-oxohexan-2-yl)amino)-3-methyl-1-oxobutan-2-yl)-3,6,9,12,15,18,21,24,27-nonaoxatriacontan-30-amide (189; 0.60 g) as a gum. $^1$H NMR (400 MHz, DMSO-d$_6$): δ 9.91 (s, 1H), 8.02-8.00 (d, 2H), 7.95 (s, 2H), 7.87-7.85 (d, 1H), 7.64-7.63 (d, 4H), 7.57-7.55 (d, 2H), 7.46-7.32 (m, 11H), 7.26-7.24 (m, 8H), 7.15-7.11 (t, 2H), 7.05-7.03 (d, 2H), 4.71 (s, 2H), 4.35-4.33 (m, 1H), 4.19 (s, 1H), 3.59-3.36 (m, 38H), 2.68-2.38 (m, 6H), 2.22 (s, 3H), 1.98-1.92 (m, 2H), 1.47-1.17 (m, 4H), 1.02 (s, 9H), 0.85-0.80 (m, 6H). LCMS: MH$^+$ 1338, retention time 2.92 min.

Synthesis of 1-azido-N—((S)-1-(((S)-6-((diphenyl(p-tolyl)methyl)amino)-1-((4-(hydroxymethyl)phenyl)amino)-1-oxohexan-2-yl)amino)-3-methyl-1-oxobutan-2-yl)-3,6,9,12,15,18,21,24,27-nonaoxatriacontan-30-amide (190): NH$_4$F (166 mg, 4.48 mmol) was added to a solution of 1-azido-N—((S)-1-(((S)-1-((4-(((tert-butyldiphenylsilyl)oxy)methyl)phenyl)amino)-6-((diphenyl(p-tolyl)methyl)amino)-1-oxohexan-2-yl)amino)-3-methyl-1-oxobutan-2-yl)-3,6,9,12,15,18,21,24,27-nonaoxatriacontan-30-amide (189) (600 mg, 0.44 mmol) in methanol (10 mL) at room temperature, and the reaction mixture was stirred at room temperature for 6 h. The progress of the reaction was monitored by TLC. After completion of starting material, the reaction mixture was concentrated under reduced pressure, and the residue obtained was diluted with water (15 mL) and extracted with EtOAc (2×20 mL). The combined organic layers were dried over anhydrous Na$_2$SO$_4$, concentrated under reduced pressure, and purified by flash chromatography eluting with 5% MeOH in DCM to afford 1-azido-N—((S)-1-(((S)-6-((diphenyl(p-tolyl)methyl)amino)-1-((4-(hydroxymethyl)phenyl)amino)-1-oxohexan-2-yl)amino)-3-methyl-1-oxobutan-2-yl)-3,6,9,12,15,18,21,24,27-nonaoxatriacontan-30-amide (190; 0.40 g) as a gum. $^1$H NMR (400 MHz, DMSO-d$_6$): δ 9.81 (s, 1H), 7.96-7.94 (d, 1H), 7.84-7.81 (d, 1H), 7.53-7.51 (d, 2H), 7.37-7.35 (d, 4H), 7.26-7.12 (m, 9H), 7.096-7.04 (d, 2H), 5.06-5.04 (t, 1H), 4.43-4.41 (d, 2H), 4.35 (m, 1H), 4.18-4.16 (t, 1H), 3.60-3.46 (m, 33H), 3.39-3.36 (t, 2H), 2.50-2.23 (m, 2H), 2.23 (s, 3H), 2.23-1.93 (m, 2H), 1.48-1.23 (m, 6H), 0.85-0.80 (m, 6H). LCMS: MH$^+$ 1100, retention time 3.72 min.

Synthesis of 4-((32S,35S)-1-azido-35-(4-((diphenyl(p-tolyl)methyl)amino)butyl)-32-isopropyl-30,33-dioxo-3,6,9,12,15,18,21,24,27-nonaoxa-31,34-diazahexatriacontan-36-amido)benzyl (4-nitrophenyl) carbonate (191): Pyridine (0.14 mL, 1.80 mmol) and 4-nitrophenyl chloroformate (14) (145 mg, 0.72 mmol) were added to a solution of 1-azido-N—((S)-1-(((S)-6-((diphenyl(p-tolyl)methyl)amino)-1-((4-(hydroxymethyl)phenyl)amino)-1-oxohexan-2-yl)amino)-3-methyl-1-oxobutan-2-yl)-3,6,9,12,15,18,21,24,27-nonaoxatriacontan-30-amide (190) (400 mg, 0.36 mmol) in DCM (10 mL) at 0° C., and the reaction mixture was stirred at room temperature for 6 h. The progress of the reaction was monitored by TLC. After completion of starting material, the reaction mixture was concentrated under reduced pressure, and purified by flash chromatography eluting with 3% MeOH in DCM to afford 4-((32S,35S)-1-azido-35-(4-((diphenyl(p-tolyl)methyl)amino)butyl)-32-isopropyl-30,33-dioxo-3,6,9,12,15,18,21,24,27-nonaoxa-31,34-diazahexatriacontan-36-amido)benzyl (4-nitrophenyl) carbonate (191; 0.34 g) as a gum. LCMS: MH$^+$ 1265, retention time 1.33 min.

Synthesis of 4-((32S,35S)-35-(4-aminobutyl)-1-azido-32-isopropyl-30,33-dioxo-3,6,9,12,15,18,21,24,27-nonaoxa-31,34-diazahexatriacontan-36-amido)benzyl ((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamate (202).

Scheme 4: Synthesis of protease-cleavable linker-payload conjugate precursor (202).

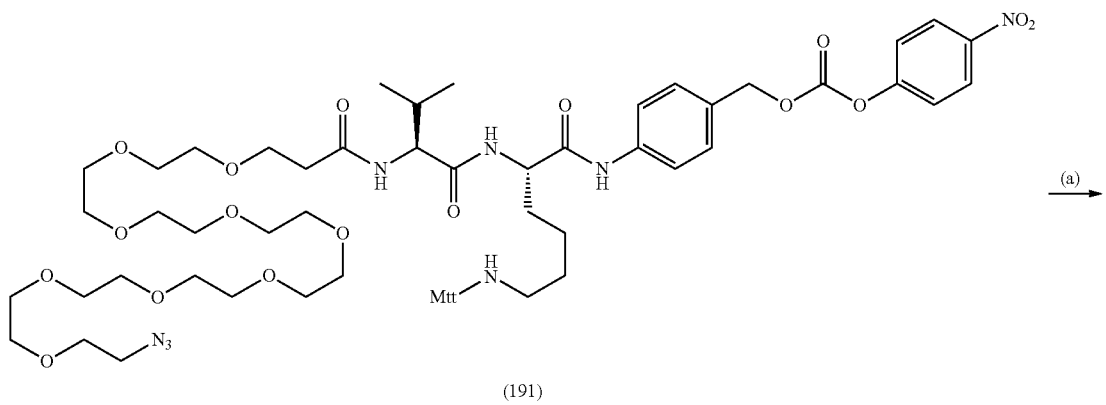

(191)

-continued

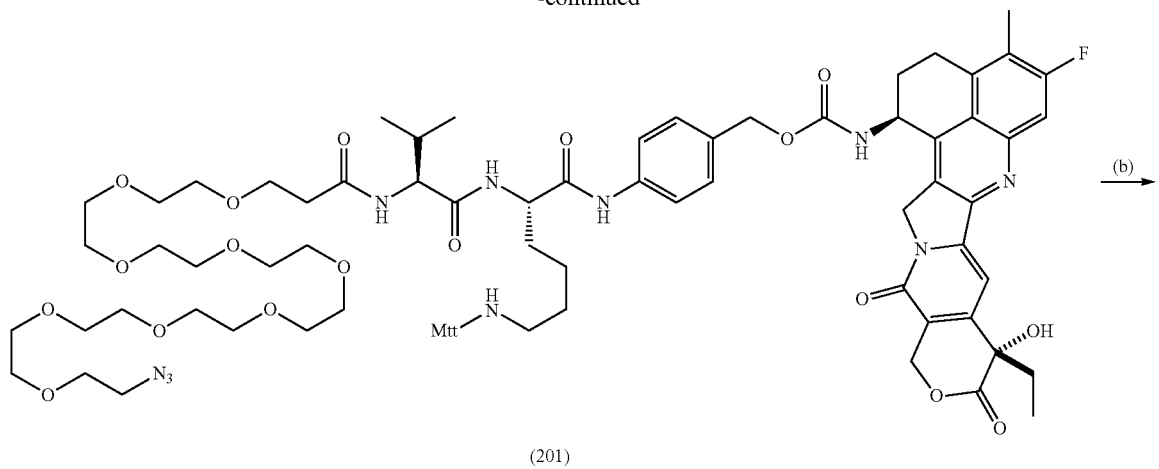

(201)

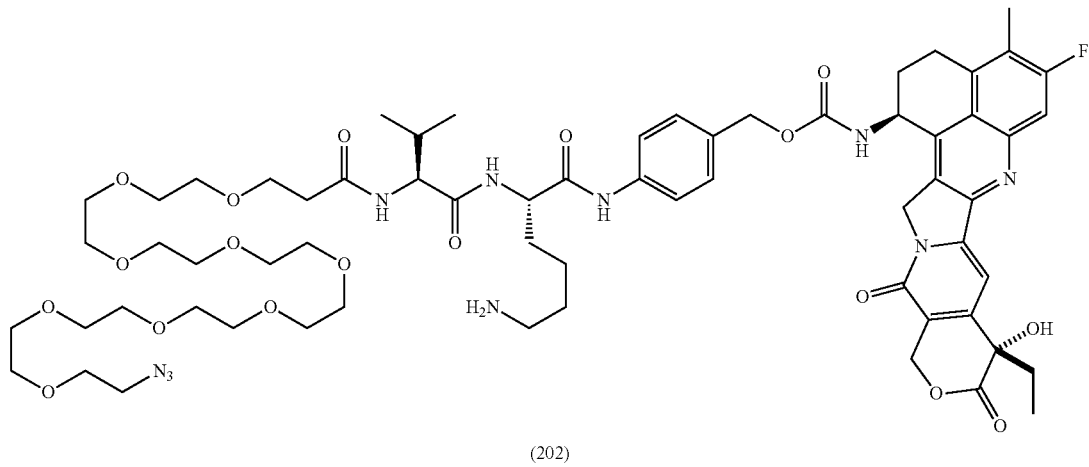

(202)

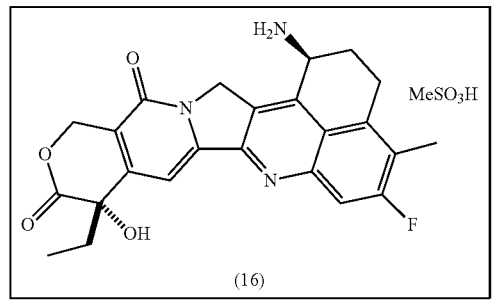

(16)

(a) (16), NMP, Et₃N, RT;
(b) 1% TFA, DCM, 0° C. to RT;

Synthesis of 4-((32S,35S)-1-azido-35-(4-(((diphenyl(p-tolyl)methyl)amino)butyl)-32-isopropyl-30,33-dioxo-3,6,9,12,15,18,21,24,27-nonaoxa-31,34-diazahexatriacontan-36-amido)benzyl ((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl) carbamate (201): Triethylamine (0.09 mL, 0.62 mmol) and (1R,9R)-1-amino-9-ethyl-5-fluoro-9-hydroxy-4-methyl-1,2,3,9,12,15-hexahydro-10H,13H-benzo[de]pyrano[3',4':6,7]indolizino[1,2-b]quinoline-10,13-dione methanesulfonate (exatecan mesylate; 16; 131 mg, 0.25 mmol) were added to a solution 4-((32S,35S)-1-azido-35-(4-(((diphenyl(p-tolyl)methyl)amino)butyl)-32-isopropyl-30,33-dioxo-3,6,9,12,15,18,21,24,27-nonaoxa-31,34-diazahexatriacontan-36-amido)benzyl (4-nitrophenyl) carbonate (191; 311 mg, 0.25 mmol) in NMP (2.5 mL) at 0° C., and the mixture was stirred at room temperature for 8 h. The progress of the reaction was monitored by LCMS. After completion of starting material, the reaction mixture was quenched with water (15 mL) and extracted with 10% methanol in chloroform (2×20 mL). The combined organic layers were dried over anhydrous sodium sulfate (Na₂SO₄) and concentrated under reduced pressure. Diethyl ether was added to the crude material, and the resulting precipitate was filtered and purified using column chromatography (Combi-Flash) eluting with 5% MeOH in DCM to provide 4-((32S,35S)-1-azido-35-(4-(((diphenyl(p-tolyl)methyl)amino)butyl)-32-isopropyl-30,33-dioxo-3,6,9,12,15,18,21,24,27-nonaoxa-31,34-diazahexatriacontan-36-amido)benzyl ((1S,9S)-9-ethyl-5-fluoro-9-hydroxy-4-methyl-10,13-dioxo-2,3,9,10,13,15-hexahydro-1H,12H- benzo[de]pyrano[3',4':6,7]indolizino[1,2-b]quinolin-1-yl) carbamate (201) as a solid (0.3 g). LCMS: MH+ 1561, retention time 2.18 min.

Synthesis of 4-((32S,35S)-35-(4-aminobutyl)-1-azido-32-isopropyl-30,33-dioxo-3,6,9,12,15,18,21,24,27-nonaoxa-31,34-diazahexatriacontan-36-amido)benzyl ((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamate (202): A 1% solution of trifluoroacetic acid (TFA) in DCM was added to a solution of 4-((32S,35S)-1-azido-35-(4-(((diphenyl(p-tolyl)methyl)amino)butyl)-32-isopropyl-30,33-dioxo-3,6,9,12,15,18,21,24,27-nonaoxa-31,34-diazahexatriacontan-36-amido)benzyl ((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl) carbamate (201; 300 mg, 0.19 mmol) in DCM (5 mL) at 0° C., and the reaction mixture was stirred at room temperature for 1 h. The progress of the reaction was monitored by LCMS. After completion of starting material, the reaction mixture was concentrated under reduced pressure, and the residue was triturated with diethyl ether and purified by RP-prep-HPLC to provide 4-((32S,35S)-35-(4-aminobutyl)-1-azido-32-isopropyl-30,33-dioxo-3,6,9,12,15,18,21,24,27-nonaoxa-31,34-diazahexatriacontan-36-amido)benzyl ((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamate (202) (70 mg) as a solid. $^1$H NMR (400 MHz, DMSO-d$_6$): δ 9.96 (s, 1H), 8.12-8.10 (q, 2H), 7.89-7.87 (d, 1H), 7.76-7.61 (d, 1H), 7.59-7.31 (m, 7H), 6.51 (s, 1H), 5.44 (s, 2H), 5.29 (s, 3H), 5.09 (s, 2H), 4.37-4.20 (m, 1H), 4.18-4.16 (t, 1H), 3.49-3.44 (m, 4H), 3.12-2.55 (m, 39H), 2.40-1.34 (m, 15H), 0.89-0.82 (m, 9H), LCMS: MH+ 1305, retention time 5.33 and 5.47 min.

Example 2: Synthesis of Folic Acid Conjugate Precursors

Folic acid conjugate precursors suitable for preparing a folate receptor targeting NDC disclosed herein can be prepared according to one of the following synthetic protocols. As the folic acid conjugate precursors comprise a terminal azide group, they are suitable for attaching to a nanoparticle functionalized with alkyne moieties (e.g., DBCO), using click chemistry.

Synthesis of (S)-16-(4-((((2-amino-4-oxo-3,4-dihydropteridin-6-yl)methyl)amino)benzamido)-1-azido-13-oxo-3,6,9-trioxa-12-azaheptadecan-17-oic acid (606)

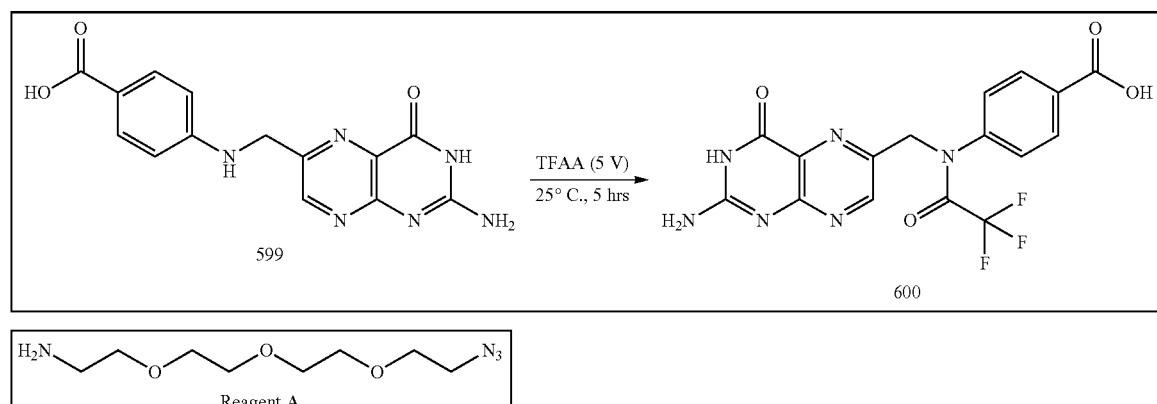

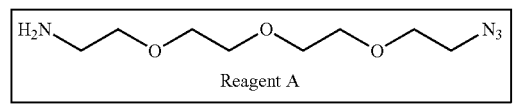

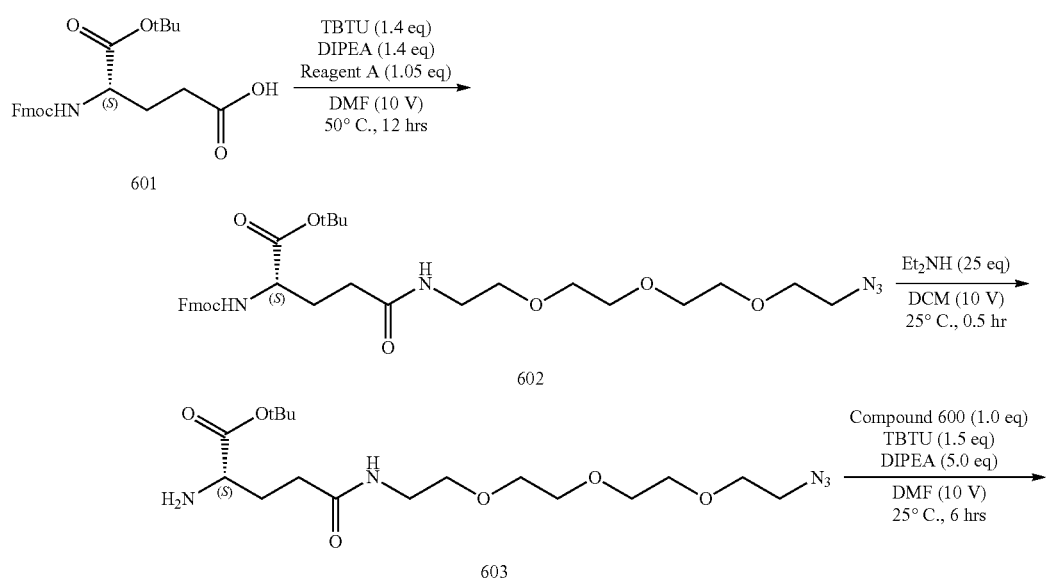

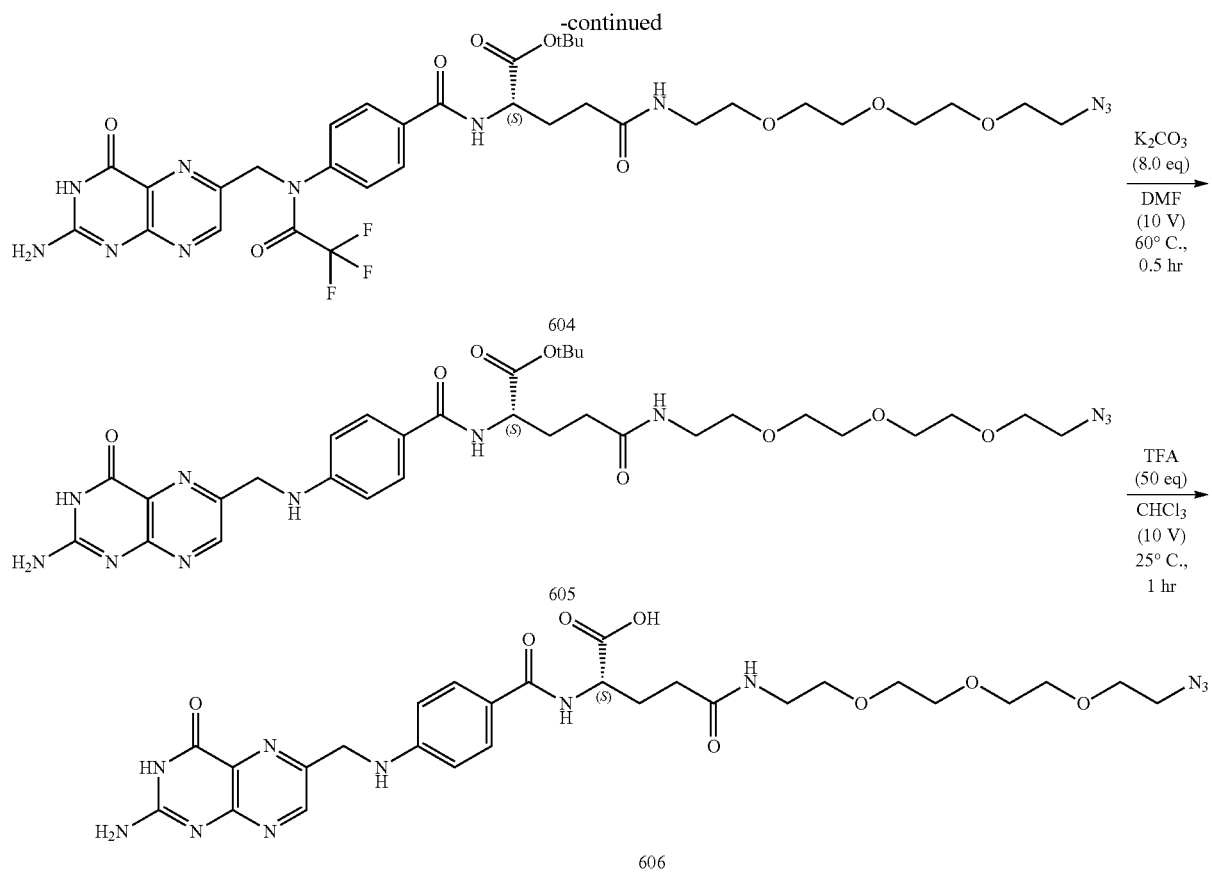

Preparation of compound 600: Compound 599 (160 g, 512 mmol) was dissolved in TFAA (800 mL) at 25° C. and stirred under a nitrogen atmosphere in the dark for 5 hrs. The solvent was then removed at 50° C. in vacuo to give the crude product. The crude product was triturated with MTBE (750 mL) for 60 min and then filtered to afford compound 600 (203 g, crude) as a solid, which was used in next step without further purification. LC-MS: $^1$H NMR: (400 MHz, CDCl$_3$) δ 12.74 (br s, 1H), 8.88 (s, 1H), 7.97-8.05 (m, 2H), 7.66-7.74 (m, 2H), 5.26 (s, 1H).

Preparation of Compound 602: TBTU (238 g, 740 mmol) and DIPEA (95.7 g, 740 mmol) were added to a solution of compound 601 (225 g, 529 mmol) in DMF (2.25 L). After 30 min stirring at 20° C., 2-(2-(2-(2-azidoethoxy)ethoxy)ethoxy)ethan-1-amine (Reagent A; 121 g, 555 mmol) was added and the mixture was stirred at 50° C. for 12 hrs. Two reaction mixtures were combined and worked up, and the residue was diluted with H$_2$O (3 L) and extracted with ethyl acetate (1500 mL×3). The combined organic layers were washed with brine (800 mL×3), dried over Na$_2$SO$_4$, filtered and concentrated under reduced pressure, and purified by column chromatography (SiO$_2$, Petroleum ether/Ethyl acetate=100/1 to 1/1) to afford compound 602 (590 g) as an oil. $^1$H NMR: (400 MHz, CDCl$_3$) (7.76-7.78 (m, 2H), 7.63-7.60 (m, 2H), 7.41-7.27 (m, 4H), 6.43 (s, 1H), 5.70 (s, 1H), 4.42-4.38 (m, 2H), 4.24-4.23 (m, 2H), 3.63-3.36 (m, 16H), 2.28-2.18 (m, 3H), 1.98-1.96 (m, 1H), 1.48 (s, 9H).

Preparation of Compound 603: N-ethylethanamine (1.27 kg, 17.4 mol) was added to a solution of compound 602 (435 g, 695 mmol) in DCM (4.35 L) and the mixture was stirred at 25° C. 3 hrs. The solvent was then removed at room temperature in vacuo, and the residue was purified by flash column chromatography (DCM/MeOH=100/1 to 1/1) to afford compound 603 (245 g) as an oil. $^1$H NMR: (400 MHz, CDCl$_3$) δ 6.55 (s, 1H), 3.67-3.30 (m, 17H), 2.34-2.30 (m, 2H), 2.10-2.06 (m, 1H), 1.87 (s, 2H), 1.77-1.73 (m, 1H), 1.44 (s, 9H).

Preparation of compound 604: TBTU (119 g, 372 mmol) and DIEA (160 g, 1.24 mol) were added to a solution of compound 600 (101 g, 248 mmol) in DMF (900 mL) and the mixture was stirred for 30 minutes. Then compound 603 (100 g, 248 mmol) in DMF (100 mL) was added. The mixture was stirred at 25° C. for 12 hrs. Two reaction mixtures were combined and concentrated and the residue was diluted with H$_2$O (2.5 L) and extracted with ethyl acetate (1 L×5). The combined organic layers were washed with brine (600 mL×3), dried over Na$_2$SO$_4$, filtered and concentrated under reduced pressure to afford compound 4 (420 g, crude) as a solid, which was used in next step without further purification.

Preparation of compound 605: K$_2$CO$_3$ (585 g, 4.23 mol) was added to a solution of compound 604 (420 g, 529 mol) in THF (4.2 mL) and H$_2$O (500 mL) and the mixture was stirred at 60° C. for 0.5 hr. The reaction mixture was concentrated under reduced pressure to remove THF and the residue was diluted with H$_2$O (500 mL) and adjusted the pH to 3 with HCl (M=1), filtered and concentrated under reduced pressure to afford compound 605 (260 g, crude) as a solid, which was used directly without purification.

Preparation of compound 606: Trifluoroacetic acid (2.12 kg, 18.6 mol) was added in one portion to a mixture of compound 605 (260 g, 373 mmol) in CH$_2$Cl$_2$ (2.6 L) at 20°

C. under nitrogen, and the mixture was stirred at 20° C. for 5 hrs. The reaction mixture was concentrated under reduced pressure and purified by HPLC (column: Agela DuraShell C18 250*80 mm*10 um; mobile phase: [water (10 mM NH4HCO3)-MeOH]; B %: 5%-40%, 20 min) to give afford compound 606 (52.5 g, 81.82 mmol, 21.96% yield) as a solid. (M+H) 642.80; IR: 2107 (N₃ Bond).

Synthesis of (S)-38-(4-(((2-amino-4-oxo-3,4-dihydropteridin-6-yl)methyl)amino)benzamido)-1-azido-30,35-dioxo-3,6,9,12,15,18,21,24,27-nonaoxa-31,34-diazanonatriacontan-39-oic acid (472)

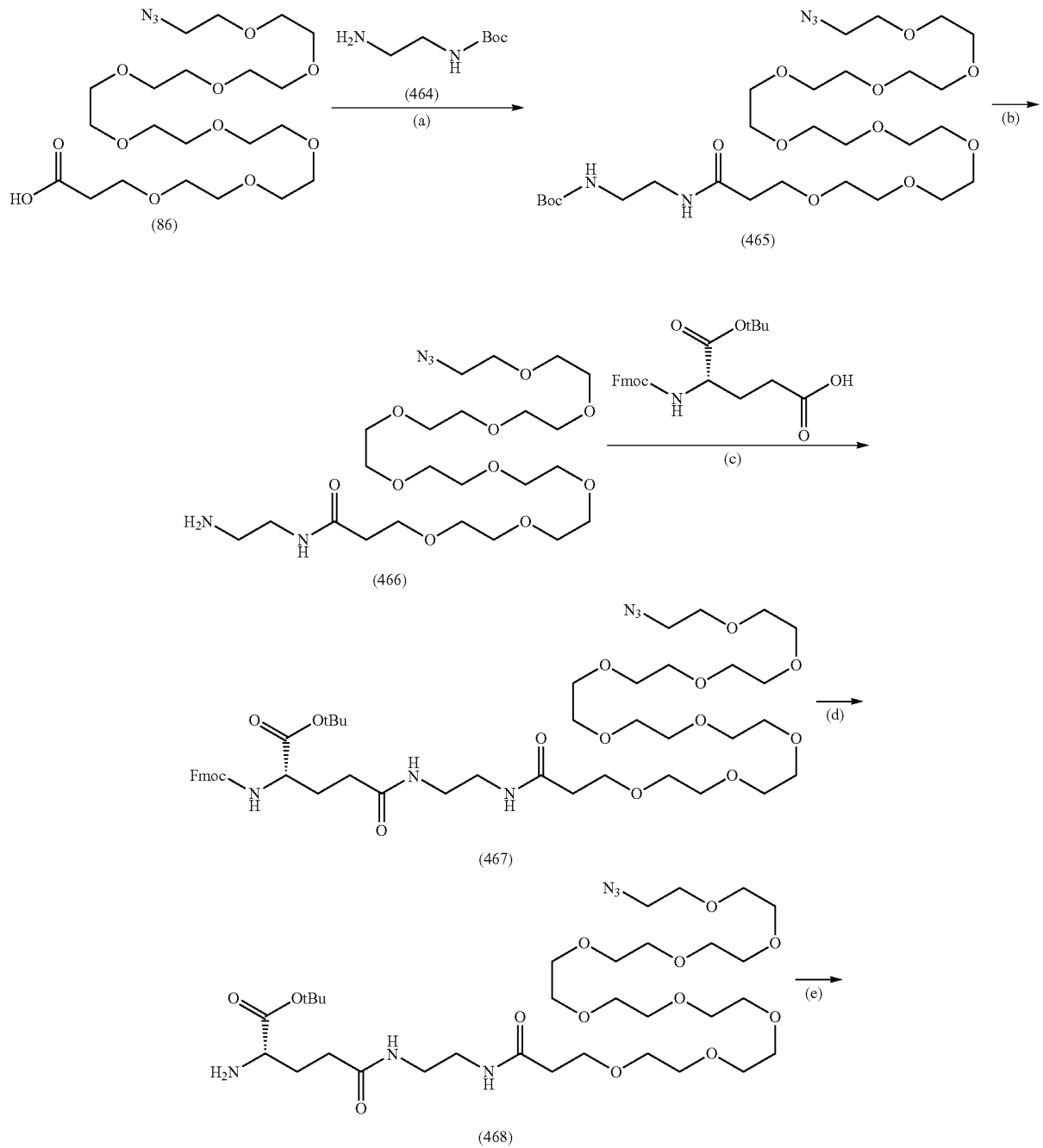

-continued

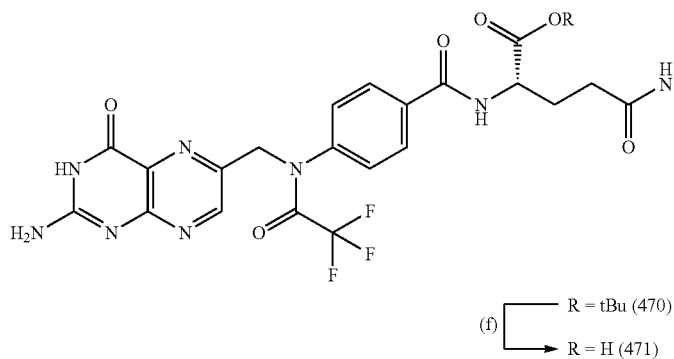

R = tBu (470)
(f)
R = H (471)

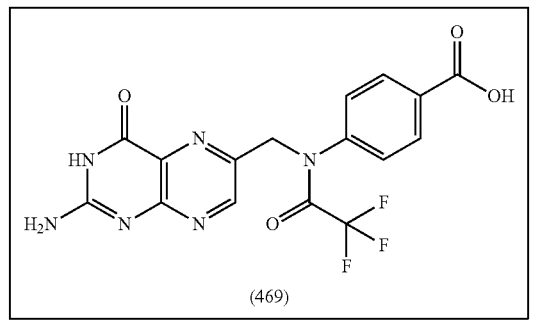

(469)

(g)

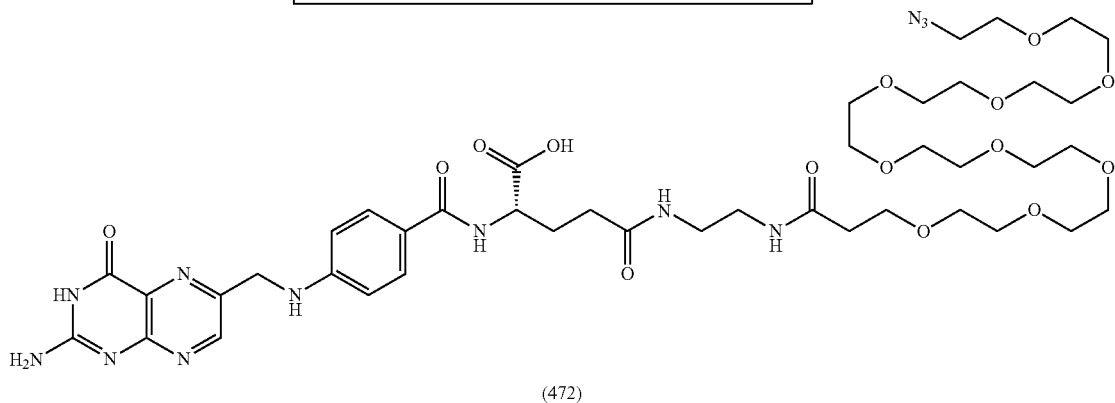

(472)

(a) ECD, HOBT, EA, DCM, RT;
(b) TFA, DCM, RT;
(c) PyBOP, DIPEA, DMF, RT;
(d) Piperidine, DMF, 0° C. to RT;
(e) (469), PyBOP, DIPEA, DMF, RT;
(f) TFA, DCM, RT;
(g) Liq•NH$_3$, DMF, RT;
then RP-prep HPLC.

Synthesis of tert-butyl (1-azido-30-oxo-3,6,9,12,15,18,21,24,27-nonaoxa-31-azatritriacontan-33-yl)carbamate (465): Triethylamine (0.36 mL, 2.64 mmol), EDC (218 mg, 1.14 mmol), HOBT (154 mg, 1.14 mmol) and tert-butyl (2-aminoethyl)carbamate (464) (124 mg, 0.881 mmol) were added to a solution of 1-azido-3,6,9,12,15,18,21,24,27-nonaoxatriacontan-30-oic acid (86; 450 mg, 0.881 mmol), in DCM (20 mL) at 0° C., and the reaction mixture was stirred at room temperature for 16 h. The progress of the reaction was monitored by TLC. After consumption of starting material, the reaction mixture was extracted with DCM and water, and the organic layer was dried over Na$_2$SO$_4$, and evaporated under vacuum. The residue was purified by flash chromatography and dried under vacuum to provide tert-butyl (1-azido-30-oxo-3,6,9,12,15,18,21,24,27-nonaoxa-31-azatritriacontan-33-yl)carbamate (465; 0.45 g) as a liquid. $^1$H NMR (400 MHz, DMSO-d$_6$): 7.83 (t, 1H), 6.75 (t, 1H), 3.61-3.31 (m, 38H), 3.02-2.97 (t, 4H), 2.28 (t, 2H), 1.37 (s, 9H).

Synthesis of N-(2-Aminoethyl)-1-azido-3,6,9,12,15,18,21,24,27-nonaoxatriacontan-30-amide (466): A solution of tert-butyl (1-azido-30-oxo-3,6,9,12,15,18,21,24,27-nonaoxa-31-azatritriacontan-33-yl)carbamate (465) (350 mg, 0.462 mmol) in DCM was cooled to 0° C. and TFA was added to it by dropwise, and the reaction mixture was then stirred at RT for 16 h. The progress of the reaction was monitored by TLC. After consumption of starting material, the reaction mixture was concentrated under reduced pressure and azeotroped with DCM (3 times) to provide crude (466), which was purified by flash chromatography eluting with 5% MeOH in DCM to provide N-(2-aminoethyl)-1-azido-3,6,9,12,15,18,21,24,27-nonaoxatriacontan-30-amide (466; 0.25 g) as a liquid. $^1$H NMR (400 MHz, DMSO-d$_6$): 8.02 (t, 1H), 7.73 (t, 2H), 3.71-3.26 (m, 40H), 2.86 (t, 2H), 2.35 (t, 2H).

Synthesis of tert-butyl (S)-38-((((9H-fluoren-9-yl)methoxy)carbonyl)amino)-1-azido-30,35-dioxo-3,6,9,12,15,18,21,24,27-nonaoxa-31,34-diazanonatriacontan-39-oate (467): Diisopropylethylamine (0.174 mL, 1.0 mmol), PyBOP (416 mg, 0.8 mmol) and N-(2-aminoethyl)-1-azido-3,6,9,12,15,18,21,24,27-nonaoxatriacontan-30-amide (466) (331 mg, 0.6 mmol) were added to a solution of (S)-4-((((9H-fluoren-9-yl)methoxy)carbonyl)amino)-5-(tert-butoxy)-5-oxopentanoic acid (170 mg, 0.4 mmol), in DMF (5 mL) at 0° C., and the reaction mixture was stirred at rt for 16 h. The progress of the reaction was monitored by TLC. After consumption of starting material, the reaction mixture was evaporated under vacuum at low temperature, and purified by flash chromatography eluting with 5% MeOH in DCM to afford tert-butyl (S)-38-((((9H-fluoren-9-yl)methoxy)carbonyl)amino)-1-azido-30,35-dioxo-3,6,9,12,15,18,21,24,27-nonaoxa-31,34-diazanonatriacontan-39-oate (467; 0.35 g) as a liquid. MH$^+$ 962, retention time 1.81 min.

Synthesis of tert-butyl (S)-38-amino-1-azido-30,35-dioxo-3,6,9,12,15,18,21,24,27-nonaoxa-31,34-diazanonatriacontan-39-oate (468): A 30% solution of piperidine in DMF (1 ml) was added to a solution of tert-butyl (S)-38-((((9H-fluoren-9-yl)methoxy)carbonyl)amino)-1-azido-30,35-dioxo-3,6,9,12,15,18,21,24,27-nonaoxa-31,34-diazanonatriacontan-39-oate (467; 350 mg, 3.65 mmol) in DMF (5 mL) at room temperature, and the reaction mixture was stirred at room temperature for 3 h. The progress of the reaction was monitored by TLC. After completion of starting material, the reaction mixture was concentrated under reduced pressure to afford tert-butyl (S)-38-amino-1-azido-30,35-dioxo-3,6,9,12,15,18,21,24,27-nonaoxa-31,34-diazanonatriacontan-39-oate (468; 250 mg), which was used in the next step without further purification. MH$^+$ 739, retention time 1.50 min.

Synthesis of tert-butyl (S)-38-(4-(N-((2-amino-4-oxo-3,4-dihydropteridin-6-yl)methyl)-2,2,2-trifluoroacetamido)benzamido)-1-azido-30,35-dioxo-3,6,9,12,15,18,21,24,27-nonaoxa-31,34-diazanonatriacontan-39-oate (470): Diisopropylethylamine (0.107 mL, 0.613 mmol), PyBOP (254 mg, 0.49 mmol) and tert-butyl (S)-38-amino-1-azido-30,35-dioxo-3,6,9,12,15,18,21,24,27-nonaoxa-31,34-diazanonatriacontan-39-oate (468) (271 mg, 0.368 mmol) were added to a solution of 4-(N-((2-amino-4-oxo-3,4-dihydropteridin-6-yl)methyl)-2,2,2-trifluoroacetamido)benzoic acid (469;100 mg, 0.245 mmol) in DMF (5 mL) at 0° C., and the reaction mixture was stirred at room temperature for 16 h. The progress of the reaction was monitored by TLC. After completion of starting material, the reaction mixture was concentrated under vacuum at low temperature, then purified by flash chromatography eluting with 10% MeOH in DCM to afford tert-butyl (S)-38-(4-(N-((2-amino-4-oxo-3,4-dihydropteridin-6-yl)methyl)-2,2,2-trifluoroacetamido)benzamido)-1-azido-30,35-dioxo-3,6,9,12,15,18,21,24,27-nonaoxa-31,34-diazanonatriacontan-39-oate (470; 180 mg) as a solid. MH$^+$ 1129, retention time 2.61 min.

Synthesis of (S)-38-(4-(N-((2-Amino-4-oxo-3,4-dihydropteridin-6-yl)methyl)-2,2,2-trifluoroacetamido)benzamido)-1-azido-30,35-dioxo-3,6,9,12,15,18,21,24,27-nonaoxa-31,34-diazanonatriacontan-39-oic acid (471): Trifluoroacetic acid (0.123 mL, 1.59 mmol) was added to a solution of tert-butyl (S)-38-(4-(N-((2-amino-4-oxo-3,4-dihydropteridin-6-yl)methyl)-2,2,2-trifluoroacetamido)benzamido)-1-azido-30,35-dioxo-3,6,9,12,15,18,21,24,27-nonaoxa-31,34-diazanonatriacontan-39-oate (470) (180 mg, 0.16 mmol) in DCM was added at room temperature, and the reaction mixture was stirred at room temperature for 16 h. The progress of the reaction was monitored by TLC. After completion of starting material, the reaction mixture was concentrated under reduced pressure and azeotroped with DCM (3 times) to afford crude product (471; 100 mg), that was used in the next step without further purification. MH$^+$ 1073, retention time 2.34 min.

Synthesis of (S)-38-(4-(((2-Amino-4-oxo-3,4-dihydropteridin-6-yl)methyl)amino)benzamido)-1-azido-30,35-dioxo-3,6,9,12,15,18,21,24,27-nonaoxa-31,34-diazanonatriacontan-39-oic acid (472): Aqueous NH$_3$ (dissolved in DMF) (0.01 mL, 0.71 mmol) was added to a solution of (S)-38-(4-(N-((2-amino-4-oxo-3,4-dihydropteridin-6-yl)methyl)-2,2,2-trifluoroacetamido)benzamido)-1-azido-30,35-dioxo-3,6,9,12,15,18,21,24,27-nonaoxa-31,34-diazanonatriacontan-39-oic acid (471; 80 mg, 0.071 mmol) in DMF (3 mL) at 0° C., and the reaction mixture was stirred at room temperature for 6 h. After completion of starting material, the reaction mixture was concentrated under reduced pressure, and the residue was purified by RP-prep-HPLC to afford (S)-38-(4-(((2-Amino-4-oxo-3,4-dihydropteridin-6-yl)methyl)amino)benzamido)-1-azido-30,35-dioxo-3,6,9,12,15,18,21,24,27-nonaoxa-31,34-diazanonatriacontan-39-oic acid (472; 15 mg) as a solid. $^1$H NMR (400 MHz, DMSO-d$_6$): 8.62 (S, 1H), 8.01 (d, 1H), 7.98 (t, 11 H), 7.64 (d, 2H), 6.64 (d, 2H), 4.47 (d, 2H), 4.21 (t, 1H), 3.68-3.35 (r, 38H), 3.07 (t, 4H), 2.32-2.11 (t, 6H), 1.86 (t, 1H). LCMS: MH$^+$ 977, retention time 1.96 min.

LCMS Method: Column—YMC TRIART C18 (33×2.1 mm, 3 u); (mobile phase: 95% [0.1% HCOOH in water] and 5% [0.1% HCOOH in CH3CN] held for 0.50 min then to 1% [0.1% HCOOH in water] and 99% [0.1% HCOOH in CH3CN] in 3.0 min, held this composition up to 4.00 min and finally back to initial condition in 4.10 min, held for 4.50 min). Flow rate—1.0 ml/min.

Example 3: Synthesis of Nanoparticle Drug Conjugates (NDCs)

Preparation of Nanoparticles

Aqueous synthesis methodology can be used for the preparation and functionalization of ultrasmall nanoparticles of the present disclosure. For example, methodology based on the procedures outlined in WO 2016/179260 A1 and WO 2018/213851 A1 (the contents of which are incorporated herein by reference in their entireties) may be used.

For example, a fluorescent compound such as, but not limited to Cy5, can be functionalized with a maleimide group, to provide a maleimide-functionalized fluorescent compound that has a net positive charge. This can be conjugated with a thiol-silane, such as (3-mercaptopropyl) trimethoxysilane (MPTMS) to produce a silane-functionalized fluorescent compound such as Cy5-silane. The conjugation may be performed in dimethyl sulfoxide (DMSO) in a glovebox under inert atmosphere overnight (16-24 hours) and at room temperature (18-25° C.).

On the following day, the next step of the synthesis can be performed in a suitable chamber, such as a glass flask, container, or reactor, and can involve stirring deionized water with a pH of around 8.5-10.5 which can be achieved using an aqueous solution of ammonium hydroxide of pH 7.5-8.5. A silica precursor, such as a tetraalkyl orthosilicate, e.g., tetramethyl orthosilicate (TMOS), can then be added into the reaction chamber under vigorous stirring at room temperature, followed by immediately adding the silane-functionalized fluorescent compound, e.g., Cy5-silane. The reaction can be left stirring at room temperature overnight (1-48 hours), to provide silica cores encapsulating the fluorescent compound, e.g., Cy5 dye.

The following day, a PEG-silane can be added into the reaction under stirring at room temperature to coat the silica core with PEG molecules, and the reaction can be left stirring for 1-48 hours. This step may be followed by heating between 75-85° C. for 1-48 hours. The reaction can then be cooled down to room temperature and purified (e.g., including sterile filtration to remove aggregates formed as side-product of the reaction, and bacteria if any present). Further functionalization of the nanoparticle may then be performed.

Functionalization of Nanoparticles

Figure 2:
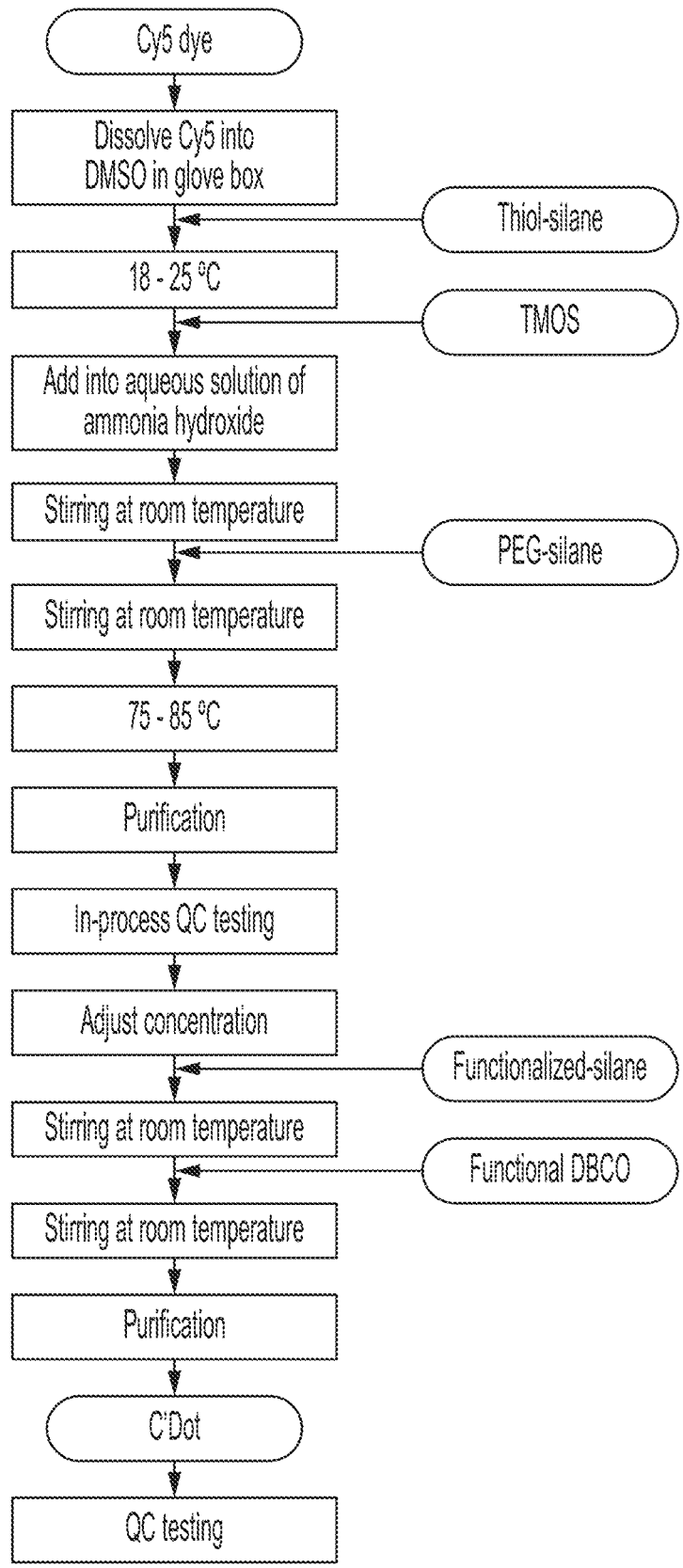
FIG. 2 depicts a flow chart for the synthesis of an exemplary functionalized nanoparticle (dibenzocyclooctyne (DBCO)-functionalized C'Dot).
Figure 3:
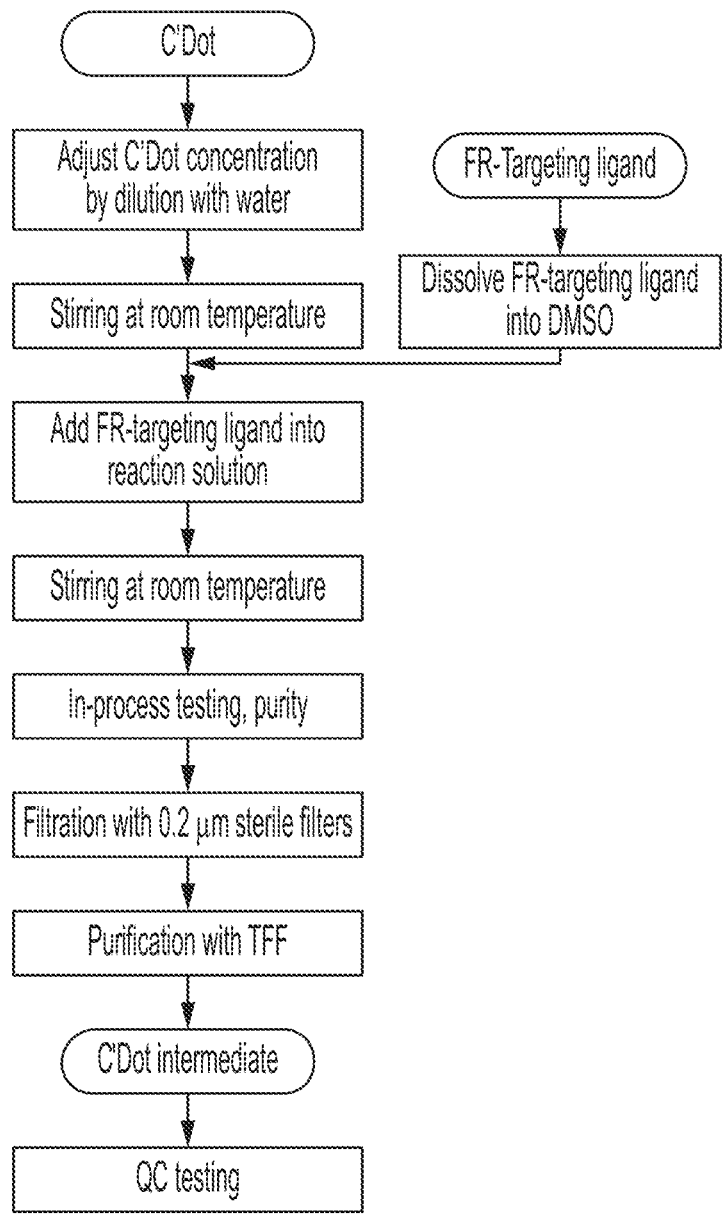
FIG. 3 depicts a flow chart for the synthesis of an exemplary NDC (FA-CDC) comprising a C'Dot functionalized with folic acid (FA) and exatecan.
Figure 3:
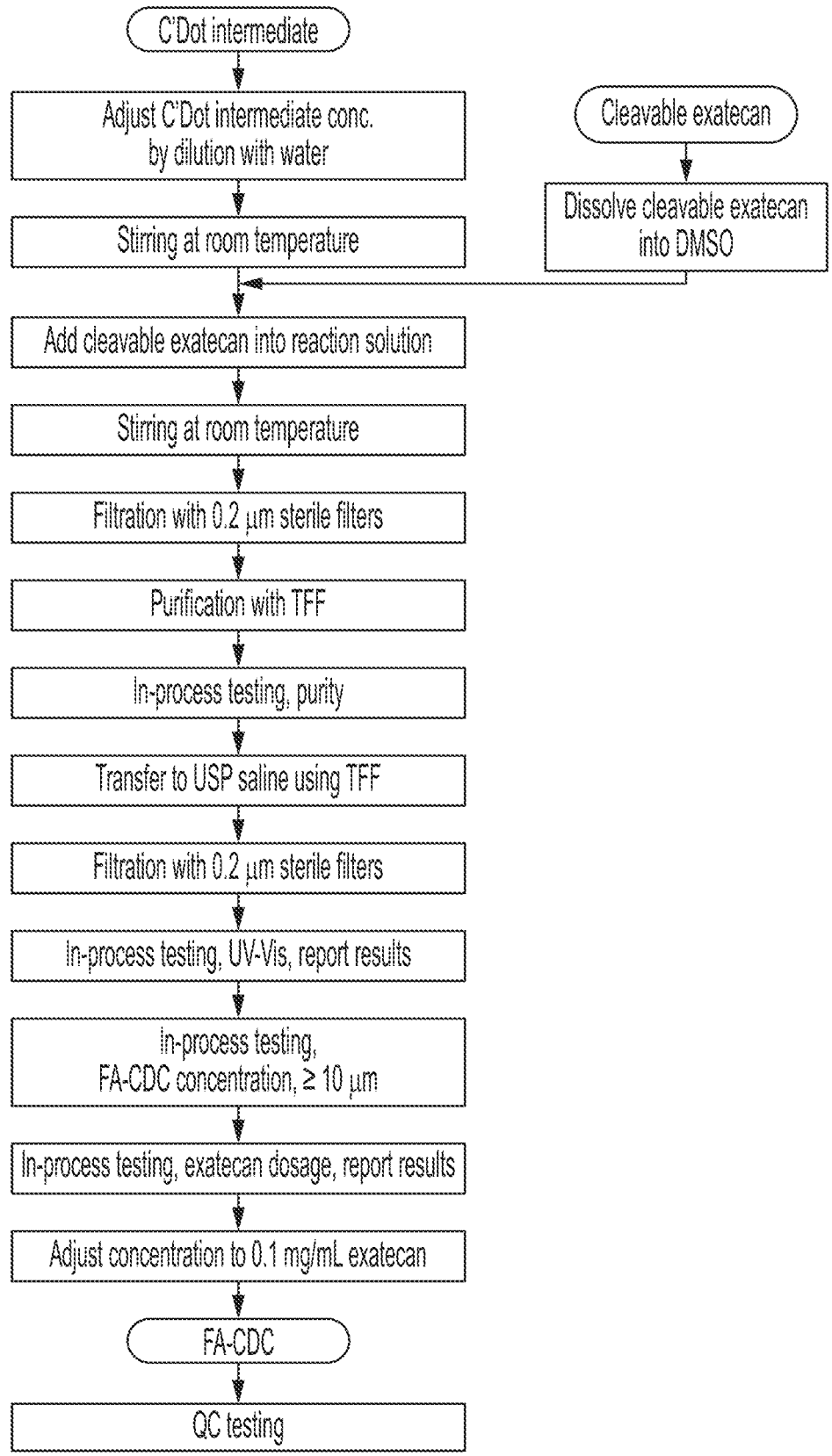

A nanoparticle prepared using a method disclosed herein may be further functionalized, e.g., using a method outlined in FIG. 2 or 3, or in Scheme 6 below. For example, (3-cyclopentadienylpropyl)triethoxysilane ("diene-silane") can be used to functionalize a nanoparticle (e.g., C'Dot) with cyclopentadiene groups, then DBCO-PEG-maleimide can be reacted with the diene-functionalized nanoparticle to provide a DBCO-functionalized nanoparticle.

Scheme 6. An exemplary method of functionalizing a nanoparticle with DBCO.

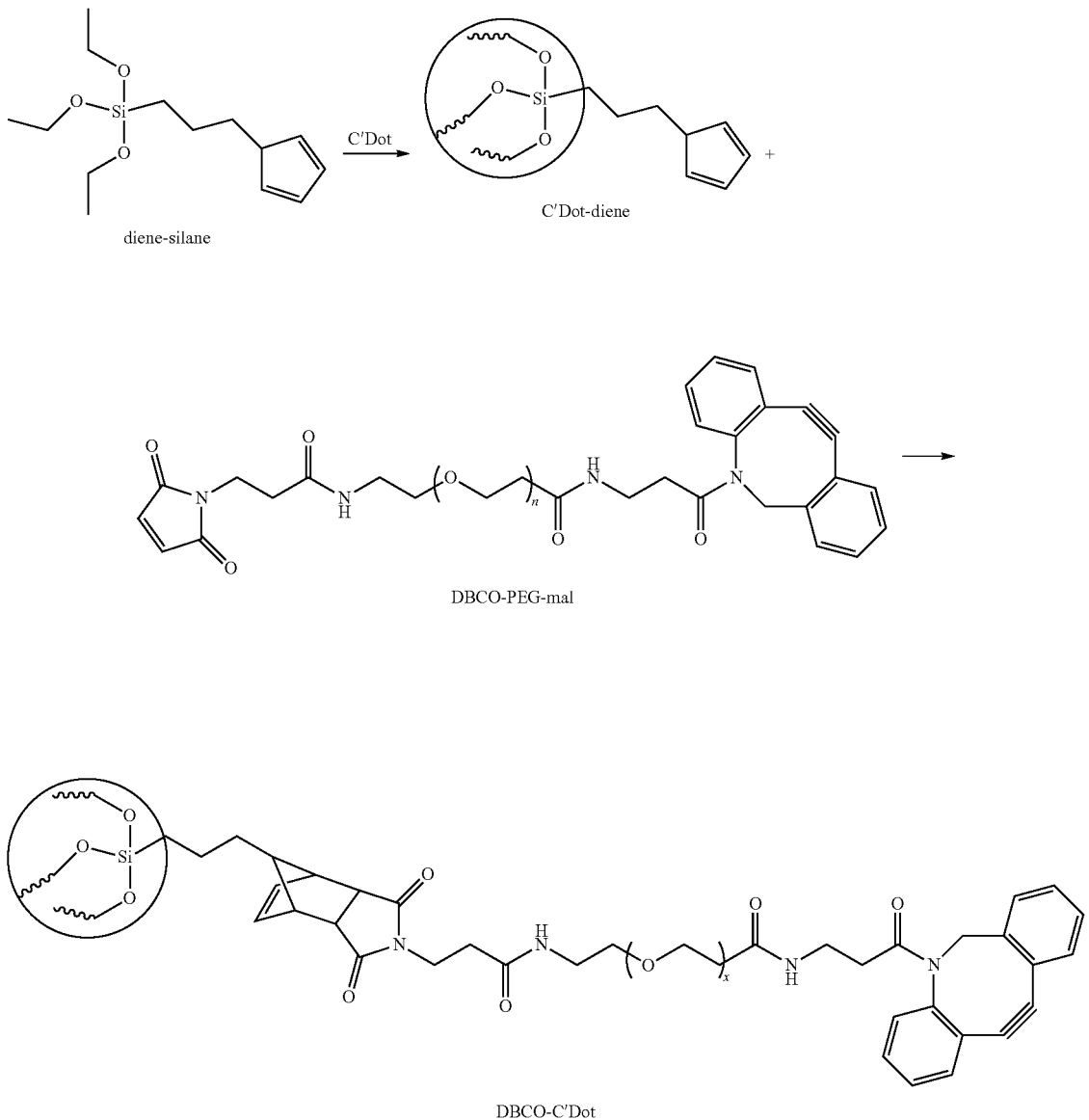

For example, Cy5-C'Dot (which may be prepared using a method described herein) was diluted with deionized water to a desired concentration, typically between 15 to 30 µM, in a round-bottom flask with a stir bar. (3-Cyclopentadienyl-propyl)triethoxysilane (cyclopentadiene) was first diluted 100× in DMSO and then added into the reaction with stirring, to reach a desired particle to cyclopentadiene molar ratio. After overnight reaction, 10×PBS was added into the reaction to achieve a final concentration of 1×PBS. Next, a DBCO-maleimide precursor (e.g., DBCO-PEG4-maleimide) was dissolved in DMSO and added into the reaction to reach a desired particle to DBCO molar ratio. After mixing for about 30 min to 1 hour, the reaction mixture was heated to 80° C. while stirring overnight. The reaction solution was then concentrated and purified using gel permeation chromatography (GPC) to obtain diene-based DBCO-C'Dot.

The purification may be performed based on the principle of size separation. Aggregates and free small molecules having molecular weight different than that of the pegylated nanoparticles are separated using gel permeation chromatography columns (GPC) or Tangential Flow Filtration (TFF) system. Two different membranes, 300 kDa, and 50 kDa cut-off sizes were employed for the removal of large aggregates and free small molecules respectively. Both GPC and TFF systems can be used to transfer the aqueous medium to water, saline etc. Purified DBCO-C'Dot in deionized water can be sterile filtered again and the quality control (QC) steps can be performed, followed by storage in refrigerator at 2-8° C.

Without wishing to be bound by theory, it is believed that the neutral charge of the cyclopentadiene groups averts hydrolysis of the amide bonds in the linkage, that can be accelerated by other types of precursors (e.g., when using amine-silanes instead of diene-silanes, the primary amine groups can cause hydrolysis). Thus, the NDCs produced using this method are highly stable (see, e.g., comparison in FIGS. 33A-33B). Additionally, using diene-functionalized nanoparticles (e.g., cyclopentadiene-functionalized nanoparticles) in the preparation of NDCS greatly diminishes the self-condensation of silane during the reaction, and improves the stability, size homogeneity, reaction yield, and purity of the functionalized nanoparticles, relative to other methods (e.g., using amine-silanes).

Preparation of Targeted NDCs

NDCs of the present disclosure comprising the nanoparticle (also referred as C'Dot), targeting ligand (folic acid) and linker-drug conjugates can be prepared as outlined in the flow chart presented in FIG. 3, and in Scheme 7 below. By adjusting the amount of targeting ligand precursor used in the functionalization step, a desired number of targeting ligands per nanoparticle can be achieved. For example, nanoparticles of the present disclosure may be functionalized to contain about 10 to about 20 folic acid moieties, e.g., about 10, about 11, about 12, about 13, about 14, or about 15 folic acid moieties. Similarly, by adjusting the amount of payload-linker conjugate precursor used in the functionalization step, a desired number of payload moieties per nanoparticle can be achieved. For example, nanoparticles of the present disclosure may be functionalized to contain about 10 to about 40 exatecan-linker moieties, e.g., about 20, about 21, about 22, about 23, about 24, or about 25 exatecan moieties.

Scheme 7. An exemplary method of functionalizing a nanoparticle with folic acid moieties and exatecan-linker moieties.

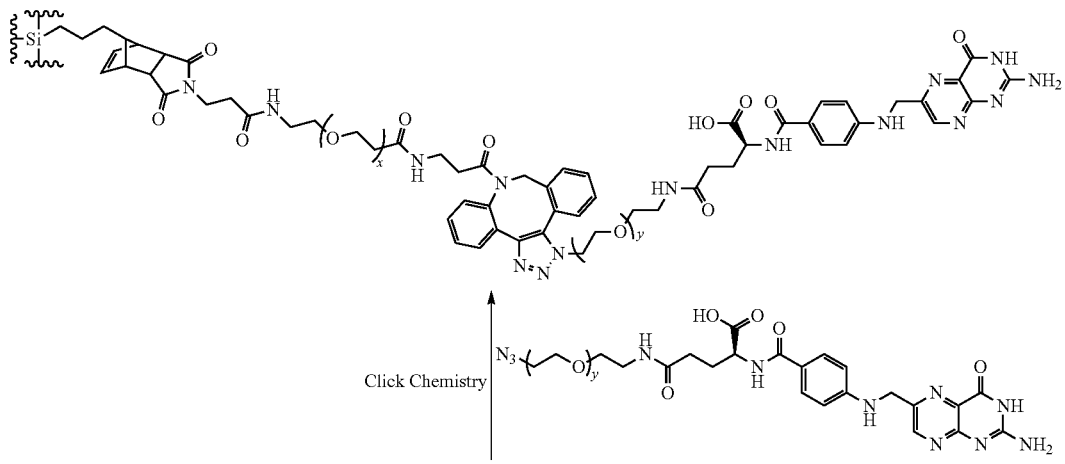

-continued
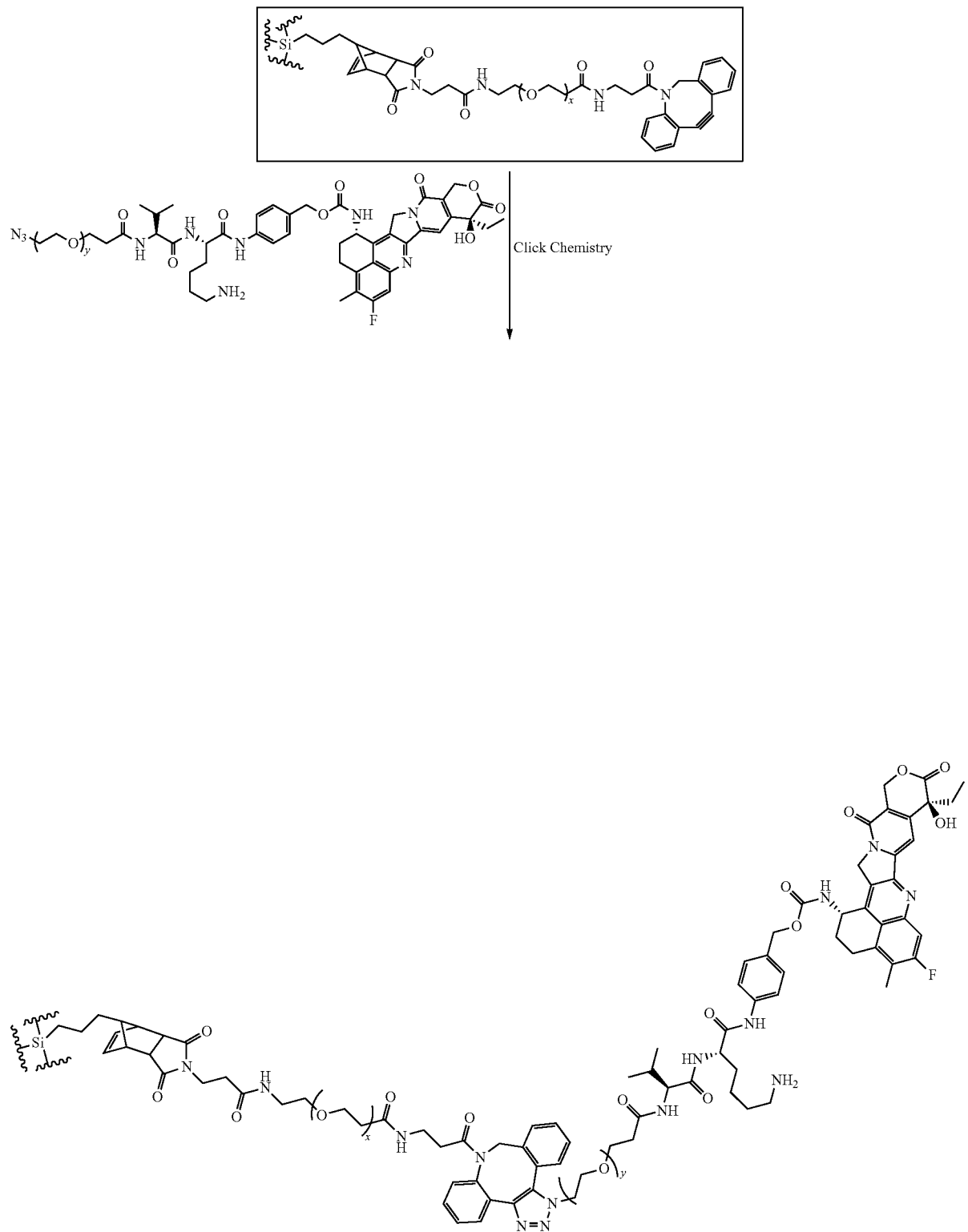

Synthesis of folic-acid conjugated nanoparticle: DBCO-C'Dot (referred as C'Dot in FIG. 3) was diluted using deionized water to a concentration of 15-45 µM. After the temperature of DBCO-C'Dot solution was around 18-25° C., folate receptor (FR)-targeting ligand precursor such as, folic acid (FA) functionalized with an azide (compound 606 prepared in Example 2) was dissolved in DMSO (0.021 M) and was then added into the reaction with stirring at room temperature, providing a C'Dot functionalized with FA via the DBCO group on the surface. The reaction ratio between DBCO-C'Dot and FA was kept from 1:5 to 1:30, and the solution was stirred for 16-24 hours at temperature of 18-25° C. FR-targeting ligand addition is followed by sterile filtration, purification and QC testing to yield FA-C'Dot (referred as C'Dot intermediate in FIG. 3), and can be stored in a refrigerator at 2-8° C. FA-C'Dot comprises a portion of DBCO groups that are available for further click-reactions, e.g., with molecules with azide functionality. It will be understood that the folate-targeting ligand (e.g., folic acid) can be conjugated to the nanoparticle after conjugation with, e.g., a payload-linker conjugate.

The volume of the FR-targeting ligand conjugation reaction can range from 5 mL to 30 L, and the concentration of DBCO-C'Dot can range from 15 to 45 µM. The following parameters are given for a typical reaction volume of 600 mL and a DBCO-C'Dot concentration of 25 µM. The ratio of DBCO-C'Dot to FR-targeting ligands was precisely controlled to obtain the desired number of FR-targeting ligands per particle, and typically can range from 1:5 to 1:30. For a typical ratio of 1:12, folate-PEG-azide was dissolved in DMSO to a concentration of 0.021 M, and 8.571 mL of the folate-PEG-azide/DMSO solution was added into the reaction. After stirring overnight at room temperature, the reaction mixture was either purified to obtain FA-C'Dot or continue directly to next conjugation step if the purity of FA-C'Dot is no less than 95%. The conversion rate of FR-targeting ligand is typically higher than 95%.

Figure 4:
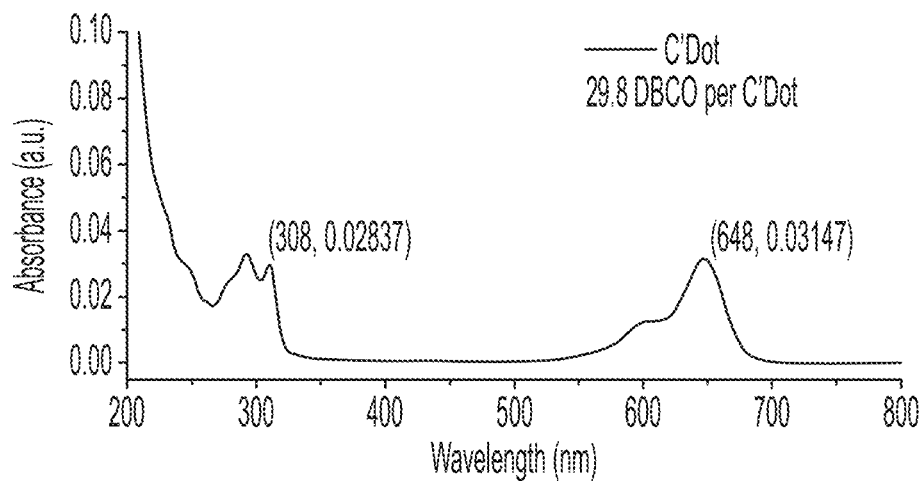
FIG. 4 illustrates a representative UV-Vis absorbance spectrum of an exemplary functionalized nanoparticle (DBCO-functionalized C'Dot). The absorption peak at 648 nm correspond to the Cy5 dye that is covalently encapsulated within the core of the C'Dot. The absorption peaks around 270 to 320 nm correspond to DBCO groups.

The number of folic acid groups attached onto each FA-C'Dot was characterized by UV-Vis, and a representative UV-Vis absorbance spectrum is shown in FIG. 4. The number of DBCO groups on each C'Dot can be calculated using the extinction coefficient of C'Dot and DBCO groups Synthesis of FA-targeted NDC (or FA-CDC) comprising exatecan: FA-C'Dots were diluted using deionized water to a concentration of 15-45 µM. After the FA-C'Dot solution temperature reached around 18-25° C., exatecan-linker conjugate precursor (e.g., compound 202 described in Example 1) cathepsin dissolved in DMSO (0.04 M) was added into the reaction under stirring at room temperature. This step functionalized the FA-C'Dot with the linker-drug conjugate via the available DBCO groups on the surface. The reaction ratio between FA-C'Dot and linker-drug conjugate was kept around 1:10-1:50 and the solution was stirred for 16-24 hours. The addition of linker-drug conjugate was followed by sterile filtration, and purification. FA-CDC (also referred as NDC) in deionized water is QC tested, and stored in refrigerator at 2-8° C.

The volume of the cleavable exatecan conjugation reaction can range from 5 mL to 30 L, and the concentration of FA-C'Dot can range from 15 to 45 µM. The following parameters are given for a typical reaction volume of 600 mL and a FA-C'Dot concentration of 25 µM. The ratio of FA-C'Dot to cleavable exatecan was precisely controlled to obtain the desired number of cleavable exatecan per particle, and typically can range from 1:10 to 1:60. For a typical ratio of 1:40, cleavable exatecan was dissolved in DMSO to a concentration of 0.04 M, and 15 mL of the cleavable exatecan/DMSO solution was added into the reaction. After stirring overnight at room temperature, the reaction mixture was purified to obtain FA-CDC.

Figure 5:
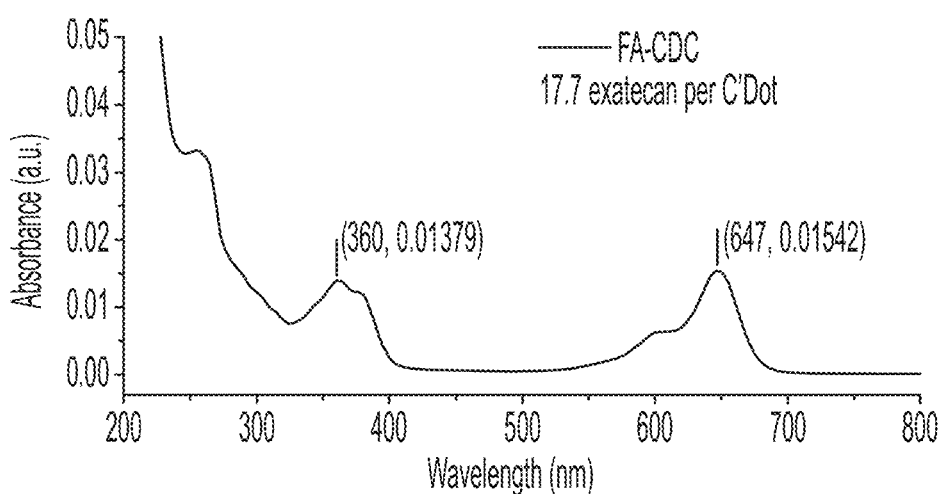
FIG. 5 illustrates a representative UV-Vis absorbance spectrum of an exemplary NDC (folic acid (FA)-functionalized C'Dot comprising exatecan (FA-CDC)). The absorption peak at 648 nm correspond to the Cy5 dye that is covalently encapsulated within the core of C'Dot. The absorption peaks around 330 to 400 nm correspond to exatecan.

The number of exatecan payloads attached onto each NDC, e.g., folic acid (FA)-functionalized drug-linker conjugated C'Dot (FA-CDC), may be characterized by UV-Vis. A representative UV-Vis absorbance spectrum is shown in FIG. 5. The number of exatecan payloads on each C'Dot can be calculated using the extinction coefficient of C'Dot and Exatecan at 360 nm after the subtraction of the absorption of Folic Acid at the same wavelength.

As stated above, a nanoparticle may be functionalized with a folate receptor targeting ligand and a payload-linker conjugate in any order (e.g., the protocol outlined above for functionalizing the nanoparticle with exatecan may be carried out prior to the protocol for conjugating folic acid).

Particle Size Determination: The average diameter of NDCs can be measured by any suitable methods, such as, but not limited to fluorescence correlation spectroscopy (FCS) (FIG. 6) and gel permeation chromatography (GPC) (FIG. 7).

FCS detects the fluorescence fluctuation resulted from particle diffusion through the focal spot on the objective. Particle diffusion information is then extracted from the autocorrelation of signal intensity fluctuations, from which the average hydrodynamic particle size can be obtained by fitting the autocorrelation curve using a single-modal FCS correlation function. The average hydrodynamic diameter of NDC was about 6 nm to about 7 nm (FIG. 6).

GPC is a type of molecular sieving chromatography, where the separation mechanism is based on the size of the analyte (here NDC's). The elution time of NDC is compared to a series of proteins with varying molecular weight. The results suggest that the elution time of NDC's is comparable to that of protein standards with molecular weight between 158 kDa and 44 kDa, consistent with the particle size average hydrodynamic size of about 6.4 nm (FIG. 7).

Figure 8:
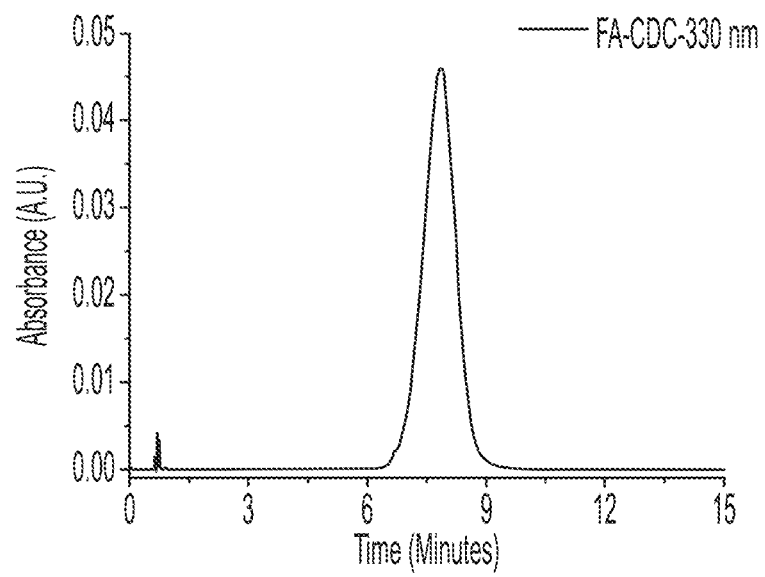
FIG. 8 depicts a reversed phase HPLC chromatogram of a purified exemplary NDC (folic acid (FA)-functionalized exatecan-linker conjugated C'Dot (FA-CDC)) at 330 nm. This wavelength can be used to monitor both the FA-CDC and impurities that may be present after the synthesis or due to any degradation of the NDC.

Purity Analysis: The purity of NDCs was analyzed using reverse phase HPLC (RP-HPLC). RP-HPLC is coupled to a photodiode array detector, using a commercially available Waters Xbridge Peptide BEH C18 column. RP-HPLC separates molecules with different polarities and is suitable as an analytical method for NDCs because of its ultrasmall sub-10 nm particle size. Using RP-HPLC, the nanoparticles are well separated from aggregates and other chemical moieties such as targeting ligands that are non-covalently associated with the nanoparticles and degraded products. Different chemical moieties are identified based on their elution time and unique UV/Vis spectra. The photodiode array detector collects UV-Vis spectra from 210 to 800 nm, and impurities of interest are measured at 330 nm. A representative chromatogram shown for the NDCs in FIG. 8, suggests that the purity of NDCs of the present disclosure is higher than 99.0%.

Example 4: Drug-Release Assays

NDCs of the present disclosure comprise a linker-payload conjugate, e.g., a protease-cleavable linker, such as cathepsin-B (Cat-B) cleavable linker. Upon contact with a protease, the NDCs may release the payload (i.e., exatecan). The drug-releasing profile and the stability of linker-drug conjugates on the nanoparticle were tested according to the following protocols.

The NDCs were prepared using methods described in Example 3, and then incubated under the desired releasing conditions for release kinetics tests. The NDCs tested in the assay are provided in Table 2 below.

TABLE 2
Exemplary NDCs used in drug-release assays.
| NDC | Exatecan-Linker Conjugate Structure |
|---|---|
| B | 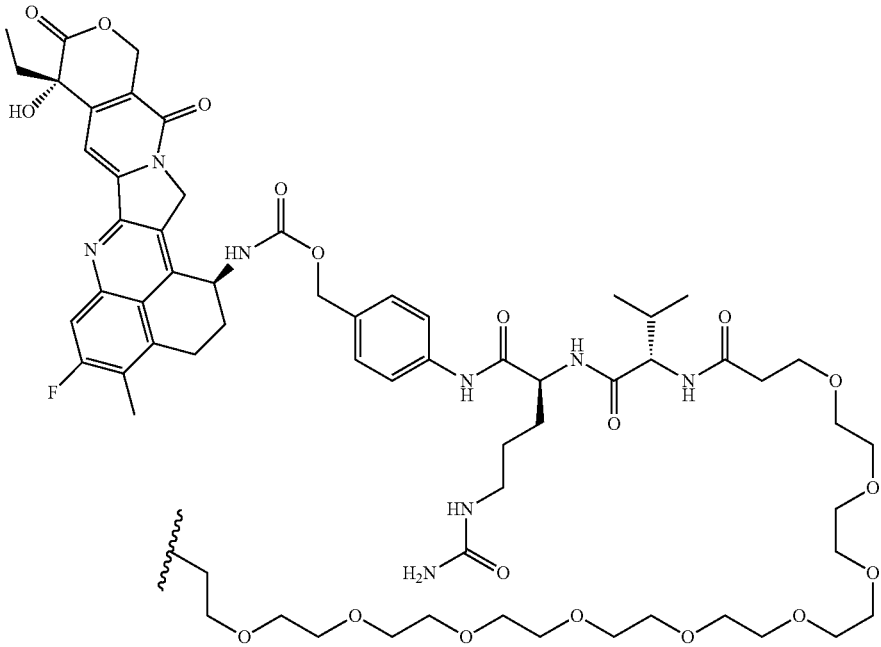 [SMILES: *CCOCCOCCOCCOCCOCCOCCOCCOCCOCCC(=O)N[C@H](C(=O)N[C@@H](CCCNC(N)=O)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C] |
| C | 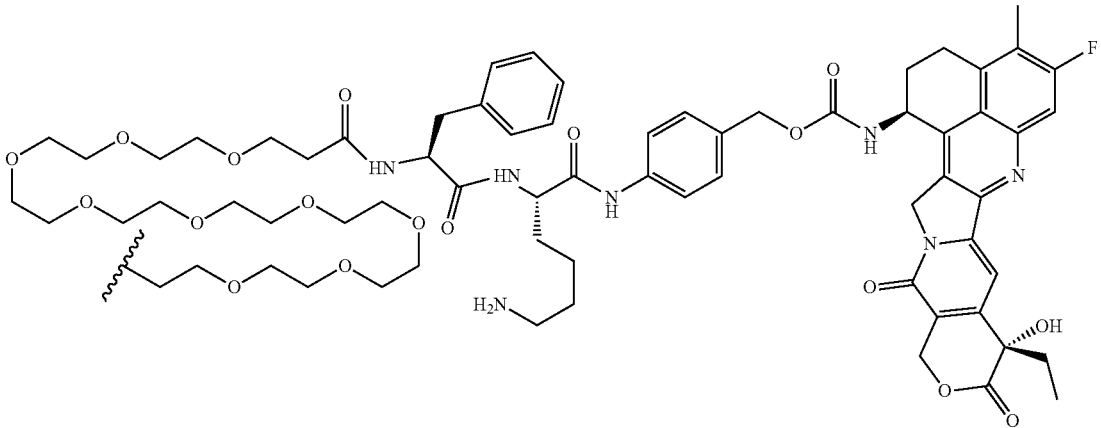 [SMILES: *CCOCCOCCOCCOCCOCCOCCOCCOCCOCCC(=O)N[C@@H](Cc1ccccc1)C(=O)N[C@@H](CCCCN)C(=O)Nc1ccc(COC(=O)N[C@H]2CCc3c(C)c(F)cc4nc5c(c2c34)Cn2c-5cc3c(c2=O)COC(=O)[C@]3(O)CC)cc1] |
| D | 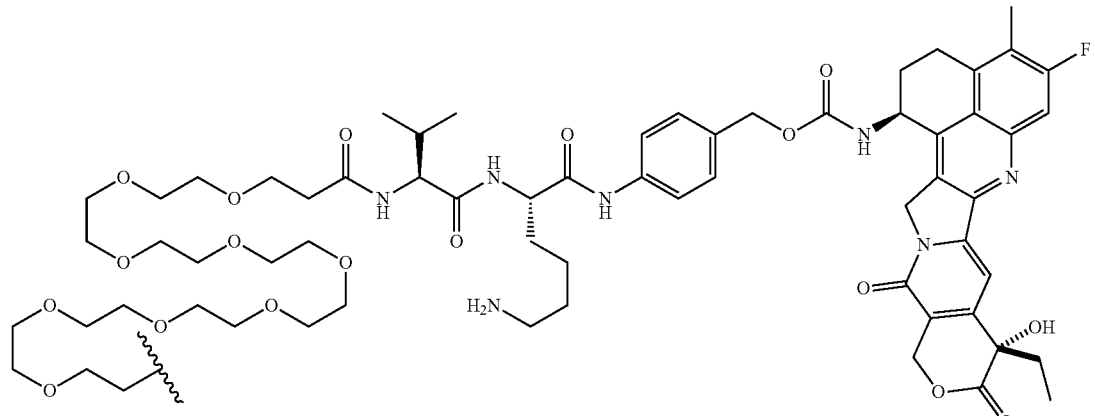 (prepared from 202, Example 1) |

Number of FA ligands per particle is between 12 and 22; Number of linker-drug conjugates per particle is between 17 and 25. Each payload-linker is conjugated to the NDC via a DBCO moiety (prepared according to the protocol outlined in Example 3).

Figure 9:
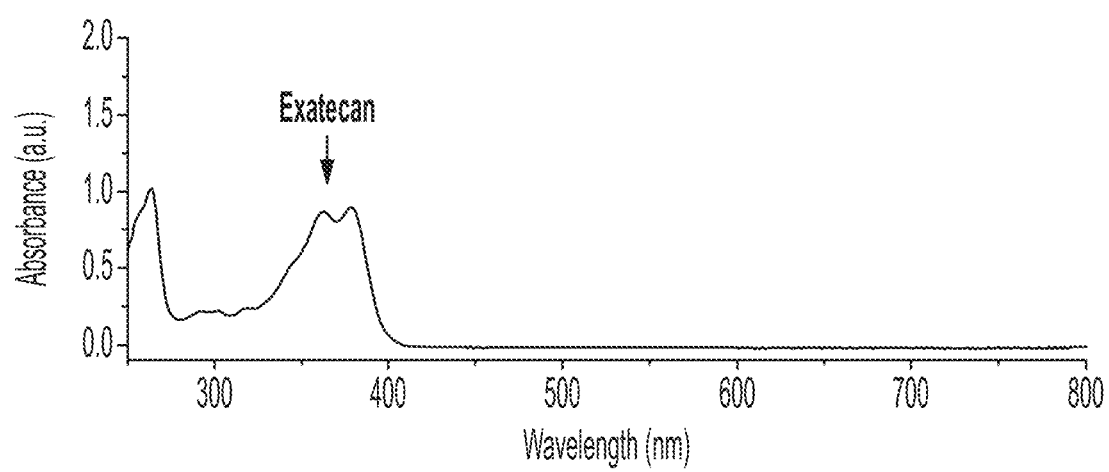
FIG. 9 illustrates the UV-Vis absorbance spectra of an exemplary exatecan-payload conjugate. Exatecan has an absorption maximum around 360 nm.
Figure 10A:
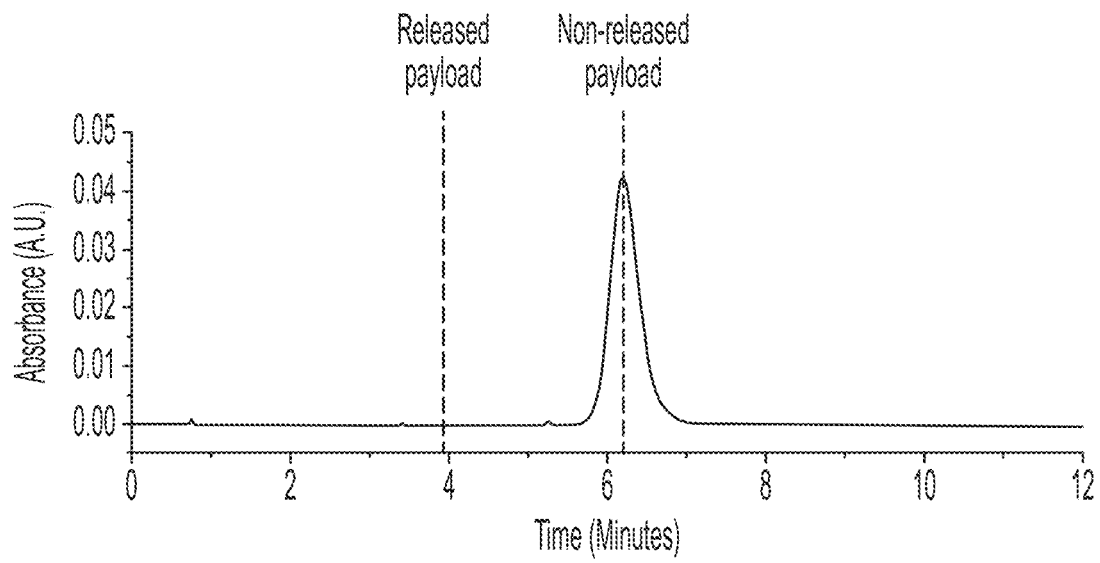
FIGS. 10A-10B illustrate a representative HPLC chromatographs providing analysis of an exemplary NDC prepared according to Example 3, that is conjugated with folic acid as targeting ligand and with exatecan as a payload (NDC prepared using the exatecan-linker conjugate precursor 202, from Example 1).
Figure 10B:
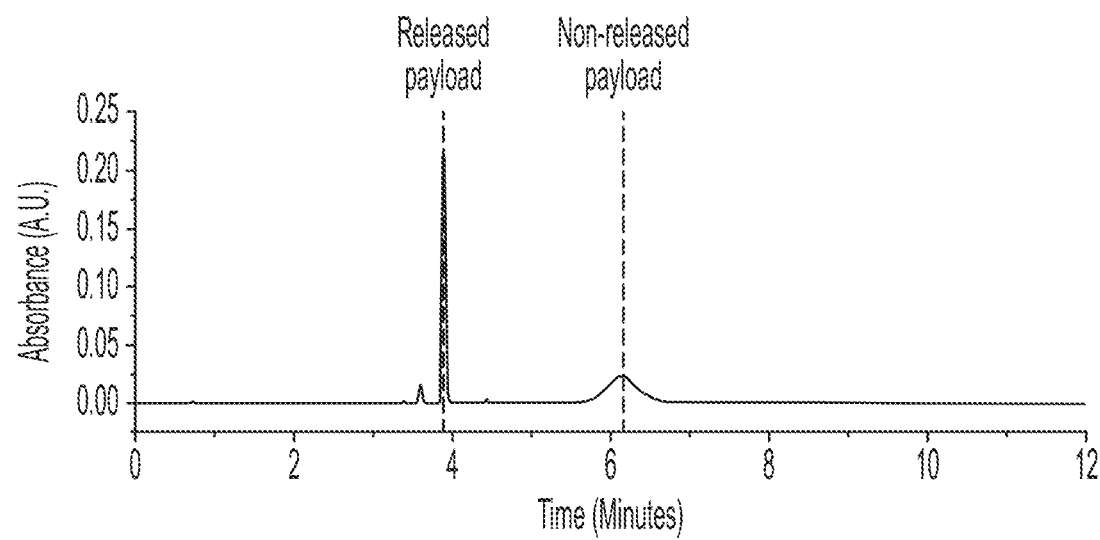

Exatecan exhibits an absorption maximum at a wavelength of around 360 nm (FIG. 9), and this signal can be used to trace the payloads in high-performance liquid chromatography (HPLC) for releasing and stability studies. The amount of released drugs vs non-released drugs was measured using reverse phase HPLC by analyzing the area under curve (AUC) (FIG. 10A and FIG. 10B).

General Method: A Waters Xbridge Peptide BEH C18 column with 4.6 mm×50 mm dimensions, a particle size of 5 μm, and a pore size of 300 Å was used (part number 186003622). Acetonitrile (VWR HiPerSolv Chromanorm, UHPLC Grade) was used as received without further preparation, 0.010% trifluoroacetic acid in deionized water was prepared by adding 1 mL of trifluoroacetic acid (HPLC grade, Millipore-Sigma) into 999 mL 18.2 MΩ·cm deionized water that was generated using an IQ7000 Millipore deionized water system and passed through a 0.2 μm filter before use. The seal wash used for the system was composed of 90% 18.2 MΩ·cm deionized water and 10% methanol (HPLC grade, VWR). The injection needle was washed using a mixture of 25 vol % 18.2 MΩ·cm deionized water, 25 vol % acetonitrile, 25 vol % methanol, and 25 vol % 2-propanol. Samples were prepared in a concentration range of 0.25 to 2 μM and the injection volume ranges from 60 μL to 10 μL, respectively. Higher sample concentration can be used if detector signal is low. Vials used for all injections are fresh Waters Total Recovery vials with screw caps that have pre-slit PTFE septa (part number 186000385C).

Before any sample injections were started, the PDA lamp was turned on and allowed to warm up for at least 30 minutes. The system and column were equilibrated with 95% 0.01% TFA in deionized water, 5% acetonitrile for at least 10 minutes at a flow rate of 1.0 mL/min after the PDA lamp had warmed up. Two blank injections, with injection volumes of 10 μL containing only 18.2 MΩ·cm deionized water, were performed before the injection of any samples for analysis. The gradient used began at 95% 0.01% TFA in deionized water and 5% acetonitrile and linearly changed to 15% 0.01% TFA in deionized water, 85% acetonitrile over 8 minutes. Acetonitrile composition was increased to 95% over an additional minute and held at 95% for an additional 2 minutes to ensure that any strongly retained compounds are eluted. The composition of the solvent was then changed back to the starting composition of the gradient over an additional minute and allowed to equilibrate for 3 minutes before another injection began. Between sample injections a blank injection was run to ensure that no carryover occurred.

For atypical cathepsin B (Cat-B) protease cleaving study, 2 μL, 0.33 μg/μL of Cat-B (sigma Aldrich) was first added with 300 μL of activation buffer (25 mM MES, 5 mM DTT, pH 5.0), forming 2.2 μg/mL of Cat-B. The mixture was kept at room temperature for 15 min before use. After activation, 100 μL of 2 μM drug-nanoparticle-conjugate was mixed with 100 μL of activated Cat-B. The mixture was then transferred to 37° C. To monitor the cleaving kinetics, at selected post-incubation time points (e.g., 2, 4, 24 h), 10 μL of mixture was sampled and injected in HPLC (TFA/acetonitrile). For the analysis of cleaving data, Empower 3 ApexTrack integration was used to determine peak areas for all relevant components.

Figure 11C:
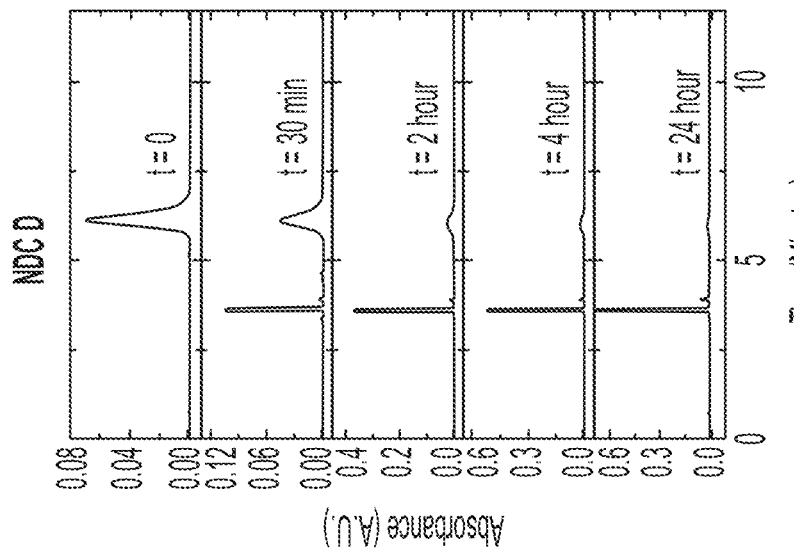
FIGS. 11A-11C are plots illustrating a drug releasing analysis of exemplary NDCs loaded with folic acid as targeting ligand and protease (cathepsin-B) cleavable exatecan-linker conjugates, at different time points after incubation with cathepsin-B.
Figure 11B:
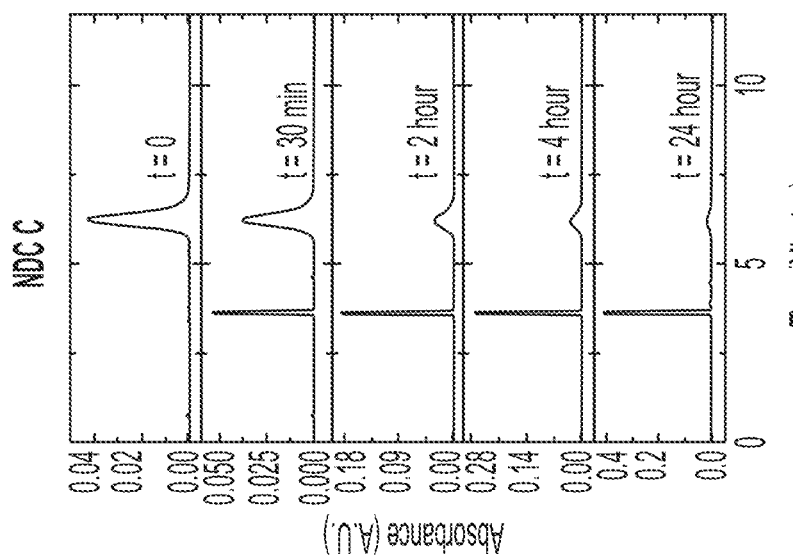
Figure 11A:
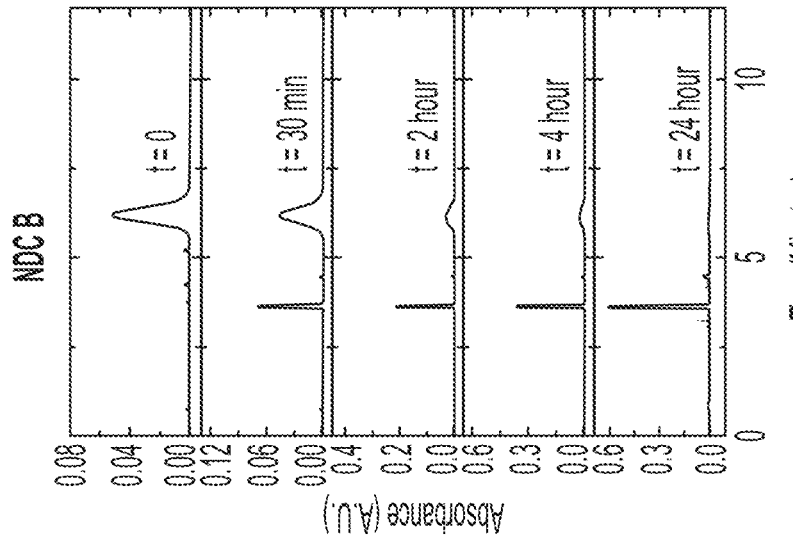
Figure 12C:
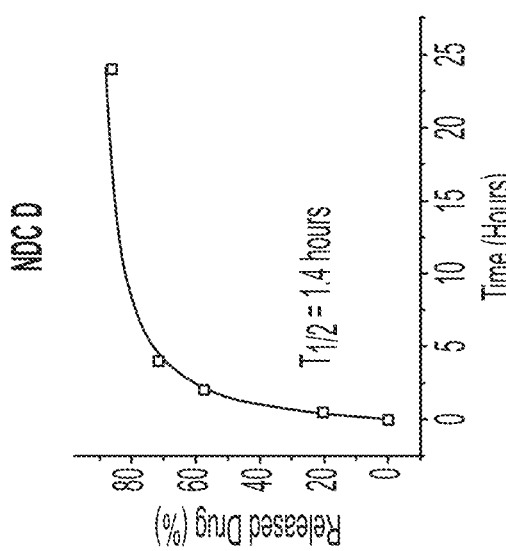
FIGS. 12A-12C are plots illustrating a drug releasing kinetics of exemplary NDCs loaded with protease (cathepsin-B) cleavable exatecan-linker conjugates, at different time points after incubation with cathepsin-B enzyme, and depicts the time for half of the payloads to be released, i.e., $T_{1/2}$.
Figure 12B:
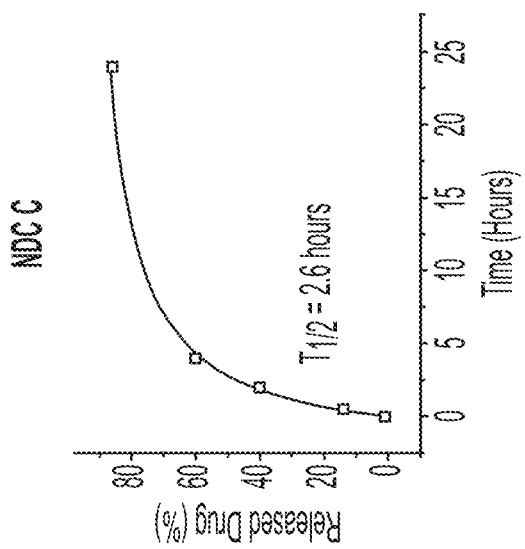
Figure 12A:
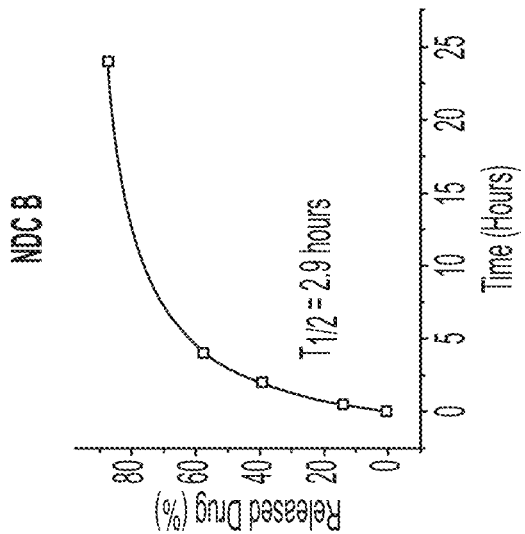

The RP-HPLC chromatograph of three representative NDCs (NDC B, NDC C, and NDC D) at different time points after incubation with cathepsin-B is depicted in FIGS. 11A-11C, respectively. The time for half of the payloads to be released from each NDC, i.e., $T_{1/2}$, under the specific experimental condition was analyzed by fitting and is depicted in FIGS. 12A-12C respectively. FIG. 12A depicts the $T_{1/2}$ as 2.9 hours for NDC B. FIG. 12B depicts the $T_{1/2}$ as 2.6 hours for NDC C. FIG. 12C depicts the $T_{1/2}$ as 1.4 hours for NDC D.

Stability Test: To assess the drug releasing profile and stability of the linker-drug conjugates under non-cleavage conditions, an exemplary NDC was incubated in phosphate-buffered saline (PBS) buffer or animal serum at 37° C. The NDC was prepared according to Example 3, using the exatecan-linker conjugate precursor 202 from Example 1)

For a typical stability test in PBS buffer, 600 μL of PBS mixture (drug-nanoparticle-conjugate concentration was kept at 2 μM, while the volume percentage of PBS was kept as 50%) was prepared and kept at 37° C. To monitor the stability of the linker-drug conjugates attached to nanoparticles, at selected post-incubation time points (e.g., 4, 24, 48 and 72 h), 10 μL of mixture was sampled and injected in HPLC (TFA/acetonitrile). For the analysis of cleaving data, Empower 3 ApexTrack integration is used to determine peak areas for all relevant components.

For a typical stability test in plasma from varied species (e.g., mouse, rat, dog, monkey and human), 600 μL plasma mixture (drug-nanoparticle-conjugate concentration was kept at 2 μM, while the volume percentage of plasma was kept as 62.5%) was prepared and kept at 37° C. To monitor the stability of linker-drug conjugates, at selected post-incubation time points (e.g., 4, 24, 48 and 72 h), 80 μL of mixture was first mixed with 80 μL of cold acetonitrile, and then went through 30 min of centrifugation at 10,000 rpm. After removal of the proteins, 60 μL of supernatant was carefully sampled and injected in HPLC. For cathepsin-B-cleavable NDC, TFA/acetonitrile was used. For the analysis of stability data, Empower 3 ApexTrack integration was used to determine peak areas for all relevant components.

The linker-payload conjugate of the NDC (as prepared in Example 3, using the exatecan-linker conjugate precursor 202 from Example 1) is stable, as 5% of less of the exatecan was released from the linker drug conjugate after 24 hours under non-cleavage conditions, i.e., when maintained in PBS, human serum, or mouse serum.

Example 5: In Vitro Flow Cytometry Cell Binding Study

Cell-binding activity of the NDCs disclosed herein was tested according to the following protocols. NDCs used were prepared according to Example 3, using the exatecan-linker conjugate precursor 202 of Example 1. The amount of folic acid per nanoparticle, and the amount of exatecan per nanoparticle, could be adjusted according to the protocol outlined in Example 3.

Cells and Cell Culture: Human KB cell line, SKOV-3 cells and TOV-112 cell line were purchased from ATCC. I-GROV1, human ovarian carcinoma cell line was purchased from EMD Millipore. Cells were maintained in Folic Acid free RPMI 1640 media/10% FBS, and 1% of penicillin/streptomycin, unless otherwise specified. Cancer cells were cultured in folic acid-free medium (RPMI1640, ThermoFisher, GIBCO) for at least one week before the study. Cell binding studies were performed by incubating 5×105 cells (total of 500 uL, 1 Million/mL) in cold PBS (with 1% of BSA) with FA-CDC prepared in Example 3 (concentration: 1 nM) for 60 min at 4° C. (n=3). After that, the cell suspension was stained with viability kit (LIVE/DEAD™ Fixable Violet Dead Cell Stain Kit, Thermo Fisher) for 10-15 min. Then, cells were centrifuged (2000 rpm, 5 min), washed (2-3 times) using cold PBS (with 1% of BSA) before resuspending in PBS (with 1% of BSA). Triplicate samples were analyzed on a LSRFortessa flow cytometer (BD Biosciences) (Cy5 channel, 633 nm/647 nm, Live/dead cell stain, 405 nm). Results were processed using FlowJo and Prism 7 software (GraphPad).

The competitive binding study (FIG. 13) was performed using the NDC of Example 3. The active targeting of NDC can be fully blocked by incubating with the presence of 1 mM free Folic Acid.

Figure 13:
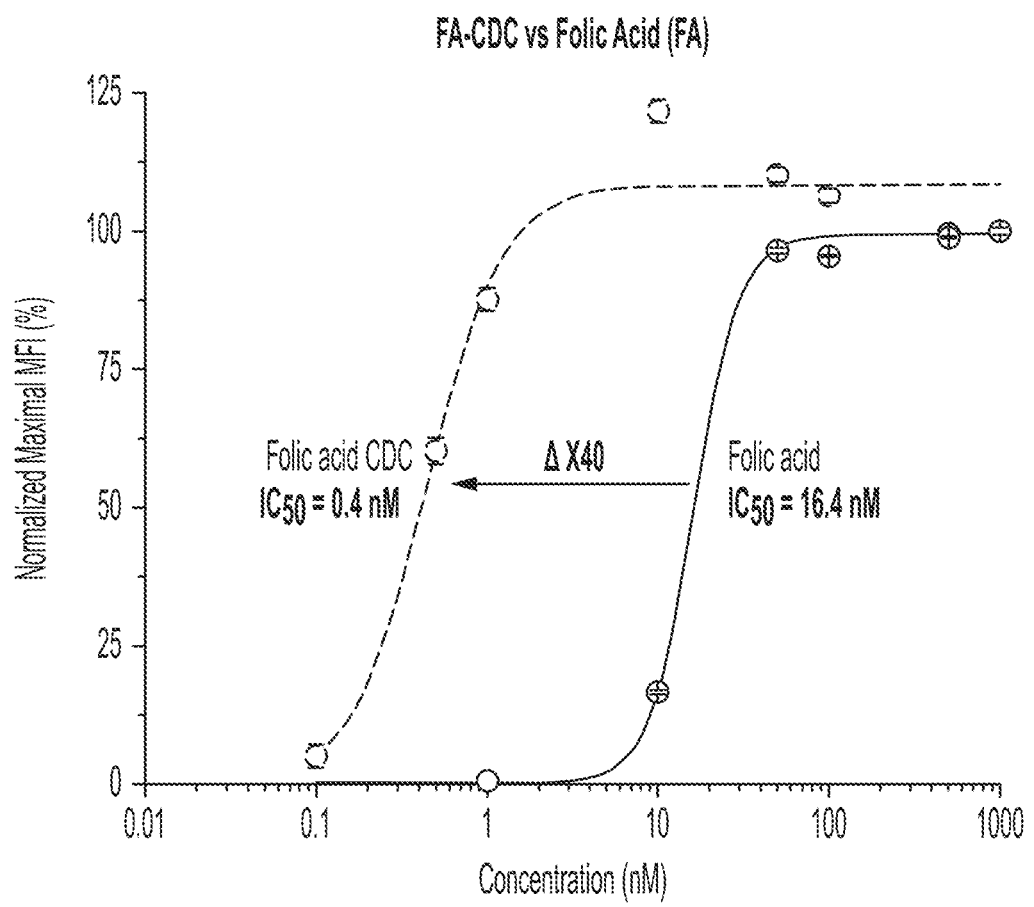
FIG. 13 depicts the competitive binding of an exemplary NDC (folic acid (FA)-functionalized drug-linker conjugated C'Dot (FA-CDC)) in a FR alpha positive (KB) cell line, when compared with free folic acid.

The competitive binding study shows >40-fold enhancement in binding capability of the NDC when compared with free folic acid, demonstrating the presence of a multivalent effect when conjugating multiple folic acid ligands on each ultrasmall C'Dot (FIG. 13).

These results demonstrate the advantages of conjugating multiple small tumor-directing ligands on the surface of nanoparticle (C'Dots) for enhancing the targeting capability using the multivalent effect. The folate receptor targeting can be blocked by competitive binding of free folic acid, such as by incubating with the presence of 1 mM free Folic Acid.

Figure 14:
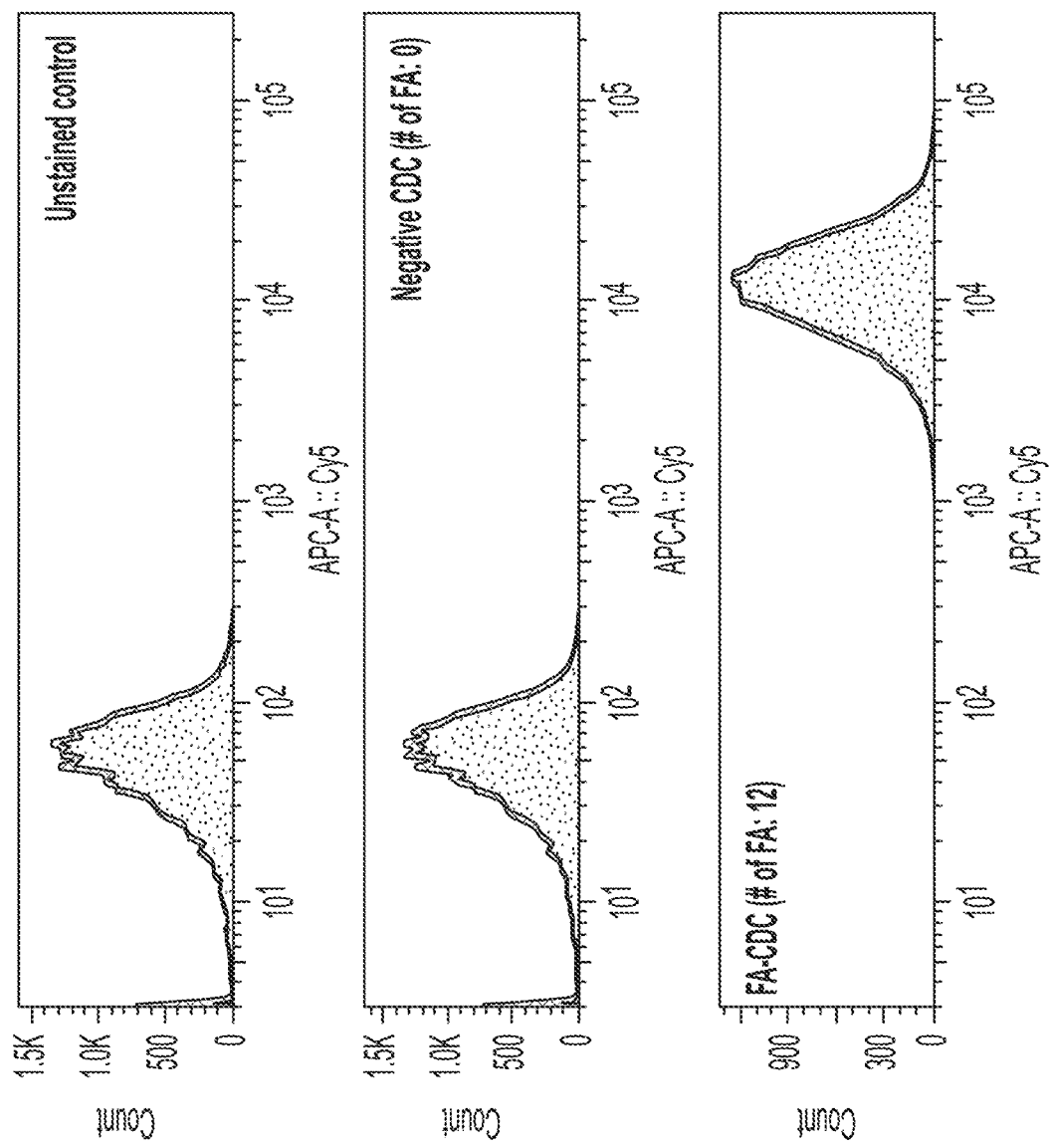
FIG. 14 depicts the flow cytometry of representative NDCs (two folic acid (FA)-functionalized drug-linker conjugated C'Dot (FA-CDCs)) in KB cell line with varied folic acid ligand density (either an average of 0, 12, or 25 folic acid molecules per nanoparticle). The exatecan-linker conjugate precursor used to prepare each NDC used in the study is described in Example 1 (Compound 202). Blocking in the blocking group was achieved using 1 mM of free folic acid. A CDC with no folic acid, but same amount of exatecan-linker conjugate, was used as the negative control group.
Figure 14:
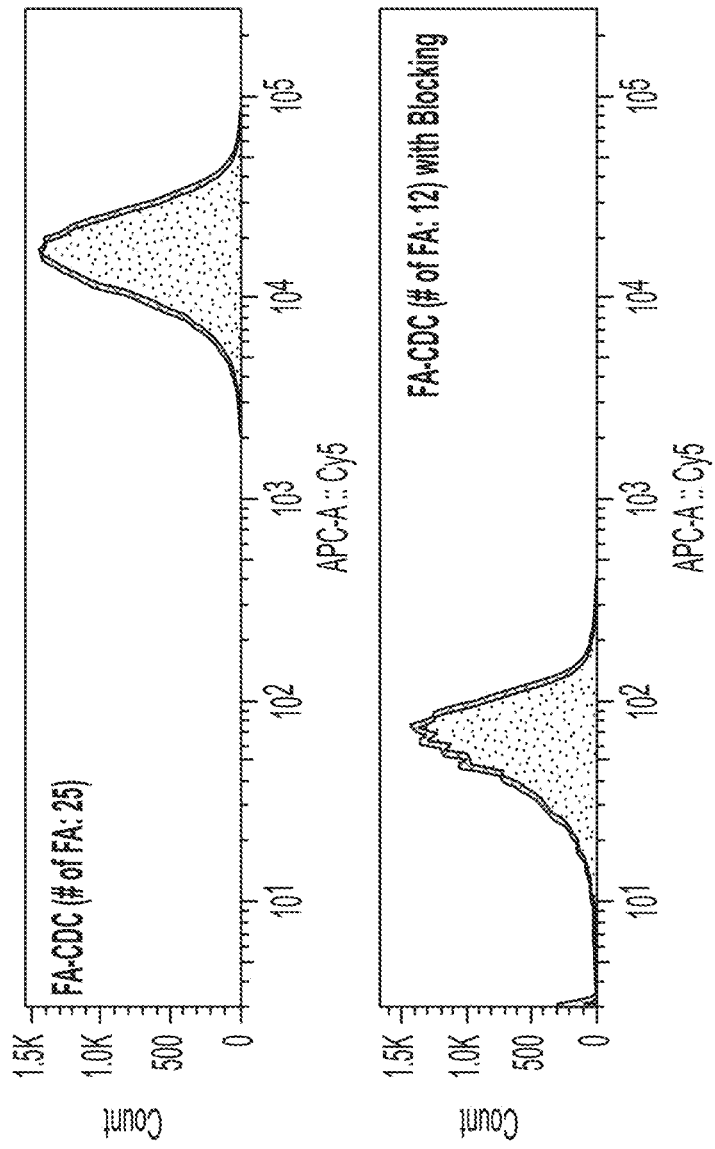

The flow cytometry shows comparable folate receptor targeting efficacy of two NDC formulations with varied folic acid ligand density, in KB cell line. The linker-exatecan conjugate precursor used to prepare the NDCs in this study is described in Example 1 (Compound 202). The blocking group has 1 mM of free Folic Acid. (FIG. 14).

The results demonstrated dramatic increase (>300-fold of MFI) in folate receptor-alpha active targeting when the folic acid ligand density was increased from zero to 12 (i.e., 12 folic acid molecules per nanoparticle), while little difference was observed upon further increasing that density to 25 folic acid molecules per nanoparticle.

Figure 15:
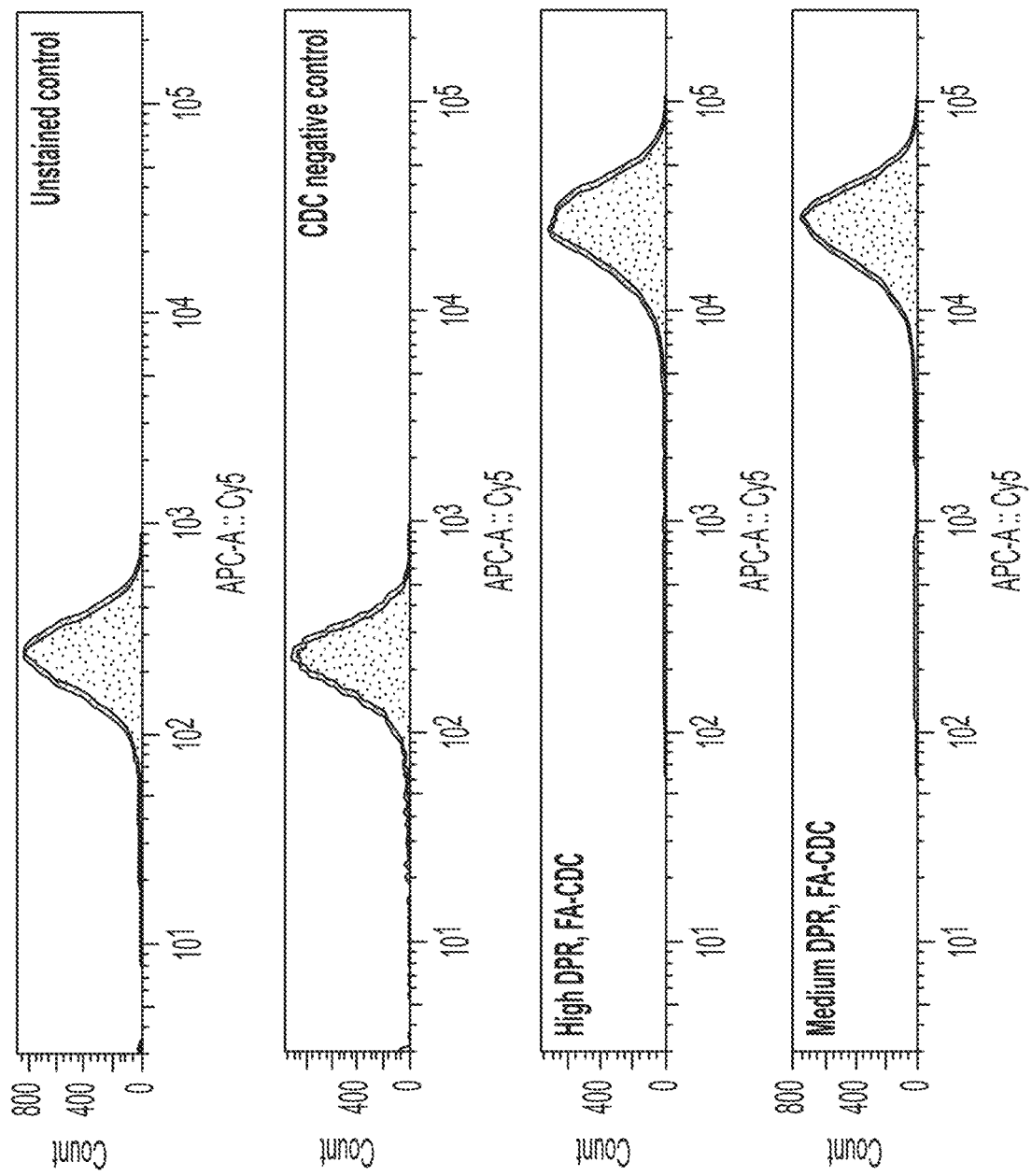
FIG. 15 depicts the flow cytometry of representative NDCs (three folic acid (FA)-functionalized drug-linker conjugated C'Dots (FA-CDCs) in KB cell line with varied drug per particle ratio (DPR). The exatecan-linker conjugate precursor used to prepare the NDCs used in the study is described in Example 1 (Compound 202). Blocking in the blocking group was achieved using 1 mM of free folic acid. All FA-CDCs comprise between 12 and 22 folic acid moieties. FA-CDCs with high drug-particle ratio (DPR) comprise between 35 and 50 exatecan-linker conjugate groups. FA-CDCs with medium DPR comprise between 17 and 25 exatecan-linker conjugate groups. FA-CDCs with low DPR have between 5 and 10 exatecan-linker conjugate groups. CDCs with no folic acid, and 17 to 25 drug linkers, was used as the negative control group.
Figure 15:
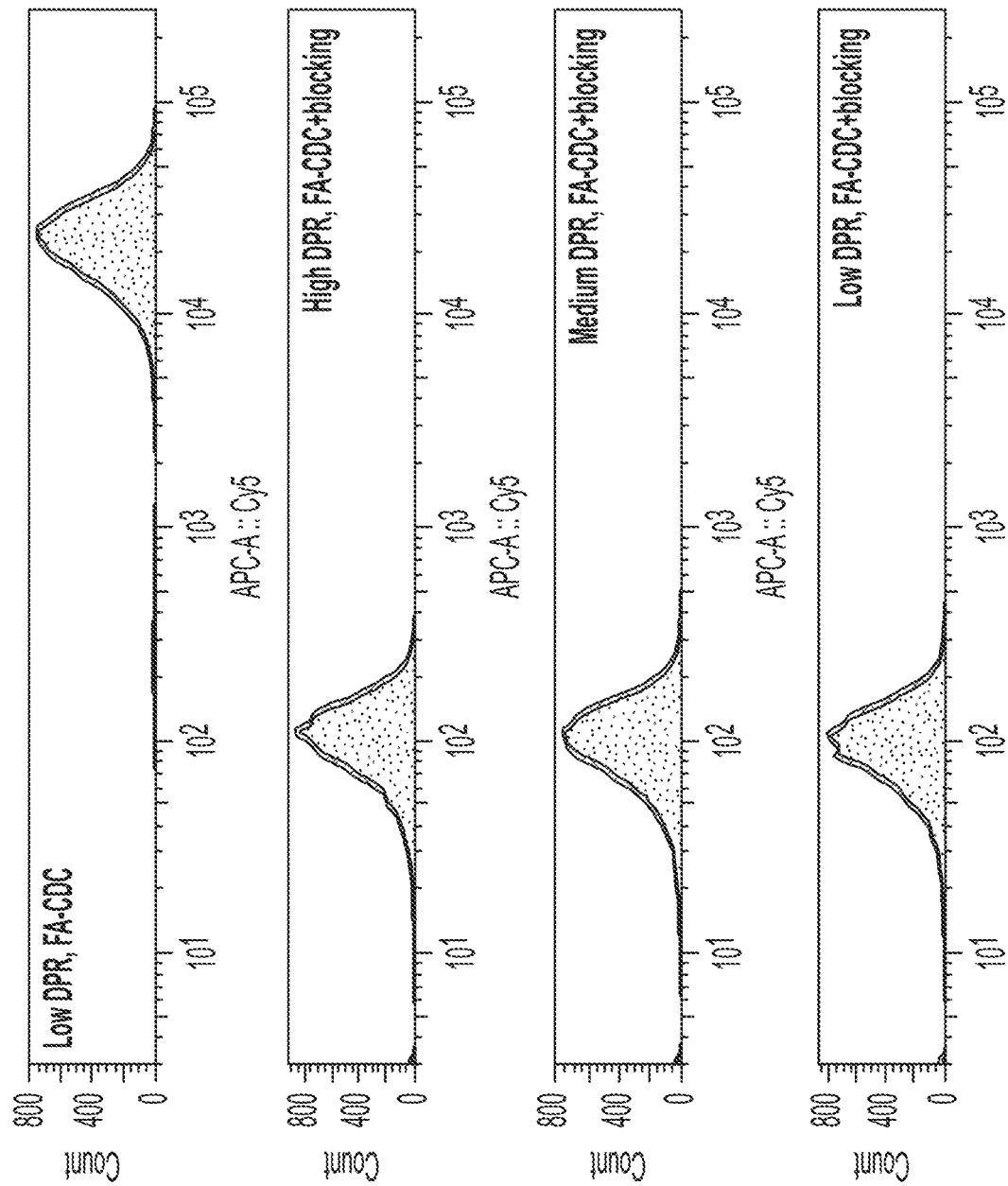

The flow cytometry shows comparable folate receptor targeting efficacy of three NDCs in KB cell line with varied drug per particle (DPR) (i.e., number of exatecan molecules per nanoparticle). The blocking group involved blocking receptors with 1 mM of free folic acid. The NDCs with different ratios of exatecan per nanoparticle were prepared using Compound 202 described in Example 1, and the results of the study are provided in FIG. 15. All FA-CDCs comprise between 12 and 22 folic acid moieties. FA-CDCs with high drug-particle ratio (DPR) comprise between 35 and 50 exatecan-linker conjugate groups. FA-CDCs with medium DPR comprise between 17 and 25 exatecan-linker conjugate groups. FA-CDCs with low DPR have between 5 and 10 exatecan-linker conjugate groups.

These results together with the nearly unchanged FCS sizing changes of the three NDCs demonstrate the robust surface chemistry and maintained folate receptor targeting capability of NDCs disclosed herein, which is surprisingly not perturbed by altering the loading capacity of payload and demonstrates a significant advantage of the NDCs disclosed herein over other drug delivery platforms.

Figure 16:
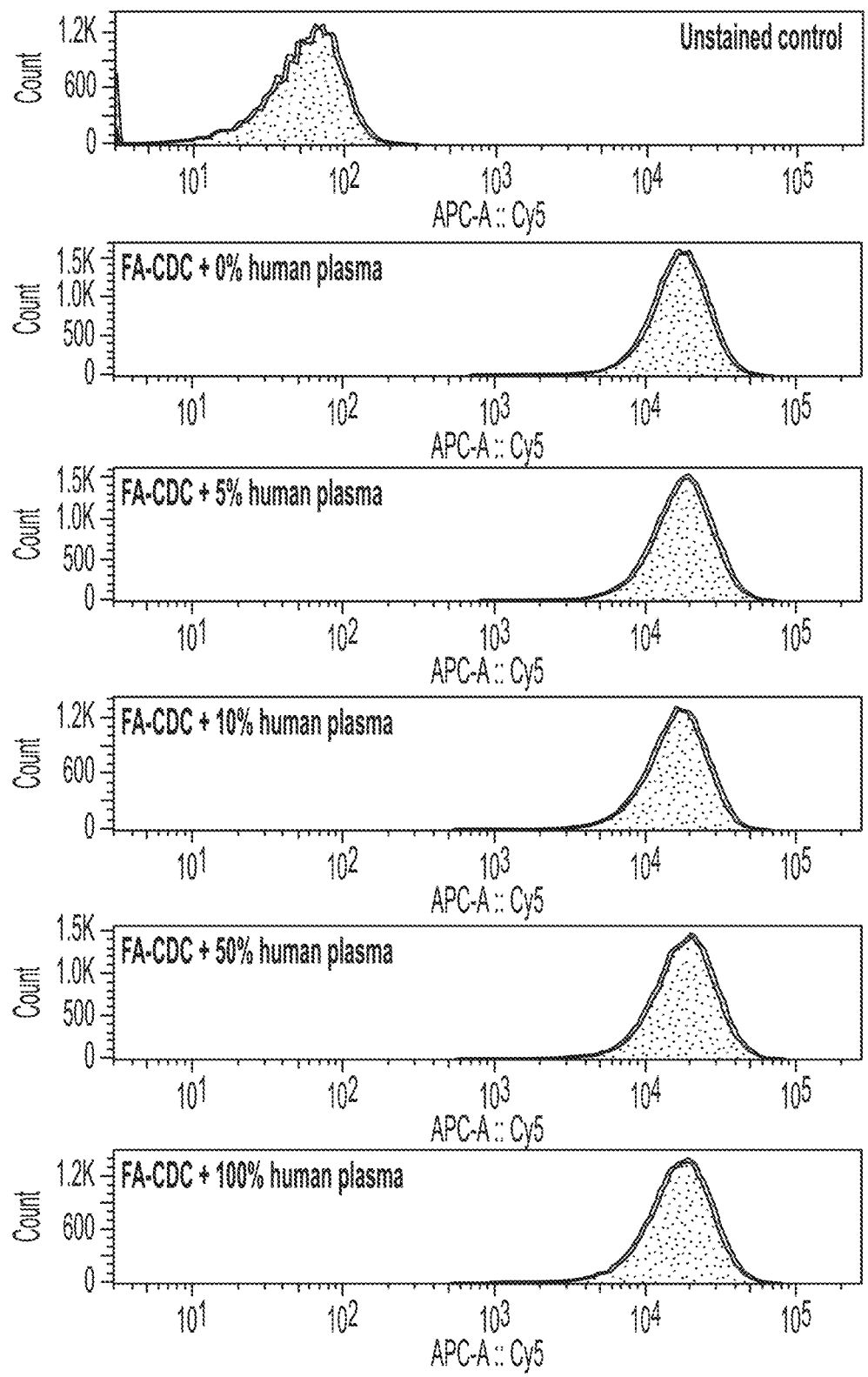
FIG. 16 depicts the flow cytometry of a representative NDC (folic acid (FA)-functionalized drug-linker conjugated C'Dot (FA-CDC)) at 1 nM that was pre-incubated with varied amounts of human plasma for 24 hours. Blocking in the blocking group was achieved with 1 mM of free folic acid. The exatecan-linker conjugate precursor used to prepare the NDC used in the study is described in Example 1 (Compound 202), to provide an average of 25 exatecan molecules per nanoparticle. The average number of folic acid ligands per nanoparticle was 15. CDC with no folic acid, but same amount of drug linkers was used as the negative control group.
Figure 16:
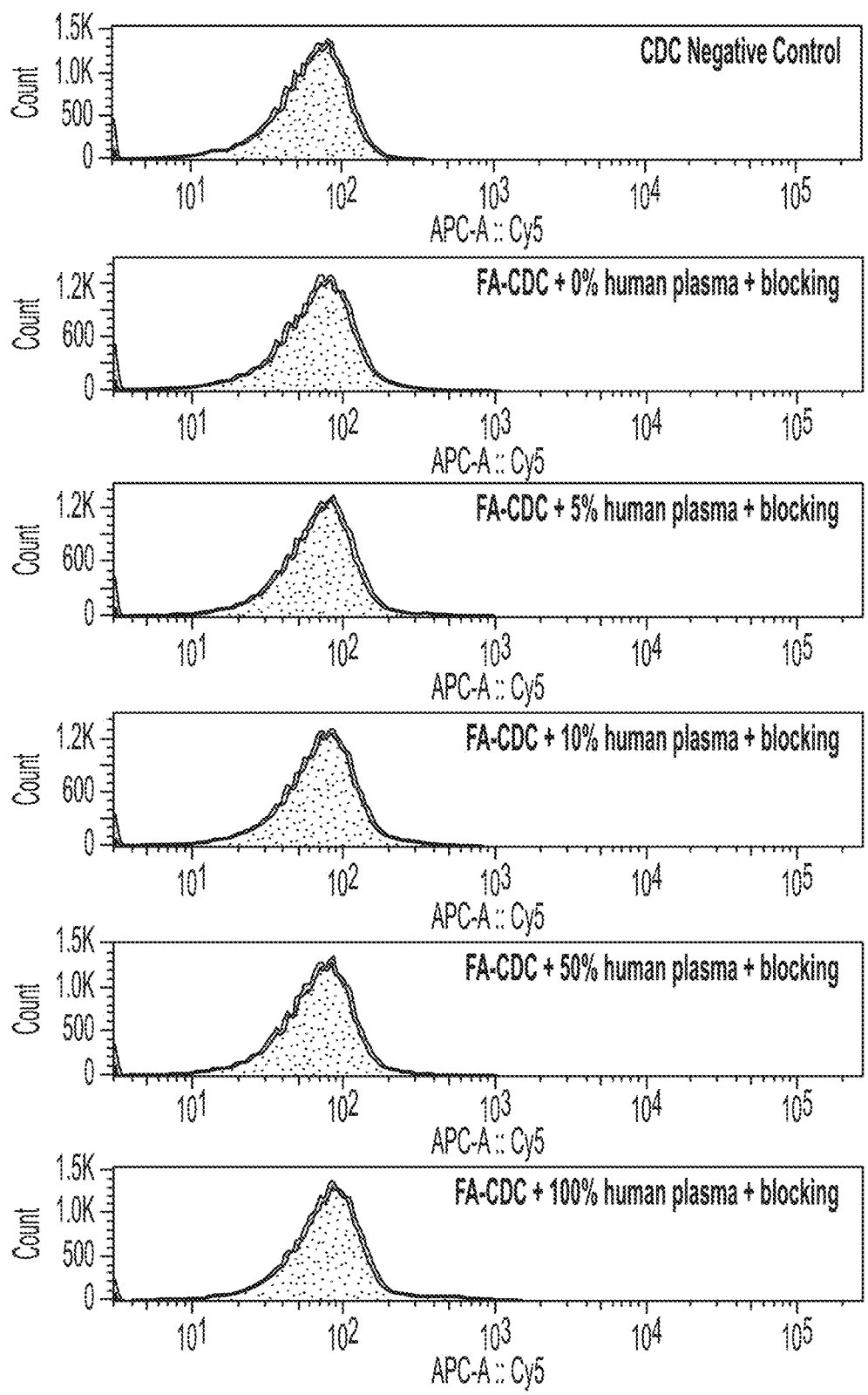

Pre-incubating NDCs in human plasma did not negatively affect folate receptor targeting ability. This study was designed to test the possible negative impact of human plasma on the NDCs, such as the formation of protein corona. The formation of protein corona and its negative impact on the designed active targeting capability of drug delivery system has been well documented in the literature. The results of this flow cytometry study are depicted in FIG. 16, which show nearly unchanged folate receptor targeting efficacy of NDCs at 1 nM, after pre-incubation with varied amounts of human plasma for 24 hours. The NDCs were prepared according to the method of Example 3, using the exatecan-payload conjugate precursor of Example 1 (Compound 202). The blocking group involved blocking with 1 mM of free folic acid. This study clearly demonstrated that the formation of a protein corona (if any) on the NDC had nearly no negative impact on the in vitro targeting capability of the NDCs.

Example 6: In Vitro Cell Viability Assay

The in vitro cytotoxicity of the NDCs disclosed herein were tested in cancer cells. The cancer cells were cultured in folic acid-free medium (RPMI1640, ThermoFisher, GIBCO) for at least one week before the study. Cells were plated in opaque 96-well plates at a density of $3 \times 10^3$ cells per well (total of 90 mL) and allowed to attach overnight. The following day, cells were treated with NDC (prepared according to Example 3) at a concentration range of 0-50 nM (0, 0.001, 0.005, 0.01, 0.05, 0.1, 0.5, 1, 5, 10, 50 nM) by adding 10 mL of 10× stock FA-CDC solution.

Cells were treated for a pre-defined exposure time (depending on the study design, e.g., 4-6 hours, or 7 days). In the case of short-exposure-time viability study, cancer cells in each wells were washed with 100 mL PBS and refreshed with 100 mL of cell medium. After washing, the plates were returned back to 37° C. incubator for 7 days before the viability assay. In the case of 7-day-exposure-time viability study, no additional washing step was performed. After 7 days, the cell viability was assessed using the CellTiter-Glo2.0 assay (Promega) according to manufacturer's instructions. Data for both viability and proliferation were plotted using Prism7 software (GraphPad). Representative cell viability results of six FA-CDCs with similar surface density of Folic Acid targeting ligands and drug linkers is presented in provided in Table 3.

TABLE 3
Representative cell viability results of NDCs with similar surface density of folic acid targeting ligands and linker-drug conjugates.
| Payload-Linker Conjugate | IC$_{50}$ in KB cell line (nM) | IC$_{50}$ in SKOV-3 cell line (nM) |
|---|---|---|
| 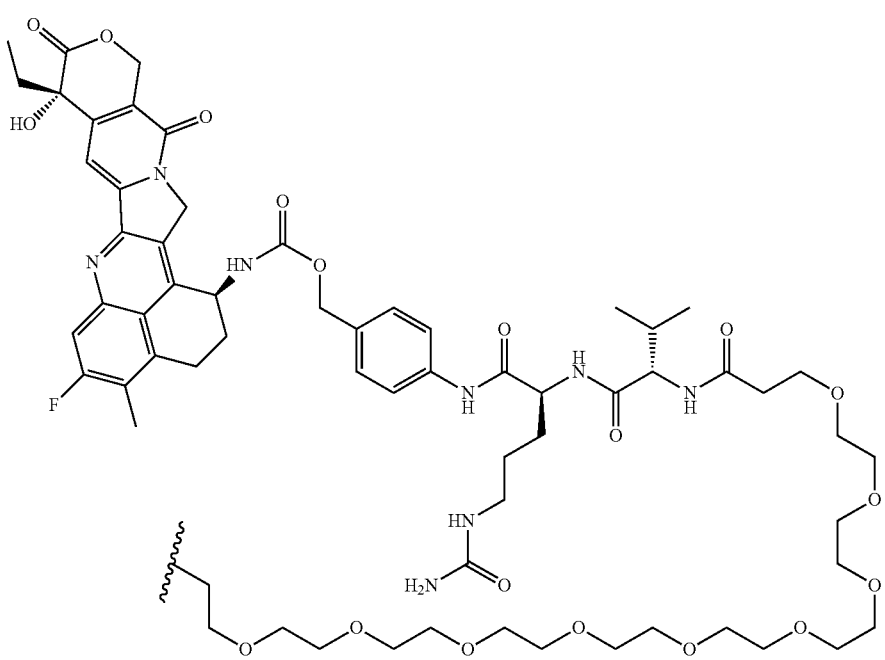 [SMILES: *CCOCCOCCOCCOCCOCCOCCOCCOCCOCCC(=O)N[C@H](C(=O)N[C@@H](CCCNC(N)=O)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C] | 0.2-5.2 | 10.7 |
| 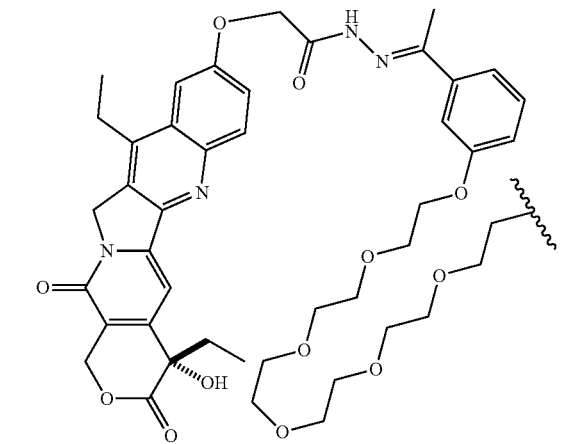 [SMILES: *CCOCCOCCOCCOCCOCCOc1cccc(/C(C)=N/NC(=O)COc2ccc3nc4c(c(CC)c3c2)Cn2c-4cc3c(c2=O)COC(=O)[C@]3(O)CC)c1] | 0.5-1.0 | 17.9 |

TABLE 3-continued

Representative cell viability results of NDCs with similar surface density of folic acid targeting ligands and linker-drug conjugates.

| Payload-Linker Conjugate | IC$_{50}$ in KB cell line (nM) | IC$_{50}$ in SKOV-3 cell line (nM) |
| --- | --- | --- |
| | 0.7-7.2 | n.t. |
| | 17.5 | n.t. |
| | 0.2-2.2 | 0.4 |

TABLE 3-continued
Representative cell viability results of NDCs with similar surface density of folic acid targeting ligands and linker-drug conjugates.
| Payload-Linker Conjugate | IC$_{50}$ in KB cell line (nM) | IC$_{50}$ in SKOV-3 cell line (nM) |
|---|---|---|
| 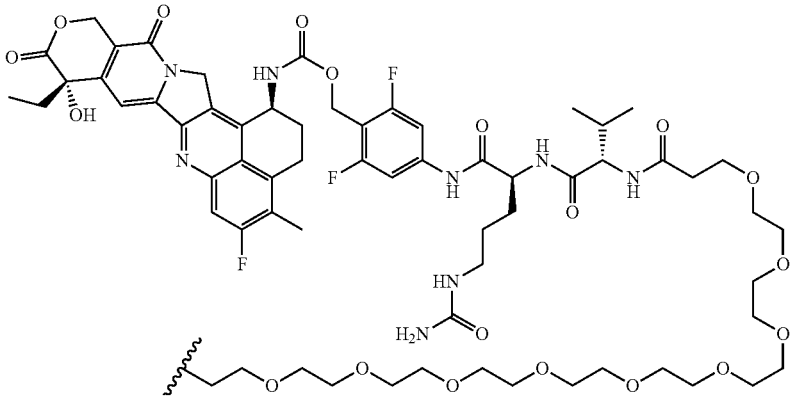 [SMILES: *CCOCCOCCOCCOCCOCCOCCOCCOCCOCCC(=O)N[C@H](C(=O)N[C@@H](CCCNC(N)=O)C(=O)Nc1cc(F)c(COC(=O)N[C@H]2CCc3c(C)c(F)cc4nc5c(c2c34)Cn2c-5cc3c(c2=O)COC(=O)[C@]3(O)CC)c(F)c1)C(C)C] | 5.2 | n.t. |
| 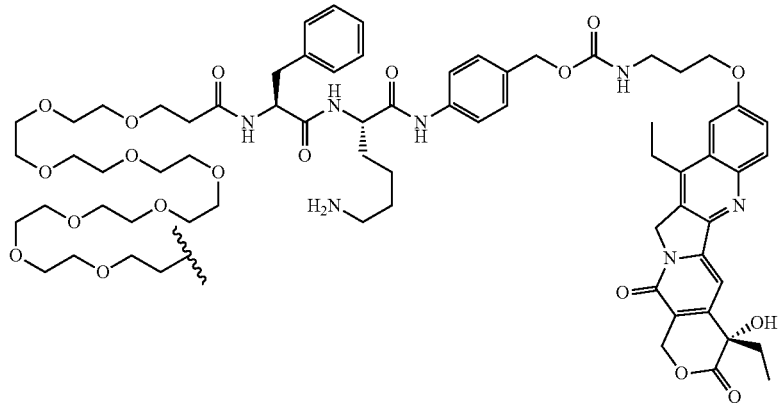 [SMILES: *CCOCCOCCOCCOCCOCCOCCOCCOCCOCCC(=O)N[C@@H](Cc1ccccc1)C(=O)N[C@@H](CCCCN)C(=O)Nc1ccc(COC(=O)NCCCOc2ccc3nc4c(c(CC)c3c2)Cn2c-4cc3c(c2=O)COC(=O)[C@]3(O)CC)cc1] | 72.2 | n.t. |
| 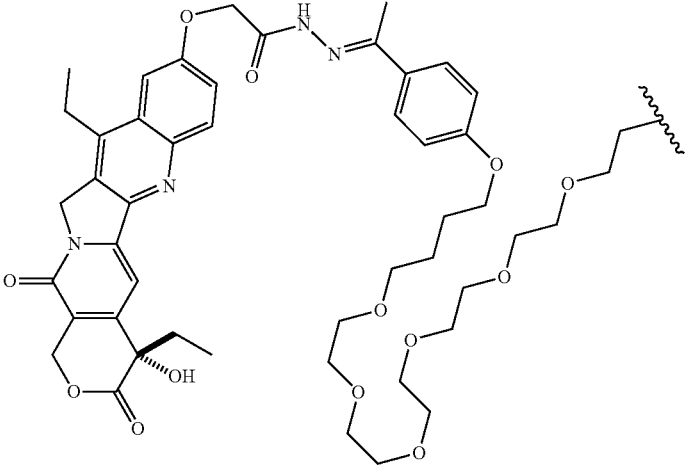 [SMILES: *CCOCCOCCOCCOCCOCCOCCCCOc1ccc(/C(C)=N/NC(=O)COc2ccc3nc4c(c(CC)c3c2)Cn2c-4cc3c(c2=O)COC(=O)[C@]3(O)CC)cc1] | 42.7 | n.t. |

TABLE 3-continued
Representative cell viability results of NDCs with similar surface density of folic acid targeting ligands and linker-drug conjugates.
| Payload-Linker Conjugate | IC$_{50}$ in KB cell line (nM) | IC$_{50}$ in SKOV-3 cell line (nM) |
|---|---|---|
| 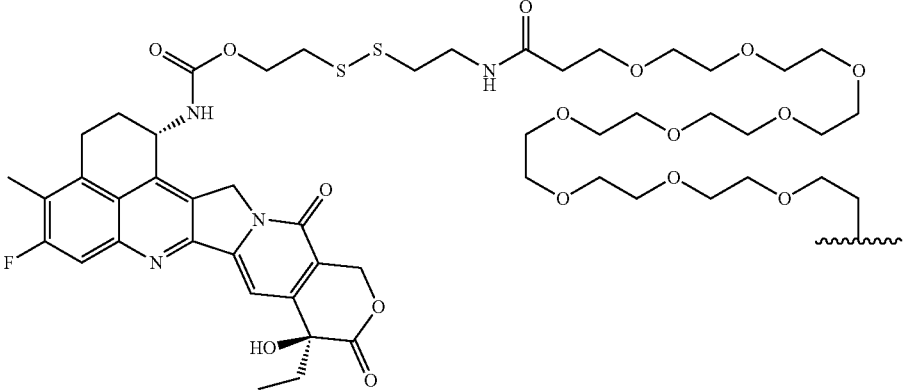 [SMILES: *CCOCCOCCOCCOCCOCCOCCOCCOCCOCCC(=O)NCCSSCCOC(=O)N[C@H]1CCc2c(C)c(F)cc3nc4c(c1c23)Cn1c-4cc2c(c1=O)COC(=O)[C@]2(O)CC] | 0.6 | 0.9 |
| 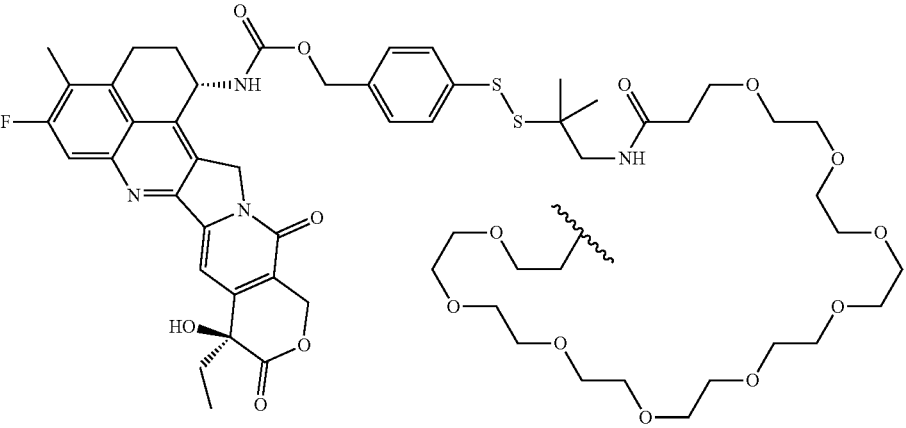 [SMILES: *CCOCCOCCOCCOCCOCCOCCOCCOCCOCCC(=O)NCC(C)(C)SSc1ccc(COC(=O)N[C@H]2CCc3c(C)c(F)cc4nc5c(c2c34)Cn2c-5cc3c(c2=O)COC(=O)[C@]3(O)CC)cc1] | 49.4 | n.t. |
| 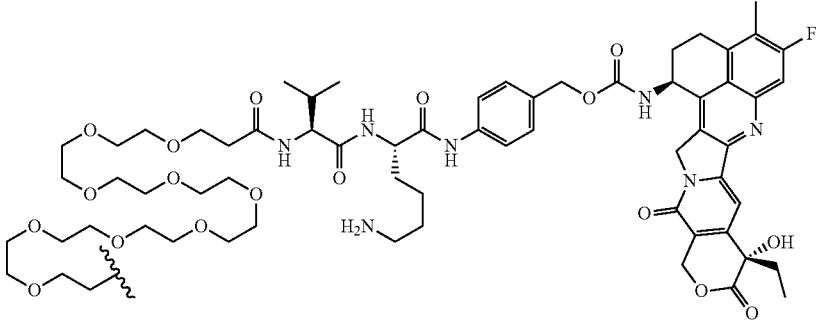 [SMILES: *CCOCCOCCOCCOCCOCCOCCOCCOCCOCCC(=O)N[C@H](C(=O)N[C@@H](CCCCN)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C] (prepared from 202, Example 1) | 0.3 | 0.13 |

Number of FA ligands per particle is between 12 and 22; Number of linker-drug conjugates per particle is between 17 and 25. Each payload-linker is conjugated to the NDC via a DBCO moiety (prepared according to the protocol outlined in Example 3).

Example 7: Two-Dimensional (2D) Confocal Imaging of NDC in Cancer Cells

A 2D confocal imaging study was carried out to determine the targeting of cells with varying levels of folate-receptor availability, using two exemplary NDCs. The cells with high folate-receptor expression (denoted ++++) were KB cells. The cells with no FR expression (denoted (–)) were TOV-112D cell line. FR-blocked cells were also used.

KB cells were maintained in folic acid free RPMI 1640 media with 10% FBS, 1% penicillin/streptomycin. TOV-112D cells were maintained in 1:1 mixture of MCDB 105 medium containing a final concentration of 1.5 g/L sodium bicarbonate and Medium 199 containing a final concentration of 2.2 g/L sodium bicarbonate, supplemented with 15% FBS and 1% penicillin/streptomycin. Cells were trypsinized and seeded in 8-well Lab-Tek chambered coverglass, at 1.0×105 cells per well, and cultured overnight to allow for attachment.

The NDCs were prepared according to Example 3 and are displayed below in Table 4. NDC D was prepared using the linker-payload conjugate (202) described in Example 1.

TABLE 4

Exemplary NDCs used in 2D Confocal Imaging Assay.

| NDC | Exatecan-Linker Conjugate |
|---|---|
| B | 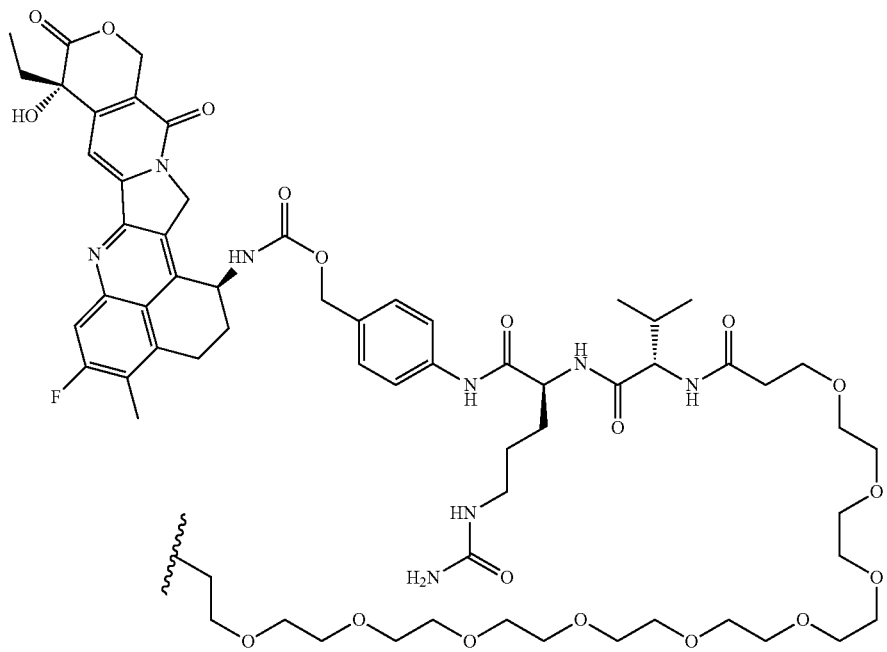 [SMILES: *CCOCCOCCOCCOCCOCCOCCOCCOCCOCCC(=O)N[C@H](C(=O)N[C@@H](CCCNC(N)=O)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C] |
| D | 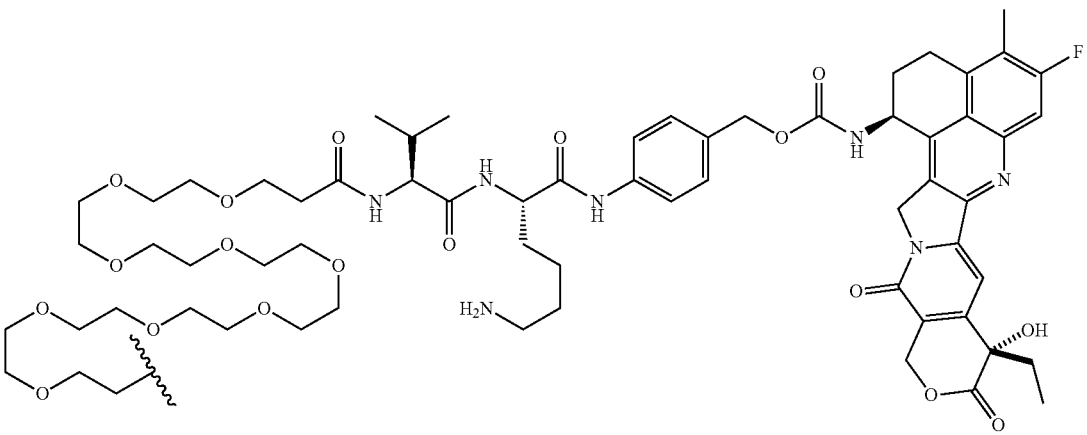 [SMILES: *CCOCCOCCOCCOCCOCCOCCOCCOCCOCCC(=O)N[C@H](C(=O)N[C@@H](CCCCN)C(=O)Nc1ccc(COC(=O)N[C@H]2CCc3c(C)c(F)cc4nc5c(c2c34)Cn2c-5cc3c(c2=O)COC(=O)[C@]3(O)CC)cc1)C(C)C] (prepared from 202, Example 1) |

Before incubation with NDC, cells were washed once with folic acid free RPMI 1640 media. The NDC was added into folic acid free RPMI 1640 media to final concentration of 50 nM. For blocking conditions, folic acid (20 mM stock dissolved in 0.1 M NaOH) was added to final concentration of 0.1 mM and co-incubated with NDC. Cells were incubated with NDC at 37° C. for either 1 hours or 24 hours. After incubation, cells were washed three times. To stain lysosomes, LysoTracker Green DND-26 (Thermo Fisher Cat. L7526, ex/em504/511 nm) was added to final concentration of 100 nM in folic acid free RPMI 1640 media with 10% FBS, 1% P/S, and incubated at 37° C. for 45 min. Cells were washed once to remove remaining lysotracker dyes. To stain nuclei, Hoechst 33342 solution (Thermo Fisher Cat. 62249, 20 mM) was diluted 1:4000 in Folic Acid free RPMI 1640 media with 10% FBS, 1% P/S, and incubated at 37° C. for 10 min. Cells were washed once, and media was exchanged to phenol red free RPMI 1640 media for confocal imaging using Nikon spinning disk confocal microscope, 60× objective, 405 nm, 488 nm, 640 nm laser lines, exposure time 100 ms for 405 channel, 500 ms for 488 channel, and 600 ms for 640 channel.

Results from confocal microscope imaging of NDC in KB (++++) and TOV-112D(−) cell lines at 1 hour time point showed that NDC were mainly present at the cell membrane of KB cells, which express high level of folate receptors, but not in blocking conditions or folate negative cell line TOV-112D, suggesting specific binding of NDC to folate receptors. After 24 hours, membrane bound NDC were internalized and the amount of internalized NDC significantly increased as compared with 1 hour time point. The internalized NDC were localized in acidic organelles stained by LysoTracker, indicating that the trafficking of NDC occurred though the endo-lysosomal pathway. The effect of serum on the binding capability of NDC was also investigated by pre-incubating NDCs in media supplemented with 10% FBS overnight, prior to incubating them with cells, and no significant difference was observed (data not shown), suggesting that the presence of serum had no impact on the binding capability of NDCs.

Figure 17:
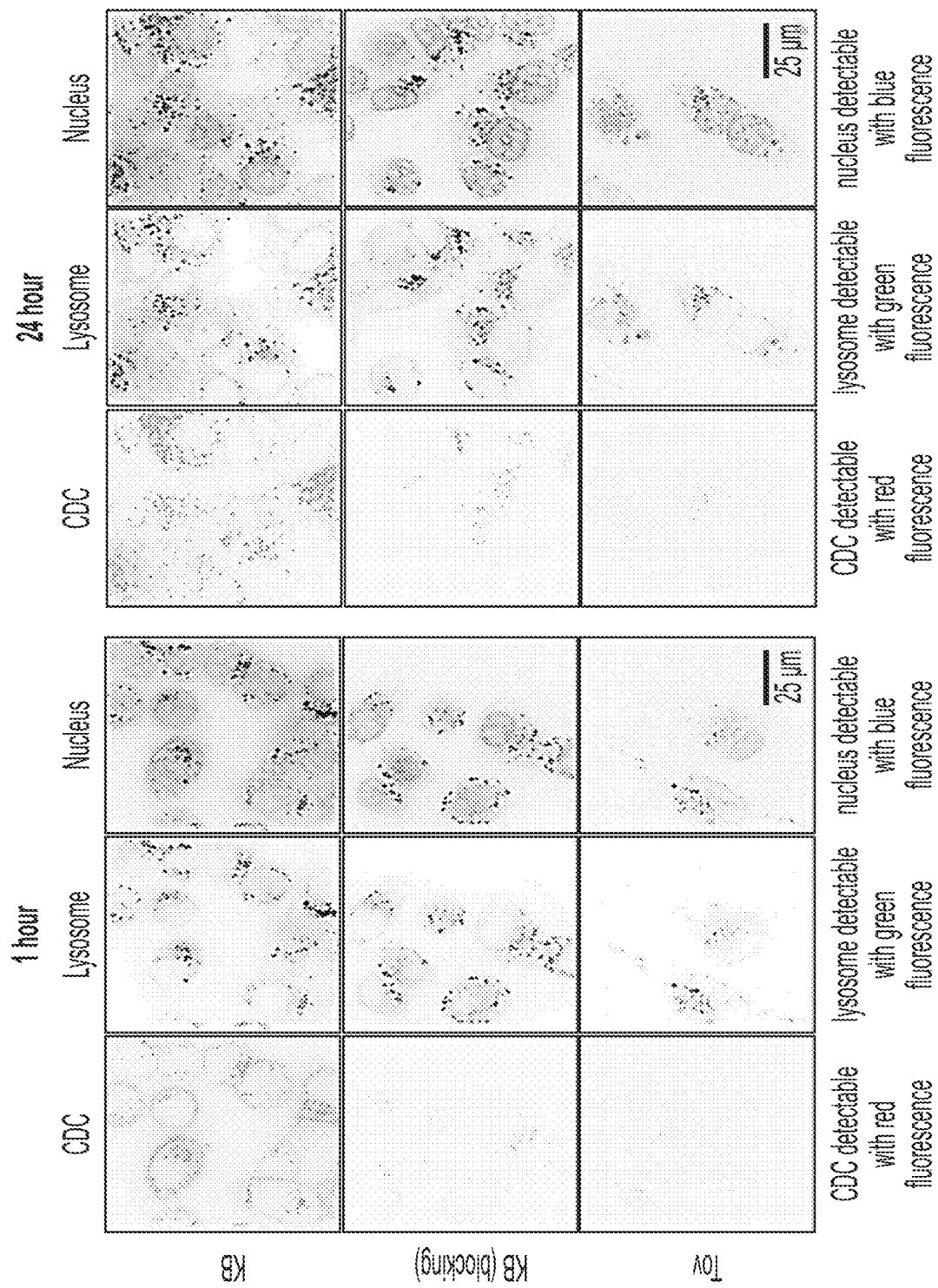
FIG. 17 shows the confocal microscopy images of an exemplary NDC (folic acid (FA)-functionalized drug-linker conjugated C'Dot (FA-CDC), shown in Examples as NDC B) in KB (++++) and TOV-112D (−) cell lines at 1 hour and 24 hours. Blocking in the blocking group was achieved using 0.1 mM of free folic acid. The average number of folic acid ligands on the FA-CDC (NDC B) is 12, and the number of exatecan-linker conjugates is 40). The lysosome was stained by using LysoTracker® Green, which is a green-fluorescent dye for labeling and tracking acidic organelles in live cells. With color images (not shown), the CDC appears red, the lysosome appears green, and the nucleus appears blue, due to fluorescence.
Figure 32:
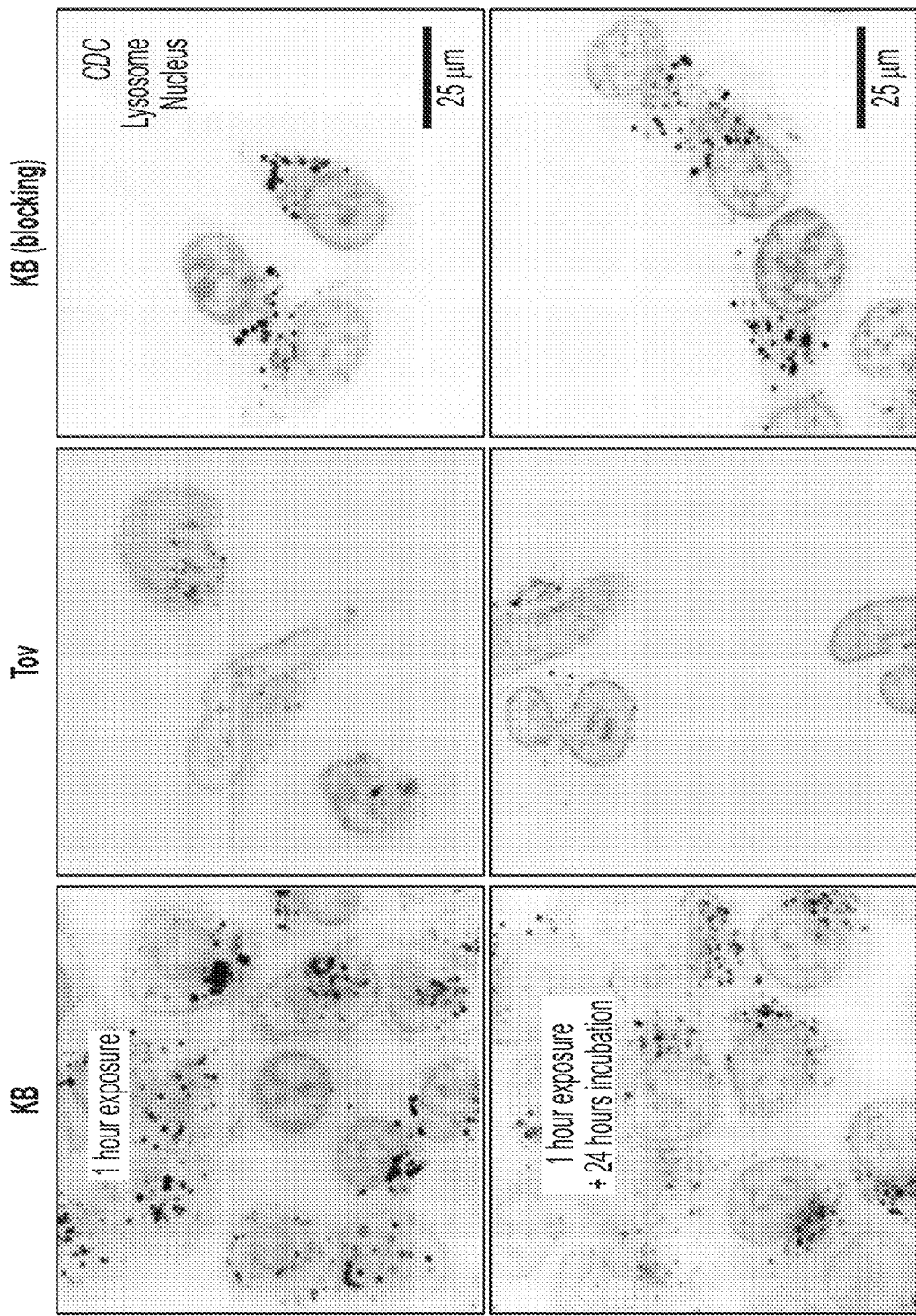
FIG. 32 shows the confocal microscopy images of an exemplary NDC (folic acid (FA)-functionalized drug-linker conjugated C'Dot (FA-CDC), shown in Examples as NDC D, prepared using exatecan-linker conjugate precursor 202) in KB (++++) and TOV-112D (−) cell lines after 1 hour and 24 hours. Blocking in the blocking group was achieved using 0.1 mM of free folic acid. The lysosome was stained by using LysoTracker® Green, which is a green-fluorescent dye for labeling and tracking acidic organelles in live cells. With color images (not shown), the CDC appears red, the lysosome appears green, and the nucleus appears blue, due to fluorescence.

These results of confocal microscopy of NDC B are provided in FIG. 17, and results for NDC D are provided in FIG. 32. These images demonstrated the highly specific active targeting and lysosome trafficking of the NDCs of the present disclosure, indicating that once the FA-targeting NDCs bind to cells they become internalized in folate receptor positive cell lines, where the exatecan payload may be cleaved (e.g., by cathepsin-B) to release free exatecan in the cancerous cell.

Example 8: Confocal Imaging of FA-CDC in 3D Tumor Spheroid Model in KB Cells

A 3D tumor spheroid model assay was conducted to determine the tumor penetration of the NDCs disclosed herein. The assay compared an exemplary NDC (prepared according to Example 3, using exatecan-linker conjugate precursor 202 of Example 1), with a payload-free FA-targeting nanoparticle (also prepared according to Example 3, with only the FA precursor and without exatecan-payload conjugate precursor); a folate receptor (FR)-targeting ADC; and the corresponding payload-free FR-targeting antibody. The FR-targeting antibody was prepared based upon the published sequence of mirvetuximab (provided in U.S. Pat. No. 9,637,547 as huMov19; the contents of which are incorporated herein by reference in its entirety). The ADC was prepared with the same antibody and was conjugated to the maytansinoid drug DM4 (created by Syngene International Ltd.) via a 4-(pyridin-2-yldisulfanyl)-2-sulfo-butyric acid (sSPDB) linker (based on the linker used in U.S. Pat. No. 9,637,547). The ADC and antibody were each conjugated with Cy5 organic dye, by reaction with Cy5-NHS ester, and were purified by a PD-10 column.

Coming ultra-low attachment surface 96-well spheroid microplates were utilized in seeding KB cells for having KB spheroids with cell density 10,000/well. Single-cell suspensions were generated from trypsinized monolayers and diluted to 100,000 cells/mL using RPMI medium (folic acid free). 100 mL of cell suspension were dispensed into each well of a microplate. The plate was kept in an incubator for 24 hours for cells forming spheroids. KB cell spheroids can be easily observed by microscope with 10× objective.

3D KB spheroids formed after overnight culturing in an ultra-low 96-well microplates. NDC (prepared according to Example 3, using exatecan-linker conjugate precursor 202 of Example 1), folate-targeted nanoparticles ("FA-C'Dot"), FR-targeted ADC, or payload-free FR-targeted-antibody were added into wells (n=3) with 50 nM final concentration and incubated for 4 hours at 37° C. Each treated KB spheroid and control spheroid were washed with PBS for three times and then carefully transferred to a glass bottom 96-well plate (Cellvis) for observation by Nikon AIR-STED confocal microscope, using laser line 640 nm, 20× objective. Z-stacks were acquired by taking 2-dimensional images each separated by 1 m in the Z-direction.

Figure 18:
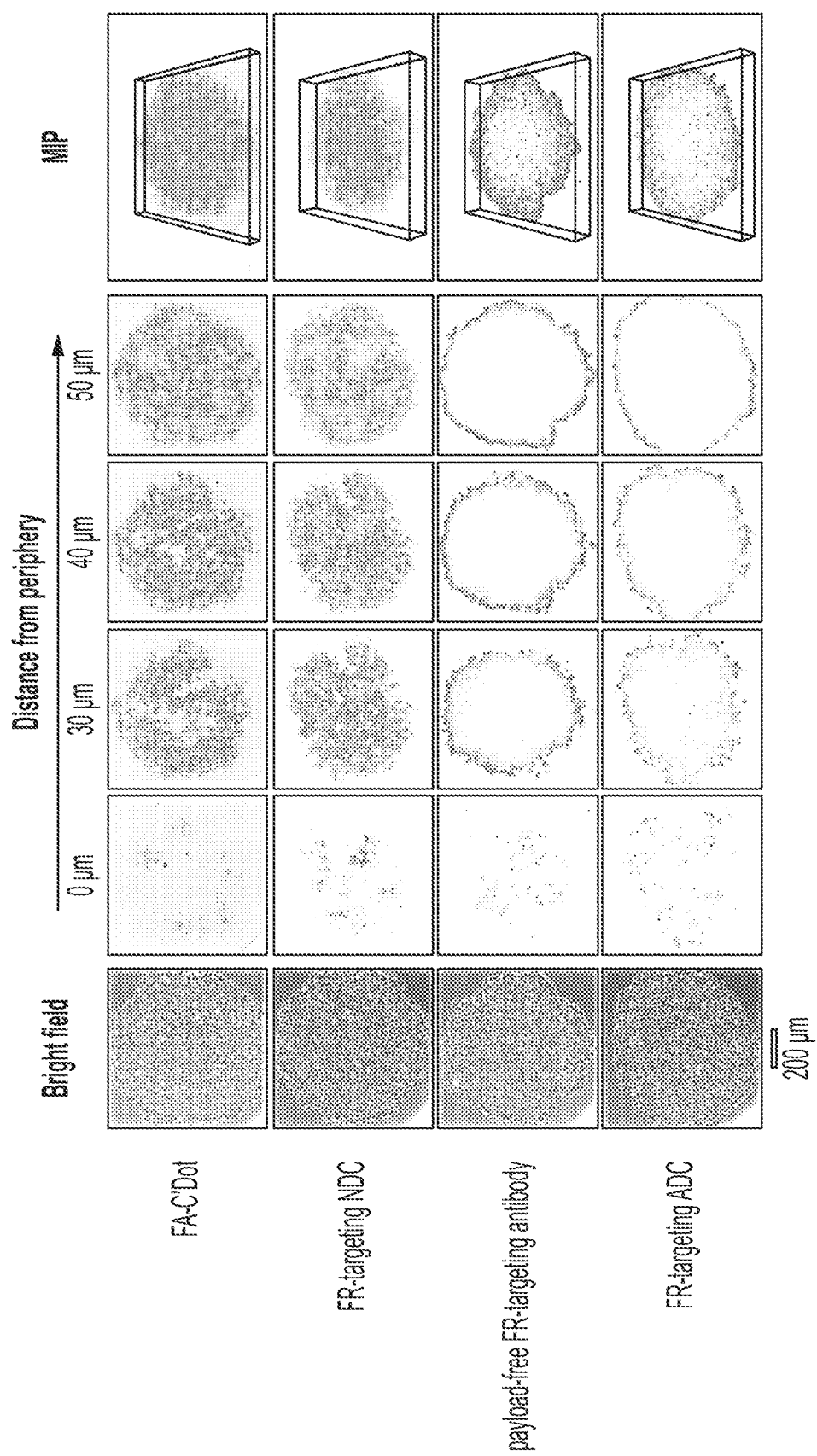
FIG. 18 is an image comparing the Z-stack confocal microscopic imaging of KB tumor spheroids treated with an exemplary folate-receptor (FR)-targeting NDC (NDC D, prepared according to Example 3 using the exatecan-linker conjugate precursor 202), a payload-free FR-targeting nanoparticle (FA-C'Dot), a FR-targeting ADC, or the corresponding payload-free FR-targeting antibody, at 37° C. for 4 hours, followed by washing. Scale bar: 200 m.

Results from the Z-stack confocal microscope imaging of KB tumor spheroid treated with the NDC, FA-C'Dot, FR-targeted ADC, and payload-free FR-targeted antibody is depicted in FIG. 18. The results show that the penetration and well diffusion of NDC and FA-C'Dots throughout the whole >800 mm of tumor spheroids. In contrast, labeled antibody and ADC merely accumulated around, but not inside of, the tumor spheroids. The ability of the NDCs disclosed herein to achieve efficient tumor penetration is highly advantageous, and shows significant improvement compared to conventional drug delivery platforms.

Example 9: $^{89}$Zr Radiolabeling of DFO-FA-CDC and In Vivo Static PET/CT and Biodistribution Studies A radiolabeling assay was conducted to determine the in vivo biodistribution of the folate receptor-targeting NDCs of the present disclosure. The NDCs used for the assay were conjugated with the chelator desferrioxamine (DFO) and then bound with a radionuclide ($^{89}$Zr).

For a typical $^{89}$Zr labeling, about 1 nmol of DFO-conjugated NDC were mixed with 1 mCi of $^{89}$Zr-oxalate (produced and provided by University of Wisconsin-Madison Cyclotron group) in HEPES buffer (pH 8) at 37° C. for 60 min; final labeling pH was kept at 7-7.5. The labeling yield could be monitored by using radio instant thin-layer chromatography (iTLC). An ethylenediaminetetraacetic acid (EDTA) challenge procedure was then introduced to remove any nonspecifically bound $^{89}$Zr from the particle surface. As-synthesized labeled NDC ($^{89}$Zr-DFO-FA-CDC) were then purified by using a PD-10 column. The final radiochemical purity was quantified by using iTLC.

For PET/CT imaging, healthy nude mice (n=3) were i.v.-injected with 200-300 µCi (7.4-11.1 MBq) $^{89}$Zr-DFO-FA-CDC. Approximately 5 min prior to the acquisition of PET/CT images, mice were anesthetized by inhalation of 2% isoflurane/oxygen gas mixture and placed on the scanner bed; anesthesia was maintained using 1% isoflurane/gas mixture. PET/CT imaging was performed in a small-animal PET/CT scanner (Inveon microPET/microCT) at 1-2, 24, 48, and 72 h post-injection. An energy window of 350-700 keV and a coincidence timing window of 6 ns were used. Data were sorted into 2D histograms by Fourier rebinning, and transverse images were reconstructed by filtered back-projection into a 128×128×63 (0.72×0.72×1.3 mm3) matrix. The PET/CT imaging data were normalized to correct for nonuniformity of response, dead-time count losses, positron branching ratio, and physical decay to the time of injection; no attenuation, scatter, or partial-volume averaging corrections were applied. The counting rates in the reconstructed images were converted to activity concentrations (percentage injected dose per gram of tissue, % ID/g) by use of a system calibration factor derived from the imaging of a mouse-sized water-equivalent phantom containing $^{89}$Zr. Region-of-interest (ROI) analyses of the PET data were performed using IRW software. At 72 h post-injection, organs from each individual mouse were collected, wet-weighted and gamma counted (Automatic Wizard2 γ-Counter, PerkinElmer). The uptake of $^{89}$Zr-DFO-FA-CDC was presented as % ID/g (mean±SD).

The NDCs of the present disclosure enable precise tumor targeting, deep tumor penetration and high tumor killing efficacy. The NDCs can be cleared rapidly and efficiently from the body, which reduces the potential for off-target toxicities and results in an improved safety profile. The NDCs disclosed herein (comprising targeting ligands (folic acid) and payload (exatecan)) can be administered to a subject and circulate through the blood stream, target the cancer (e.g., tumor), diffuse, penetrate, internalize, and cleave the exatecan payload, killing the cancer cells.

Figure 19A:
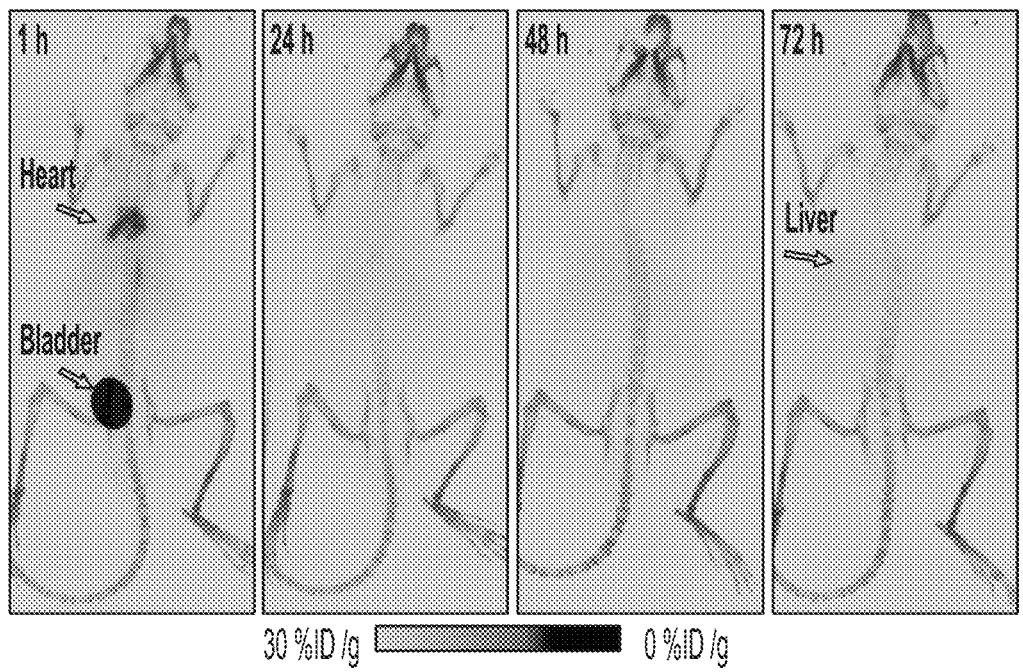
FIG. 19A depicts a representative maximum intensity projection (MIP) PET/CT imaging of healthy nude mice injected with $^{89}$Zr-DFO-FA-CDC at 1, 24, 48 and 72 hours post-injection.
Figure 19B:
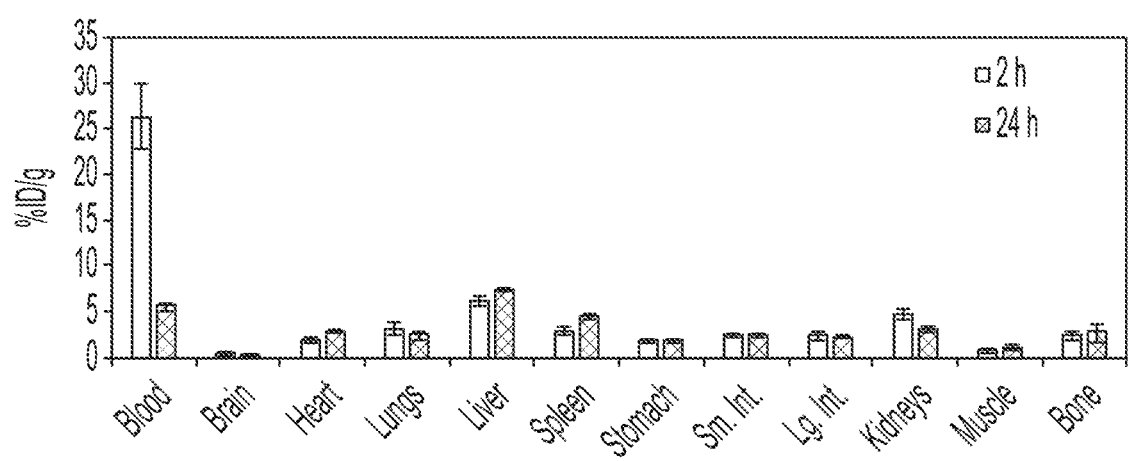
FIG. 19B illustrates the biodistribution pattern of $^{89}$Zr-DFO-FA-CDC in healthy nude mice at 2 and 24 hour post-injection (n=3). The exatecan-linker conjugate precursor used to prepare the NDC used in the study is described in Example 1 (Compound 202); the average number of folic acid ligands on each NDC (FA-CDC) is 12; and the average number of exatecan-linker conjugates on each NDC is 25.

In this study, the renal clearance and biodistribution pattern of FA-CDC were tested. As shown in FIG. 19A, after the intravenous injection, the $^{89}$Zr-DFO-FA-CDC circulated in the blood stream of healthy nude mouse, as indicated by the high radioactive signal from the heart and artery. Dominant radioactive signal can also be seen from the mouse bladder, demonstrate the renal clearance of the NDC. After 24 h, the majority of the injected $^{89}$Zr-DFO-FA-CDC was cleared out of the mouse body. The changes in biodistribution pattern at 2 hours and 24 hours post-injection is also shown in FIG. 19B. As expected, the NDC can circulate in the blood stream with a dominant renal clearance pathway, whilst avoiding clearance by the mononuclear phagocytic system (MPS) (i.e., liver and spleen).

Example 10: Human KB Tumor Model and In Vivo Efficacy Study

The in vivo efficacy of the NDC was carried out using a human KB tumor mouse model. The assay compared the NDC prepared according to Example 3 using the exatecan-payload conjugate precursor 202 (Example 1; here labeled D, and shown in FIG. 20D, with the NDCs indicated in Table 5 below (NDCs A-C and E-F). Each NDC was compared to a control and free exatecan, and NDCs E and F were compared to free exatecan and irinotecan (CPT-11).

TABLE 5

Exemplary NDCs used in the in vivo efficacy study.

| NDC | Payload-Linker Conjugate |
|---|---|
| A | |

TABLE 5-continued
Exemplary NDCs used in the in vivo efficacy study.
| NDC | Payload-Linker Conjugate |
|---|---|
| B | 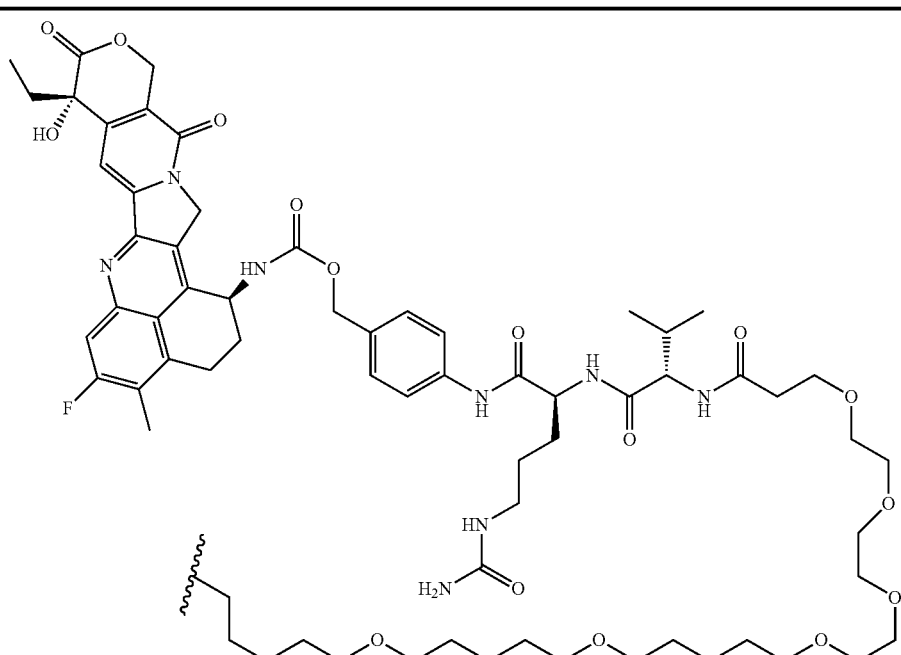 |
| C | 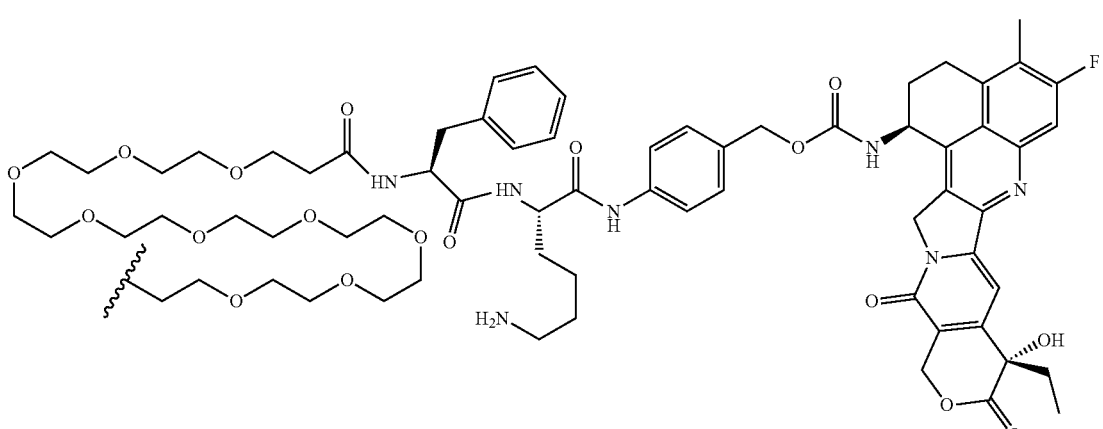 |
| D | 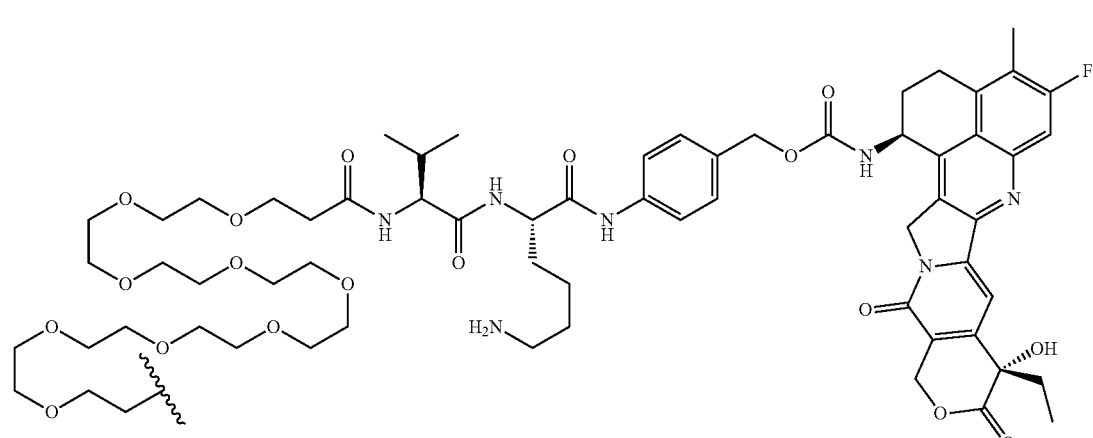 |
(prepared from 202, Example 1)

TABLE 5-continued

Exemplary NDCs used in the in vivo efficacy study.

| NDC | Payload-Linker Conjugate |
| --- | --- |
| E | [chemical structure] |
| F | [chemical structure] |

Number of FA ligands per particle is between 12 and 22; Number of linker-drug conjugates per particle is between 17 and 25. Each payload-linker is conjugated to the NDC via a DBCO moiety (prepared according to the protocol outlined in Example 3).

Human KB cell line was purchased from ATCC and maintained in folic acid free RPMI 1640 media/10% FBS, and 1% of penicillin/streptomycin, unless otherwise specified. Once the KB cells were cultured to reach an adequate cell count, the cell viability was confirmed by a hemocytometer and trypan blue staining assay. For subcutaneous implantation, each mouse was injected with KB cells at a density of 2×106 cells/mice at 0.1 mL Matrigel/cell dilution volume per injection on the left lower flank of the thigh. Once a subcutaneous tumor volume has reached a palpable size of 75 to 150 mm$^3$ in a required number of mice for this study, the mice was randomized and assigned to each treatment cohort resulting with comparable tumor volume statistics. Following randomization and study cohort assignment, each dose cohort was treated according to the routes of administration, dosage and schedule.

Two dose levels of each of NDCs B-D were used in the efficacy study (only one dose level for NDCs A, E and F). Tumor volume measurements were performed using a calibrated caliper every second day during the dose treatment period, followed by twice weekly measurements during the recovery period of the in-life phase, and tumor volumes were determined using the formula length (mm)×width (mm)×width (mm)×0.50. Body weight measurements were performed every second day during the dose treatment period, followed by twice weekly measurements during the recovery period of the in-life phase. Mice were euthanized when the end points of the study reached 1000 mm$^3$. Tumors were harvested and tumor size was measured. Tumor were surgically excised and snap-frozen for storage at −80° C. until future analysis.

Figures 20A, 20B, 20C:
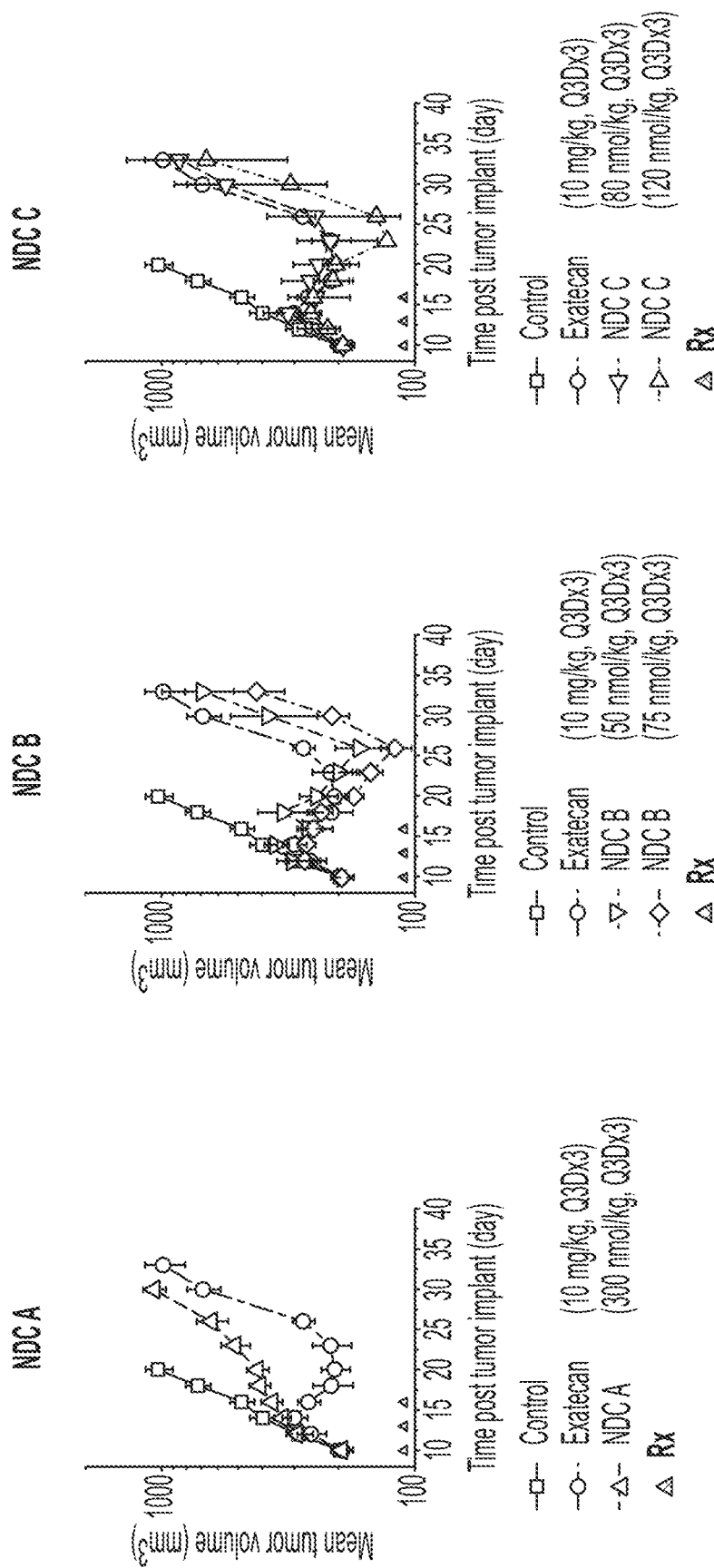
FIGS. 20A-20F depicts the in vivo tumor growth inhibition studies of six exemplary folate receptor targeting NDCs (NDCs A-F) in KB tumor-bearing mice (n=7). NDC-A comprises about 19 drug-linker conjugate groups and about 18 folic acid ligands per nanoparticle. NDC B comprises about 25 drug-linker groups and about 15 folic acid ligands per nanoparticle. NDC C comprises about 19 drug-linker conjugate groups and about 13 folic acid ligands per nanoparticle. NDC D comprises about 25 drug-linker conjugate groups and about 12 folic acid ligands per nanoparticle. NDC E comprises about 17 drug-linker conjugate groups and about 17 folic acid ligands per nanoparticle. NDC F comprises about 23 drug-linker conjugate groups and about 20 folic acid ligands per nanoparticle.
Figure 20F:
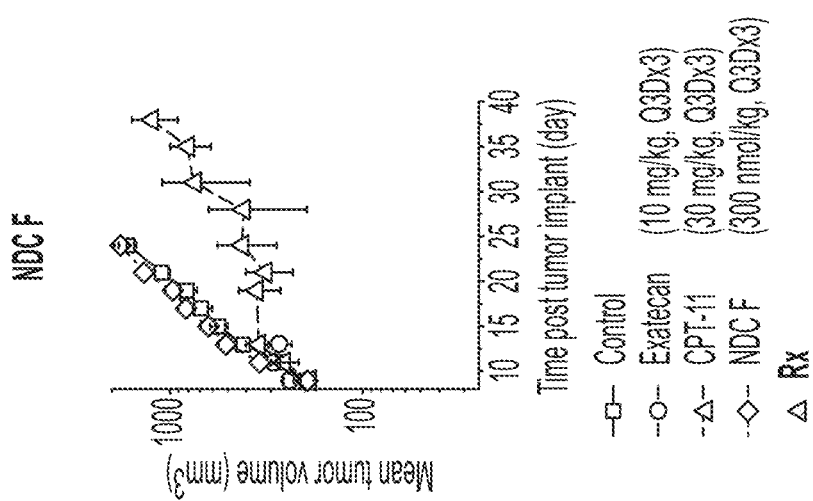
Figure 20E:
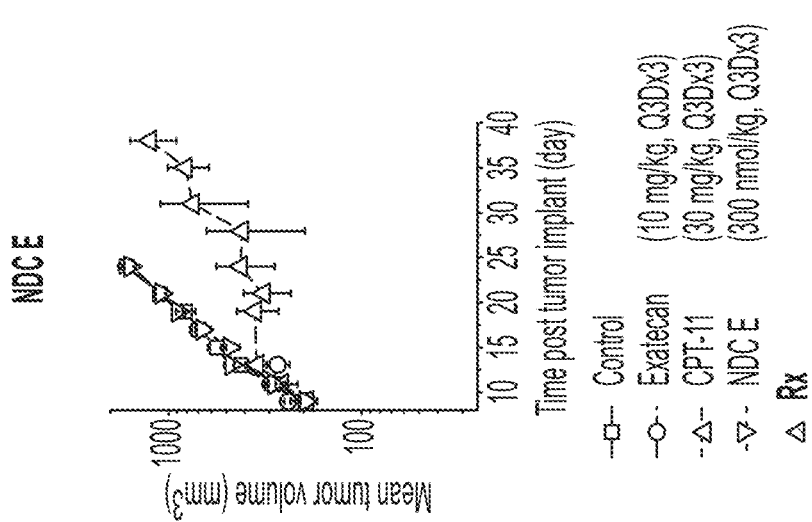
Figure 20D:
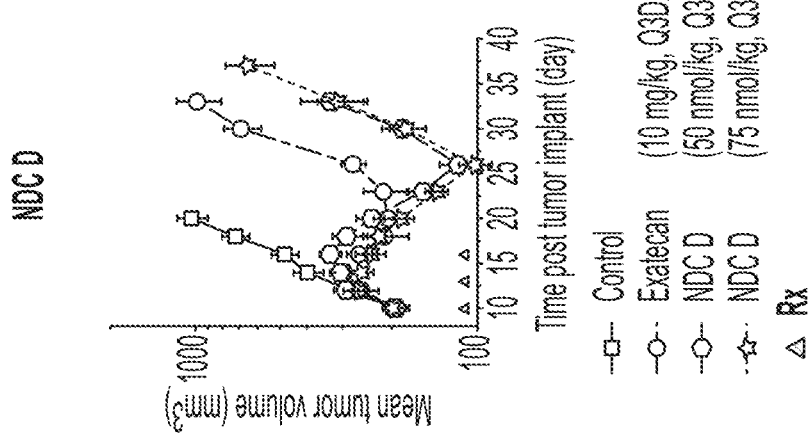

FIGS. 20A-20F depicts the in vivo tumor growth inhibition studies of the six folate receptor-targeting NDCs in KB tumor-bearing mice (n=7). The tumor growth charts depicted for the in vivo efficacy study shows a clear response of tumor growth inhibition in mice treated with the NDC prepared according to Example 3 using the exatecan-payload conjugate precursor 202 (from Example 1), which is shown in FIG. 20D. Similarly, growth inhibition was observed in NDC A (FIG. 20A), NDC B (FIG. 20B), and NDC C (FIG. 20C). In contrast, mice treated with NDC E (FIG. 20E), and NDC F (FIG. 20F) showed no significant inhibition in tumor growth. Doses for the NDCs are provided in FIGS. 20A-20F. Clear response of tumor growth inhibition was observed in mice treated with NDCs A-D. Control group mice received normal saline follow the same Q3DX3 dose regimen.

Example 11: Activity of NDCs in Drug-Resistant Cell Lines

An assay was carried out using the NDCs disclosed herein to determine their activity in drug-resistant cancer cells (specifically, irinotecan-resistant KB cells and exatecan-resistant KB cells). The NDCs used in this assay were prepared according to Example 3, using the exatecan-linker conjugate precursor 202 (from Example 1).
Development of TOP1 Inhibitor-Resistant Folate Receptor Alpha Positive Cancer Cells.

Naïve human KB cell line were purchased from ATCC and maintained in folic acid free RPMI 1640 media/10% FBS, and 1% of penicillin/streptomycin. To develop the TOP1 inhibitor resistant KB cells, the cells in flask (50-60% confluence) were repeatedly treated with increasing concentration of exatecan, topotecan, SN-38 or irinotecan for over 4 months. The starting TOP1 inhibitor treatment concentration was close to the KB cell's $IC_{90}$ values. After each treatment, the cells were carefully washed with fresh RPMI 1640 media and left to proliferate for an additional 2-3 days until reaching 50-60% confluence. The next round of TOP1 inhibitor treatment was started with 2-10× higher TOP1 inhibitor concentration.
Resistant Factor and $IC_{50}$ Assay.

Both naïve and TOP1 inhibitor resistant KB cell were cultured in folic acid-free medium (RPMI1640, ThermoFisher, GIBCO). Cells were plated in opaque 96-well plates at a density of 3×10³ cells per well (total of 90 µL) and allowed to attach overnight. The following day, cells were treated with selected TOP1 inhibitors (e.g., free exatecan) or NDC at suitable concentration ranges. After exposing the TOP1 inhibitors with both types of cells for the same period of time, the cell viability was assessed using the CellTiter-Glo2.0 assay (Promega) according to manufacturer's instructions. Data for both viability and proliferation were plotted using Prism7 software (GraphPad). The resistant factor can be calculated by using the following equation:

$$\text{Resistant factor} = \frac{IC_{50} \text{ of resistant } KB \text{ cell}}{IC_{50} \text{ of naïve } KB \text{ cell}}$$

Irinotecan-Resistant KB Cell Line and Potency Test of NDC

Figure 21B:
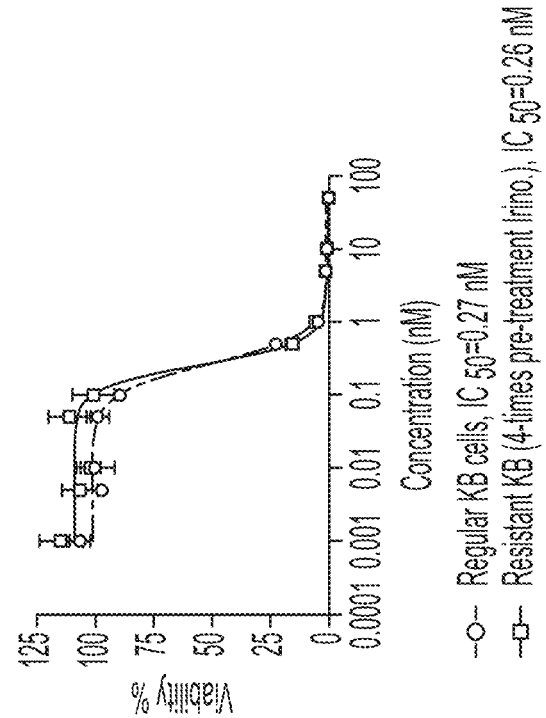
FIGS. 21A-21B depict the $IC_{50}$ curves of an exemplary NDC in irinotecan-resistant and naïve KB cells, compared to non-conjugated irinotecan.
Figure 21A:
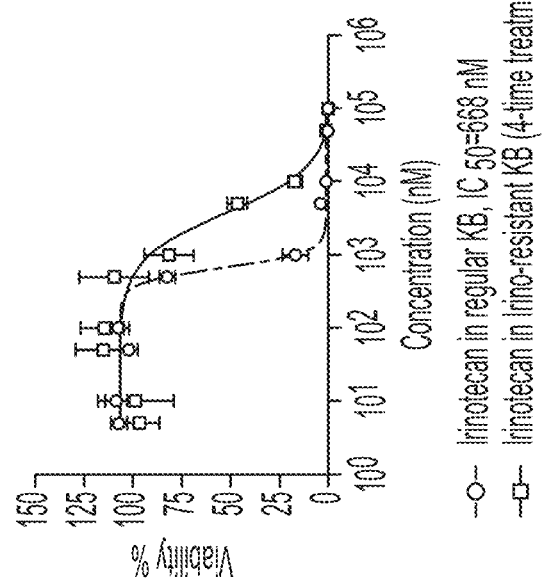
Figure 22B:
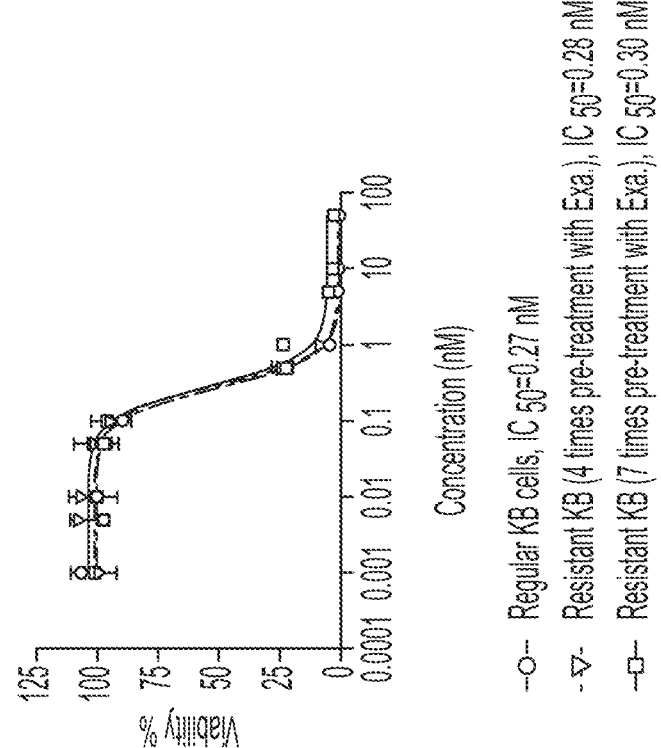
FIGS. 22A-22B depict the $IC_{50}$ curves of an exemplary NDC in exatecan-resistant and naïve KB cells, compared to non-conjugated exatecan.
Figure 22A:
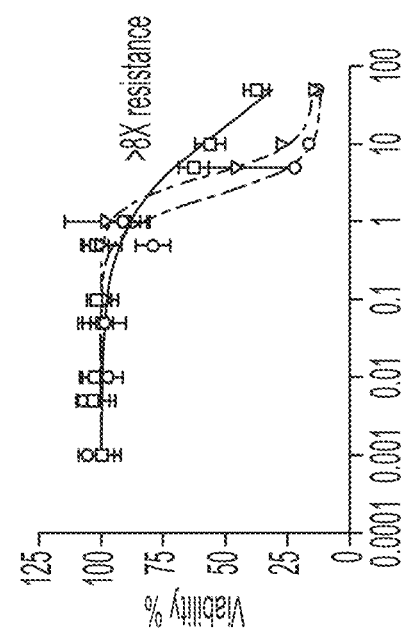
Figure 25A:
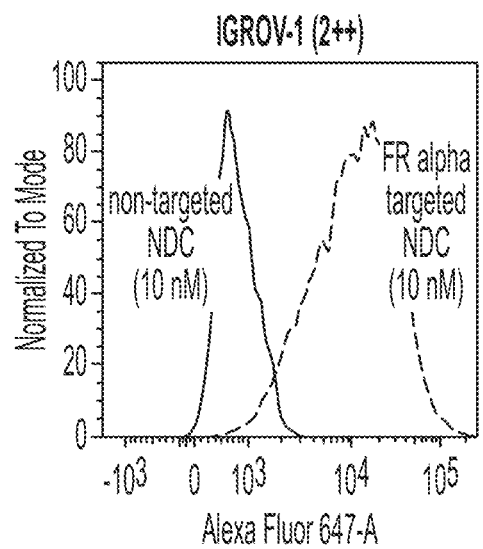
FIGS. 25A-25D provide flow cytometry histograms demonstrating the specific folate receptor (FR) alpha targeting capability of an exemplary FR-targeting NDC (prepared according to Example 3, using the exatecan-linker conjugate precursor 202 of Example 1) to both the IGROV-1 (FR alpha positive human ovarian cancer) and the engineered AML MV4;11 cell line that overexpresses FR alpha.
Figure 25B:
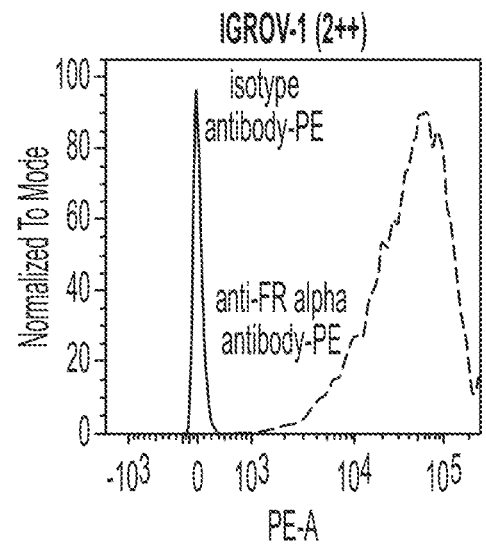
Figure 25C:
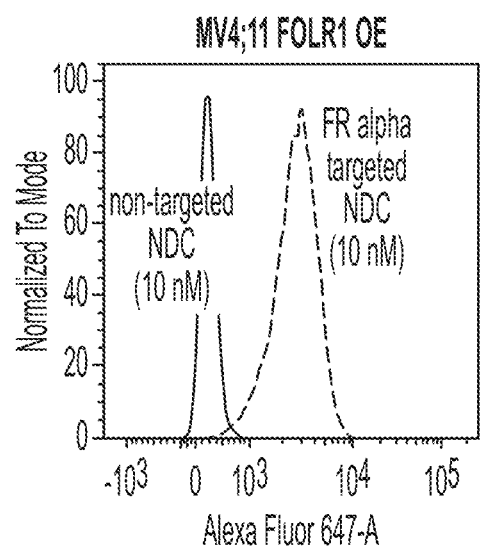
Figure 25D:
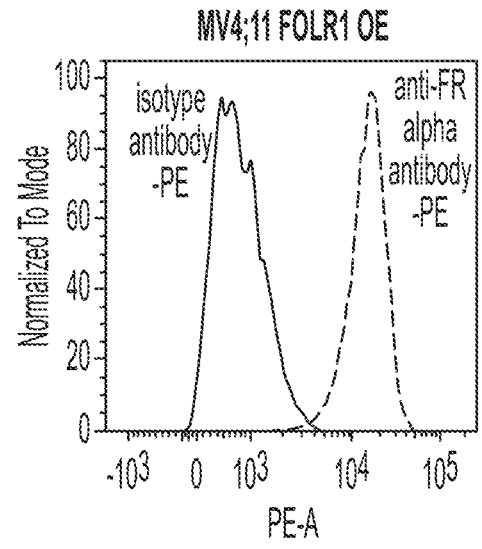

FIG. 21A shows the $IC_{50}$ curves of irinotecan in both naïve and resistant KB cells, which demonstrates the successful development of 5× irinotecan-resistant KB cells, where $IC_{50}$ free irinotecan in irinotecan-resistant KB cells was 3,618 nM, compared to 668 nM in naïve cells. FIG. 21B provides the $IC_{50}$ curves of the NDC (FA-CDC) (prepared according to Example 3, using the exatecan-linker conjugate precursor 202 of Example 1) in the naïve KB cells ($IC_{50}$=0.27 nM) and resistant KB cells (IC50=0.26 nM), indicating the NDC has a high potency that is uniform across both naïve KB cells and TOP1 inhibitor-resistant KB cells.
Exatecan-Resistant KB Cell Line and Potency Test of NDC FIG. 22A shows the $IC_{50}$ curves of exatecan in both naïve and resistant KB cells, which demonstrates the successful development of >8× exatecan-resistant KB cells, where $IC_{50}$ of exatecan in regular KB cells was 2 nM, compared with 4 nM in KB cells pretreated 4× with exatecan, and 16.9 nM in KB cells pretreated 7× with exatecan. FIG. 22B shows the $IC_{50}$ curves of the NDC (FA-CDC) (prepared according to Example 3, using the exatecan-linker conjugate precursor 202 of Example 1) in both naïve and resistant KB cells (4× or 7× pretreatment), where the $IC_{50}$ of the FA-CDC was 0.27 nM, 0.28 nM, and 0.30 nM, respectively. The results indicated the NDC possesses high potency uniformly in both the naïve and resistant KB cells.

Example 12: Activity of NDCs in Cancer Cells with Varied Folate Receptor Expression Levels An assay was conducted to determine the cytotoxicity of exemplary NDCs (FA-CDCs), with varying levels of drug-to-particle ratio, in different FR-alpha overexpressing cancer cell lines, compared to non-conjugated exatecan. The NDCs were prepared according to Example 3, using the payload-linker conjugate precursor 202, of Example 1. The NDCs (FA-CDCs) tested had a drug-to-particle ratio (DPR) of 43, 20, 8, and 1 (i.e., 43, 20, 8, and 1 exatecan-linker groups per nanoparticle).

Cancer cells with varied FR alpha expression levels (KB (++++), IGROV-1(++), SK-OV-3(++), HCC827(++), A549 (−), and BT549(−)) were cultured in folic acid-free medium (RPMI1640, ThermoFisher, GIBCO) for at least one week before the study. Assays for 7-day exposure and 6-hour exposure were both conducted.

Cells were plated in opaque 96-well plates at a density of 3×103 cells per well (total of 90 µL) and allowed to attach overnight. The following day, cells were treated with NDC with varied drug-to-particle ratio (DPR) at a concentration ranging from 0-50 nM (0, 0.001, 0.005, 0.01, 0.05, 0.1, 0.5, 1, 5, 10, 50 nM) by adding 10 µL of 10× stock compounds.

For the 6-hour exposure viability study cells were treated for 6 hours and washed (3×) with 100 µL PBS. 100 µL of fresh cell medium was then added to each well and the plate was incubated for an additional 7 days at 37° C. before performing the CellTiter-Glo® cytotoxic assay (Promega) according to manufacturer's instructions. The results of the 7-day exposure assay are presented in FIG. 23, which demonstrate that the NDC was highly potent across all cell lines, despite differing levels of FR expression in the cells.

For the 7-day exposure viability study, the cells were incubated with compounds for the entire 7-day period, followed by the CellTiter-Glo® cytotoxic assay. Data for half maximal inhibitory concentration (IC50) was plotted using Prism7 software (GraphPad). The results of the 6-hour exposure assay are presented in FIG. 23, which demonstrate that the NDC was highly potent across all cell lines, despite differing levels of FR expression in the cells.

Example 13: Cytotoxicity of NDCs in Patient-Derived Pt-Resistant Tumor Cell Lines An assay was conducted to establish the cytotoxicity of an exemplary NDC (prepared according to Example 1, using the exatecan-linker conjugate precursor Compound 202 from Example 1) in various patient derived tumor cell lines that are Pt-resistant, with comparison to non-conjugated exatecan. Cell lines were obtained from ovarian cancer, non-small cell lung cancer (NSCLC), breast cancer (both HR+, HER2+; and HR−, HER2+; and triple negative breast cancer (TNBC)), endometrial cancer, and head and neck (H&N) cancers. The results of the assay are provided in FIG. 24.

The cytotoxic efficacy was determined by KIYATEC using the KIYA-PREDICT™ assay. The FRα immunohistochemistry (ICH) scoring of tumor tissue from platinum-resistant ovarian, endometrium, non-small cell lung, breast, triple-negative breast, head & neck cancer patients were conducted by XenoSTART by using the Biocare Medical FRα IHC Assay Kit (cat #BRI4006KAA), following the manufacturer's protocol. A total of 28 PDX models from different indications were selected based on the IHC scores and provided to KIYATEC for the KIYA-PREDICT™ assay. Briefly, cryopreserved PDX tumors were thawed and enzymatically dissociated to single cells, and plated into 384-well spheroid microplates (Corning). Flow cytometry was also performed to assess the FRα levels among different PDX models. Following the 24 hours of spheroid formation, NDC or controls were added at the designed concentration range and incubated for 7 days. After that, the cell viability was measured by CellTiter-Glo® 3D (Promega). The data was analyzed in Microsoft Excel and GraphPad Prism.

Example 14: In Vitro and In Vivo Efficacy of an Exemplary NDC in Pediatric Acute Myeloid Leukemia Models Assays were carried out to establish the in vitro and in vivo efficacy of an exemplary NDC (prepared according to the protocol in Example 3, using the exatecan-linker conjugate precursor 202 from Example 1) in folate-receptor alpha-positive pediatric acute myeloid leukemia models.

In Vitro Flow Cytometry Cell Binding Study

Cancer cells (IGROV-1 and AML MV4;11 cell lines) were cultured in folic acid-free medium (RPMI1640, ThermoFisher, GIBCO) for at least one week before the study. Cell binding studies were performed by incubating $5 \times 10^5$ cells (total of 500 µL, 1 million/mL) in cold phosphate-buffered saline (PBS) (with 1% of bovine serum albumin (BSA)) with the exemplary NDC or with anti-FR alpha phycoerythrin (PE)-conjugated antibodies (anti-FR alpha antibody-PE) (concentration: 10 nM) for 60 min at 4° C. (n=3). A non-targeted CDC and isotype antibody-PE were used as negative controls for the exemplary NDC and anti-FR alpha antibody-PE, respectively. The cell suspension was then stained with viability kit (LIVE/DEAD™ Fixable Violet Dead Cell Stain Kit, Thermo Fisher) for 10-15 min. The cells were next centrifuged (2000 revolutions per minute, 5 min), washed (2-3 times) using cold PBS (with 1% of BSA) before resuspending in PBS (with 1% of BSA). Triplicate samples were analyzed on a LSRFortessa flow cytometer (BD Biosciences) (Cy5 channel, 633 nm/647 nm, Live/dead cell stain, 405 nm). Results were processed using FlowJo and Prism 7 software (GraphPad).

The flow cytometry histograms of the exemplary NDC and anti-FR alpha antibody-PE compared with the respective negative controls (non-targeted NDC or isotype antibody-PE) are shown in FIGS. 25A-25D. The flow study demonstrates the specific FR alpha targeting capability of the exemplary NDC to both the IGROV-1 (FR alpha positive human ovarian cancer) and the AML MV4;11 cell lines.

In Vitro CellTiter-Glo® Cytotoxic Assay

Cancer cells (IGROV-1 and AML MV4;11 cell lines) were cultured in folic acid-free medium (RPMI1640, ThermoFisher, GIBCO) for at least one week before the study. Cells were plated in opaque 96-well plates at a density of $3 \times 10^3$ cells per well (total of 90 µL) and allowed to attach overnight. The following day, cells were treated with the exemplary NDC at a concentration ranging from 0-100 nM, by adding 10 µL of 10× stock NDC solution. For the shorter exposure viability study, cells were treated for 4 hours and washed (3×) with 100 µL PBS. 100 µL of fresh cell medium without the NDC was then added to each well and the plate was incubated for an additional 5 days at 37° C. before performing the CellTiter-Glo® cytotoxic assay (Promega) according to manufacturer's instructions. Data for half maximal inhibitory concentration ($IC_{50}$) was plotted using Prism7 software (GraphPad).

Figure 26A:
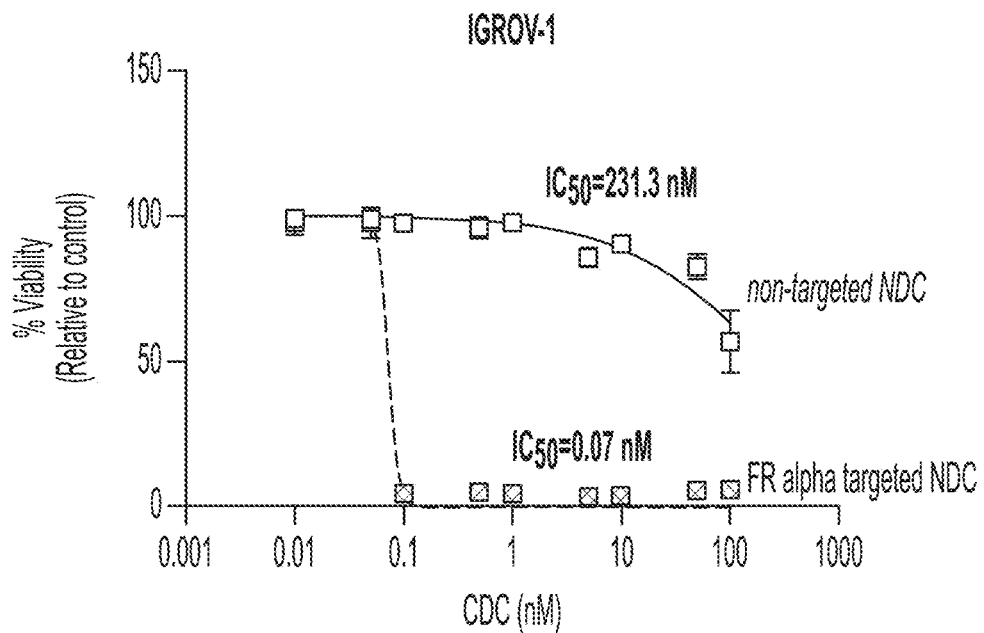
FIGS. 26A-26B are graphs illustrating the in vitro cytotoxic activity of an exemplary NDC (prepared according to Example 3 using the exatecan-linker conjugate precursor of Example 1, Compound 202) in IGROV-1 (FR alpha positive human ovarian cancer) cell line (FIG. 26A) and MV4; 11 engineered AML MV4;11 cell line that overexpresses FR alpha (FIG. 26B) using non-targeted NDC as negative control.
Figure 26B:
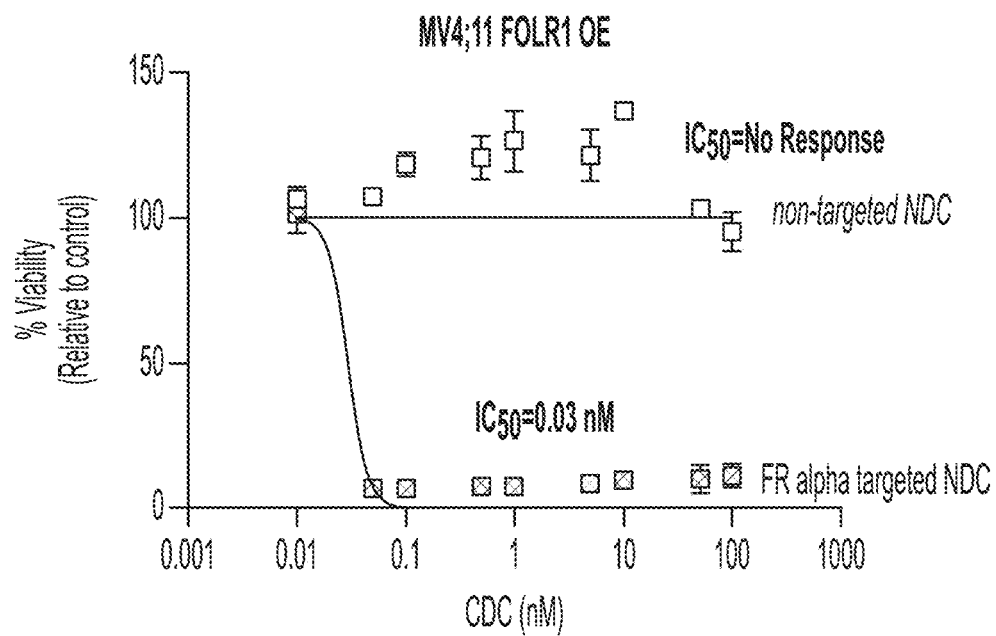

The in vitro specific cytotoxic activity of the exemplary NDC in FR alpha positive human ovarian cancer and MV4;11 AML cell lines is displayed in FIGS. 26A-26B. Cells were treated with the exemplary NDC at the indicated concentrations, incubated at 37° C. for 4 hours, washed, and returned to the incubator for an additional 5 days, before performing the CellTiter-Glo® cytotoxic assay.

CBFA2T3-GLIS2 Fusion-Positive AML Cell Line-Derived Xenograft Models

Figure 31:
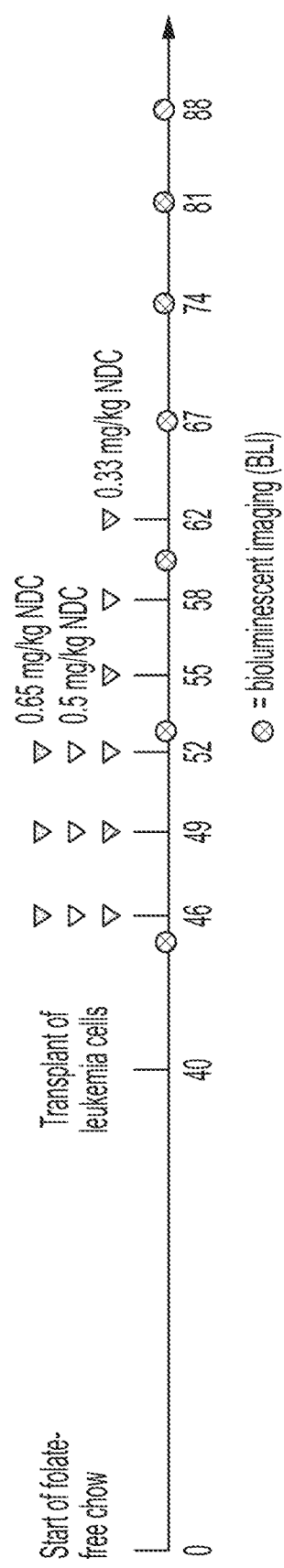
FIG. 31 is an illustration of the timeline used for preparing FR alpha overexpressing AML mice and dosing the mice with an exemplary NDC (prepared according to Example 3, using the exatecan-linker conjugate precursor of Example 1, Compound 202) at three different dose regimens (0.33 mg/kg, Q3Dx6); 0.50 mg/kg, Q3Dx3; or 0.65 mg/kg, Q3Dx3), and imaging the mice with bioluminescent imaging (BLI). Each day of dosing is denoted by a triangle (i.e., on days 46, 49, and 52 for all dose groups, and also on days 55, 58, and 62 for the 0.33 mg/kg Q3Dx6 dose group).

In vivo anti-tumor killing activity of the exemplary NDC was assessed in cell line-derived xenograft (CDX) models. NOD scid gamma (NSG) mice were fed with folate free chow for 1 week prior to injection with AML cell lines. Then 1-5 million fusion-positive cell lines (M07e, WSU-AML) and engineered cells (MV4;11 FOLR+) transduced with Luciferase reporter were transplanted into the NSG mice via tail-vein injections. Leukemia burden and response to treatments was monitored using non-invasive bioluminescent imaging (from both the front and the back of the mouse), and flow cytometry analysis of mouse peripheral blood drawn by submandibular bleeds was carried out bi-weekly, starting from the first week of CDC treatment. Mice were monitored for disease symptoms (including tachypnea, hunchback, persistent weight loss, fatigue, and hind-limb paralysis). Mice from the saline control group (Cohort 1) were euthanized due to the high AML burden on Day 44 post-leukemia injection (tissues including blood, bone marrow, thymus, liver, lungs and spleen were harvested at necropsy and analyzed for the presence of leukemia cells). Mice from the treatment groups (Cohorts 2-4) continued to receive weekly bioluminescent imaging and bodyweight monitoring. An illustration of the timeline for mice preparation, treatment, and imaging is provided in FIG. 31.

All the mice were randomized prior to dosing and weighed to provide the correct designed dose based on Table 6 below. Leukemia burden and response to treatments was monitored weekly using non-invasive bioluminescent imaging. Bodyweight was measured every other day. The mice were terminated if their weight loss was over 20%.

TABLE 6

Dose design (n = 5 per group)

| Cohort | Material Administered | Study Phase | Dose (mg/kg of Exatecan) | Regimen | IV Dose volume (mL/kg) | Clinical Observations and Study End Points |
|---|---|---|---|---|---|---|
| 1 | Normal saline | Vehicle control | n/ap | Q3D × 3 | 10 | Every other day body weight (BW) |
| 2 | NDC | escalation | 0.33 | Q3D × 6 | 10 | |

TABLE 6-continued

Dose design (n = 5 per group)

| Cohort | Material Administered | Study Phase | Dose (mg/kg of Exatecan) | Regimen | IV Dose volume (mL/kg) | Clinical Observations and Study End Points |
|---|---|---|---|---|---|---|
| 3 | NDC | escalation | 0.50 | Q3D × 3 | 10 | End point: |
| 4 | NDC | escalation | 0.65 | Q3D × 3 | 10 | BW loss >20% |

Figure 27:
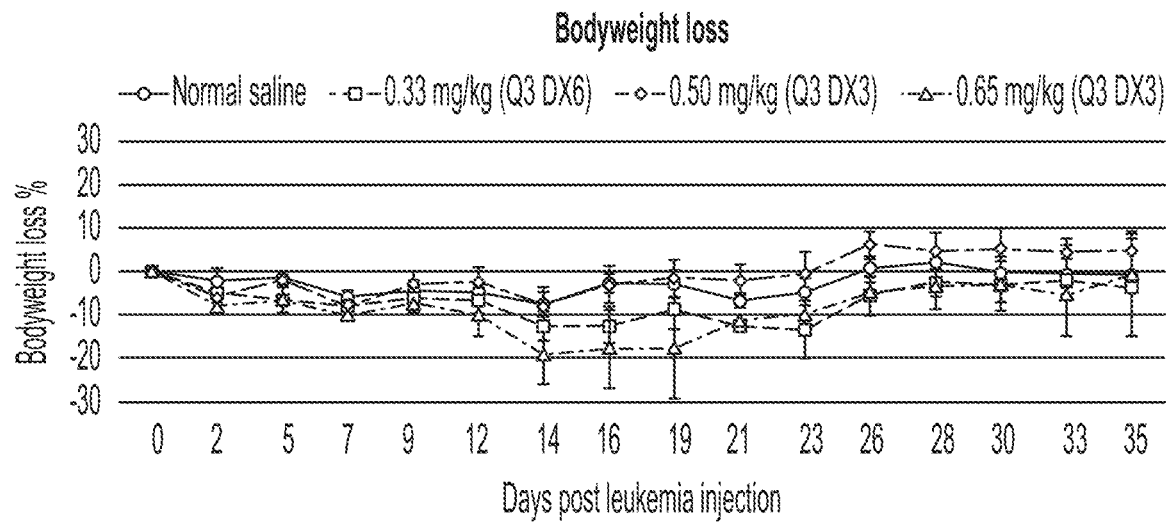
FIG. 27 is a graph providing the bodyweight change of FR alpha overexpressing AML mice over time after treatment with normal saline or an exemplary NDC (prepared according to Example 3, using the exatecan-linker conjugate precursor of Example 1, Compound 202) at three different dose regimens (0.33 mg/kg, Q3Dx6 (denoted with squares); 0.50 mg/kg, Q3Dx3 (denoted with diamonds); or 0.65 mg/kg, Q3Dx3 (denoted with triangles)).

FIG. 27 provides the bodyweight change of AML mice treated with normal saline and the exemplary NDC at the three dose levels indicated in Table 6. The normal saline group (Cohort 1) showed a bodyweight loss within 20%, mainly due to the leukemia burden. In the 0.33 mg/kg (Q3Dx6) dose group (Cohort 2), 4 of 5 mice tolerated the NDC well (<20% loss), and bodyweight was gained after 6 doses; while the remaining mouse showed >20% bodyweight loss after the 5$^{th}$ dose, and more bodyweight loss after the 6$^{th}$ dose. In the 0.50 mg/kg (Q3Dx3) dose group (Cohort 3), all 5 mice tolerated the NDC well (<20% loss), and bodyweight was gained after 3 doses. In the 0.65 mg/kg (Q3Dx3) group (Cohort 4), 2 of 5 mice tolerated the NDC well (<20% loss), and bodyweight was gained after 3 doses, while 3 of 5 mice showed >20% bodyweight loss after the 3$^{rd}$ dose.

Figure 28:
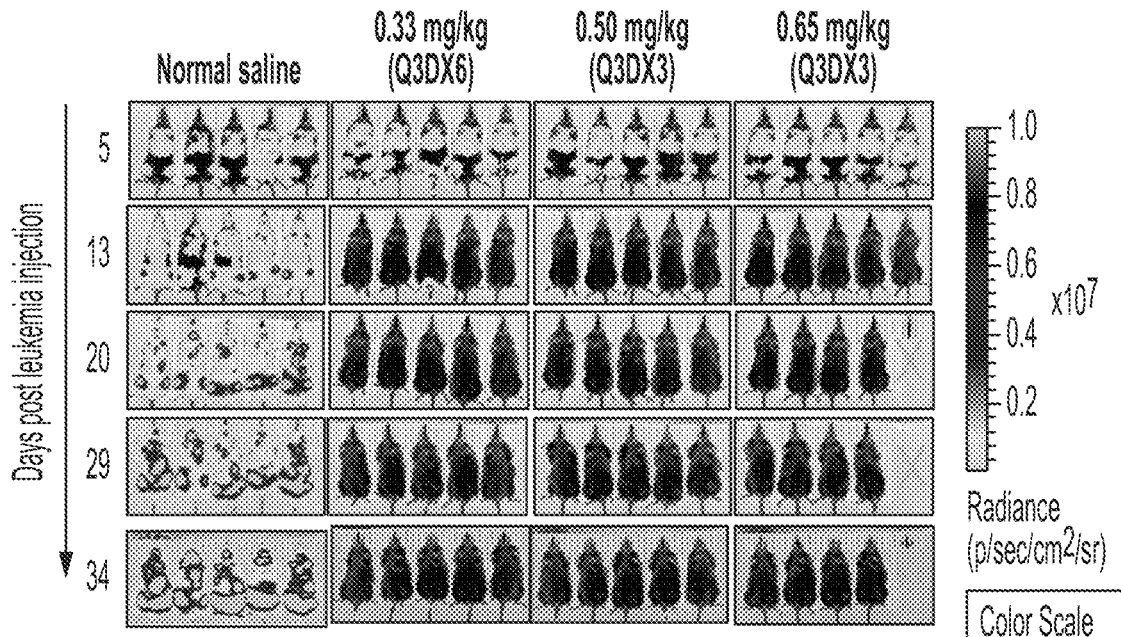
FIG. 28 provides images from in vivo bioluminescence imaging (BLI) of FR alpha overexpressing AML mice treated with normal saline or an exemplary NDC (prepared according to Example 3, using the exatecan-linker conjugate precursor of Example 1, Compound 202) at three different dose regimens (0.33 mg/kg, Q3Dx6); 0.50 mg/kg, Q3Dx3; or 0.65 mg/kg, Q3Dx3).
Figure 29:
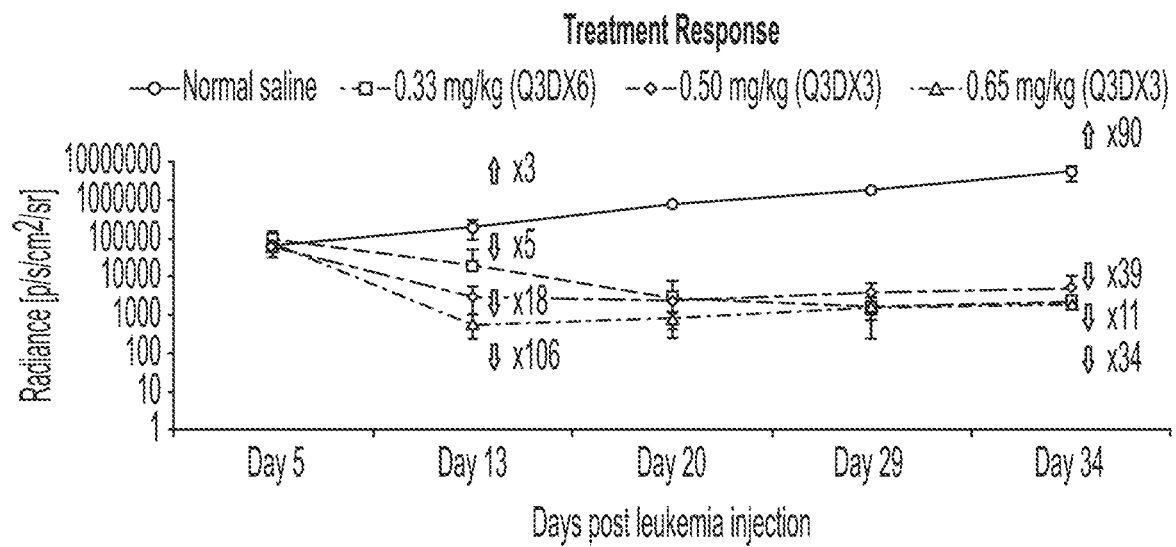
FIG. 29 is a graph providing the quantitative in vivo bioluminescence imaging analysis of FR alpha overexpressing AML mice treated with normal saline or an exemplary NDC (prepared according to Example 1, using the exatecan-linker conjugate precursor of Example 1, Compound 202) at three different dose regimens (0.33 mg/kg, Q3Dx6); 0.50 mg/kg, Q3Dx3; or 0.65 mg/kg, Q3Dx3).

FIG. 28 provides the in vivo bioluminescence images (BLI) obtained from the AML mice treated with normal saline or the exemplary NDC at each dose regimen (i.e., Cohorts 1-4 from Table 6). Quantitative in vivo bioluminescence imaging analysis of Cohorts 1-4 (i.e., AML mice treated with normal saline or the exemplary NDC at each dose regimen outlined in Table 6) is provided in FIG. 29. In the normal saline group (Cohort 1), the leukemia burden continued to progress, with the average whole-body BLI signal increasing >90 fold in 34 days, while a quick and dose-dependent suppression of the leukemia burden was achieved in all 3 treatment groups (Cohorts 2-4). The 0.5 mg/kg (Q3Dx3) dose group (Cohort 3) showed 11-fold less leukemia burden on Day 34 when compared with burden on Day 1 post-leukemia injection. When comparing the 0.33 mg/kg (Q3Dx6) dose group (Cohort 2) with the 0.65 mg/kg (Q3Dx3) dose group (Cohort 4), 0.33 mg/kg was tolerated better with a slightly better response. Taken together, these data indicate the exemplary NDC successfully suppressed the leukemia burden in the FR alpha positive AML mice, and showed quick and dose-dependent response.

Figure 30:
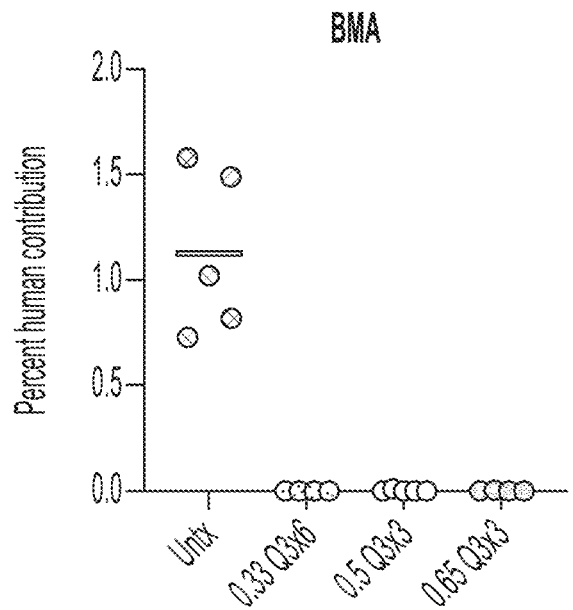
FIG. 30 is a graph indicating the leukemia detected in bone marrow aspiration at Day 42 post-leukemia cell injection, obtained from mice treated with normal saline or an exemplary NDC (prepared according to Example 3, using the exatecan-linker conjugate precursor of Example 1, Compound 202) at three different dose regimens (0.33 mg/kg, Q3Dx6); 0.50 mg/kg, Q3Dx3; or 0.65 mg/kg, Q3Dx3).

FIG. 30 provides a graph illustrating the results of bone marrow aspiration of Cohorts 1-4 (i.e., the mice treated with normal saline or the exemplary NDC at each dose group indicated in Table 6) on Day 42 post-leukemia injection. Leukemia was detected in the group of mice treated with normal saline (Cohort 1), while no detectable leukemia burden could be observed in any of the mice from the treatment groups (Cohorts 2-4).

Example 15. Stability of Linker Derived from Diene

In order to determine the stability of NDCs disclosed herein prepared using a diene-based functionalization approach, the stability of NDC prepared using a diene based functionalization approach were compared to NDC prepared using an amine-based functionalization approach.

The NDCs were incubated in 0.9% saline, PBS, human plasma (10%), and mouse plasma (10%) at 37° C. in a shaking dry bath for different time periods. Prior to analysis, plasma proteins in the samples were removed by precipitation, through addition of an equivalent volume of cold acetonitrile, followed by centrifugation at 10000 rpm in an Eppendorf 5425 microcentrifuge. Following centrifugation, the clear supernatant was transferred from the centrifuge tube into a clear total recovery HPLC vial. The supernatant free of any visible aggregation was diluted with an equivalent volume of deionized water to adjust the sample matrix to match the starting conditions of the HPLC separation and avoid loss of sensitivity. The purity and impurity of each sample is then quantified by RP-HPLC.

The targeted-NDCs produced using the methods described in Example 3, using the diene-silane precursor exhibited high stability in mouse and human plasma, and showed significant stability improvement, relative to corresponding NDCs produced using an amine-silane precursor (see FIGS. 33A and 33B)). In the NDCs prepared using the diene-silane precursor, more than 95% of exatecan drugs remain on the NDCs for up to 7 days in mouse and human plasma, obtained by the UV-Vis spectra of the NDC peaks in RP-HPLC chromatograms. Meanwhile, an independent RP-HPLC assay monitoring free exatecan suggested that the released exatecan was below detection limit of RP-HPLC, i.e., 0.02%, and the absence of non-desired free drug further demonstrates their high plasma stability. The targeted-NDCs also exhibited high storage stability at 4° C. in 0.9% saline. Their purity, size distribution, and hydrodynamic diameter were characterized by RP-HPLC, SEC and FCS respectively, and remained unchanged over 6 months under storage condition. Such high storage stability is another key parameter important for both clinical translation and commercial manufacture.

Example 16. Pharmacokinetics and Toxicology Study

The pharmacokinetics and toxicology of an exemplary NDC were assessed in a rat model and in a dog model. The NDC used in this study was prepared according to Example 3, using the exatecan-linker conjugate precursor compound 202 of Example 1. As demonstrated in the above examples, this exemplary NDC is highly stable in plasma and elicits antitumor efficacy in a variety of cell line and PDX-derived tumor models both in vitro and in vivo.

In 15-day repeat dose toxicology and toxicokinetic (TK) studies performed in Wistar Han rats and Beagle dogs, the NDC was tolerated at up to 0.87 mg/kg/day in rats and 0.174 mg/kg/day in dogs based upon conjugated exatecan concentration when administered on a QWx3 schedule via a 1-hour infusion. Observed dose-related toxicities for both species were limited to the bone marrow and gastrointestinal tract. These are the same organs as those observed when free payload (exatecan) was administered, suggesting that the delivery of exatecan conjugated to the NDC did not broaden the tissue toxicity profile. Observed toxicities were recovered or substantially reduced by the end of a two-week recovery period. No drug-related hepatic, renal, pulmonary or ocular toxicities were observed, and there were no drug-related deaths in the repeat dose toxicity study.

TK parameters, estimated in the 15-day GLP study, revealed similar plasma exposure values in males and females for the NDC, total exatecan (conjugated and released) and released exatecan. The NDC exhibited an average circulatory half-life ranging from approximately 15 to 20 hours in rats, and 24 to 29 hours in dogs, with no accumulation of the NDC, total exatecan, or free exatecan observed from day 1 to day 15. Based upon $AUC_{0-last}$ (hr*ng/mL) released payload levels in the circulation were less than approximately 0.3% and 0.10% of the total payload levels in the rat and the dog respectively. No NDC anti-drug antibodies were induced in either species. In summary, the NDC has a favorable nonclinical safety/TK profile.

While the invention has been particularly shown and described with reference to specific preferred embodiments, it should be understood by those skilled in the art that various changes in form and detail may be made therein without departing from the spirit and scope of the invention as defined by the appended claims.

```
                              SEQUENCE LISTING

Sequence total quantity: 15
SEQ ID NO: 1            moltype =    length =
SEQUENCE: 1
000

SEQ ID NO: 2            moltype =    length =
SEQUENCE: 2
000

SEQ ID NO: 3            moltype =    length =
SEQUENCE: 3
000

SEQ ID NO: 4            moltype =    length =
SEQUENCE: 4
000

SEQ ID NO: 5            moltype =    length =
SEQUENCE: 5
000

SEQ ID NO: 6            moltype =    length =
SEQUENCE: 6
000

SEQ ID NO: 7            moltype =    length =
SEQUENCE: 7
000

SEQ ID NO: 8            moltype = AA   length = 4
FEATURE                 Location/Qualifiers
source                  1..4
                        mol_type = protein
                        organism = synthetic construct
SITE                    4
                        note = MeGly
SEQUENCE: 8
VFGG                                                                      4

SEQ ID NO: 9            moltype =    length =
SEQUENCE: 9
000

SEQ ID NO: 10           moltype = AA   length = 4
FEATURE                 Location/Qualifiers
source                  1..4
                        mol_type = protein
                        organism = synthetic construct
SITE                    4
                        note = MeGly
SEQUENCE: 10
VKGG                                                                      4

SEQ ID NO: 11           moltype = AA   length = 4
FEATURE                 Location/Qualifiers
source                  1..4
                        mol_type = protein
                        organism = synthetic construct
SITE                    4
                        note = MeGly
SEQUENCE: 11
VAGG                                                                      4

SEQ ID NO: 12           moltype = AA   length = 4
FEATURE                 Location/Qualifiers
source                  1..4
                        mol_type = protein
                        organism = synthetic construct
```

```
SEQUENCE: 12
VFGP                                                                          4

SEQ ID NO: 13          moltype =    length =
SEQUENCE: 13
000

SEQ ID NO: 14          moltype = AA   length = 4
FEATURE                Location/Qualifiers
source                 1..4
                       mol_type = protein
                       organism = synthetic construct
SEQUENCE: 14
VKGP                                                                          4

SEQ ID NO: 15          moltype = AA   length = 4
FEATURE                Location/Qualifiers
source                 1..4
                       mol_type = protein
                       organism = synthetic construct
SEQUENCE: 15
VAGP                                                                          4
```

What is claimed is:

1. A nanoparticle-drug conjugate (NDC) comprising:
   (a) a silica nanoparticle;
   (b) polyethylene glycol (PEG) that is covalently bonded to the surface of the silica nanoparticle;
   (c) a targeting ligand comprising folic acid, wherein the targeting ligand is attached to the silica nanoparticle through a first spacer group; and
   (d) a linker-payload conjugate, wherein:
      (i) the payload is exatecan;
      (ii) the linker-payload conjugate is attached to the silica nanoparticle through a second spacer group;
      (iii) the linker is a protease-cleavable linker; and
      (iv) the exatecan is released upon cleavage of the linker,
   wherein the first spacer group and the second spacer group each comprise a structure of Formula (NP):

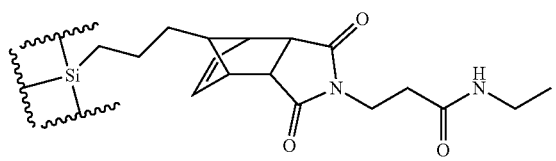

(NP)

-continued

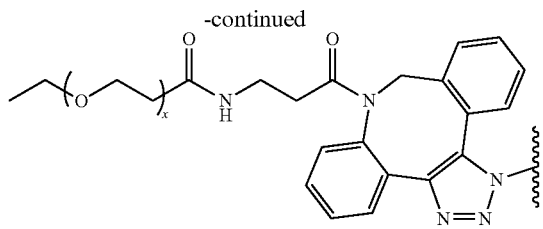

wherein
  x is an integer of 0 to 20;
  the silicon atom (Si) is a part of the silica nanoparticle; and
  the ⸹ adjacent to the triazole moiety denotes a point of attachment to the targeting ligand or the linker-payload conjugate, either directly or indirectly.

2. A nanoparticle-drug conjugate (NDC) comprising:
   (a) a silica nanoparticle;
   (b) polyethylene glycol (PEG) that is covalently bonded to the surface of the silica nanoparticle;
   (c) a targeting ligand comprising folic acid, wherein the targeting ligand is attached to the silica nanoparticle through a spacer group; and
   (d) a structure of Formula (S-1):

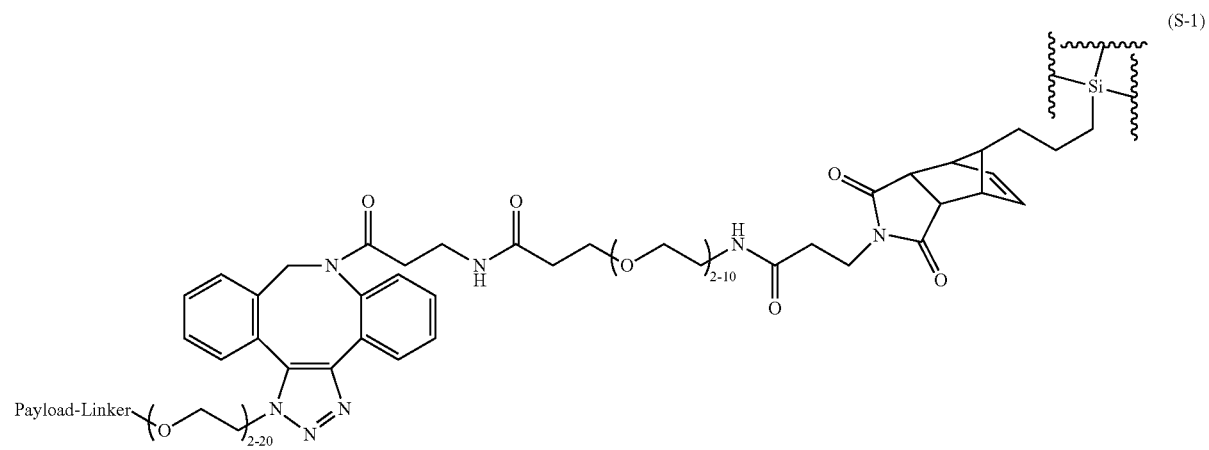

(S-1)

wherein
Payload comprises exatecan;
Linker comprises a protease-cleavable linker, wherein the exatecan is released upon cleavage of the linker; and
the silicon atom (Si) is a part of the silica nanoparticle.

3. A nanoparticle-drug conjugate (NDC) comprising:
(a) a silica nanoparticle;
(b) polyethylene glycol (PEG) that is covalently bonded to the surface of the silica nanoparticle;
(c) a structure of Formula (S-2):

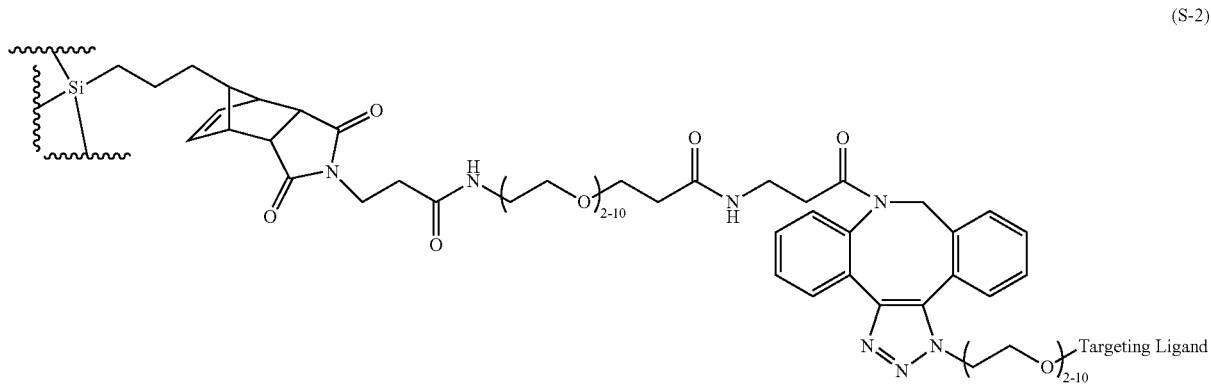

(S-2)

wherein
Targeting Ligand comprises folic acid; and
the silicon atom (Si) is a part of the silica nanoparticle; and
(d) a linker-payload conjugate, wherein:
(i) the payload is exatecan;
(ii) the linker-payload conjugate is attached to the silica nanoparticle through a spacer group;
(iii) the linker is a protease-cleavable linker; and
(iv) the exatecan is released upon cleavage of the linker.

4. A nanoparticle-drug conjugate (NDC) comprising:
(a) a silica nanoparticle;
(b) polyethylene glycol (PEG) that is covalently bonded to the surface of the silica nanoparticle;
(c) a targeting ligand comprising folic acid, wherein the targeting ligand is attached to the silica nanoparticle through a first spacer group; and
(d) a linker-payload conjugate that is attached to the silica nanoparticle through a second spacer group, wherein the payload is exatecan, the linker is a protease-cleavable linker, the exatecan is released upon cleavage of the linker, and wherein the linker-payload conjugate comprises a structure of Formula (I):

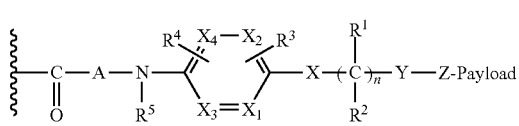

(I)

or a salt thereof,
wherein,
} denotes a point of attachment to the second spacer group;
A is Val-Lys;
Payload comprises a residue of the exatecan;
Z is an —NH— group of the exatecan;

$R^1$, $R^2$, $R^3$, $R^4$, and $R^5$ in each occurrence is independently hydrogen;
X is absent;
Y is

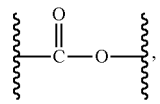

wherein the carbonyl in

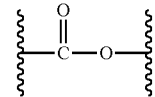 [SMILES: *OC(*)=O]

is bonded to Z;
$X_1$, $X_2$, $X_3$, and $X_4$ are each independently —CH—; and
n is 1.

5. The NDC of claim 1, wherein the protease comprises a serine protease or a cysteine protease.

6. A pharmaceutical composition comprising an NDC of claim 1, and a pharmaceutically acceptable excipient.

7. The pharmaceutical composition of claim 6, wherein the pharmaceutical composition is for intravenous administration.

8. The NDC of claim 1, wherein the NDC has an average diameter between about 1 nm and about 10 nm.

9. The NDC of claim 2, wherein the NDC has an average diameter between about 1 nm and about 10 nm.

10. The NDC of claim 3, wherein the NDC has an average diameter between about 1 nm and about 10 nm.

11. The NDC of claim 4, wherein the NDC has an average diameter between about 1 nm and about 10 nm.

12. The NDC of claim 1, wherein the NDC comprises from about 1 to about 40 linker-payload conjugates.

13. The NDC of claim 2, wherein the NDC comprises from about 1 to about 40 moieties with the structure of Formula (S-1).

14. The NDC of claim 3, wherein the NDC comprises from about 1 to about 40 linker-payload conjugates.

15. The NDC of claim 4, wherein the NDC comprises from about 1 to about 40 linker-payload conjugates.

16. The NDC of claim 1, wherein the NDC comprises from about 1 to about 30 targeting ligands.

17. The NDC of claim 2, wherein the NDC comprises from about 1 to about 30 targeting ligands.

18. The NDC of claim 3, wherein the NDC comprises from about 1 to about 30 moieties with the structure of Formula (S-2).

19. The NDC of claim 4, wherein the NDC comprises from about 1 to about 30 targeting ligands.

20. The NDC of claim 1, further comprising a fluorescent compound that is covalently encapsulated within the silica nanoparticle.

21. The NDC of claim 2, further comprising a fluorescent compound that is covalently encapsulated within the silica nanoparticle.

22. The NDC of claim 3, further comprising a fluorescent compound that is covalently encapsulated within the silica nanoparticle.

23. The NDC of claim 4, further comprising a fluorescent compound that is covalently encapsulated within the silica nanoparticle.

24. The NDC of claim 1, wherein x is an integer of 4.

25. A pharmaceutical composition comprising an NDC of claim 2, and a pharmaceutically acceptable excipient.

26. The pharmaceutical composition of claim 25, wherein the pharmaceutical composition is for intravenous administration.

27. A pharmaceutical composition comprising an NDC of claim 3, and a pharmaceutically acceptable excipient.

28. The pharmaceutical composition of claim 27, wherein the pharmaceutical composition is for intravenous administration.

29. A pharmaceutical composition comprising an NDC of claim 4, and a pharmaceutically acceptable excipient.

30. The pharmaceutical composition of claim 29, wherein the pharmaceutical composition is for intravenous administration.

* * * * *